US012674149B2

(12) United States Patent
Doudna et al.

(10) Patent No.: US 12,674,149 B2
(45) Date of Patent: Jul. 7, 2026

(54) CRISPR-CAS EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Evangelina Nogales De La Morena, Berkeley, CA (US); Jun-Jie Liu, Albany, CA (US); Connor Andrew Tsuchida, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 408 days.

(21) Appl. No.: 18/038,398

(22) PCT Filed: Dec. 1, 2021

(86) PCT No.: PCT/US2021/061455
§ 371 (c)(1),
(2) Date: May 23, 2023

(87) PCT Pub. No.: WO2022/119957
PCT Pub. Date: Jun. 9, 2022

(65) Prior Publication Data
US 2023/0407276 A1     Dec. 21, 2023

Related U.S. Application Data

(60) Provisional application No. 63/272,900, filed on Oct. 28, 2021, provisional application No. 63/120,638, filed on Dec. 2, 2020.

(51) Int. Cl.
*C12N 9/22*      (2006.01)
*C12N 15/10*     (2006.01)
*C12N 15/63*     (2006.01)

(52) U.S. Cl.
CPC ............ *C12N 9/22* (2013.01); *C12N 15/102* (2013.01); *C12N 15/63* (2013.01); *C12N 2310/20* (2017.05)

(58) Field of Classification Search
CPC ...................................................... C12N 9/22
See application file for complete search history.

(56) References Cited

U.S. PATENT DOCUMENTS 11,535,835 B1 * 12/2022 Oakes ..................... A61P 27/02
11,795,472 B2 * 10/2023 Doudna ................. C07K 19/00
(Continued)

FOREIGN PATENT DOCUMENTS

WO      WO 2018/064371 A1      4/2018
WO      WO 2020/247882 A1      12/2020

OTHER PUBLICATIONS

Fransceus. J Ind Microbiol Biotechnol. May 2017;44(4-5):687-695. (Year: 2017).*
(Continued)

*Primary Examiner* — Yong D Pak
(74) *Attorney, Agent, or Firm* — Kyle A. Gurley; Bozicevic, Field & Francis LLP

(57) ABSTRACT

The present disclosure provides variant CRISPR-Cas effector polypeptides, as well as engineered guide nucleic acids, and systems comprising the same. The present disclosure provides methods of modifying a target nucleic acid, using a variant CRISPR-Cas effector polypeptide of the present disclosure.

65 Claims, 52 Drawing Sheets
Specification includes a Sequence Listing.

DpbCasXv2
MENRINKIRKKLSADNATKPVSRSGPMKTLLVRVMTDDLKKRLEKRRKKPEVMPQVISN
NAANNLRMLLDDYTKMKEAILQVYWQEFKDDHVGLMCKFAQPASKKIDQNKLKPEMDEK
GNLTTAGFACSQCGQPLFVYKLEQVSENGRAYTNYFGRCNVAEHEKLILLLAQLKPEKDS
DEAVTYSLGKFCQRALDFYSIHVTKESTHPVKPLAQIAGNRYASGPVGKALSDACMGTI
ASFLSKYQDIIIEHQKVVKGNQKRLESLRELAGKENLEYPSVTLPPQPHIKEGVDAYNE
VIARVRMWVNLNIWQKLKLSRDDAKPLLRLKGPPSPPVVERRENEVDWWNTINEVKKLI
DAKRDMGRVFWSGVTAEKRNTILEGYNYLPNENDHKKREGSLENPKKPAKRQFGDLLLY
LEKKYAGDWGKVPDEAWERIDKKIAGLTSHIEREEARNAEDAQSKAVLTDWLRAKASFV
LERLKEMDEKEFYACSIQLQKWYGDLRGNPFAVEAENRVVDISGFSIGSDGHSIQYRNL
LAWKYLENGKRSFYILMNYGKRGRIRFTDGTDIKKSGKWQGLLYGGGKAKVIDLTFDPD
DEQLIILPLAFGTRQGREFIWNDLLSLETGLIKLANGRVISKIIYNKKIGRDEPALFVA
LTFERREVVDPSNIKPVNLIGVDRGENIPAVIALTDPEGCPLPEFKDSSGGPTDILRIG
EGYKEKQRAIQAAKEVEQRRAGGYSRKFASKSRNLADDMVRNSARDLFYBAVTHDAVLV
FENLSRGFGRQGKRTFMTEPQYIKMEDWLTAKLAYEGLTSKTYLSKTLAQYTSKTCSNC
GFTITTADYDGMLVRLKKTSOGWATTLNNKELKAEGQITYYNRYKRQTVEKELSAELDR
LSEESGMNDISKWTRGRRDEALFLLKKPFSHRPVQEQFVCLDCGHEVHADEQAALNIAR
SWLFLREQEYKKYQINKTTGNTBKRAPVEIWQSFYKRRLKEVWKPWA

DpbCasXv1
MEKRINKIRKKLSADNATKPVSRSGPMKTLLVRVMTDDLKKRLEKPRKKPEVMPQVISN
NAANNLRMLLDDYTKMKEAILQVYWQEFKDDHVGLMCKFAQPASKKIDQNKLKPEMDEK
GNLTTAGFACSQCGQPLFVYKLEQVSEKGKAYTNYFGRCHVAEHEKLILLLAQLKPEKDS
DEAVTYSLGKFGQRALDFYSIHVTKESTHPVKPLAQIAGNRYASGPVGKALSDACMGTI
ASFLSKYQDIIIEHQKVVKGNQKRLESLRELAGKENLEYPSVTLPPQPHIKEGVDAYNE
VIARVRMWVNLNLWQKLKLSRDDAKPLLRLKGPFSPPVVERRENEVDWWNTINEVKKLI
DAKRDMGRVFWSGVIAEKRNTILEGYNYLPNENDHKKREGSLENPKKPAKRQFGDLLLY
LEKKYAGDWGKVPDEAWERIDKKIAGLTSHIEREEAPNAEDAQSKAVLTDWLPAKASFV
LERLKEMDEKEFYACEIQLQKWYGDLRGNPFAVEAENRVVDISGFSIGSDGHSIQYRNL
LAWKYLENGKREFYLLMNYGKKGRIPFTDGTDIKKSGKWQGLLYGGGKAKVIDLTFDPD
DEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIG
EGYKEKQRAIQAAKEVEQRRAGGYSRKFASKSRNLADOMVRNSARDLFYHAVTHDAVLV
FENLSRGFGPQGKRTFMTERQYTKMEDWLTAKLAYEGLTSKTYLSKTLAQYTSKTCSNC
GFTITTADYDGMLVRLKKTSDGRATTLNNKELKAEGQITYYNRYKKQTVEKELSAELDR
LSEESGNNDISKWTKGPRDEALFLLKKRFSHRPVQEQFVCLDCGHEVHADEQAALNIAR
SWLF LNSNSTEFKSYKSGKQPFVGAWQA FYKRRLKEVWKPNA

(56)     References Cited

U.S. PATENT DOCUMENTS

| | | | | |
|---|---|---|---|---|
| 11,873,504 B2 * | 1/2024 | Doudna | ................. | C12N 15/88 |
| 2018/0346927 A1 * | 12/2018 | Doudna | .............. | C12N 9/1007 |
| 2019/0010471 A1 | 1/2019 | Zhang et al. | | |

OTHER PUBLICATIONS

Sanavia. Computational and Structural Biotechnology Journal, vol. 18, 2020, pp. 1968-1979 (Year: 2020).*

Studer. Residue mutations and their impact on protein structure and function: detecting beneficial and pathogenic changes. Biochem. J. (2013) 449, 581-594. (Year: 2013).*

Liu, et al.; "CasX enzymes comprise a distinct family of RNA-guided genome editors"; Nature; vol. 566, pp. 218-223 (Feb. 14, 2019).

Tsuchida, et al.; "Chimeric CRISPR-CasX enzymes and guide RNAs for improved genome editing activity"; Molecular Cell; vol. 82, No. 6, pp. 1199-1209 (Mar. 17, 2022).

Liu, et al.; "CRISPR-CasX is an RNA-dominated enzyme active for human genome editing"; Nature; vol. 566, No. 7743, pp. 218-223 (Feb. 2019).

UniProt A0A1G3BXR9. Uncharacterized protein, Oct. 20, 2020 [online]. [Retrieved on Feb. 11, 2022]. Retrieved from the internet: <URL: https://www.uniprot.org/uniprot/A0A1G3BXR9> Especially p. 1-3.

* cited by examiner

FIG. 1A

DpbCasXv2

MEKRINKIRKKLSADNATKPVSRSGPMKTLLVRVMTDDLKKRLEKRRKKPEVMPQVISN
NAANNLRMLLDDYTKMKEAILQVYWQEFKDDHVGLMCKFAQPASKKIDQNKLKPEMDEK
GNLTTAGFACSQCGQPLFVYKLEQVSEKGKAYTNYFGRCNVAEHEKLILLAQLKPEKDS
DEAVTYSLGKFGQRALDFYSIHVTKESTHPVKPLAQIAGNRYASGPVGKALSDACMGTI
ASFLSKYQDIIIEHQKVVKGNQKRLESLRELAGKENLEYPSVTLPPQPHTKEGVDAYNE
VIARVRMWVNLNLWQKLKLSRDDAKPLLRLKGFPSFPVVERRENEVDWWNTINEVKKLI
DAKRDMGRVFWSGVTAEKRNTILEGYNYLPNENDHKKREGSLENPKKPAKRQFGDLLLY
LEKKYAGDWGKVFDEAWERIDKKIAGLTSHIEREEARNAEDAQSKAVLTDWLRAKASFV
LERLKEMDEKEFYACEIQLQKWYGDLRGNPFAVEAENRVVDISGFSIGSDGHSIQYRNL
LAWKYLENGKREFYLLMNYGKKGRIRFTDGTDIKKSGKWQGLLYGGGKAKVIDLTFDPD
DEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIG
EGYKEKQRAIQAAKEVEQRRAGGYSRKFASKSRNLADDMVRNSARDLFYHAVTHDAVLV
FENLSRGFGRQGKRTFMTERQYTKMEDWLTAKLAYEGLTSKTYLSKTLAQYTSKTCSNC
GFTITTADYDGMLVRLKKTSDGWATTLNNKELKAEGQITYYNRYKRQTVEKELSAELDR
LSEESGNNDISKWTKGRRDEALFLLKKRFSHRPVQEQFVCLDCGHEVHADEQAALNIAR
SWLFLR<u>SQEYKKYQTNKTTGNTDKRAFVETWQS</u>FYKRRLKEVWKPNA

FIG. 1B

DpbCasXv1

MEKRINKIRKKLSADNATKPVSRSGPMKTLLVRVMTDDLKKRLEKRRKKPEVMPQVISN
NAANNLRMLLDDYTKMKEAILQVYWQEFKDDHVGLMCKFAQPASKKIDQNKLKPEMDEK
GNLTTAGFACSQCGQPLFVYKLEQVSEKGKAYTNYFGRCNVAEHEKLILLAQLKPEKDS
DEAVTYSLGKFGQRALDFYSIHVTKESTHPVKPLAQIAGNRYASGPVGKALSDACMGTI
ASFLSKYQDIIIEHQKVVKGNQKRLESLRELAGKENLEYPSVTLPPQPHTKEGVDAYNE
VIARVRMWVNLNLWQKLKLSRDDAKPLLRLKGFPSFPVVERRENEVDWWNTINEVKKLI
DAKRDMGRVFWSGVTAEKRNTILEGYNYLPNENDHKKREGSLENPKKPAKRQFGDLLLY
LEKKYAGDWGKVFDEAWERIDKKIAGLTSHIEREEARNAEDAQSKAVLTDWLRAKASFV
LERLKEMDEKEFYACEIQLQKWYGDLRGNPFAVEAENRVVDISGFSIGSDGHSIQYRNL
LAWKYLENGKREFYLLMNYGKKGRIRFTDGTDIKKSGKWQGLLYGGGKAKVIDLTFDPD
DEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIG
EGYKEKQRAIQAAKEVEQRRAGGYSRKFASKSRNLADDMVRNSARDLFYHAVTHDAVLV
FENLSRGFGRQGKRTFMTERQYTKMEDWLTAKLAYEGLTSKTYLSKTLAQYTSKTCSNC
GFTITTADYDGMLVRLKKTSDGWATTLNNKELKAEGQITYYNRYKRQTVEKELSAELDR
LSEESGNNDISKWTKGRRDEALFLLKKRFSHRPVQEQFVCLDCGHEVHADEQAALNIAR
SWLFL<u>NSNSTEFKSYKSGKQPFVGAWQA</u>FYKRRLKEVWKPNA

FIG. 2A

PlmCasXv2

MQEIKRINKIRRRLVKDSNTKKAGKTGPMKTLLVRVMTPDLRERLENLRKKPENIPQPI
SNTSRANLNKLLTDYTEMKKAILHVYWEEFQKDPVGLMSRVAQPAPKNIDQRKLIPVKD
GNERLTSSGFACSQCCQPLYVYKLEQVNDKGKPHTNYFGRCNVSEHERLILLSPHKPEA
NDELVTYSLGKFGQRALDFYSIHVTRESNHPVKPLEQIGGNSCASGPVGKALSDACMGA
VASFLTKYQDIILEHQKVIKKNEKRLANLKDIASANGLAFPKITLPPQPHTKEGIEAYN
NVVAQIVIWVNLNLWQKLKIGRDEAKPLQRLKGFPSFPLVERQANEVDWWDMVCNVKKL
INEKKEDGKVFWQNLAGYKRQEALLPYLSSEED<u>HKKREGSLENP</u>KKFARYQFGDLLLHL
EKKHGEDWGKVYDEAWERIDKKVEGLSKHIKLEEERRSEDAQSKAALTDWLRAKASFVI
EGLKEADKDEFCRCELKLQKWYGDLRGKPFAIEAENSILDISGFSKQYNCAFIWQKDGV
KKLNLYLIINYFKGGKLRFKKIKPEAFEANRFYTVINKKSGEIVPMEVNFNFDDPNLII
LPLAFGKRQGREFIWNDLLSLETGSLKLANGRVIEKTLYNRRTRQDEPALFVALTFERR
EVLDSSNIKPMNLIGIDRGENIPAVIALTDPEGCPLSRFKDSLGNPTHILRIGESYKEK
QRTIQAAKEVEQRRAGGYSRKYASKAKNLADDMVRNTARDLLYYAVTQDAMLIFENLSR
GFGRQGKRTFMAERQYTRMEDWLTAKLAYEGLPSKTYLSKTLAQYTSKTCSNCGFTITS
ADYDRVLEKLKKTATGWMTTINGKELKVEGQITYYNRYKRQNVVKDLSVELDRLSEESV
NNDISSWTKGRSGEALSLLKKRFSHRPVQEKFVCLNCGFETHADEQAALNIARSWLFLR
SQEYKKYQTNKTTGNTDKRAFVETWQSFYRKKLKEVWKPAV

FIG. 2B

PlmCasXv1

MQEIKRINKIRRRLVKDSNTKKAGKTGPMKTLLVRVMTPDLRERLENLRKKPENIPQPI
SNTSRANLNKLLTDYTEMKKAILHVYWEEFQKDPVGLMSRVAQPAPKNIDQRKLIPVKD
GNERLTSSGFACSQCCQPLYVYKLEQVNDKGKPHTNYFGRCNVSEHERLILLSPHKPEA
NDELVTYSLGKFGQRALDFYSIHVTRESNHPVKPLEQIGGNSCASGPVGKALSDACMGA
VASFLTKYQDIILEHQKVIKKNEKRLANLKDIASANGLAFPKITLPPQPHTKEGIEAYN
NVVAQIVIWVNLNLWQKLKIGRDEAKPLQRLKGFPSFPLVERQANEVDWWDMVCNVKKL
INEKKEDGKVFWQNLAGYKRQEALLPYLSSEED<u>RKKG</u>KKFARYQFGDLLLHLEKKHGED
WGKVYDEAWERIDKKVEGLSKHIKLEEERRSEDAQSKAALTDWLRAKASFVIEGLKEAD
KDEFCRCELKLQKWYGDLRGKPFAIEAENSILDISGFSKQYNCAFIWQKDGVKKLNLYL
IINYFKGGKLRFKKIKPEAFEANRFYTVINKKSGEIVPMEVNFNFDDPNLIILPLAFGK
RQGREFIWNDLLSLETGSLKLANGRVIEKTLYNRRTRQDEPALFVALTFERREVLDSSN
IKPMNLIGIDRGENIPAVIALTDPEGCPLSRFKDSLGNPTHILRIGESYKEKQRTIQAA
KEVEQRRAGGYSRKYASKAKNLADDMVRNTARDLLYYAVTQDAMLIFENLSRGFGRQGK
RTFMAERQYTRMEDWLTAKLAYEGLPSKTYLSKTLAQYTSKTCSNCGFTITSADYDRVL
EKLKKTATGWMTTINGKELKVEGQITYYNRYKRQNVVKDLSVELDRLSEESVNNDISSW
TKGRSGEALSLLKKRFSHRPVQEKFVCLNCGFETHADEQAALNIARSWLFLRSQEYKKY
QTNKTTGNTDKRAFVETWQSFYRKKLKEVWKPAV

FIG. 3
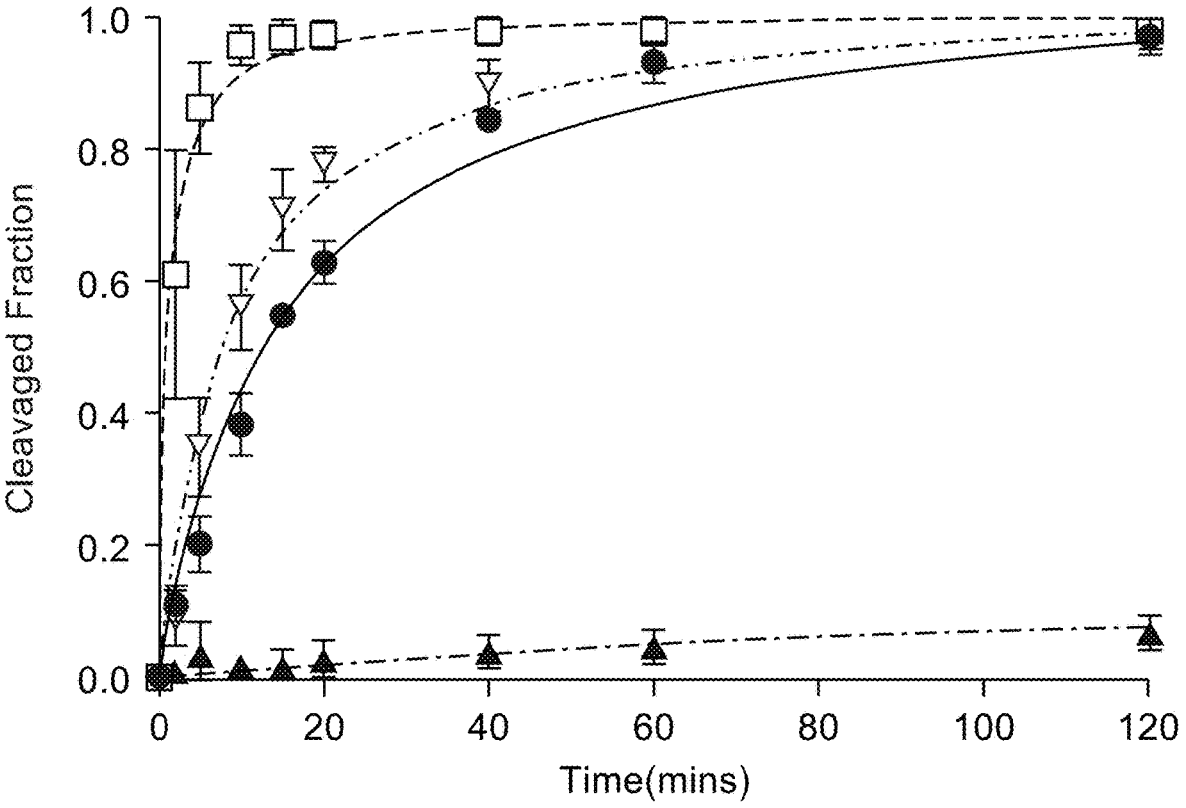
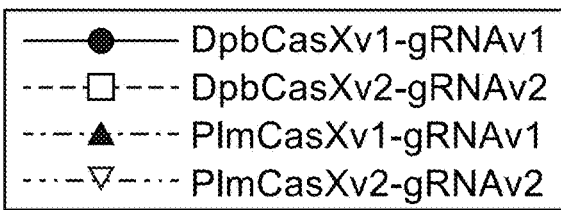

FIG. 4
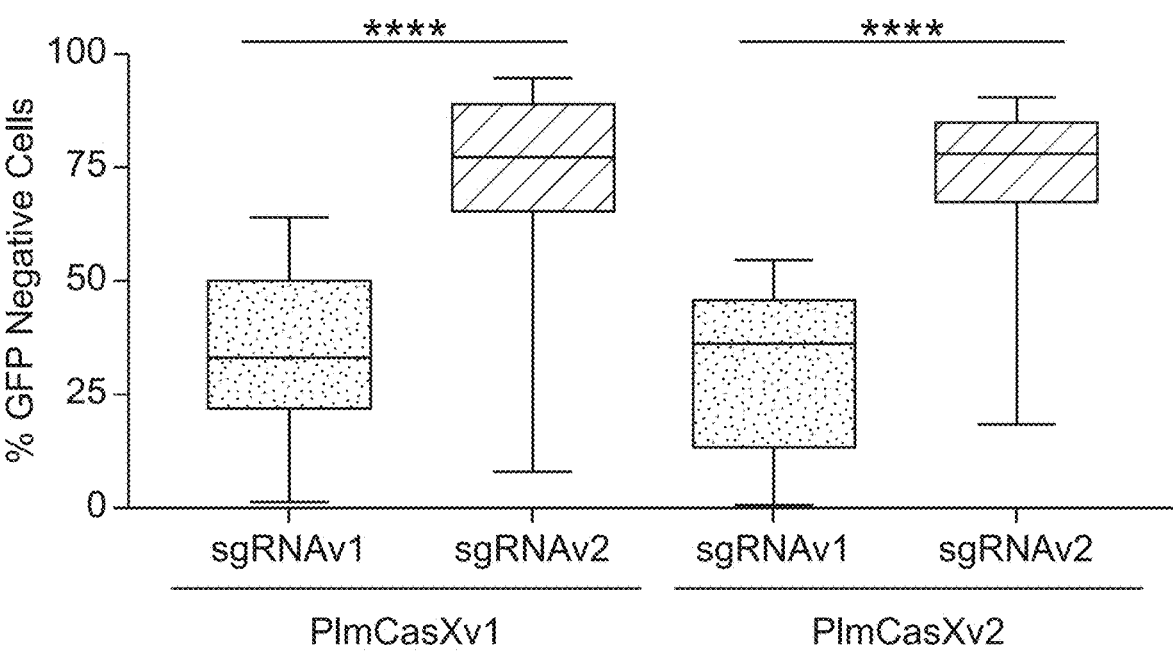
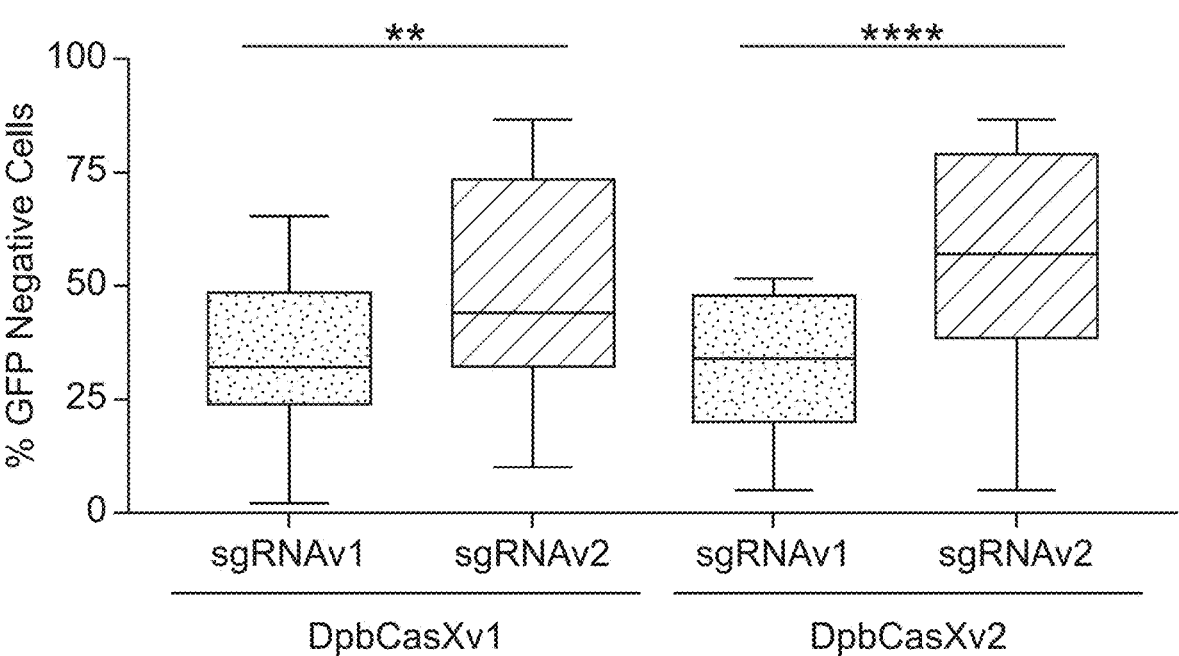

FIG. 8D
State I
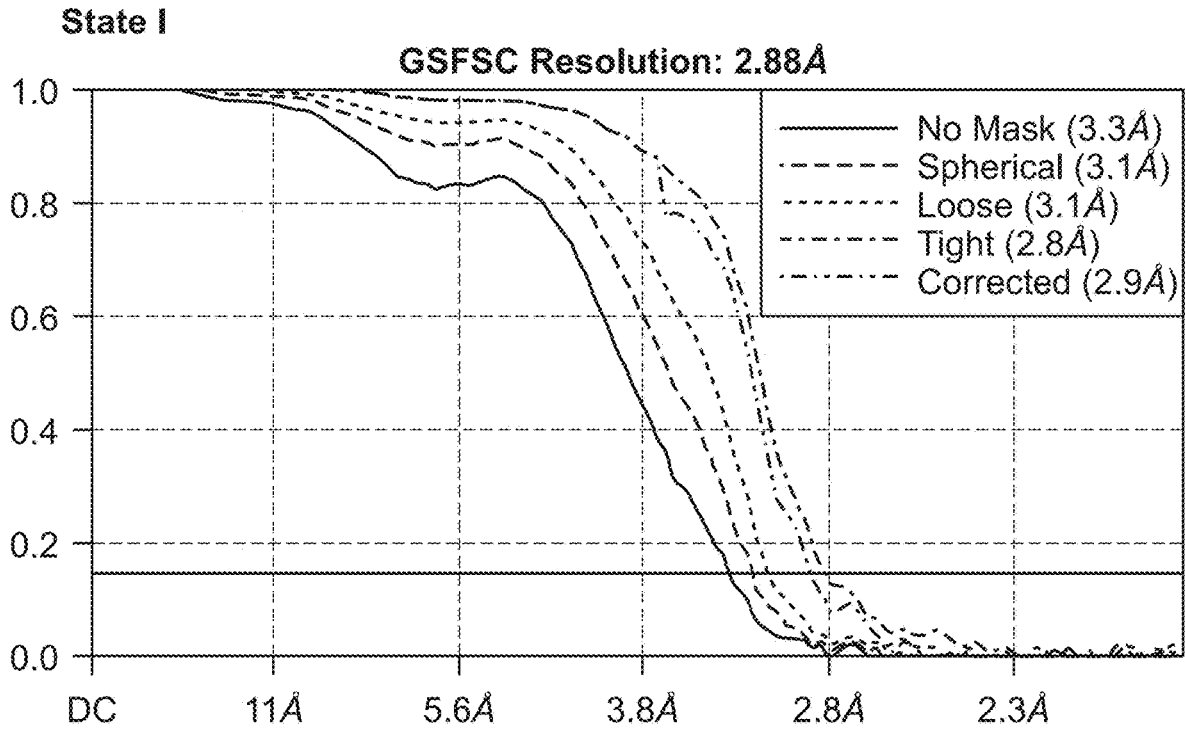
State II
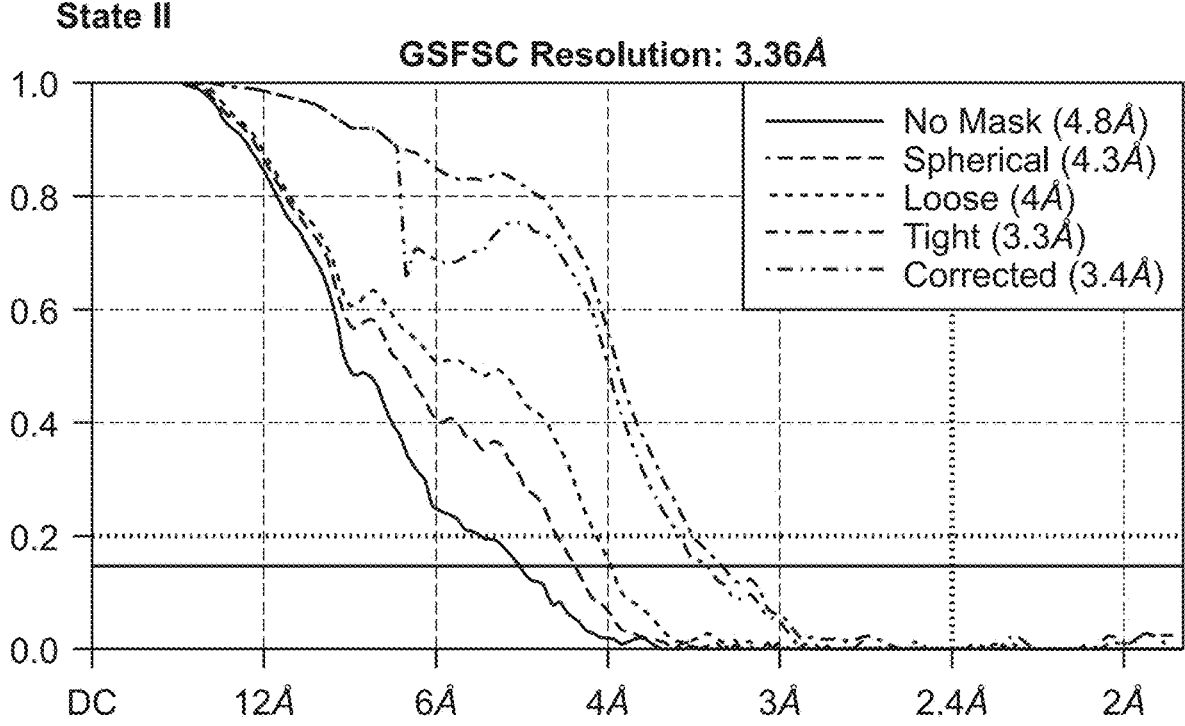

State I         State II         State III

FIG. 9B

Target Strand Cleavage

FIG. 12A

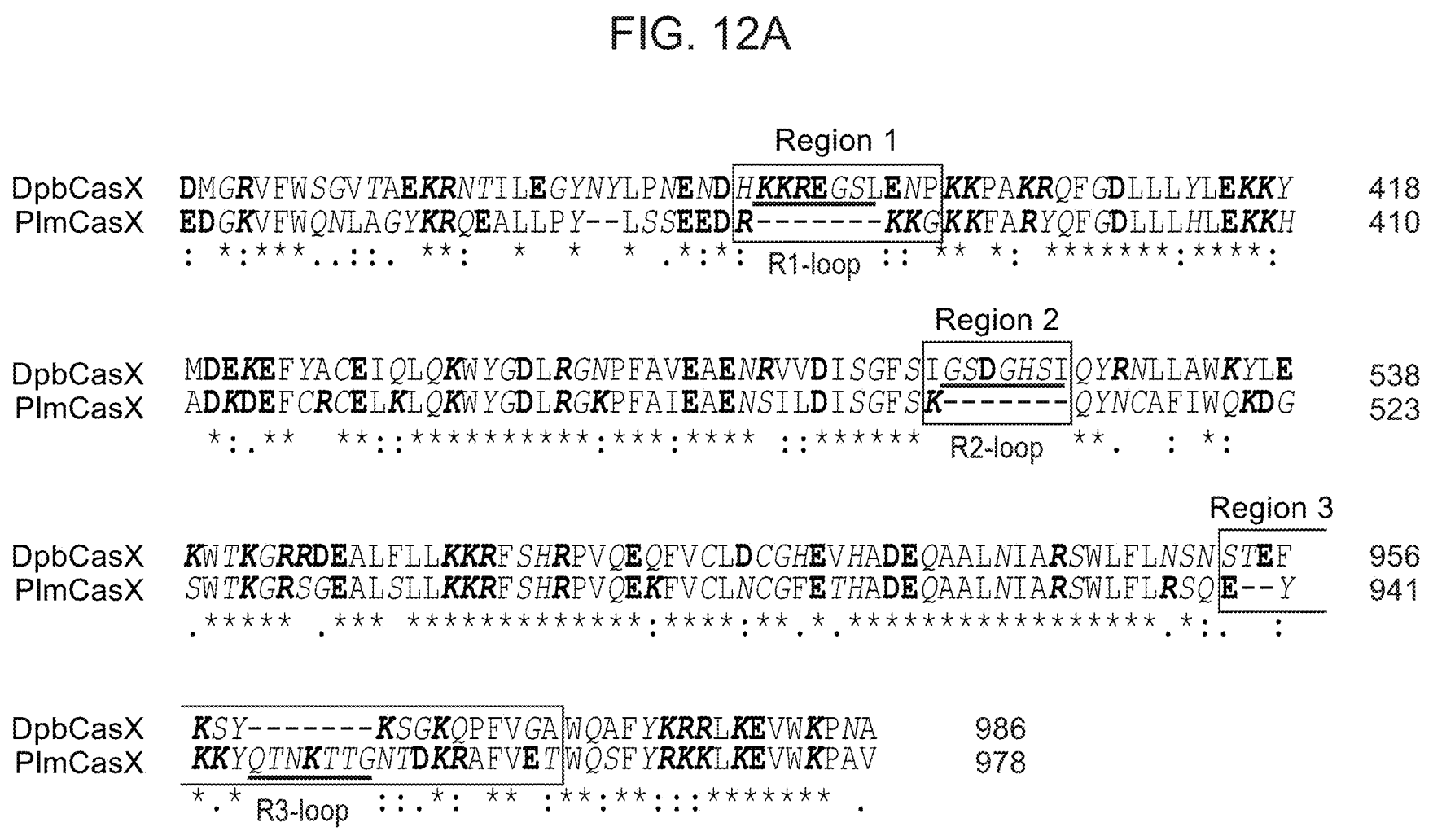

Region 1

DpbCasX    DMGRVFWSGVTAEKRNTILEGYNYLPNENDHKKREGSLENPKKPAAKRQFGDLLLYLEKKY**   418
PlmCasX    ED*GK*VFWQNLAGYKR*Q*EALLPY--LSSEED*R*------KKGKKFARYQFGDLLHLEKKH   410
   :  **** . : : .. *    *    *    ** *:  . ** ***:.*
   R1-loop Region 2

DpbCasX    MDEKEFYACEIQLQ*KW*Y*GD*LRGNP*FAVEA*E*NRV*VDISGF*SI*GSD*QYRNLLAW*KYLE**   538
PlmCasX    ADKDEFCRC*E*L*KL*Q*KW*Y*GD*I*SGF*S**K*------QYNCAFIWQ*KDG*   523
   * . :  *** : * ***** .: ** . * .  :.  . : 
   R2-loop Region 3

DpbCasX    KNTKGRRDEALFLLKKRFSHRPVQE*QFVCLDCGHEVHADE*QAALNIARSWLFLNSN*STEF*   956
PlmCasX    SNTKGR*SG*E*A*LSLLKKRFSHRPVQE**KFVCLNCGFE*THADE*QAALNIARSWLFLRS*Q*E--Y   941
   . *** .:  * * ** . * . * **** * .: :.: :* .:

DpbCasX    KSY------KSGK*Q*PFVGAWQAF*Y*KRRLKEVWKPNA   986
PlmCasX    KK*Y*Q*TN*K*TT*GNTDKRA*FVETWQSF*Y*RKKLKEVWKPAV   978
   * * .: . : : .::: .* ** .
   R3-loop

FIG. 14B
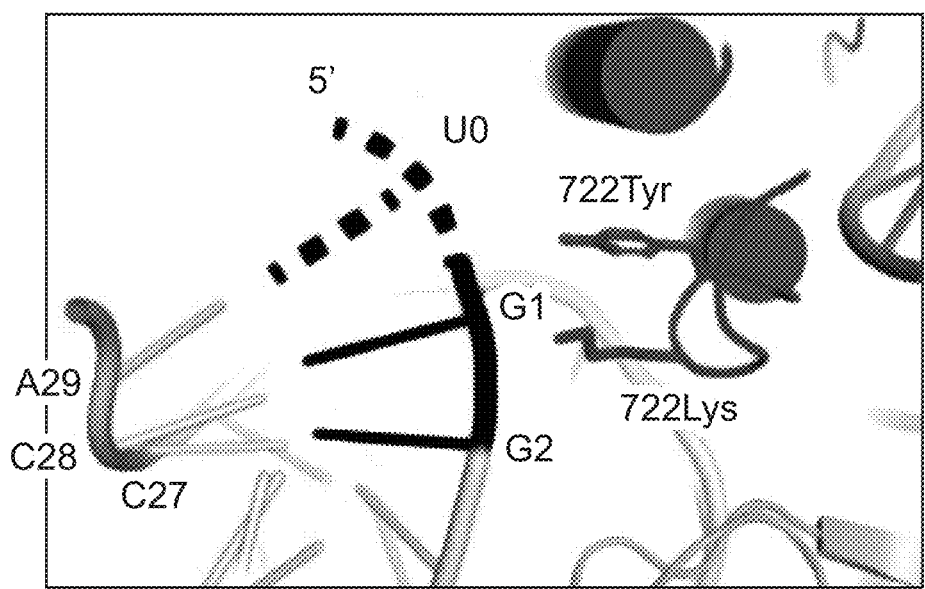
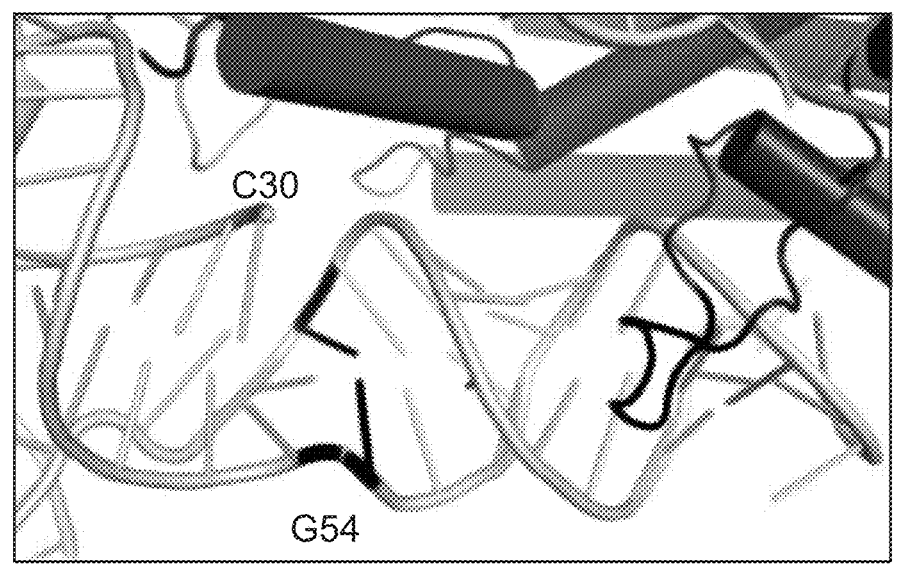

FIG. 14D
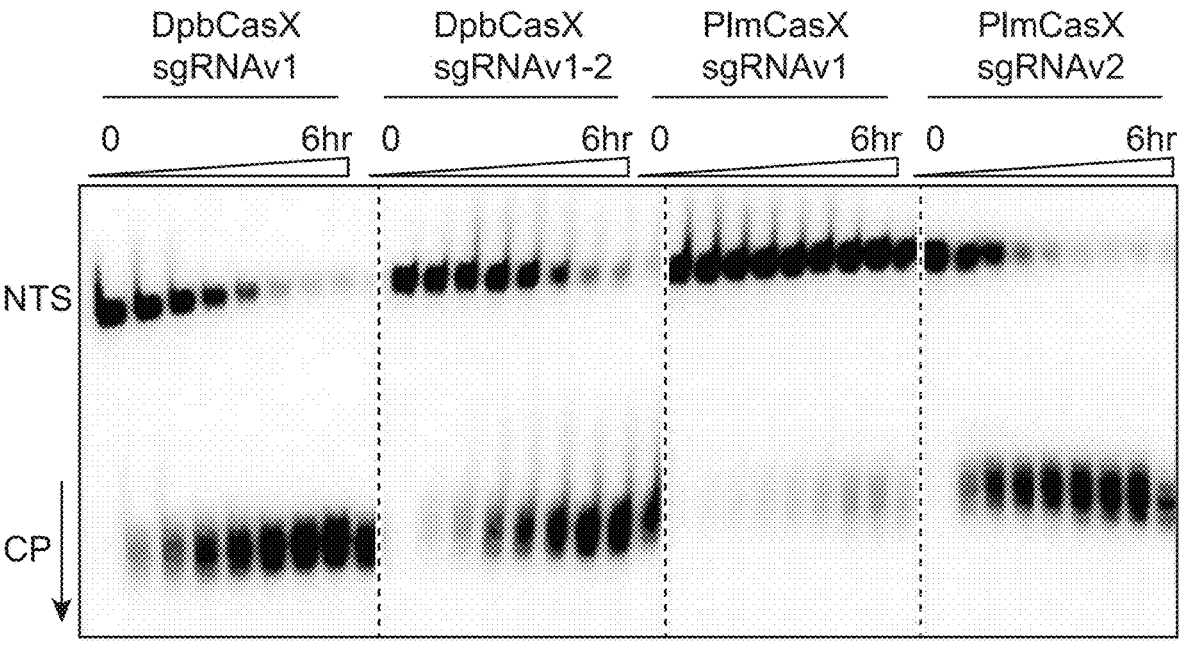
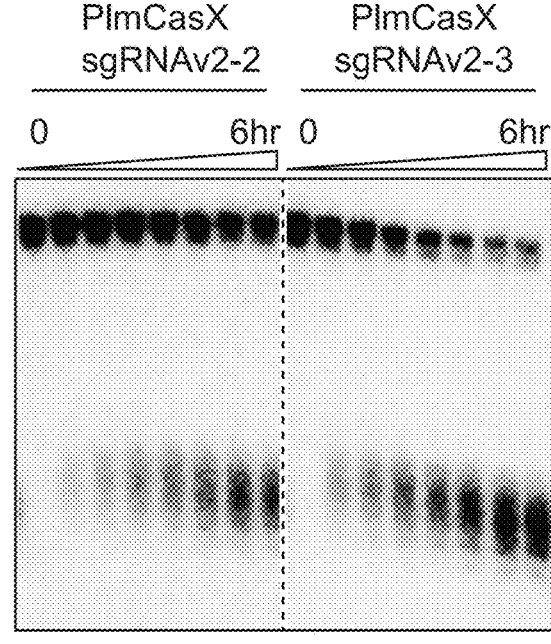

*Without Cross-linking*

FIG. 17B
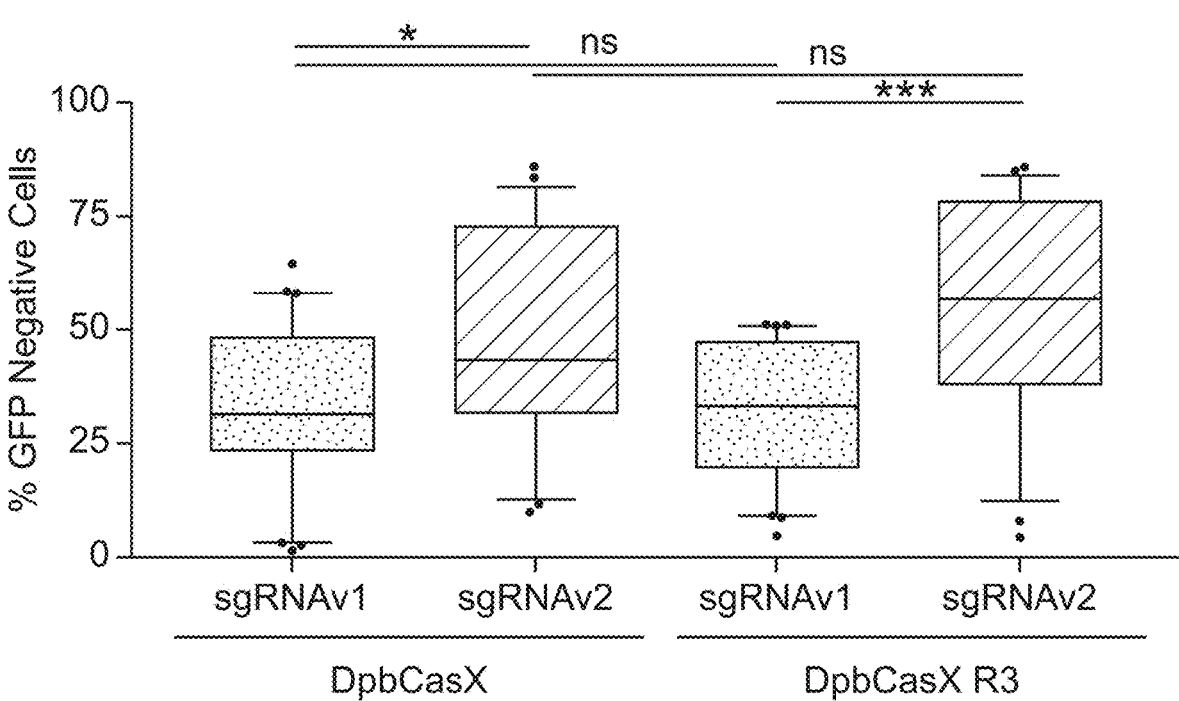
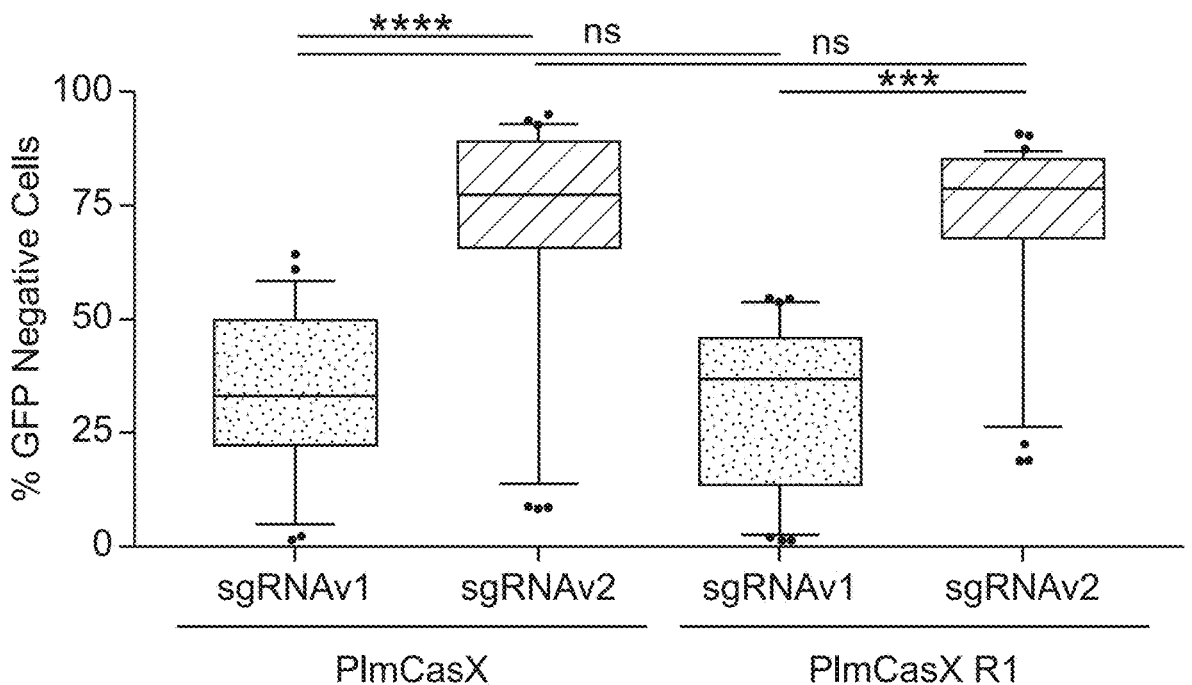

FIG. 18C
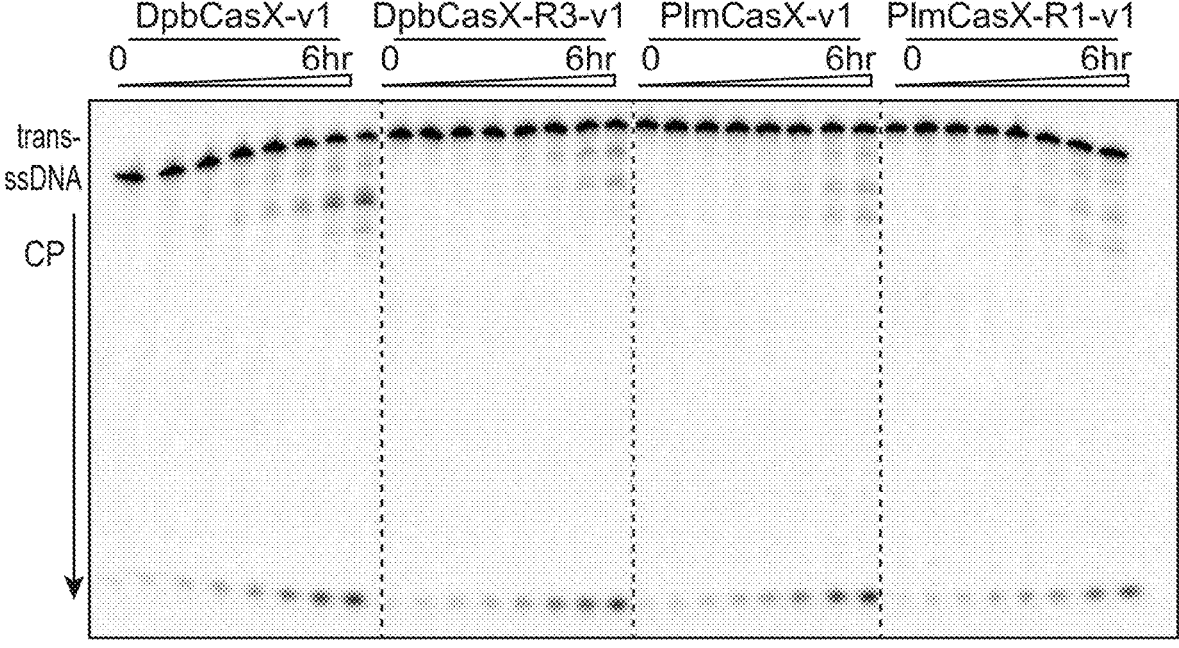
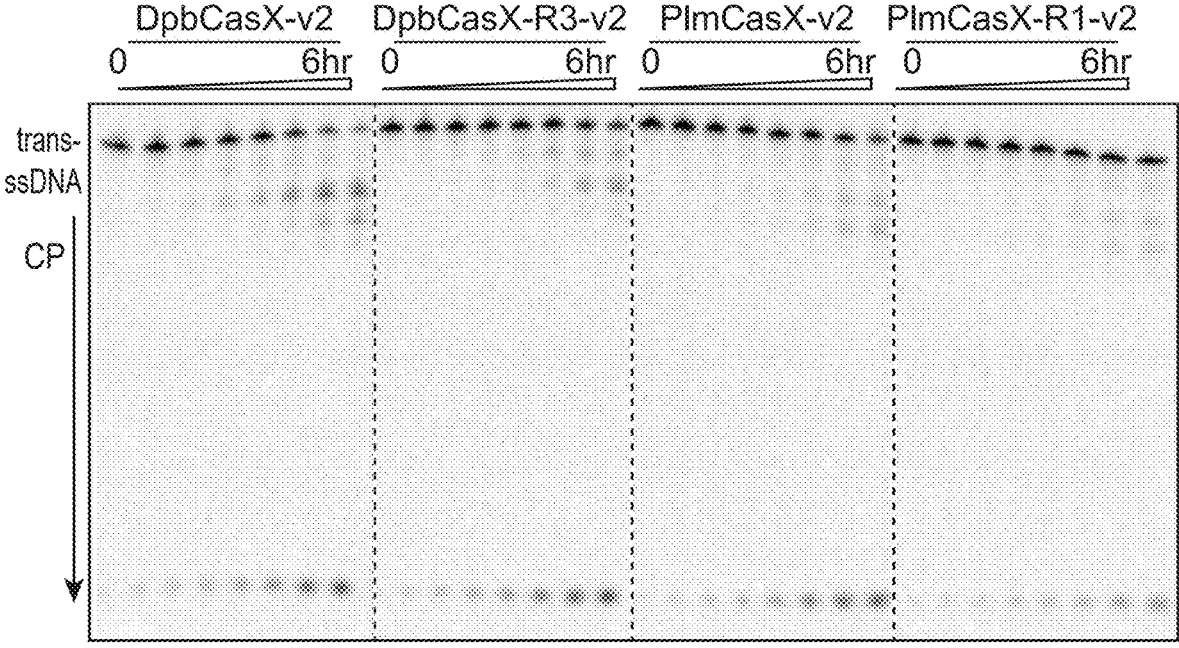

| Experiment | Name | Sequence/comments |
|---|---|---|
| Preparation of the ternary complex for cryoEM | TS DNA | ATCGTTATAC TTTGATTTTCTGCTGCAGGA TGAA ATCCCG |
| Preparation of ternary complex for cryoEM | NTS-DNA | CGGGAT TTCA TCCTGCAGCA TCCCCGACCC GTATAACGAT |
| sgRNAv1 used for EM complex preparations, and most of cleavage assays | sgRNAv1 | ggCGCGUUUAUUCCAUUACUUUGGAGCCAGUCCCAGCGACU AUGUCGUAUGGACGAAGCGCUUAUUUAUCGGAGAGAAACC GAUAAGUAAAACGCAUCAAAGUCCUGCAGCAGAAAAUCAA A |
| DNA cleavage in vitro | NTS DNA | GCCCGCGGGAT TTCA TCCTGCAGCAGAAAAUCAAA GACAAT GAATATTTCGGCGC |
| DNA cleavage in vitro | TS DNA | GCGCCGAAATATTCATTGTC TTTGATTTTCTGCTGCAGGA TG AA ATCCCGCGGGC |
| The secondary architecture of gRNAv1 | gRNAv1 | ggCGCGUUUAUUCCAUUACUUUGGAGCCAGUCCCAGCGACU AUGUCGUAUGGACGAAGCGCUUAUUUAUCGGAGAGAAACC GAUAAGUAAAACGCAUCAAAG |
| The secondary architecture of gRNAv1 | gRNAv1-2 | UggCGCGUUUAUUCCAUUACUUUGGAGCCAGUCCCAGCGAC UAUGUCGUAUGGACGAAGCGCUUAUUUAUCGGAGAGAAAC CGAUAAGUAAAACGCAUCAAAG |
| The hypothetical secondary architecture gRNAv2 | gRNAv2 | ggCGCUUUUAUCUCAUUACUUUGAGAGCCAUCACCAGCGAC UAUGUCGUAUGGGUAAAGCGCUUAUUUAUCGGAGAAACCG AUAAAUAAGAAGCAUCAAAG |
| The hypothetical secondary architecture gRNAv2 | gRNAv2-2 | UggCGCUUUUAUCUCAUUACUUUGAGAGCCAUCACCAGCGA CUAUGUCGUAUGGGUAAAGCGCUUAUUUAUCGGAGAAACC GAUAAAUAAGAAGCAUCAAAG |
| The hypothetical secondary architecture gRNAv2 | gRNAv2-3 | UACUGGCGCUUUUAUCUCAUUACUUUGAGAGCCAUCACCA GCGACUAUGUCGUAUGGGUAAAGCGCUUAUUUAUCGGAGA AACCGAUAAAUAAGAAGCAUCAAAG |
| sgRNAv2 used for cleavage assays | sgRNAv2 | ggCGCUUUUAUCUCAUUACUUUGAGAGCCAUCACCAGCGAC UAUGUCGUAUGGGUAAAGCGCUUAUUUAUCGGAGAAACCG AUAAAUAAGAAGCAUCAAAGUCCUGCAGCAGAAAAUCAAA |

FIG. 19 (Cont.)

| trans- cleavage assay | random-ssDNA | GTTTATTTACTTTAGTCACTCCAGGATTCCAATAGATATTTAC TTTGAAG |
|---|---|---|
| CasX human GFP targeting | CasX-g1 | CCGGGGTGGTGCCCATCCTG |
| CasX human GFP targeting | CasX-g2 | GCGTGTCCGGCGAGGGCGAG |
| CasX human GFP targeting | CasX-g3 | GGGTCAGCTTGCCGTAGGTG |
| CasX human GFP targeting | CasX-g4 | TCTGCACCACCGGCAAGCTG |
| CasX human GFP targeting | CasX-g5 | GCCGCTACCCCGACCACATG |
| CasX human GFP targeting | CasX-g6 | GGCATGGCGGACTTGAAGAA |
| CasX human GFP targeting | CasX-g7 | CCTCGGCGCGGGTCTTGTAG |
| CasX human GFP targeting | CasX-g8 | AGGGCGACACCCTGGTGAAC |
| CasX human GFP targeting | CasX-g9 | GCTCGATGCGGTTCACCAGG |
| CasX human GFP targeting | CasX-g10 | AGGAGGACGGCAACATCCTG |
| CasX EMX1 targeting | sgRNA 1 | CTCTGGCCCACTGTGTCCTC |
| CasX EMX1 targeting | sgRNA 2 | CAGAAGGGGATGGCAGGGCA |
| CasX-EMX1 targeting | sgRNA 3 | CCTGGGCCAGGGAGGGAGGG |
| | | |
| Plasmid | Contains | Comments |

FIG. 19 (Cont.)

| | | |
|---|---|---|
| 2CT-10-DpbCasX | His-MBP-TEV-DpbCasX, expression vector | This study |
| 2CT-10-PlmCasX | His-MBP-TEV-PlmCasX, expression vector | This study |
| 2CT-10-DpbCasX- HII truncation | His-MBP-TEV-DpbCasX- HII truncation, expression vector | This study |
| 2CT-10-PlmCasX-HII truncation | His-MBP-TEV-PlmCasX-HII truncation, expression vector | This study |
| 2CT-10-DpbCasX+Plm R3 insertion | His-MBP-TEV-DpbCasX+Plm R3 insertion, expression vector | This study |
| 2CT-10-PlmCasX+Dpb R1 insertion | His-MBP-TEV-PlmCasX+Dpb R1 insertion, expression vector | This study |
| 2CT-10-PlmCasX+Dpb R1+2 insertion | His-MBP-TEV-PlmCasX+Dpb R1+2 insertion, expression vector | This study |
| pBLO62.4 | U6-sgRNAv1-CAG-DpbCasX-PuroR | Liu et al., 2019 |
| pBLO62.5 | U6-sgRNAv1-CAG-PlmCasX-PuroR | Liu et al., 2019 |
| pCAT042 | U6-sgRNAv1-CAG-DpbCasX(H2T)-PuroR | This study |

FIG. 19 (Cont.)

| pCAT043 | U6-sgRNAv1-CAG-DpbCasX(R3)-PuroR | This study |
|---|---|---|
| pCAT033 | U6-sgRNAv1-CAG-PlmCasX(H2T)-PuroR | This study |
| pCAT034 | U6-sgRNAv1-CAG-PlmCasX(R1)-PuroR | This study |
| pCAT035 | U6-sgRNAv1-CAG-PlmCasX(R1+2)-PuroR | This study |
| pCAT079 | U6-sgRNAv2-CAG-DpbCasX-PuroR | This study |
| pCAT105 | U6-sgRNAv2-CAG-DpbCasX(R3)-PuroR | This study |
| pCAT077 | U6-sgRNAv2-CAG-PlmCasX-PuroR | This study |
| pCAT100 | U6-sgRNAv2-CAG-PlmCasX(R1)-PuroR | This study |
| pCAT526 | U6-sgRNAv1-CAG-PlmCasX-mNeon-PuroR | This study |
| pCAT527 | U6-sgRNAv2-CAG-PlmCasX(R1)-mNeon-PuroR | This study |

FIG. 20

```
         10          20          30          40
GGCGCGUUUAUUCCAUUACUUUG GAGCCAGUC CCAGCGACUAUGUCGU
GGCGCUUUUAUCUCAUUACUUUGAGAGCCA UCACCAGCGACUAUGUCGU
     *       * *                *          ** *
```

```
   50          60          70          80          90
AUGGACGAAGCGCUUAUUUAUCGGAGAGAAACCGAUAAGUAAAACGCA
AUGGGUAAAGCGCUUAUUUAUCGGAGA   AACCGAUAAAUAAGAAGCA
      * * *                       * *      *   *  *
```

```
  100
UCAAAG(N)ₓ (sgRNAv1)
UCAAAG(N)ₓ (sgRNAv2)
```

CRISPR-CAS EFFECTOR POLYPEPTIDES AND METHODS OF USE THEREOF

CROSS-REFERENCE

This application is a national stage application under 35 U.S.C. § 371 of PCT/US2021/061455, filed Dec. 1, 2021, which claims the benefit of U.S. Provisional Patent Application No. 63/120,638, filed Dec. 2, 2020, and U.S. Provisional Patent Application No. 63/272,900, filed Oct. 28, 2021, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-438WO_SEQLIST_ST25.txt" created on Nov. 24, 2021 and having a size of 72 KB. The contents of the text file are incorporated by reference herein in their entirety.

INTRODUCTION

Clustered Regularly Interspaced Short Palindromic Repeats (CRISPR)-Cas systems comprise a CRISPR-associated (Cas) effector polypeptide and a guide nucleic acid. The CRISPR-Cas system confers on bacteria and archaea an acquired immunity against phage and viruses. Intensive research over the past decade has uncovered the biochemistry of this system. CRISPR-Cas systems consist of Cas proteins, which are involved in acquisition, targeting, and cleavage of foreign DNA or RNA, and a CRISPR array, which includes direct repeats flanking short spacer sequences that guide Cas proteins to their targets. Class 2 CRISPR-Cas effector polypeptide systems, comprising a CRISPR-Cas effector polypeptide bound to a guide RNA, bind to and cleave a targeted nucleic acid. The programmable nature of these CRISPR-Cas effector polypeptide systems has facilitated their use as a versatile technology for use in, e.g., gene editing.

There is a need in the art for additional CRISPR-Cas effector polypeptides and guide RNAs.

SUMMARY

The present disclosure provides variant CRISPR-Cas effector polypeptides, as well as engineered guide nucleic acids, and systems comprising the same. The present disclosure provides methods of modifying a target nucleic acid, using a variant CRISPR-Cas effector polypeptide of the present disclosure.

BRIEF DESCRIPTION OF THE DRAWINGS

FIG. 1A-1B provide amino acid sequences of DpbCasXv2 (SEQ ID NO:1) and DpbCasXv1 (SEQ ID NO:2), respectively.

FIG. 2A-2B provide amino acid sequences of PlmCasXv2 (SEQ ID NO:3) and PlmCasXv1 (SEQ ID NO:4), respectively.

FIG. 3 depicts in vitro DNA cleavage activity of DpbCasXv2, DpvCasXv2, PlmCasXv1, and PlmCasXv2, complexed with gRNAv1 or gRNAv2.

FIG. 4 depicts target nucleic acid editing in a living cell, using DpbCasXv1 or DpbCasXv2, complexed with either single-guide RNA (sgRNA) v1 or sgRNA v2.

FIG. 9A-9B depict overall structures of the PlmCasX-dsDNA-sgRNAv1 complex.

FIG. 12A-12C depict design of CasX protein chimeras (FIG. 12A from top to bottom SEQ ID NOs:93-94).

FIG. 14A-14G depict design of the CasX sgRNA (FIG. 14C from left to right SEQ ID NOs:95-96; FIG. 14F from left to right SEQ ID NOs:97-99).

FIG. 17A-17B depict genome editing by engineered DpbCasX and PlmCasX.

FIG. 18A-18E depict a CasX platform with enhanced gene editing efficacy (FIG. 18E from top to bottom SEQ ID NOs:100, 100, 101-110).

FIG. 19 provides a Table showing plasmids and oligonucleotides used in the Examples (from top to bottom SEQ ID NOs:5-29).

FIG. 20 depicts sgRNAv1 (SEQ ID NO:89) and sgRNAv2 (SEQ ID NO:90) and illustrates changes that provide for increased gene editing.

DEFINITIONS

Figures 5, 6A, 6B:
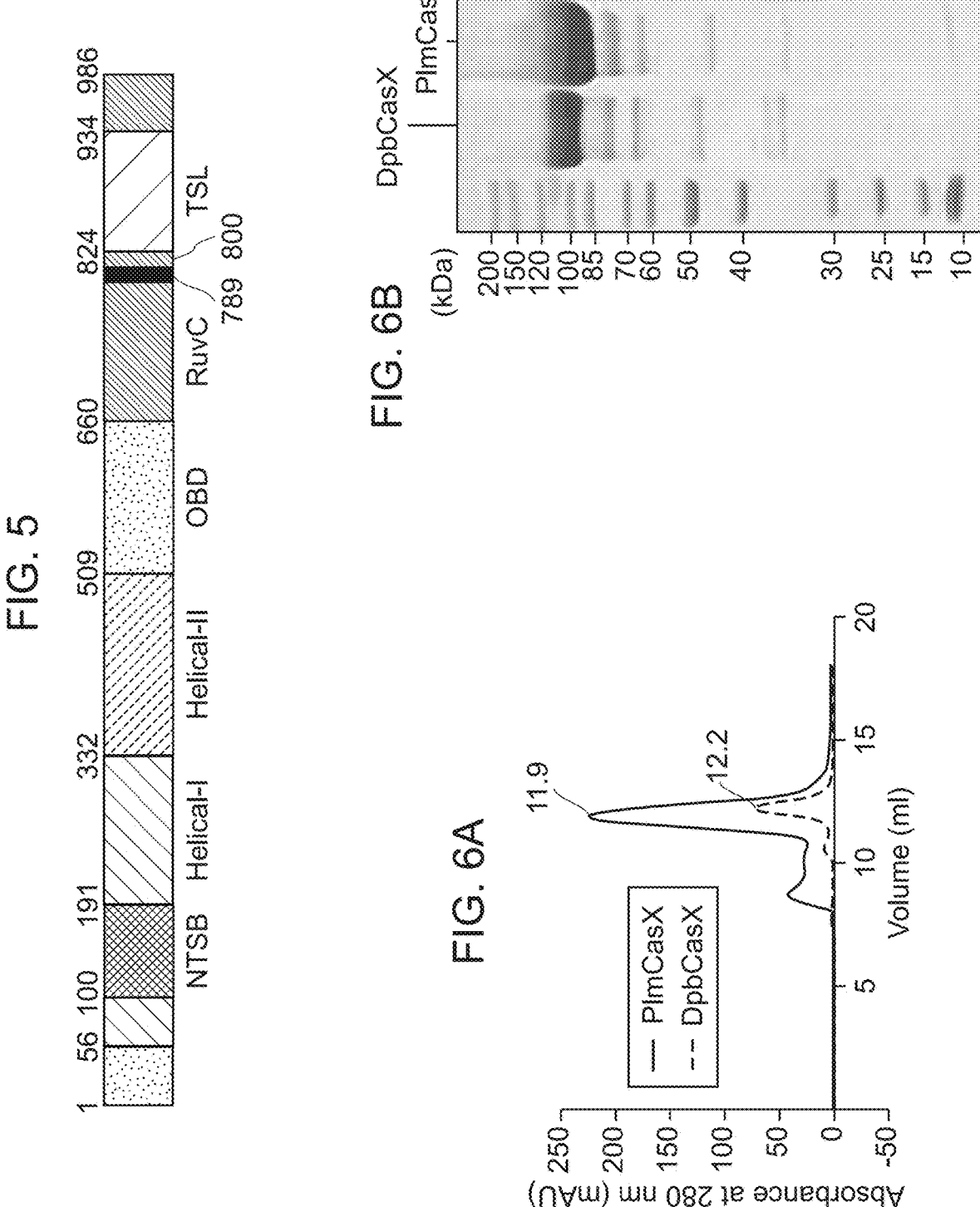
FIG. 5 provides a schematic depiction of domains of a reference CRISPR-Cas effector polypeptide.
FIG. 6A-6F depict targeted DNA cleavage by DpbCasX and PlmCasX.

"Heterologous," as used herein, means a nucleotide or polypeptide sequence that is not found in the native nucleic acid or protein, respectively. For example, relative to a variant CRISPR-Cas effector polypeptide, a heterologous polypeptide comprises an amino acid sequence from a protein other than the variant CRISPR-Cas effector polypeptide. As an example, a variant CRISPR-Cas effector polypeptide can be fused to a polypeptide other than a variant CRISPR-Cas effector polypeptide (e.g., a nuclear localization signal; an enzyme other than a variant CRISPR-Cas effector polypeptide; a transcription modulatory polypeptide; and the like.

The terms "polynucleotide" and "nucleic acid," used interchangeably herein, refer to a polymeric form of nucleotides of any length, either ribonucleotides or deoxynucleotides. Thus, the term "polynucleotide" includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature. The terms "non-naturally occurring" and "engineered," as used herein as applied to a nucleic acid, a protein, a cell, or an organism, refers to a nucleic acid, cell, protein, or organism that is not found in nature, but includes one or more modifications made by human intervention.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified prokaryotic host cell (e.g., a bacterium) is genetically modified by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell. Similarly, a genetically modified eukaryotic host cell is genetically by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant CRISPR-Cas effector polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant CRISPR-Cas effector polypeptides, as well as engineered (non-naturally-occurring) guide nucleic acids, and systems comprising the same. The present disclosure provides methods of modifying a target nucleic acid, using a variant CRISPR-Cas effector polypeptide of the present disclosure.

Variant Crispr-Cas Effector Polypeptides

The present disclosure provides variant CRISPR-Cas effector polypeptides that exhibits increased target nucleic acid binding and/or increased guide RNA binding, relative to a reference CRISPR-Cas effector polypeptide. In some cases, a reference CRISPR-Cas effector polypeptide is a CasX polypeptide. In some cases, a reference CRISPR-Cas effector polypeptide comprises the amino acid sequence depicted in FIG. 1B; such a reference CRISPR-Cas effector polypeptide is also referred to herein as "DpbCasXv1." In some cases, a reference CRISPR-Cas effector polypeptide comprises the amino acid sequence depicted in FIG. 2B; such a reference CRISPR-Cas effector polypeptide is also referred to herein as "PlmCasXv1." The present disclosure provides a ribonucleoprotein (RNP) comprising: a) a variant CRISPR-Cas effector polypeptide of the present disclosure (which may be a fusion polypeptide comprising a variant CRISPR-Cas effector polypeptide of the present disclosure); and b) a guide RNA.

A variant CRISPR-Cas effector polypeptide of the present disclosure comprises modifications in the RuvC-III domain or the helical-II domain, relative to a reference CRISPR-Cas effector polypeptide. FIG. 5 provides a schematic depiction of domains of a reference CRISPR-Cas effector polypeptide. OBD: oligonucleotide binding domain; TSL: target-strand loading; BH: bridge helix (amino acids 789-800). RuvC domains are: RuvC-I (amino acids 660-789; RuvC-II (amino acids 800-824); and RuvC-III (amino acids 934-986). See, e.g., Liu et al. (2019) *Nature* 566:218.

In some cases, a variant CRISPR-Cas effector polypeptide of the present disclosure, when complexed with a guide nucleic acid (e.g., a guide RNA) cleaves a target nucleic acid more efficiently than a reference CRISPR-Cas effector polypeptide (e.g., a polypeptide comprising the amino acid sequence depicted in FIG. 1B; or a polypeptide comprising the amino acid sequence depicted in FIG. 2B). For example, in some cases, a variant CRISPR-Cas effector polypeptide of the present disclosure, when complexed with a guide nucleic acid (e.g., a guide RNA) exhibits at least 1.5-fold, at least 2.0-fold, at least 2.5-fold, at least 3.0-fold, at least 3.5-fold, at least 4.0-fold, at least 4.5-fold, at least 5.0-fold, at least 6-fold, at least 7-fold, at least 8-fold, at least 9-fold, at least 10-fold, or more than 10-fold, greater enzymatic activity (i.e., cleavage of a target nucleic acid), compared to the enzymatic activity of a CRISPR-Cas effector polypeptide comprising the amino acid sequence depicted in FIG. 1B (DpbCasXv1) when complexed with the same guide nucleic acid, for cleavage of the same target nucleic acid.

For example, in some cases, a variant CRISPR-Cas effector polypeptide of the present disclosure, when complexed with a guide nucleic acid (e.g., a guide RNA), cleaves 50% of the copies of a target nucleic acids within a time period that is at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, or at least 90% less, than the time period required by a CRISPR-Cas effector polypeptide comprising the amino acid sequence depicted in FIG. 1B (DpbCasXv1) when complexed with the same guide nucleic acid, to cleave 50% of the copies of the same target nucleic acid.

As another example, in some cases, a variant CRISPR-Cas effector polypeptide of the present disclosure, when complexed with a guide nucleic acid (e.g., a guide RNA), cleaves 50% of the copies of a target nucleic acids within a time period that is at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, or at least 90% less, than the time period required by a CRISPR-Cas effector polypeptide comprising the amino acid sequence depicted in FIG. 2B (PlmCasXv1) when complexed with the same guide nucleic acid, to cleave 50% of the copies of the same target nucleic acid.

In some cases, a variant CRISPR-Cas effector polypeptide of the present disclosure, when complexed with a guide nucleic acid (e.g., a guide RNA), cleaves 50% of the copies of a target nucleic acids within a time period of from about 10 seconds to about 2 minutes (e.g., from about 10 seconds to about 15 seconds, from about 15 seconds to about 30 seconds, from about 30 seconds to about 45 seconds, from about 45 seconds to about 60 seconds, from about 60 seconds to about 75 seconds, from about 75 seconds to about 90 seconds, from about 90 seconds to about 105 seconds, or from about 105 seconds to about 120 seconds. In some cases, a variant CRISPR-Cas effector polypeptide of the present disclosure, when complexed with a guide nucleic acid (e.g., a guide RNA), cleaves 50% of the copies of a target nucleic acids within a time period of from about 2 minutes to about 10 minutes (e.g., from about 2 minutes to about 3 minutes, from about 3 minutes to about 4 minutes, from about 4 minutes to about 5 minutes, from about 5 minutes to about 6 minutes, from about 6 minutes to about 7 minutes, from about 7 minutes to about 8 minutes, from about 8 minutes to about 9 minutes, or from about 9 minutes to about 10 minutes. The copies of the target nucleic acids can be in an in vitro, cell-free sample. The copies of the target nucleic acids can be in living cells (e.g., a plurality of living cells, where each cell of the plurality of living cells includes a copy of the target nucleic acid), where the living cells can be in vitro or in vivo.

RuvC-III Modifications

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1A. A variant CRISPR-Cas effector polypeptide comprising the amino acid sequence depicted in FIG. 1A is also referred to herein as "DpbCasXv2." In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1A; and comprises a RuvC domain (in particular, a RuvC-III domain) comprising the amino acid sequence RSQEYKKYQTNKTTGNTDKRAFVETWQS (SEQ ID NO:30), or an amino acid sequence having from 1 to 10 amino acid substitutions compared to RSQEYKKYQTNKTTGNTDKRAFVETWQS (SEQ ID NO:30). For example, in some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1A; and comprises a RuvC (e.g., a RuvC-III) domain comprising the amino acid sequence $X_1SQEYKX_2YX_3X_4X_5KTTGNTDKX_6X_7FVX_8X_9WQX_{10}$ (SEQ ID NO:31), where $X_1$ is Arg, Gln, or Asn; $X_2$ is Lys, His, or Ser; $X_3$ is Gln, Arg, or Asn; $X_4$ is Thr or Ser; $X_5$ is Arg, Asn, Gln, or Gly; $X_6$ is Arg, Gln, or Asn; $X_7$ is Ala, Val, or Pro; $X_8$ is Glu, Asp, or Gly; $X_9$ is Thr, Ser, Ala, or Val; and $X_{10}$ is Ser, Thr, Ala, or Val.

In some cases, a variant CRISPR-Cas effector polypeptide of the present disclosure comprises, in order from N-terminus to C-terminus: i) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 1-933 of the amino acid sequence depicted in FIG. 1A; ii) a 28-amino acid sequence comprising the amino acid sequence RSQEYKKYQTNKTTGNTDKRAFVETWQS (SEQ ID NO:30), or an amino acid sequence having from 1 to 10 amino acid substitutions (e.g., conservative amino acid substitutions) compared to (SEQ ID NO: 30)
RSQEYKKYQTNKTTGNTDKRAFVETWQS (e.g.,
$X_1SQEYKX_2YX_3X_4X_5KTTGNTDKX_6X_7FVX_8X_9WQX_{10}$
(SEQ ID NO:31), where $X_1$ is Arg, Gln, or Asn; $X_2$ is Lys, His, or Ser; $X_3$ is Gln, Arg, or Asn; $X_4$ is Thr or Ser; $X_5$ is Arg, Asn, Gln, or Gly; $X_6$ is Arg, Gln, or Asn; $X_7$ is Ala, Val, or Pro; $X_8$ is Glu, Asp, or Gly; $X_9$ is Thr, Ser, Ala, or Val; and $X_{10}$ is Ser, Thr, Ala, or Val); and iii) the amino acid sequence FYKRRLKEVWKPNA (SEQ ID NO:32), or an amino acid sequence having from 1 to 5 amino acid substitutions (e.g., conservative amino acid substitutions) compared to FYKRRLKEVWKPNA (SEQ ID NO:32).

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1A; and comprises a RuvC-III domain at its C-terminus, where the RuvC-III domain comprises an amino acid sequence having at least 80%, at least 85%, at least 90%, at least 95%, at least 98%, at least 99%, or 100%, amino acid sequence identity to the amino acid sequence DEQAALNIARSWLFLFR-SQEYKKYQTNKTTGNTDKRAFVETWQSYKRRLKEV-WKPNA (SEQ ID NO:33), and where the RuvC-III domain has a length of from about 55 amino acids to about 70 amino acids (e.g., from about 55 amino acids to about 57 amino acids, from about 57 amino acids to about 60 amino acids, from about 60 amino acids to about 65 amino acids, or from about 65 amino acids to about 70 amino acids).

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1B; and comprises a substitution of the amino acid sequence NSNSTEFKSYKSGKQPFVGAWQA (SEQ ID NO:34) of the reference amino acid sequence of FIG. 1B; where the amino acid sequence NSN-STEFKSYKSGKQPFVGAWQA (SEQ ID NO:34) is substituted with the amino acid sequence $X_1SQEYKX_2YX_3X_4X_5KTTGNTDKX_6X_7FVX_8X_9WQX_{10}$ (SEQ ID NO:31), where $X_1$ is Arg, Gln, or Asn; $X_2$ is Lys, His, or Ser; $X_3$ is Gln, Arg, or Asn; $X_4$ is Thr or Ser; $X_5$ is Arg, Asn, Gln, or Gly; $X_6$ is Arg, Gln, or Asn; $X_7$ is Ala, Val, or Pro; $X_8$ is Glu, Asp, or Gly; $X_9$ is Thr, Ser, Ala, or Val; and $X_{10}$ is Ser, Thr, Ala, or Val. In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1B; and comprises a substitution of the amino acid sequence NSN-STEFKSYKSGKQPFVGAWQA (SEQ ID NO:34) of the reference amino acid sequence of FIG. 1B; where the amino acid sequence NSNSTEFKSYKSGKQPFVGAWQA (SEQ ID NO:34) is substituted with the amino acid sequence (SEQ ID NO: 30)
RSQEYKKYQTNKTTGNTDKRAFVETWQS.

Helical-II Modifications

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2A. A variant CRISPR-Cas effector polypeptide comprising the amino acid sequence depicted in FIG. 2A is also referred to herein as "PlmCasXv2." In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2A; and comprises a helical-II comprising the amino acid sequence HKKREGSLENP (SEQ ID NO:35), or an amino acid sequence having from 1 to 4 amino acid substitutions (e.g., conservative amino acid substitutions) compared to HKKREGSLENP (SEQ ID NO:35). For example, in some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2A; and comprises a helical-II domain comprising the amino acid sequence $X_1KKREGX_2X_3EX_4P$ (SEQ ID NO:36), where $X_1$ is His or Arg; $X_2$ is Ser or Thr; $X_3$ is Leu, Val, or Ile; and $X_4$ is Asn, Arg, or Gln.

In some cases, a variant CRISPR-Cas effector polypeptide of the present disclosure comprises, in order from N-terminus to C-terminus: i) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 1-331 of the amino acid sequence depicted in FIG. 2A; ii) an 11-amino acid sequence comprising the amino acid sequence HKKREGSLENP (SEQ ID NO:35), or an amino acid sequence having from 1 to 4 amino acid substitutions (e.g., conservative amino acid substitutions) compared to HKKREGSLENP (SEQ ID NO:35) (e.g., $X_1$KKREGX$_2$X$_3$EX$_4$P (SEQ ID NO:36), where $X_1$ is His or Arg; $X_2$ is Ser or Thr; $X_3$ is Leu, Val, or Ile; and $X_4$ is Asn, Arg, or Gln); and iii) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to amino acids 399-985 of the amino acid sequence depicted in FIG. 2A.

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2A; and comprises a helical II domain, where the helical-II domain comprises an amino acid sequence having at least 80%, at least 85%, at least 90%, at least 95%, at least 98%, at least 99%, or 100%, amino acid sequence identity to the amino acid sequence PLVERQA-NEVDWWDMVCNVKKLINEKKEDGKVFWQN-LAGYKRQEALLPYLSSEEDHKKRE GSLENPKK-FARYQFGDLLLHLEKKHGEDWGKVYDEAWERI DKKVEGLSKHIKLEEERRSEDA QSKAALTDWL-RAKASFVIEGLKEADKDEFCR-CELKLQKWYGDLRGKPFAIEAENSILDISGF (SEQ ID NO:37), where the helical-II domain comprises an 11-amino acid sequence comprising the amino acid sequence HKKREGSLENP (SEQ ID NO:35), or an amino acid sequence having from 1 to 4 amino acid substitutions (e.g., conservative amino acid substitutions) compared to HKKREGSLENP (SEQ ID NO:35) (e.g., $X_1$KKREGX$_2$X$_3$EX$_4$P (SEQ ID NO:36), where $X_1$ is His or Arg; $X_2$ is Ser or Thr; $X_3$ is Leu, Val, or Ile; and $X_4$ is Asn, Arg, or Gln); and where the helical-II domain has a length of from about 180 amino acids to about 1900 amino acids (e.g., from about 180 amino acids to about 185 amino acids, or from about 185 amino acids to about 190 amino acids).

In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2B; and comprises a substitution of the amino acid sequence RKKG (SEQ ID NO:38) of the reference amino acid sequence of FIG. 2B; where the amino acid sequence RKKG (SEQ ID NO:38) is substituted with the amino acid sequence $X_1$KKREGX$_2$X$_3$EX$_4$P (SEQ ID NO:36), where $X_1$ is His or Arg; $X_2$ is Ser or Thr; $X_3$ is Leu, Val, or Ile; and $X_4$ is Asn, Arg, or Gln. In some cases, a variant CRISPR-Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2B; and comprises a substitution of the amino acid sequence RKKG (SEQ ID NO:38) of the reference amino acid sequence of FIG. 1B; where the amino acid sequence RKKG (SEQ ID NO:38) is substituted with the amino acid sequence HKKREGSLENP (SEQ ID NO:35).

Variants—Catalytic Activity

In some cases, a variant CRISPR-Cas effector polypeptide of the present disclosure is a catalytically 'dead' protein (has substantially no cleavage activity) and can be referred to as a "dead" variant CRISPR-Cas effector polypeptide. In some cases, variant CRISPR-Cas effector polypeptide of the present disclosure is a nickase (cleaves only one strand of a double stranded target nucleic acid, e.g., a double stranded target DNA). As described in more detail herein, in some cases, a variant CRISPR-Cas effector polypeptide of the present disclosure (in some case a variant CRISPR-Cas effector polypeptide with target nucleic acid cleavage activity; and in some cases a variant CRISPR-Cas effector polypeptide with reduced cleavage activity, e.g., a "dead" variant CRISPR-Cas effector polypeptide or a nickase variant CRISPR-Cas effector polypeptide) is fused (conjugated) to a heterologous polypeptide that has an activity of interest (e.g., a catalytic activity of interest) to form a fusion protein (a chimeric variant CRISPR-Cas effector polypeptide).

Conserved catalytic residues of a variant CRISPR-Cas effector polypeptide include D672, E769, and D935, when numbered according to the amino acid sequence depicted in FIG. 1A (DpbCasXv2); and D666, E763, and D929, when numbered according to the amino acid sequence depicted in FIG. 2A (PlmCasXv2).

Thus, in some cases, a variant CRISPR-Cas effector polypeptide of the present disclosure has reduced activity and one or more of the above described amino acids are mutated (e.g., substituted with another amino acid, such as alanine). In some cases, a variant CRISPR-Cas effector polypeptide of the present disclosure is a catalytically 'dead' protein (is catalytically inactive) and is referred to as a "dead" variant CRISPR-Cas effector polypeptide. A dead variant CRISPR-Cas effector polypeptide can be fused to a fusion partner that provides an activity, and in some cases, the dead variant CRISPR-Cas effector polypeptide (e.g., one without a fusion partner that provides catalytic activity—but which can have a nuclear localization signal(s) when produced in a eukaryotic cell) can bind to target DNA and can block RNA polymerase from transcribing from a target DNA. In some cases, the variant CRISPR-Cas effector polypeptide is a nickase (cleaves only one strand of a double stranded target nucleic acid, e.g., a double stranded target DNA).

Variants—Chimeric Variant CRISPR-Cas Effector Polypeptides (i.e., Fusion Proteins)

As noted above, in some cases, a variant CRISPR-Cas effector polypeptide of the present disclosure is fused (conjugated) to one or more heterologous polypeptides that has/have an activity of interest (e.g., a catalytic activity of interest; a localization activity) to form a fusion protein (a chimeric variant CRISPR-Cas effector polypeptide). A heterologous polypeptide to which a variant CRISPR-Cas effector polypeptide is fused is referred to herein as a "fusion partner."

In some cases, the fusion partner can modulate transcription (e.g., inhibit transcription, increase transcription) of a target DNA. For example, in some cases the fusion partner is a protein (or a domain of a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases, the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric variant CRISPR-Cas effector polypeptide of the present disclosure includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric variant CRISPR-Cas effector polypeptide includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFκB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SETIB, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable chimeric variant CRISPR-Cas effector polypeptide), and a chloroplast transit peptide. Suitable chloroplast transit peptides include, but are not limited to:

```
                                    (SEQ ID NO: 39)
MASMISSSAVTTVSRASRGQSAAMAPFGGLKSMTGFPVR

KVNTDITSITSNGGRVKCMQVWPPIGKKKFETLSYLPPL

TRDSRA;
                                    (SEQ ID NO: 40)
MASMISSSAVTTVSRASRGQSAAMAPFGGLKSMTGFPVR

KVNTDITSITSNGGRVKS;
                                    (SEQ ID NO: 41)
MASSMLSSATMVASPAQATMVAPFNGLKSSAAFPATRKA

NNDITSITSNGGRVNCMQVWPPIEKKKFETLSYLPDLTD

SGGRVNC;
                                    (SEQ ID NO: 42)
MAQVSRICNGVQNPSLISNLSKSSQRKSPLSVSLKTQQH

PRAYPISSSWGLKKSGMTLIGSELRPLKVMSSVSTAC;
                                    (SEQ ID NO: 43)
MAQVSRICNGVWNPSLISNLSKSSQRKSPLSVSLKTQQH

PRAYPISSSWGLKKSGMTLIGSELRPLKVMSSVSTAC;
                                    (SEQ ID NO: 44)
MAQINNMAQGIQTLNPNSNFHKPQVPKSSSFLVFGSKKL

KNSANSMLVLKKDSIFMQLFCSFRISASVATAC;
                                    (SEQ ID NO: 45)
MAALVTSQLATSGTVLSVTDRFRRPGFQGLRPRNPADAA

LGMRTVGASAAPKQSRKPHRFDRRCLSMVV;
                                    (SEQ ID NO: 46)
MAALTTSQLATSATGFGIADRSAPSSLLRHGFQGLKPRS

PAGGDATSLSVTTSARATPKQQRSVQRGSRRFPSVVVC;
                                    (SEQ ID NO: 47)
MASSVLSSAAVATRSNVAQANMVAPFTGLKSAASFPVSR

KQNLDITSIASNGGRVQC;
                                    (SEQ ID NO: 48)
MESLAATSVFAPSRVAVPAARALVRAGTVVPTRRTSSTS

GTSGVKCSAAVTPQASPVISRSAAAA;
and
                                    (SEQ ID NO: 49)
MGAAATSMQSLKFSNRLVPPSRRLSPVPNNVTCNNLPKS

AAPVRTVKCCASSWNSTINGAAATTNGASAASS.
```

In some cases, a variant CRISPR-Cas effector polypeptide of the present disclosure comprises: a) a variant CRISPR-Cas effector polypeptide of the present disclosure; and b) a chloroplast transit peptide. Thus, for example, a ribonucleoprotein (RNP) complex (comprising a variant CRISPR-Cas effector polypeptide and a guide nucleic acid) can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast can be accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a variant CRISPR-Cas effector polypeptide of the present disclosure can comprise: a) a variant CRISPR-Cas effector polypeptide of the present disclosure; and b) an endosomal escape peptide. In some cases, an endosomal escape polypeptide comprises the amino acid sequence GLFXALLXLLXSLWXLLLXA (SEQ ID NO:50), wherein each X is independently selected from lysine, histidine, and arginine. In some cases, an endosomal escape polypeptide comprises the amino acid sequence GLF-HALLHLLHSLWHLLLHA (SEQ ID NO:51).

For examples of fusion partners used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et. al., Cell. 2013 Jul. 18; 154(2):442-51; Kearns et al., Nat Methods. 2015 May; 12(5):401-3; Mendenhall et. al., Nat Biotechnol. 2013 December; 31(12):1133-6; Hilton et. al., Nat Biotechnol. 2015 May; 33(5):510-7; Gordley et. al., Proc Natl Acad Sci USA. 2009 Mar. 31; 106(13):5053-8; Akopian et. al., Proc Natl Acad Sci USA. 2003 Jul. 22; 100(15):8688-91; Tan et., al., J Virol. 2006 February; 80(4):1939-48; Tan et. al., Proc Natl Acad Sci USA. 2003 Oct. 14; 100(21):11997-2002; Papworth et. al., Proc Natl Acad Sci USA. 2003 Feb. 18; 100(4):1621-6; Sanjana et. al., Nat Protoc. 2012 Jan. 5; 7(1):171-92; Beerli et. al., Proc Natl Acad Sci USA. 1998 Dec. 8; 95(25):14628-33; Snowden et. al., Curr Biol. 2002 Dec. 23; 12(24):2159-66; Xu et. al., Xu et. al., Cell Discov. 2016 May 3; 2:16009; Komor et al., Nature. 2016 Apr. 20; 533(7603):420-4; Chaikind et. al., Nucleic Acids Res. 2016 Aug. 11; Choudhury et. al., Oncotarget. 2016 Jun. 23; Du et. al., Cold Spring Harb Protoc. 2016 Jan. 4; Pham et. al., Methods Mol Biol. 2016; 1358:43-57; Balboa et al., Stem Cell Reports. 2015 Sep. 8; 5(3):448-59; Hara et. al., Sci Rep. 2015 Jun. 9; 5:11221; Piatek et. al., Plant Biotechnol J. 2015 May; 13(4):578-89; Hu et al., Nucleic Acids Res. 2014 April; 42(7):4375-90; Cheng et. al., Cell Res. 2013 October; 23(10):1163-71; cheng et. al., Cell Res. 2013 October; 23(10):1163-71; and Maeder et. al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric variant CRISPR-Cas effector polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide present in a subject chimeric variant CRISPR-Cas effector polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric variant CRISPR-Cas effector polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes).

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject variant CRISPR-Cas effector polypeptide include, but are not limited to those described in the following applications (which publications are related to other CRISPR-Cas effector polypeptides such as Cas9; however, the described fusion partners can also be used with a variant CRISPR-Cas effector polypeptide of the present disclosure): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus; a sequence to keep the fusion protein out of the nucleus, e.g., a nuclear export sequence (NES), a sequence to keep the fusion protein retained in the cytoplasm; a mitochondrial localization signal for targeting to the mitochondria; a chloroplast localization signal for targeting to a chloroplast; an ER retention signal; or the like). In some cases, a variant CRISPR-Cas effector polypeptide of the present disclosure does not include an NLS, such that the protein is not targeted to the nucleus (which can be advantageous, e.g., when the target nucleic acid is an RNA that is present in the cytosol). In some cases, the heterologous polypeptide can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like).

In some cases, a variant CRISPR-Cas effector polypeptide of the present disclosure includes (is fused to) a nuclear localization signal (NLS) (e.g., a single NLS; or, in some cases, 2 or more, 3 or more, 4 or more, or 5 or more NLSs). Thus, in some cases, a variant CRISPR-Cas effector polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus. In some cases, a variant CRISPR-Cas effector polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a variant CRISPR-Cas effector polypeptide includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO:52); the NLS from nucleoplasmin (e.g., the nucleoplasmin bipartite NLS with the sequence KRPAATKK-AGQAKKKK (SEQ ID NO:53)); the c-myc NLS having the amino acid sequence PAAKRVKLD (SEQ ID NO:54) or RQRRNELKRSP (SEQ ID NO:55); the hRNPA1 M9 NLS having the sequence NQSSNFGPMKGGNFG-GRSSGPYGGGGQYFAKPRNQGGY (SEQ ID NO:56); the sequence RMRIZFKNKGKDTAELRRRRVEVS-VELRKAKKDEQILKRRNV (SEQ ID NO:57) of the IBB domain from importin-alpha; the sequences VSRKRPRP (SEQ ID NO:58) and PPKKARED (SEQ ID NO:59) of the myoma T protein; the sequence PQPKKKPL (SEQ ID NO:60) of human p53; the sequence SALIKKKKKMAP (SEQ ID NO:61) of mouse c-abl IV; the sequences DRLRR (SEQ ID NO:62) and PKQKKRK (SEQ ID NO:63) of the influenza virus NS1; the sequence RKLKKKIKKL (SEQ ID NO:64) of the Hepatitis virus delta antigen; the sequence REKKKFLKRR (SEQ ID NO:65) of the mouse Mx1 protein; the sequence KRKGDEVDGVDEVAKKKSKK (SEQ ID NO:66) of the human poly(ADP-ribose) polymerase; and the sequence RKCLQAGMNLEARKTKK (SEQ ID NO:67) of the steroid hormone receptors (human) glucocorticoid. In general, NLS (or multiple NLSs) are of sufficient strength to drive accumulation of the variant CRISPR-Cas effector polypeptide in a detectable amount in the nucleus of a eukaryotic cell. Detection of accumulation in the nucleus may be performed by any suitable technique. For example, a detectable marker may be fused to the variant CRISPR-Cas effector polypeptide such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a variant CRISPR-Cas effector polypeptide of the present disclosure is a fusion polypeptide that includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a variant CRISPR-Cas effector polypeptide of the present disclosure to generate a fusion protein). In some cases, a PTD is covalently linked to the carboxyl terminus of a variant CRISPR-Cas effector polypeptide of the present disclosure. In some cases, the PTD is inserted internally in the variant CRISPR-Cas effector polypeptide at a suitable insertion site. In some cases, a subject variant CRISPR-Cas effector polypeptide is a fusion polypeptide that includes (is conjugated to, is fused to) one or more PTDs (e.g., two or more, three or more, four or more PTDs). In some cases, a PTD includes a nuclear localization signal (NLS) (e.g, in some cases 2 or more, 3 or more, 4 or more, or 5 or more NLSs). Thus, in some cases, a variant CRISPR-Cas effector polypeptide is a fusion polypeptide that includes one or more NLSs (e.g., 2 or more, 3 or more, 4 or more, or 5 or more NLSs). In some cases, a PTD is covalently linked to a nucleic acid (e.g., a guide nucleic acid, a polynucleotide encoding a guide nucleic acid, a polynucleotide encoding a variant CRISPR-Cas effector polypeptide of the present disclosure, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:68); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); a *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:69); Transportan GWTLNSAGYLLGKINLKALAALAKKIL (SEQ ID NO:70); KALAWEAKLAKALAKA-LAKHLAKALAKALKCEA (SEQ ID NO:71); and RQIKIWFQNRRMKWKK (SEQ ID NO:72). Exemplary PTDs include but are not limited to, YGRKKRRQRRR (SEQ ID NO:68), RKKRRQRRR (SEQ ID NO:73); an arginine homopolymer of from 3 arginine residues to 50 arginine residues; Exemplary PTD domain amino acid sequences include, but are not limited to, any of the following: YGRKKRRQRRR (SEQ ID NO:68); RKKRRQRRR (SEQ ID NO:74); YARAAARQARA (SEQ ID NO:75); THRLPRRRRRR (SEQ ID NO:76); and GGRRARRRRRR (SEQ ID NO:77). In some cases, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject variant CRISPR-Cas effector polypeptide can be fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $(GSGGS)_n$ (SEQ ID NO:78), (GGSGGS) (SEQ ID NO:79), $(GGGGS)_n$ (SEQ ID NO:87) and $(GGGS)_n$ (SEQ ID NO:80), where n is an integer of at least one; e.g., where n is an integer from 1 to 10), glycine-alanine polymers, alanine-serine polymers. Exemplary linkers can comprise amino acid sequences including, but not limited to, GGSG (SEQ ID NO:81), GGSGG (SEQ ID NO:82), GSGSG (SEQ ID NO:83), GSGGG (SEQ ID NO:84), GGGSG (SEQ ID NO:85), GSSSG (SEQ ID NO:86), GGGGS (SEQ ID NO:87), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a variant CRISPR-Cas effector polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phyco-biliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A variant CRISPR-Cas effector polypeptide of the present disclosure binds to a target nucleic acid (e.g., a target DNA) at a target sequence defined by the region of complementarity between the DNA-targeting RNA (guide RNA) and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some cases, the PAM for a variant CRISPR-Cas effector polypeptide of the present disclosure is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some cases, the PAM sequence of the non-complementary strand is 5'-TCN-3' (and in some cases TTCN), where N is any DNA nucleotide. In some cases, the PAM sequence requirement may be different than the 5'-TCN-3' or 5'-TTCN-3' sequences described above. Various methods (including in silico and/or wet lab methods) for identification of the appropriate PAM sequence are known in the art and are routine, and any convenient method can be used.

Guide Nucleic Acid

A nucleic acid molecule that binds to a variant CRISPR-Cas effector polypeptide of the present disclosure, forming a ribonucleoprotein complex (RNP), and targets the complex to a specific location within a target nucleic acid (e.g., a target DNA) is referred to herein as a "guide RNA." It is to be understood that in some cases, a hybrid DNA/RNA can be made such that a guide RNA includes DNA bases in addition to RNA bases; nevertheless, the term "guide RNA" encompasses such a molecule herein.

A guide RNA generally includes two segments: a targeting segment and a protein-binding segment. The targeting segment of a guide RNA, for use with a variant CRISPR-Cas effector polypeptide of the present disclosure, includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a variant CRISPR-Cas effector polypeptide of the present disclosure. The protein-binding segment of a subject guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the guide RNA (the guide sequence of the guide RNA) and the target nucleic acid.

A guide RNA and a variant CRISPR-Cas effector polypeptide of the present disclosure form a complex (e.g., bind via non-covalent interactions). The guide RNA provides target specificity to the complex by including a targeting segment, which includes a guide sequence (a nucleotide sequence that is complementary to a sequence of a target nucleic acid). The variant CRISPR-Cas effector polypeptide (or the fusion partner of a chimeric variant CRISPR-Cas effector polypeptide) of the complex provides the site-specific activity. In other words, the variant CRISPR-Cas effector polypeptide is guided to a target nucleic acid sequence (e.g. a target sequence) by virtue of its association with the guide RNA.

The "guide sequence" also referred to as the "targeting sequence" of a guide RNA can be modified so that the guide RNA can target a variant CRISPR-Cas effector polypeptide to any desired sequence of any desired target nucleic acid, with the exception (e.g., as described herein) that the PAM sequence can be taken into account. Thus, for example, a guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

A subject guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA." Thus, a subject single guide RNA comprises a targeter (e.g., targeter-RNA) and an activator (e.g., activator-RNA) that are linked to one another (e.g., by intervening nucleotides), and hybridize to one another to form the double stranded RNA duplex (dsRNA duplex) of the protein-binding segment of the guide RNA, thus resulting in a stem-loop structure. Thus, the targeter and the activator each have a duplex-forming segment, where the duplex forming segment of the targeter and the duplex-forming segment of the activator have complementarity with one another and hybridize to one another.

In some cases, the linker of a single-guide RNA (sgRNA) is a stretch of nucleotides. In some cases, the targeter and activator of a single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt). Guide sequence of a guide RNA The targeting segment of a guide RNA (for use with a variant CRISPR-Cas effector polypeptide of the present disclosure) includes a guide sequence (i.e., a targeting sequence), which is a nucleotide sequence that is complementary to a sequence (a target site) in a target nucleic acid. In other words, the targeting segment of a guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the guide sequence has a length in a range of from 19-30 nucleotides (nt) (e.g., from 19-25, 19-22, 19-20, 20-30, 20-25, or 20-22 nt). In some cases, the guide sequence has a length in a range of from 19-25 nucleotides (nt) (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. The guide sequence can be represented by "Nx", where N is any nucleotide and x is an integer from 19-30 (i.e., Nx can be 19-30 nucleotides), or ranges in between, as described above.

Protein-Binding Segment of a Guide RNA

The protein-binding segment of a subject guide RNA interacts with a variant CRISPR-Cas effector polypeptide of the present disclosure. The guide RNA guides the bound variant CRISPR-Cas effector polypeptide to a specific nucleotide sequence within target nucleic acid via the above-mentioned guide sequence. The protein-binding segment of a guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In some cases, the activator-RNA (e.g., in dual or single guide format) has a length of 65 nucleotides (nt) or more (e.g., 66 or more, 67 or more, 68 or more, 69 or more, 70 or more, or 75 or more nt). In some cases, the activator-RNA (e.g., in dual or single guide format) has a length of 66 nt or more (e.g., 67 or more, 68 or more, 69 or more, 70 or more, or 75 or more nt). In some cases, the activator-RNA (e.g., in dual or single guide format) has a length of 67 nt or more (e.g., 68 or more, 69 or more, 70 or more, or 75 or more nt).

The term "activator" or "activator RNA" is used herein to mean a tracrRNA-like molecule (tracrRNA: "trans-acting CRISPR RNA") of a dual guide RNA (and therefore of a single guide RNA when the "activator" and the "targeter" are linked together by, e.g., intervening nucleotides). Thus, for example, a guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a dual guide RNA. The term "activator" is used herein to encompass naturally existing tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which a variant CRISPR-Cas effector polypeptide binds). In some cases, the activator provides one or more stem loops that can interact with variant CRISPR-Cas effector polypeptide. An activator can be referred to as having a tracr sequence (tracrRNA sequence) and in some cases is a tracrRNA, but the term "activator" is not limited to naturally existing tracrRNAs.

Example Guide RNA Sequences

Figure 14A:
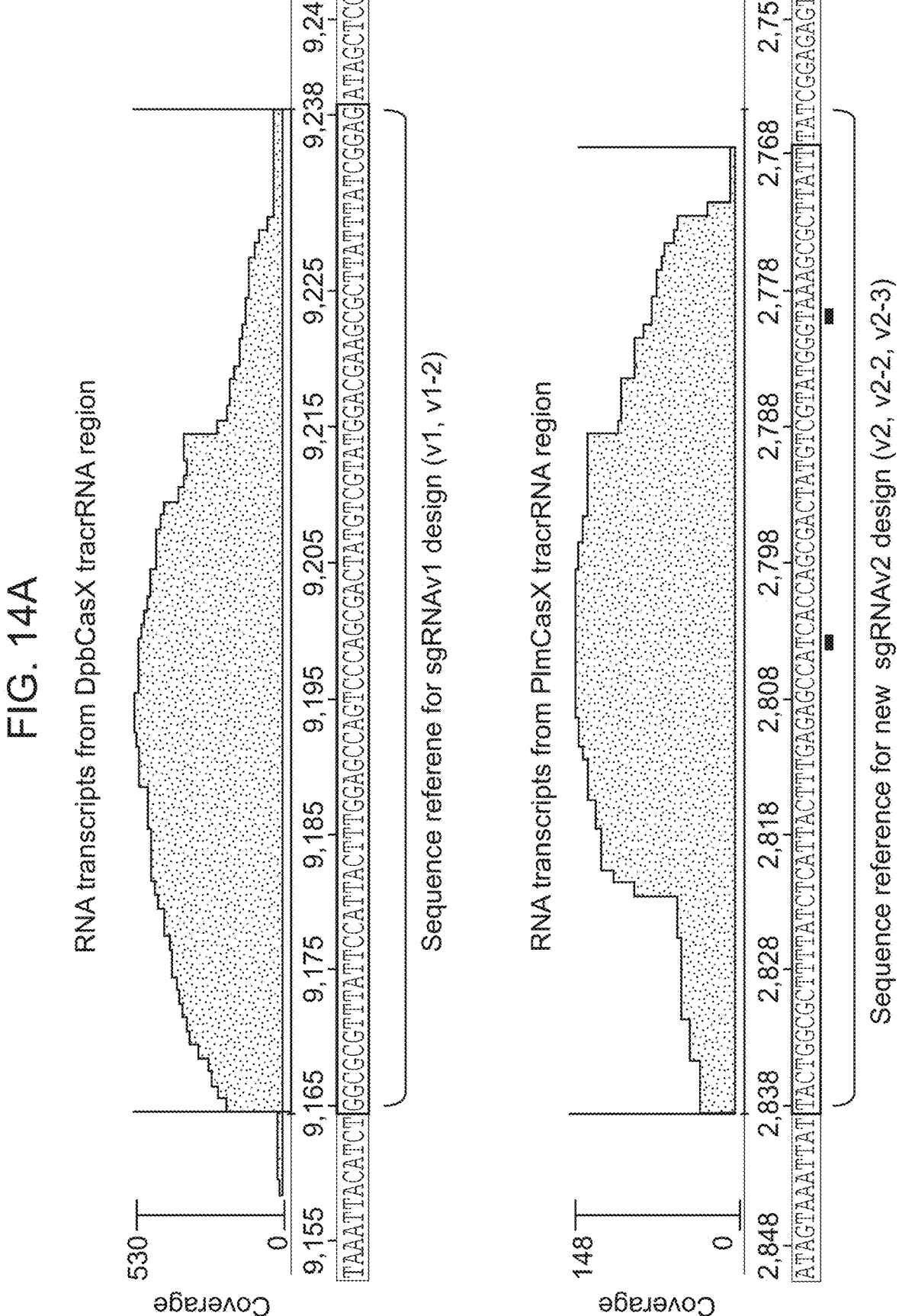
Figure 14C:
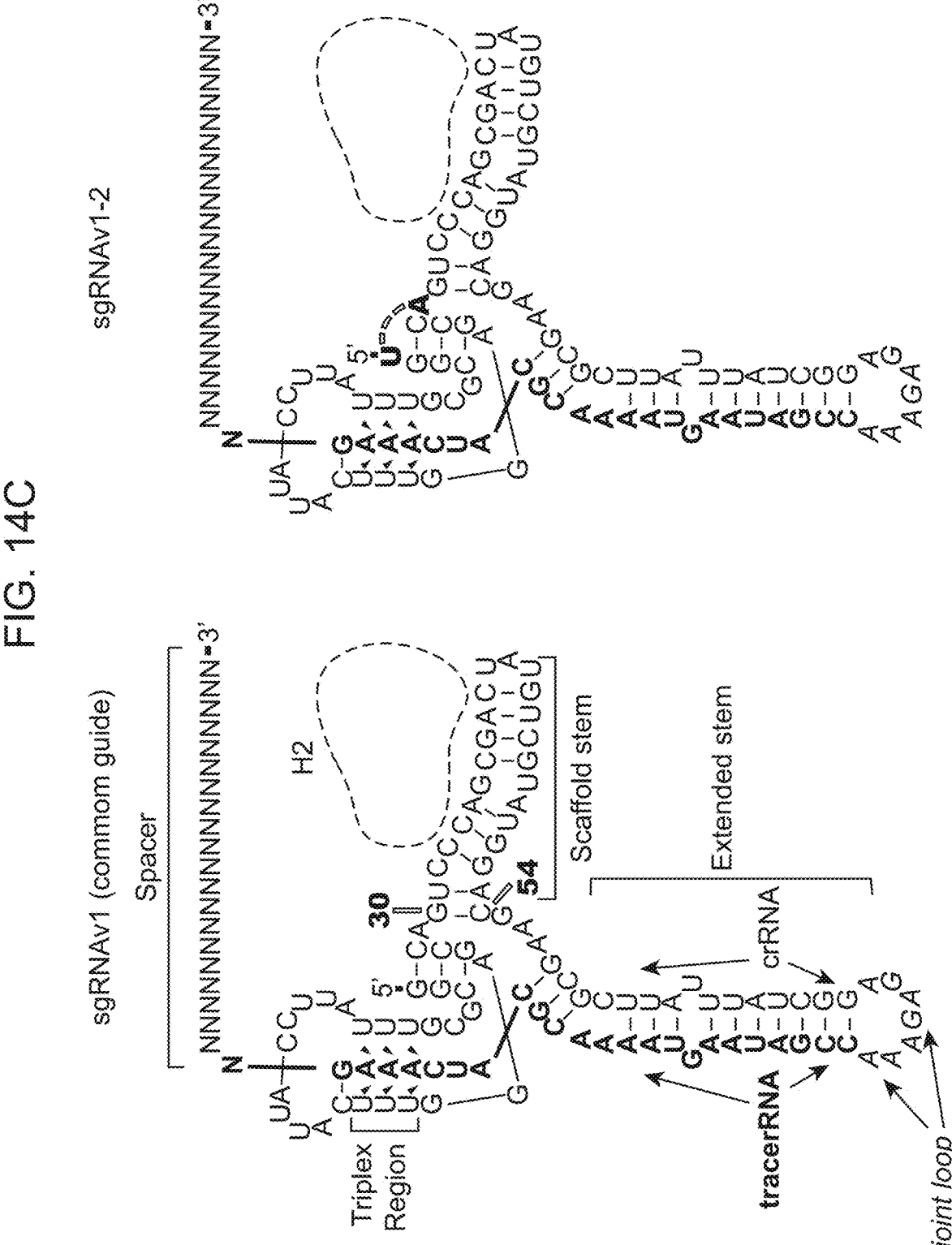
Figure 14E:
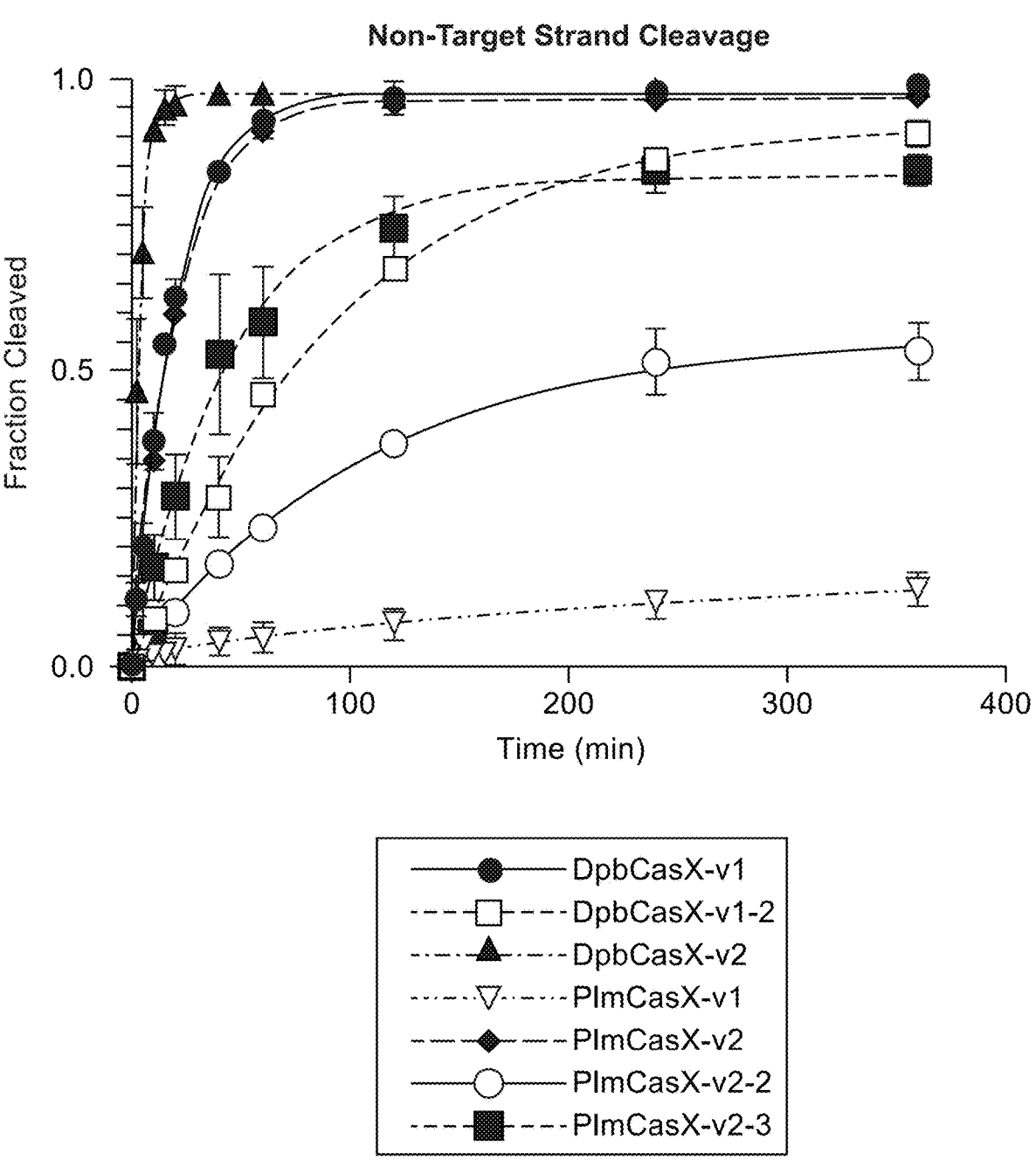

In some cases, a guide RNA suitable for use with a variant CRISPR-Cas effector polypeptide of the present disclosure has a disrupted G30-C54 base pairing. Disruption of G30-C54 base pairing can be accomplished by adding one or more nucleotides (e.g., from 1 to 10 nucleotides; e.g., 1, 2, 3, 4, 5, 6, 7, 8, 9, or 10 nucleotides) after G23, thereby increasing the single stranded linker, as shown in FIG. 14D and FIG. 14E.

In some cases, a guide RNA suitable for use with a variant CRISPR-Cas effector polypeptide of the present disclosure includes one or more modifications, compared to sgRNAv1 (e.g., compared to a sgRNA comprising a protein-binding region (protein-binding segment) comprising the sequence:

GGCGCGTTTATTCCATTACTTTG-
GAGCCAGTCCCAGCGAC-
TATGTCGTATGGACGAAGCGCT TATTTATCG-
GAGAGAAACCGATAAGTAAAACGCATCAAAG (SEQ
ID NO:88) or the sequence depicted in FIG. 20 as "sgR-
NAv1"), where the one or more modifications are those in
Table 1, below:

TABLE 1

| Modification |
| --- |
| G > T at sgRNAv1 nt position 6 |
| T > C at sgRNAv1 nt position 12 |
| C > T at sgRNAv1 nt position 13 |
| Insert A at sgRNAv2 nt position 24 |
| Remove G from sgRNAv1 nt position 30 |
| Insert A at sgRNAv2 nt position 33 |
| A > G at sgRNAv1 nt position 53 |
| C > T at sgRNAv1 nt position 54 |
| G > A at sgRNAv1 nt position 55 |
| Remove G from sgRNAv1 nt position 76 |
| Remove A from sgRNAv1 nt position 77 |
| G > A at sgRNAv1 nt position 87 |
| A > G at sgRNAv1 nt position 91 |
| C > G at sgRNAv1 nt position 93 |

In Table 1, "G>T" refers to substitution of a G with a T;
"T>C" refers to substitution of a T with a C; "C>T" refers
to substitution of a C with a T; "A>G" refers to substitution
of an A with a G; and "G>A" refers to substitution of a G
with an A.

In some cases, a guide RNA suitable for use with a
variants CRISPR-Cas effector polypeptide of the present
disclosure comprises one or more of the modifications
depicted in Table 1. The modifications may comprise any
number and combination of the modifications across the
length of the sgRNA. In some cases, a guide RNA suitable
for use with a variant CRISPR-Cas effector polypeptide of
the present disclosure includes all of the modification shown
in Table 1. As an example, the guide RNA identified as
"sgRNAv2" in FIG. 20 includes all of the modification
shown in Table 1. As those skilled in the art will appreciate,
a guide RNA can have "U" at each of the positions indicates
as "T" in FIG. 20.

A guide RNA with one or more of the modifications
shown in Table 1 can, when complexed with a CRISPR-Cas
effector polypeptide of the present disclosure, provide for
increased gene editing efficiency, compared with a guide
RNA comprising the protein-binding segment of sgRNAv1.
A guide RNA with one or more of the modifications shown
in Table 1 can provide for at least 10%, at least 25%, at least
50%, at least 2-fold, at least 2.5-fold, at least 5-fold, or more
than 5-fold, increased gene editing efficiency, compared
with the editing efficiency obtained using a guide RNA
comprising the protein-binding segment of sgRNAv1 when
complexed with the same CRISPR-Cas effector polypeptide.

Non-limiting examples of guide RNAs suitable for use
with a variant CRISPR-Cas effector polypeptide of the
present disclosure include, e.g.:

(SEQ ID NO: 89)
GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAG(N)$_x$, where N is any nucleotide, and x is an integer from 19 to 30.
For example, Nx can be 19-30 nucleotides (nt) (e.g., from 19-25, 19-22, 19-20, 20-30, 20-25, or 20-22 nt). In some
cases, the guide sequence (Nx) has a length in a range of
from 19-25 nucleotides (nt) (e.g., from 19-22, 19-20, 20-25,
20-25, or 20-22 nt). In some cases, the guide sequence has
a length of 19 or more nt (e.g., 20 or more, 21 or more, or
22 or more nt; 19 nt, 20 nt, 21 nt, 22 nt, 23 nt, 24 nt, 25 nt,
etc.). In some cases, the guide sequence has a length of 19
nt. In some cases, the guide sequence has a length of 20 nt.
In some cases, the guide sequence has a length of 21 nt. In
some cases, the guide sequence has a length of 22 nt. In
some cases, the guide sequence has a length of 23 nt.

2)

(SEQ ID NO: 90)
GGCGCUUUUAUCUCAUUACUUUGAGAGCCAUCACCAGCGACUAUGUCGU

AUGGGUAAAGCGCUUAUUUAUCGGAGAAACCGAUAAAUAAGAAGCAUCA

AAG(N)$_x$, where N is any nucleotide, and x is an integer from 19 to 30.
For example, Nx can be 19-30 nucleotides (nt) (e.g., from
19-25, 19-22, 19-20, 20-30, 20-25, or 20-22 nt). In some
cases, the guide sequence (Nx) has a length in a range of
from 19-25 nucleotides (nt) (e.g., from 19-22, 19-20, 20-25,
20-25, or 20-22 nt). In some cases, the guide sequence has
a length of 19 or more nt (e.g., 20 or more, 21 or more, or
22 or more nt; 19 nt, 20 nt, 21 nt, 22 nt, 23 nt, 24 nt, 25 nt,
etc.). In some cases, the guide sequence has a length of 19
nt. In some cases, the guide sequence has a length of 20 nt.
In some cases, the guide sequence has a length of 21 nt. In
some cases, the guide sequence has a length of 22 nt. In
some cases, the guide sequence has a length of 23 nt.

In some cases, the activator-RNA comprises a nucleotide
sequence having 80% or more identity (e.g., 85% or more,
90% or more, 93% or more, 95% or more, 97% or more,
98% or more, or 100% identity) with the sequence (SEQ ID NO: 10)
GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAG.

In some cases, the activator-RNA comprises a nucleotide
sequence having 80% or more identity (e.g., 85% or more,
90% or more, 93% or more, 95% or more, 97% or more,
98% or more, or 100% identity) with the sequence (SEQ ID NO: 12)
GGCGCUUUUAUCUCAUUACUUUGAGAGCCAUCACCAGCGACU

AUGUCGUAUGGGUAAAGCGCUUAUUUAUCGGAGAAACCGAUA

AAUAAGAAGCAUCAAAG.

Variant Crispr-Cas Effector Polypeptide Systems

The present disclosure provides a variant CRISPR-Cas
effector polypeptide system. A variant CRISPR-Cas effector
polypeptide system of the present disclosure can comprise:
a) a variant CRISPR-Cas effector polypeptide of the present
disclosure; and a guide RNA; b) a variant CRISPR-Cas
effector polypeptide of the present disclosure; a guide RNA;
and a donor template nucleic acid; c) a variant CRISPR-Cas
effector polypeptide of the present disclosure, where the
variant CRISPR-Cas effector polypeptide is a fusion poly-
peptide; and a guide RNA; d) a variant CRISPR-Cas effector polypeptide of the present disclosure, where the variant CRISPR-Cas effector polypeptide is a fusion polypeptide; a guide RNA; and a donor template nucleic acid; e) an mRNA encoding a variant CRISPR-Cas effector polypeptide of the present disclosure; and a guide RNA; f) an mRNA encoding a variant CRISPR-Cas effector polypeptide of the present disclosure; a guide RNA; and a donor template nucleic acid; g) an mRNA encoding a variant CRISPR-Cas effector polypeptide of the present disclosure, where the variant CRISPR-Cas effector polypeptide is a fusion polypeptide; and a guide RNA; h) an mRNA encoding a variant CRISPR-Cas effector polypeptide of the present disclosure, where the variant CRISPR-Cas effector polypeptide is a fusion polypeptide; a; guide RNA; and a donor template nucleic acid; i) a recombinant expression vector comprising: i) a nucleotide sequence encoding a variant CRISPR-Cas effector polypeptide of the present disclosure; and ii) a nucleotide sequence encoding a guide RNA; j) a recombinant expression vector comprising: i) a nucleotide sequence encoding a variant CRISPR-Cas effector polypeptide of the present disclosure; ii) a nucleotide sequence encoding a guide RNA; and iii) a nucleotide sequence encoding a donor template nucleic acid; k) a recombinant expression vector comprising a nucleotide sequence encoding: i) a variant CRISPR-Cas effector polypeptide fusion polypeptide of the present disclosure; and ii) a nucleotide sequence encoding a guide RNA; l) a recombinant expression vector comprising: i) a nucleotide sequence encoding a variant CRISPR-Cas effector polypeptide of the present disclosure, where the variant CRISPR-Cas effector polypeptide is a fusion polypeptide; ii) a nucleotide sequence encoding a guide RNA; and iii) a nucleotide sequence encoding a donor template nucleic acid; m) a first recombinant expression vector comprising a nucleotide sequence encoding a variant CRISPR-Cas effector polypeptide of the present disclosure; and a second recombinant expression vector comprising a nucleotide sequence encoding a guide RNA; n) a first recombinant expression vector comprising a nucleotide sequence encoding a variant CRISPR-Cas effector polypeptide of the present disclosure; and a second recombinant expression vector comprising a nucleotide sequence encoding: i) a guide RNA; and ii) a donor template nucleic acid; o) a first recombinant expression vector comprising a nucleotide sequence encoding a variant CRISPR-Cas effector polypeptide of the present disclosure, where the variant CRISPR-Cas effector polypeptide is a fusion polypeptide, and a second recombinant expression vector comprising a nucleotide sequence encoding a guide RNA; p) a first recombinant expression vector comprising a nucleotide sequence encoding a variant CRISPR-Cas effector polypeptide of the present disclosure, where the variant CRISPR-Cas effector polypeptide is a fusion polypeptide; and a second recombinant expression vector comprising a nucleotide sequence encoding: i) a guide RNA; and ii) a donor template nucleic acid; q) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or r) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or some variation of one of (a) through (r).

Nucleic Acids

The present disclosure provides one or more nucleic acids comprising one or more of: a donor polynucleotide sequence, a nucleotide sequence encoding a variant CRISPR-Cas effector polypeptide of the present disclosure, a guide RNA, and a nucleotide sequence encoding a guide RNA (which can include two separate nucleotide sequences in the case of dual guide RNA format or which can include a single nucleotide sequence in the case of single guide RNA format). The present disclosure provides a nucleic acid comprising a nucleotide sequence encoding a variant CRISPR-Cas effector polypeptide of the present disclosure, where the variant CRISPR-Cas effector polypeptide is a fusion polypeptide. The present disclosure provides a recombinant expression vector that comprises a nucleotide sequence encoding a variant CRISPR-Cas effector polypeptide. The present disclosure provides a recombinant expression vector that comprises a nucleotide sequence encoding a variant CRISPR-Cas effector polypeptide of the present disclosure, where the variant CRISPR-Cas effector polypeptide is a fusion polypeptide. The present disclosure provides a recombinant expression vector that comprises: a) a nucleotide sequence encoding a variant CRISPR-Cas effector polypeptide of the present disclosure; and b) a nucleotide sequence encoding a guide RNA(s). The present disclosure provides a recombinant expression vector that comprises: a) a nucleotide sequence encoding a variant CRISPR-Cas effector polypeptide of the present disclosure, where the variant CRISPR-Cas effector polypeptide is a fusion polypeptide; and b) a nucleotide sequence encoding a guide RNA(s). In some cases, the nucleotide sequence encoding the variant CRISPR-Cas effector polypeptide and/or the nucleotide sequence encoding the guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a variant CRISPR-Cas effector polypeptide of the present disclosure is codon optimized. This type of optimization can entail a mutation of a variant CRISPR-Cas effector polypeptide-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized variant CRISPR-Cas effector polypeptide-encoding nucleotide sequence could be used. As another non-limiting example, if the intended host cell were a mouse cell, then a mouse codon-optimized variant CRISPR-Cas effector polypeptide-encoding nucleotide sequence could be generated. As another non-limiting example, if the intended host cell were a plant cell, then a plant codon-optimized variant CRISPR-Cas effector polypeptide-encoding nucleotide sequence could be generated. As another non-limiting example, if the intended host cell were an insect cell, then an insect codon-optimized variant CRISPR-Cas effector polypeptide-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a variant CRISPR-Cas effector polypeptide of the present disclosure (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a variant CRISPR-Cas effector polypeptide of the present disclosure (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a guide RNA is operably linked to a control element, e.g., a transcriptional control element, such as a promoter. In some embodiments, a nucleotide sequence encoding a variant CRISPR-Cas effector polypeptide of the present disclosure (which in some cases can be a fusion polypeptide) is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the variant CRISPR-Cas effector polypeptide, thus resulting in a chimeric variant CRISPR-Cas effector polypeptide.

In some cases, a nucleotide sequence encoding a guide RNA and/or a variant CRISPR-Cas effector polypeptide (or a fusion polypeptide comprising a variant CRISPR-Cas effector polypeptide) is operably linked to an inducible promoter. In some embodiments, a nucleotide sequence encoding a guide RNA and/or a variant CRISPR-Cas effector polypeptide (or fusion polypeptide comprising a variant CRISPR-Cas effector polypeptide) is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500

(2002)), an enhanced U6 promoter (e.g., Xia et al., Nucleic Acids Res. 2003 Sep. 1; 31(17)), a human H1 promoter (H1), and the like.

In some cases, a nucleotide sequence encoding a guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a variant CRISPR-Cas effector polypeptide is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a variant CRISPR-Cas effector polypeptide and/or a guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some cases, a variant CRISPR-Cas effector polypeptide can be provided as RNA encoding the variant CRISPR-Cas effector polypeptide. The RNA can be provided by direct chemical synthesis or may be transcribed in vitro from a DNA (e.g., encoding the variant CRISPR-Cas effector polypeptide). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the guide RNA; recombinant expression vectors encoding the variant CRISPR-Cas effector polypeptide; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding guide RNA and/or a variant CRISPR-Cas effector polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a guide RNA and/or a variant CRISPR-Cas effector polypeptide to a cell may include nucleic acid sequences that encode for selectable markers in the target cells, so as to identify cells that have taken up the guide RNA and/or variant CRISPR-Cas effector polypeptide.

A nucleic acid comprising a nucleotide sequence encoding a variant CRISPR-Cas effector polypeptide, or a fusion polypeptide comprising a variant CRISPR-Cas effector polypeptide, is in some cases an RNA. Thus, a variant CRISPR-Cas effector polypeptide can be introduced into cells as RNA encoding the variant CRISPR-Cas effector polypeptide. Methods of introducing RNA into cells are known in the art and may include, for example, direct injection, transfection, or any other method used for the introduction of DNA. A variant CRISPR-Cas effector polypeptide may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally, or alternatively, a variant CRISPR-Cas effector polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapedia, referred to as penetratin, which comprises the amino acid sequence RQIKIWFQNRRMKWKK (SEQ ID NO:72). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A variant CRISPR-Cas effector polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a guide RNA, encoding a variant CRISPR-Cas effector polypeptide, encoding a fusion protein comprising a variant CRISPR-Cas effector polypeptide, etc.) and proteins (e.g., a variant CRISPR-Cas effector polypeptide; a fusion polypeptide comprising a variant CRISPR-Cas effector polypeptide) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g.

D-amino acids or non-naturally occurring synthetic amino acids. D-amino acids may be substituted for some or all of the amino acid residues.

A variant CRISPR-Cas effector polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus, cysteines can be used to make thioethers, histidines for linking to a metal ion complex, carboxyl groups for forming amides or esters, amino groups for forming amides, and the like.

A variant CRISPR-Cas effector polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a variant CRISPR-Cas effector polypeptide, or a fusion polypeptide comprising a variant CRISPR-Cas effector polypeptide, of the present disclosure is at least 80% pure, at least 85% pure, at least 90% pure, at least 95% pure, at least 98% pure, or at least 99% pure (e.g., free of contaminants, proteins other than a variant CRISPR-Cas effector polypeptide, or other macromolecules, etc.).

To induce cleavage or any desired modification to a target nucleic acid (e.g., genomic DNA), or any desired modification to a polypeptide associated with target nucleic acid, a guide RNA and/or a variant CRISPR-Cas effector polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a guide RNA that does not change when the guide sequence is changed to hybridized to a desired target sequence (e.g., sequences that contribute to the protein-binding aspect of the guide RNA, e.g., the sequences that contribute to the dsRNA duplex(es) of the guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a variant CRISPR-Cas effector polypeptide, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some cases, a subject nucleic acid (e.g., a guide RNA) has one or more modifications, e.g., one or more of a base modification, a sugar modification, a backbone modification, etc., to provide the nucleic acid with a new or enhanced feature (e.g., improved stability; improved nuclease resistance; etc.). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stable with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some cases, a subject nucleic acid has one or more nucleotides that are 2'-O-Methyl modified nucleotides. In some cases, a subject nucleic acid (e.g., a dsRNA, a siNA, etc.) has one or more 2' Fluoro modified nucleotides. In some cases, a subject nucleic acid (e.g., a dsRNA, a siNA, etc.) has one or more LNA bases. In some cases, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some cases, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry,* 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_n$ $ON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON$ $(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., *Chapter 15, Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N. Y Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP-cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO:68); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO:69); Transportan GWTLNSAGYLLGKINLKALAALAKKIL SEQ ID NO:70); KALAWEAKLAKALAKA-LAKHLAKALAKALKCEA SEQ ID NO:71); and RQIKIWFQNRRMKWKK SEQ ID NO:72). Exemplary PTDs include but are not limited to, YGRKKRRQRRR SEQ ID NO:68), RKKRRQRRR SEQ ID NO:73); an arginine homopolymer of from 3 arginine residues to 50 arginine residues; Exemplary PTD domain amino acid sequences include, but are not limited to, any of the following: YGRKKRRQRRR SEQ ID NO:68); RKKRRQRR SEQ ID NO:74; YARAAARQARA SEQ ID NO:75); THRL-PRRRRRR SEQ ID NO:76); and GGRRARRRRRR SEQ ID NO:77). In some cases, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A guide RNA (or a nucleic acid comprising a nucleotide sequence encoding same) and/or a variant CRISPR-Cas effector polypeptide of the present disclosure (or a nucleic acid comprising a nucleotide sequence encoding same) and/or a fusion polypeptide of the present disclosure (or a nucleic acid that includes a nucleotide sequence encoding a fusion polypeptide of the present disclosure) and/or a donor polynucleotide (donor template) can be introduced into a host cell by any of a variety of well-known methods.

Any of a variety of compounds and methods can be used to deliver to a target cell a variant CRISPR-Cas effector polypeptide system of the present disclosure (e.g., where a variant CRISPR-Cas effector polypeptide system comprises: a) a variant CRISPR-Cas effector polypeptide of the present disclosure; and a guide RNA; b) a variant CRISPR-Cas effector polypeptide of the present disclosure; a guide RNA; and a donor template nucleic acid; c) a variant CRISPR-Cas effector polypeptide of the present disclosure, where the variant CRISPR-Cas effector polypeptide is a fusion polypeptide; and a guide RNA; d) a variant CRISPR-Cas effector polypeptide of the present disclosure, where the variant CRISPR-Cas effector polypeptide is a fusion polypeptide; a guide RNA; and a donor template nucleic acid; e) an mRNA encoding a variant CRISPR-Cas effector polypeptide of the present disclosure; and a guide RNA; f) an mRNA encoding a variant CRISPR-Cas effector polypeptide of the present disclosure; a guide RNA; and a donor template nucleic acid; g) an mRNA encoding a variant CRISPR-Cas effector polypeptide of the present disclosure, where the variant CRISPR-Cas effector polypeptide is a fusion polypeptide; and a guide RNA; h) an mRNA encoding a variant CRISPR-Cas effector polypeptide of the present disclosure, where the variant CRISPR-Cas effector polypeptide is a fusion polypeptide; a; guide RNA; and a donor template nucleic acid; i) a recombinant expression vector comprising: i) a nucleotide sequence encoding a variant CRISPR-Cas effector polypeptide of the present disclosure; and ii) a nucleotide sequence encoding a guide RNA; j) a recombinant expression vector comprising: i) a nucleotide sequence encoding a variant CRISPR-Cas effector polypeptide of the present disclosure; ii) a nucleotide sequence encoding a guide RNA; and iii) a nucleotide sequence encoding a donor template nucleic acid; k) a recombinant expression vector comprising a nucleotide sequence encoding: i) a variant CRISPR-Cas effector polypeptide fusion polypeptide of the present disclosure; and ii) a nucleotide sequence encoding a guide RNA; l) a recombinant expression vector comprising: i) a nucleotide sequence encoding a variant CRISPR-Cas effector polypeptide of the present disclosure, where the variant CRISPR-Cas effector polypeptide is a fusion polypeptide; ii) a nucleotide sequence encoding a guide RNA; and iii) a nucleotide sequence encoding a donor template nucleic acid; m) a first recombinant expression vector comprising a nucleotide sequence encoding a variant CRISPR-Cas effector polypeptide of the present disclosure; and a second recombinant expression vector comprising a nucleotide sequence encoding a guide RNA; n) a first recombinant expression vector comprising a nucleotide sequence encoding a variant CRISPR-Cas effector polypeptide of the present disclosure; and a second recombinant expression vector comprising a nucleotide sequence encoding: i) a guide RNA; and ii) a donor template nucleic acid; o) a first recombinant expression vector comprising a nucleotide sequence encoding a variant CRISPR-Cas effector polypeptide of the present disclosure, where the variant CRISPR-Cas effector polypeptide is a fusion polypeptide, and a second recombinant expression vector comprising a nucleotide sequence encoding a guide RNA; p) a first recombinant expression vector comprising a nucleotide sequence encoding a variant CRISPR-Cas effector polypeptide of the present disclosure, where the variant CRISPR-Cas effector polypeptide is a fusion polypeptide; and a second recombinant expression vector comprising a nucleotide sequence encoding: i) a guide RNA; and ii) a donor template nucleic acid; q) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or r) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or some variation of one of (a) through (r). As a non-limiting example, a variant CRISPR-Cas effector polypeptide system of the present disclosure can be combined with a lipid. As another non-limiting example, a variant CRISPR-Cas effector polypeptide system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a variant CRISPR-Cas effector polypeptide of the present disclosure is provided as a nucleic acid (e.g., an mRNA, a DNA, a plasmid, an expression vector, a viral vector, etc.) that encodes the variant CRISPR-Cas effector polypeptide. In some cases, the variant CRISPR-Cas effector polypeptide of the present disclosure is provided directly as a protein (e.g., without an associated guide RNA or with an associate guide RNA, i.e., as a ribonucleoprotein complex). A variant CRISPR-Cas effector polypeptide of the present disclosure can be introduced into a cell (provided to the cell) by any convenient method; such methods are known to those of ordinary skill in the art. As an illustrative example, a variant CRISPR-Cas effector polypeptide of the present disclosure can be injected directly into a cell (e.g., with or without a guide RNA or nucleic acid encoding a guide RNA, and with or without a donor polynucleotide). As another example, a preformed complex of a variant CRISPR-Cas effector polypeptide of the present disclosure and a guide RNA (an RNP) can be introduced into a cell (e.g, eukaryotic cell) (e.g., via injection, via nucleofection; via a protein transduction domain (PTD) conjugated to one or more components, e.g., conjugated to the variant CRISPR-Cas effector polypeptide, conjugated to a guide RNA, conjugated to a variant CRISPR-Cas effector polypeptide of the present disclosure and a guide RNA; etc.).

In some cases, a fusion polypeptide of the present disclosure (where a fusion polypeptide of the present disclosure comprises: i) a variant CRISPR-Cas effector polypeptide; and ii) one or more heterologous fusion partners) is provided as a nucleic acid (e.g., an mRNA, a DNA, a plasmid, an expression vector, a viral vector, etc.) that encodes the fusion polypeptide. In some cases, a fusion polypeptide of the present disclosure is provided directly as a protein (e.g., without an associated guide RNA or with an associate guide RNA, i.e., as a ribonucleoprotein complex). A fusion polypeptide of the present disclosure can be introduced into a cell (provided to the cell) by any convenient method; such methods are known to those of ordinary skill in the art. As an illustrative example, a fusion polypeptide of the present disclosure can be injected directly into a cell (e.g., with or without nucleic acid encoding a guide RNA and with or without a donor polynucleotide). As another example, a preformed complex of a fusion polypeptide of the present disclosure and a guide RNA (an RNP) can be introduced into a cell (e.g., via injection, via nucleofection; via a protein transduction domain (PTD) conjugated to one or more components, e.g., conjugated to the fusion protein, conjugated to a guide RNA, conjugated to a fusion polypeptide of the present disclosure and a guide RNA; etc.).

In some cases, a nucleic acid (e.g., a guide RNA; a nucleic acid comprising a nucleotide sequence encoding a variant CRISPR-Cas effector polypeptide of the present disclosure; etc.) is delivered to a cell (e.g., a target host cell) and/or a polypeptide (e.g., a variant CRISPR-Cas effector polypeptide; a fusion polypeptide comprising a variant CRISPR-Cas effector polypeptide) in a particle, or associated with a particle. In some cases, a variant CRISPR-Cas effector polypeptide system of the present disclosure is delivered to a cell in a particle, or associated with a particle. The terms "particle" and nanoparticle" can be used interchangeable, as appropriate. A recombinant expression vector comprising a nucleotide sequence encoding a variant CRISPR-Cas effector polypeptide of the present disclosure and/or a guide RNA, an mRNA comprising a nucleotide sequence encoding a variant CRISPR-Cas effector polypeptide of the present disclosure, and guide RNA may be delivered simultaneously using particles or lipid envelopes; for instance, a variant CRISPR-Cas effector polypeptide and a guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a variant CRISPR-Cas effector polypeptide and a guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A variant CRISPR-Cas effector polypeptide of the present disclosure (or an mRNA comprising a nucleotide sequence encoding a variant CRISPR-Cas effector polypeptide of the present disclosure; or a recombinant expression vector comprising a nucleotide sequence encoding a variant CRISPR-Cas effector polypeptide of the present disclosure) and/or guide RNA (or a nucleic acid such as one or more expression vectors encoding the guide RNA) may be delivered simultaneously using particles or lipid envelopes. For example, a biodegradable core-shell structured nanoparticle with a poly (O-amino ester) (PBAE) core enveloped by a phospholipid bilayer shell can be used. In some cases, particles/nanoparticles based on self-assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure (as described above). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell.

In some cases, lipid nanoparticles (LNPs) are used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilinoeyl-3-dimethylammonium-propane (DLinDAP), 1,2-dilinoleyloxy-3-N,N-dimethylaminopropane (DLinDMA), 1,2- dilinoleyloxy-keto-N,N-dimethyl-3-aminopropane (DLinKDMA), and 1,2-dilinoleyl-4-(2-dimethylamino-ethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a variant CRISPR-Cas effector polypeptide of the present disclosure, a fusion polypeptide of the present disclosure, an RNP of the present disclosure (where an RNP of the present disclosure comprises: i) a variant CRISPR-Cas effector polypeptide of the present disclosure or a fusion polypeptide of the present disclosure; and ii) a guide RNA), a nucleic acid of the present disclosure, or a variant CRISPR-Cas effector polypeptide system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell have a diameter of from 25 nm to 200 nm. In some cases, nanoparticles suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell have a diameter of 100 nm or less In some cases, nanoparticles suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell have a diameter of from 35 nm to 60 nm.

Nanoparticles suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. A prototype nanoparticle of semi-solid nature is the liposome.

In some cases, an exosome is used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. Exosomes are endogenous nano-vesicles that transport RNAs and proteins, and which can deliver RNA to the brain and other target organs.

In some cases, a liposome is used to deliver variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a variant CRISPR-Cas effector polypeptide system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a variant CRISPR-Cas effector polypeptide system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A variant CRISPR-Cas effector polypeptide system of the present disclosure, or a component thereof, may be delivered encapsulated in PLGA microspheres such as that further described in US published applications 20130252281 and 20130245107 and 20130244279.

Supercharged proteins can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a variant CRISPR-Cas effector polypeptide of the present disclosure, a fusion polypeptide of the present disclosure, an RNP of the present disclosure, a nucleic acid of the present disclosure (e.g., a guide RNA, a nucleic acid encoding a guide RNA, a nucleic acid encoding a variant CRISPR-Cas effector polypeptide, a donor template, and the like), or a variant CRISPR-Cas effector polypeptide system of the present disclosure, to a target cell (e.g., a target cell in vivo, where the target cell is a target cell in circulation, a target cell in a tissue, a target cell in an organ, etc.). An implantable device suitable for use in delivering a variant CRISPR-Cas effector polypeptide of the present disclosure, a fusion polypeptide of the present disclosure, an RNP of the present disclosure, a nucleic acid of the present disclosure, or a variant CRISPR-Cas effector polypeptide system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the variant CRISPR-Cas effector polypeptide, the fusion polypeptide, the RNP, or the variant CRISPR-Cas effector polypeptide system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear-auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a variant CRISPR-Cas effector polypeptide of the present disclosure and/or a nucleic acid comprising a nucleotide sequence encoding a variant CRISPR-Cas effector polypeptide of the present disclosure. The present disclosure provides a modified cell (e.g., a genetically modified cell) comprising nucleic acid comprising a nucleotide sequence encoding a variant CRISPR-Cas effector polypeptide of the present disclosure. The present disclosure provides a genetically modified cell that is genetically modified with an mRNA comprising a nucleotide sequence encoding a variant CRISPR-Cas effector polypeptide of the present disclosure. The present disclosure provides a genetically modified cell that is genetically modified with a recombinant expression vector comprising a nucleotide sequence encoding a variant CRISPR-Cas effector polypeptide of the present disclosure. The present disclosure provides a genetically modified cell that is genetically modified with a recombinant expression vector comprising: a) a nucleotide sequence encoding a variant CRISPR-Cas effector polypeptide of the present disclosure; and b) a nucleotide sequence encoding a guide RNA of the present disclosure. The present disclosure provides a genetically modified cell that is genetically modified with a recombinant expression vector comprising: a) a nucleotide sequence encoding a variant CRISPR-Cas effector polypeptide of the present disclosure; b) a nucleotide sequence encoding a guide RNA of the present disclosure; and c) a nucleotide sequence encoding a donor template.

A cell that serves as a recipient for a variant CRISPR-Cas effector polypeptide of the present disclosure and/or a nucleic acid comprising a nucleotide sequence encoding a variant CRISPR-Cas effector polypeptide of the present disclosure and/or a guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a variant CRISPR-Cas effector polypeptide of the present disclosure and/or a nucleic acid comprising a nucleotide sequence encoding a variant CRISPR-Cas effector polypeptide of the present disclosure and/or a guide RNA of the present disclosure is referred to as a "host cell" or a "target cell." A host cell or a target cell can be a recipient of a variant CRISPR-Cas effector polypeptide system of the present disclosure. A host cell or a target cell can be a recipient of an RNP of the present disclosure. A host cell or a target cell can be a recipient of a single component of a variant CRISPR-Cas effector polypeptide system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, adult cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34$^+$ and CD3$^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf— red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, insecta,* Archaeognatha, *thysanura,* Palaeoptera, Ephemeroptera, *odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota* or *Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a variant CRISPR-Cas effector polypeptide system of the present disclosure, or a component of a variant CRISPR-Cas effector polypeptide system of the present disclosure.

A kit of the present disclosure can comprise: a) a variant CRISPR-Cas effector polypeptide of the present disclosure; and a guide RNA; b) a variant CRISPR-Cas effector polypeptide of the present disclosure; a guide RNA; and a donor template nucleic acid; c) a variant CRISPR-Cas effector polypeptide of the present disclosure, where the variant CRISPR-Cas effector polypeptide is a fusion polypeptide; and a guide RNA; d) a variant CRISPR-Cas effector polypeptide of the present disclosure, where the variant CRISPR-Cas effector polypeptide is a fusion polypeptide; a guide RNA; and a donor template nucleic acid; e) an mRNA encoding a variant CRISPR-Cas effector polypeptide of the present disclosure; and a guide RNA; f) an mRNA encoding a variant CRISPR-Cas effector polypeptide of the present disclosure; a guide RNA; and a donor template nucleic acid; g) an mRNA encoding a variant CRISPR-Cas effector polypeptide of the present disclosure, where the variant CRISPR-Cas effector polypeptide is a fusion polypeptide; and a guide RNA; h) an mRNA encoding a variant CRISPR-Cas effector polypeptide of the present disclosure, where the variant CRISPR-Cas effector polypeptide is a fusion polypeptide; a; guide RNA; and a donor template nucleic acid; i) a recombinant expression vector comprising: i) a nucleotide sequence encoding a variant CRISPR-Cas effector polypeptide of the present disclosure; and ii) a nucleotide sequence encoding a guide RNA; j) a recombinant expression vector comprising: i) a nucleotide sequence encoding a variant CRISPR-Cas effector polypeptide of the present disclosure; ii) a nucleotide sequence encoding a guide RNA; and iii) a nucleotide sequence encoding a donor template nucleic acid; k) a recombinant expression vector comprising a nucleotide sequence encoding: i) a variant CRISPR-Cas effector polypeptide fusion polypeptide of the present disclosure; and ii) a nucleotide sequence encoding a guide RNA; l) a recombinant expression vector comprising: i) a nucleotide sequence encoding a variant CRISPR-Cas effector polypeptide of the present disclosure, where the variant CRISPR-Cas effector polypeptide is a fusion polypeptide; ii) a nucleotide sequence encoding a guide RNA; and iii) a nucleotide sequence encoding a donor template nucleic acid; m) a first recombinant expression vector comprising a nucleotide sequence encoding a variant CRISPR-Cas effector polypeptide of the present disclosure; and a second recombinant expression vector comprising a nucleotide sequence encoding a guide RNA; n) a first recombinant expression vector comprising a nucleotide sequence encoding a variant CRISPR-Cas effector polypeptide of the present disclosure; and a second recombinant expression vector comprising a nucleotide sequence encoding: i) a guide RNA; and ii) a donor template nucleic acid; o) a first recombinant expression vector comprising a nucleotide sequence encoding a variant CRISPR-Cas effector polypeptide of the present disclosure, where the variant CRISPR-Cas effector polypeptide is a fusion polypeptide, and a second recombinant expression vector comprising a nucleotide sequence encoding a guide RNA; p) a first recombinant expression vector comprising a nucleotide sequence encoding a variant CRISPR-Cas effector polypeptide of the present disclosure, where the variant CRISPR-Cas effector polypeptide is a fusion polypeptide; and a second recombinant expression vector comprising a nucleotide sequence encoding: i) a guide RNA; and ii) a donor template nucleic acid; q) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or r) a recombinant expression vector comprising: i) a nucleotide sequence encoding a variant CRISPR-Cas effector polypeptide of the present disclosure; ii) a nucleotide sequence encoding a first guide RNA; and iii) a nucleotide sequence encoding a second guide RNA; or some variation of one of (a) through (r).

A kit of the present disclosure can comprise: a) a component, as described above, of a variant CRISPR-Cas effector polypeptide system of the present disclosure, or can comprise a variant CRISPR-Cas effector polypeptide system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control guide RNA; and the like. A kit of the present disclosure can comprise: a) a component, as described above, of a variant CRISPR-Cas effector polypeptide system of the present disclosure, or can comprise a variant CRISPR-Cas effector polypeptide system of the present disclosure; and b) a therapeutic agent.

A kit of the present disclosure can comprise a recombinant expression vector comprising: a) an insertion site for inserting a nucleic acid comprising a nucleotide sequence encoding a portion of a guide RNA that hybridizes to a target nucleotide sequence in a target nucleic acid; and b) a nucleotide sequence encoding the variant CRISPR-Cas effector polypeptide-binding portion of a guide RNA. A kit of the present disclosure can comprise a recombinant expression vector comprising: a) an insertion site for inserting a nucleic acid comprising a nucleotide sequence encoding a portion of a guide RNA that hybridizes to a target nucleotide sequence in a target nucleic acid; b) a nucleotide sequence encoding the variant CRISPR-Cas effector polypeptide-binding portion of a guide RNA; and c) a nucleotide sequence encoding a variant CRISPR-Cas effector polypeptide of the present disclosure.

Utility

A variant CRISPR-Cas effector polypeptide of the present disclosure, or a fusion polypeptide of the present disclosure, finds use in a variety of methods (e.g., in combination with a guide RNA and in some cases further in combination with a donor template). For example, a variant CRISPR-Cas effector polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a variant CRISPR-Cas effector polypeptide of the present disclosure; and b) one or more (e.g., two) guide RNAs. In some cases, a method of the present disclosure for modifying a target nucleic acid comprises contacting the target nucleic acid with: a) a variant CRISPR-Cas effector polypeptide of the present disclosure; b) a guide RNA; and c) a donor nucleic acid (e.g., a donor template). In some cases, the contacting step is carried out in a cell in vitro. In some cases, the contacting step is carried out in a cell in vivo. In some cases, the contacting step is carried out in a cell ex vivo.

Because a method that uses a variant CRISPR-Cas effector polypeptide includes binding of the variant CRISPR-Cas effector polypeptide to a particular region in a target nucleic acid (by virtue of being targeted there by an associated guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res.

2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. al, Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a variant CRISPR-Cas effector polypeptide of the present disclosure or with a fusion polypeptide of the present disclosure, etc., encompass all methods for contacting the target nucleic acid. For example, a variant CRISPR-Cas effector polypeptide can be provided to a cell as protein, RNA (encoding the variant CRISPR-Cas effector polypeptide), or DNA (encoding the variant CRISPR-Cas effector polypeptide); while a guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for variant CRISPR-Cas effector polypeptide; in the form of a protein for a fusion polypeptide comprising a variant CRISPR-Cas effector polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a variant CRISPR-Cas effector polypeptide or a fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a variant CRISPR-Cas effector polypeptide of the present disclosure, or with a fusion polypeptide of the present disclosure. In some cases, a method of the present disclosure for modifying a target nucleic acid comprises contacting a target nucleic acid with a variant CRISPR-Cas effector polypeptide and a guide RNA. In some cases, a method of the present disclosure for modifying a target nucleic acid comprises contacting a target nucleic acid with a variant CRISPR-Cas effector polypeptide, a first guide RNA, and a second guide RNA In some cases, a method of the present disclosure for modifying a target nucleic acid comprises contacting a target nucleic acid with a variant CRISPR-Cas effector polypeptide of the present disclosure and a guide RNA and a donor DNA template.

Target Nucleic Acids and Target Cells of Interest

A variant CRISPR-Cas effector polypeptide of the present disclosure, or a fusion polypeptide of the present disclosure, when bound to a guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject variant CRISPR-Cas effector polypeptide (and/or nucleic acid encoding the protein such as DNA and/or RNA), and/or guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota* or *Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A guide RNA (or a nucleic acid comprising a nucleotide sequence encoding same), and/or a variant CRISPR-Cas effector polypeptide of the present disclosure (or a fusion polypeptide of the present disclosure) (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a taret cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition (e.g., including any convenient combination of: a variant CRISPR-Cas effector polypeptide, a guide RNA, a donor polynucleotide, etc.) using known methods, e.g., such as nucleofection.

Donor Polynucleotide (Donor Template)

Guided by a dual or single guide RNA, a variant CRISPR-Cas effector polypeptide of the present disclosure in some cases generates site-specific double strand breaks (DSBs) or single strand breaks (SSBs) (e.g., when the variant CRISPR-Cas effector polypeptide is a nickase variant) within double-stranded DNA (dsDNA) target nucleic acids, which are repaired either by non-homologous end joining (NHEJ) or homology-directed recombination (HDR).

In some cases, contacting a target DNA (with a variant CRISPR-Cas effector polypeptide and a guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, a guide RNA (or DNA encoding same) and a variant CRISPR-Cas effector polypeptide (or a nucleic acid encoding same, such as an RNA or a DNA, e.g., one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease-causing mutation by introducing a correct sequence), and the like. As such, a complex comprising a guide RNA and variant CRISPR-Cas effector polypeptide is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the variant CRISPR-Cas effector polypeptide (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair or a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a guide RNA and/or a variant CRISPR-Cas effector polypeptide (or a fusion polypeptide comprising a variant CRISPR-Cas effector polypeptide) and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a variant CRISPR-Cas effector polypeptide of the present disclosure; a nucleic acid comprising a nucleotide sequence encoding a fusion polypeptide of the present disclosure; etc.), is used as a transgene to generate a transgenic non-human organism that produces a variant CRISPR-Cas effector polypeptide, or a fusion polypeptide, of the present disclosure. The present disclosure provides a transgenic-non-human organism comprising a nucleotide sequence encoding a variant CRISPR-Cas effector polypeptide, or a fusion polypeptide, of the present disclosure.

Transgenic, Non-Human Animals

The present disclosure provides a transgenic non-human animal, which animal comprises a transgene comprising a nucleic acid comprising a nucleotide sequence encoding a variant CRISPR-Cas effector polypeptide of the present disclosure or a fusion polypeptide comprising a variant CRISPR-Cas effector polypeptide of the present disclosure. In some cases, the genome of the transgenic non-human animal comprises a nucleotide sequence encoding a variant CRISPR-Cas effector polypeptide or a fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a variant CRISPR-Cas effector polypeptide or a fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a variant CRISPR-Cas effector polypeptide of the present disclosure; a nucleic acid comprising a nucleotide sequence encoding a fusion polypeptide of the present disclosure; etc.), is used as a transgene to generate a transgenic plant that produces a variant CRISPR-Cas effector polypeptide, or a fusion polypeptide, of the present disclosure. The present disclosure provides a transgenic plant comprising a nucleotide sequence encoding a variant CRISPR-Cas effector polypeptide, or a fusion polypeptide, of the present disclosure. In some cases, the genome of the transgenic plant comprises a subject nucleic acid. In some embodiments, the transgenic plant is homozygous for the genetic modification. In some cases, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a variant CRISPR-Cas effector polypeptide, or a fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545, 817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad.

Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a variant CRISPR-Cas effector polypeptide, or a fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a variant CRISPR-Cas effector polypeptide, or a fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant CRISPR-Cas effector polypeptide comprising an amino acid sequence having at least 50% amino acid sequence identity to the amino acid sequence depicted in FIG. 1A or FIG. 2A, wherein the variant CRISPR-Cas effector polypeptide comprises: i) one or more amino acid substitutions and/or insertions in the helical II domain relative to a reference CRISPR-Cas effector polypeptide comprising the amino acid sequence depicted in FIG. 1B or FIG. 2B; and/or ii) one or more amino acid substitutions and/or insertions in the RuvC domain relative to a reference CRISPR-Cas effector polypeptide comprising the amino acid sequence depicted in FIG. 1B or FIG. 2B, wherein said one or more amino acid substitutions and/or insertions provides for increased binding and/or cleavage of a target nucleic acid compared to the binding and/or cleavage of the target nucleic acid by the reference CRISPR-Cas effector polypeptide.

Aspect 2. The variant CRISPR-Cas effector polypeptide of aspect 1, wherein the variant CRISPR-Cas effector polypeptide exhibits at least 2-fold increased target cleavage of a target nucleic acid compared to the cleavage of the target nucleic acid by the reference CRISPR-Cas effector polypeptide.

Aspect 3. The variant CRISPR-Cas effector polypeptide of aspect 1 or aspect 2, wherein the variant CRISPR-Cas effector polypeptide comprises a substitution of the sequence NSNSTEFKSYKSGKQPFVGAWQA (SEQ ID NO:34) of the reference amino acid sequence of FIG. 1B.

Aspect 4. The variant CRISPR-Cas effector polypeptide of any one of aspects 1-3, wherein the variant CRISPR-Cas effector polypeptide comprises an amino acid sequence having at least 50% amino acid sequence identity to the amino acid sequence depicted in FIG. 1A, and wherein the RuvC domain comprises the amino acid sequence RSQEYKKYQTNKTTGNTDKRAFVETWQS (SEQ ID NO:30), or an amino acid sequence having from 1 to 10 amino acid substitutions compared to

```
                                     (SEQ ID NO: 30)
        RSQEYKKYQTNKTTGNTDKRAFVETWQS.
```

Aspect 5. The variant CRISPR-Cas effector polypeptide of aspect 4, wherein the amino acid sequence RSQEYKKYQTNKTTGNTDKRAFVETWQS (SEQ ID NO:30), or an amino acid sequence having from 1 to 10 amino acid substitutions compared to RSQEYKKYQTNKTTGNTDKRAFVETWQS (SEQ ID NO:30), replaces NSNSTEFKSYKSGKQPFVGAWQA (SEQ ID NO:34) of the amino acid sequence depicted in FIG. 1B.

Aspect 6. The variant CRISPR-Cas effector polypeptide of aspect 1 or aspect 2, wherein the variant CRISPR-Cas effector polypeptide comprises a substitution of the sequence RKKG (SEQ ID NO:38) of the reference sequence depicted in FIG. 2B.

Aspect 7. The variant CRISPR-Cas effector polypeptide of 6, wherein the variant CRISPR-Cas effector polypeptide comprises an amino acid sequence having at least 50% amino acid sequence identity to the amino acid sequence depicted in FIG. 2A, and wherein the helical II domain comprises the amino acid sequence HKKREGSLENP (SEQ ID NO:35) or an amino acid sequence having from 1 to 5 amino acid substitutions compare to HKKREGSLENP (SEQ ID NO:35).

Aspect 8. The variant CRISPR-Cas effector polypeptide of aspect 7, wherein the amino acid sequence HKKREGSLENP (SEQ ID NO:35) or an amino acid sequence having from 1 to 5 amino acid substitutions compare to HKKREGSLENP (SEQ ID NO:35), replaces HKKREGSLENP (SEQ ID NO:35) of the amino acid sequence depicted in FIG. 2B.

Aspect 9. The variant CRISPR-Cas effector polypeptide of any one of aspects 1-5, wherein the variant CRISPR-Cas effector polypeptide is a nickase that can cleave only one strand of a double-stranded target nucleic acid.

Aspect 10. The variant CRISPR-Cas effector polypeptide of any one of aspects 1-5, wherein the variant CRISPR-Cas effector polypeptide is catalytically inactive.

Aspect 11. The variant CRISPR-Cas effector polypeptide of any one of aspects 1-5, wherein the variant CRISPR-Cas effector polypeptide comprises one or more mutations at a position corresponding to those selected from: i) D672, E769, and D935 of the amino acid sequence depicted in FIG. 1A; or ii) D666, E763, and D929 of the amino acid sequence depicted in FIG. 2A.

Aspect 12. A composition comprising: a) a variant CRISPR-Cas effector polypeptide of any one of aspects 1-11, or a nucleic acid comprising a nucleotide sequence encoding the variant CRISPR-Cas effector polypeptide; and b) a guide nucleic acid, or a nucleic acid comprising a nucleotide sequence encoding the guide nucleic acid, wherein the guide nucleic acid comprises: i) an activator region that can bind to and activate the variant CRISPR-Cas effector polypeptide; and ii) a guide sequence that can hybridize with a target region of a target nucleic acid, optionally wherein the guide nucleic acid comprises the nucleotide sequence:

```
     i)
                                     (SEQ ID NO: 10)
     GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAG.
     or ii)
                                     (SEQ ID NO: 12)
     GGCGCUUUUAUCUCAUUACUUUGAGAGCCAUCACCAGCGACU

AUGUCGUAUGGGUAAAGCGCUUAUUUAUCGGAGAAACCGAUA

AAUAAGAAGCAUCAAAG.
```

Aspect 13. The composition of aspect 12, wherein the guide RNA is a single-molecule guide RNA.

Aspect 14. The composition of aspect 12 or aspect 13, wherein the composition comprises a lipid.

Aspect 15. The composition of any one of aspects 12-14, wherein a) and b) are within a liposome.

Aspect 16. The composition of any one of aspects 12-14, wherein a) and b) are within a particle.

Aspect 17. The composition of any one of aspects 12-16, comprising one or more of: a buffer, a nuclease inhibitor, and a protease inhibitor.

Aspect 18. The composition of any one of aspects 12-17, comprising a DNA donor nucleic acid.

Aspect 19. A nucleic acid comprising a nucleotide sequence encoding the variant CRISPR-Cas effector polypeptide of any one of aspects 1-11.

Aspect 20. The nucleic acid of aspect 19, wherein the nucleotide sequence is operably linked to a promoter.

Aspect 21. The nucleic acid of aspect 20, wherein the promoter is functional in a eukaryotic cell.

Aspect 22. The nucleic acid of aspect 20, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 23. The nucleic acid of any one of aspects 20-22, wherein the promoter is one or more of: a constitutive promoter, an inducible promoter, a cell type-specific promoter, and a tissue-specific promoter.

Aspect 24. A recombinant expression vector comprising the nucleic acid of any one of aspects 19-23.

Aspect 25. The recombinant expression vector of aspect 24, wherein the recombinant expression vector is a recombinant adenoassociated viral vector, a recombinant retroviral vector, or a recombinant lentiviral vector.

Aspect 26. A fusion polypeptide comprising: a) a variant CRISPR-Cas effector polypeptide of any one of aspects 1-11; and b) one or more heterologous polypeptides.

Aspect 27. The fusion polypeptide of aspect 26, wherein the variant CRISPR-Cas effector polypeptide is a nickase that can cleave only one strand of a double-stranded target nucleic acid.

Aspect 28. The fusion polypeptide of aspect 26, wherein the variant CRISPR-Cas effector polypeptide is catalytically inactive.

Aspect 29. The fusion polypeptide of aspect 27 or aspect 28, wherein the variant CRISPR-Cas effector polypeptide comprises one or more mutations at a position corresponding to those selected from: i) D672, E769, and D935 of the amino acid sequence depicted in FIG. 1A; or ii) D666, E763, and D929 of the amino acid sequence depicted in FIG. 2A.

Aspect 30. The fusion polypeptide of any one of aspects 26-29, wherein the heterologous polypeptide is fused to the N-terminus and/or the C-terminus of the variant CRISPR-Cas effector polypeptide.

Aspect 31. The fusion polypeptide of any one of aspects 26-30, wherein at least one of the one or more heterologous polypeptides is a nuclear localization signal.

Aspect 32. The fusion polypeptide of any one of aspects 26-31, wherein the one or more heterologous polypeptides is a targeting polypeptide that provides for binding to a cell surface moiety on a target cell or target cell type.

Aspect 33. The fusion polypeptide of any one of aspects 26-31, wherein the one or more heterologous polypeptides exhibits an enzymatic activity that modifies target DNA.

Aspect 34. The fusion polypeptide of aspect 33, wherein the heterologous polypeptide exhibits an enzymatic activity selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 35. The fusion polypeptide of aspect 33, wherein the heterologous polypeptide exhibits an enzymatic activity selected from: nuclease activity, methyltransferase activity, demethylase activity, deamination activity, depurination activity, integrase activity, transposase activity, and recombinase activity Aspect 36. The fusion polypeptide of any one of aspects 26-31, wherein the heterologous polypeptide exhibits an enzymatic activity that modifies a target polypeptide associated with a target nucleic acid.

Aspect 37. The fusion polypeptide of aspect 34, wherein the heterologous polypeptide exhibits histone modification activity.

Aspect 38. The fusion polypeptide of aspect 36 or aspect 37, wherein the heterologous polypeptide exhibits an enzymatic activity selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

Aspect 39. The fusion polypeptide of any one of aspects 26-30, wherein at least one of the one or more heterologous polypeptides is an endosomal escape polypeptide.

Aspect 40. The fusion polypeptide of any one of aspects 26-30, wherein the one or more heterologous polypeptides is a protein that increases or decreases transcription.

Aspect 41. The fusion polypeptide of aspect 40, wherein the one or more heterologous polypeptides is a transcriptional repressor polypeptide.

Aspect 42. The fusion polypeptide of aspect 40, wherein the one or more heterologous polypeptides is a transcriptional activation polypeptide.

Aspect 43. The fusion polypeptide of any one of aspects 26-30, wherein the one or more heterologous polypeptides is a protein binding polypeptide.

Aspect 44. A nucleic acid comprising a nucleotide sequence encoding the fusion polypeptide of any one of aspects 26-43.

Aspect 45. A recombinant expression vector comprising the nucleic acid of aspect 44.

Aspect 46. A cell comprising one or more of:
a) a variant CRISPR-Cas effector polypeptide of any one of aspects 1-11;
b) a nucleic acid comprising a nucleotide sequence encoding a variant CRISPR-Cas effector polypeptide of any one of aspects 1-11;
c) a fusion polypeptide of any one of aspects 26-43;
d) a nucleic acid comprising a nucleotide sequence encoding a fusion polypeptide of any one of aspects 23-43;
e) a guide nucleic acid, wherein the guide nucleic acid comprises: i) an activator region that can bind to and activate the variant CRISPR-Cas effector polypeptide of any one of aspects 1-11; and ii) a guide sequence that can hybridize with a target region of a target nucleic acid; and
f) a nucleic acid encoding a guide nucleic acid, wherein the guide nucleic acid comprises: i) an activator region that can bind to and activate the variant CRISPR-Cas effector polypeptide of any one of aspects 1-11; and ii) a guide sequence that can hybridize with a target region of a target nucleic acid.

Aspect 47. The cell of aspect 46, wherein the cell is a eukaryotic cell.

Aspect 48. The cell of aspect 47, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

Aspect 49. The cell of any one of aspects 46-48, wherein the cell is in vitro.

Aspect 50. The cell of any one of aspects 46-48, wherein the cell is in vivo.

Aspect 51. A method of modifying a target nucleic acid, the method comprising contacting the target nucleic acid with: a) a variant CRISPR-Cas effector polypeptide of any one of aspects 1-11; and b) a guide nucleic acid, wherein the guide nucleic acid comprises: i) an activator region that can bind to and activate the variant CRISPR-Cas effector polypeptide; and ii) a guide sequence that can hybridize with a target region of a target nucleic acid.

Aspect 52. The method of aspect 51, wherein said modification is cleavage of the target nucleic acid.

Aspect 53. The method of aspect 51 or aspect 52, wherein the target nucleic acid is selected from: double stranded DNA, single stranded DNA, RNA, genomic DNA, and extrachromosomal DNA.

Aspect 54. The method of any one of aspects 51-53, wherein said contacting takes place in vitro outside of a cell.

Aspect 55. The method of any one of aspects 51-53, wherein said contacting takes place inside of a cell in vitro.

Aspect 56. The method of any one of aspects 51-53, wherein said contacting takes place inside of a cell in vivo.

Aspect 57. The method of aspect 52 or aspect 53, wherein the cell is a eukaryotic cell.

Aspect 58. The method of aspect 57, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 59. The method of aspect 55 or aspect 56, wherein the cell is a prokaryotic cell.

Aspect 60. The method of any one of aspects 51-59, wherein said contacting results in genome editing.

Aspect 61. The method of any one of aspects 55-60, wherein said contacting comprises introducing into the cell: a) the variant CRISPR-Cas effector polypeptide, or a nucleic acid comprising a nucleotide sequence encoding the variant CRISPR-Cas effector polypeptide; and b) the guide RNA, or a nucleic acid comprising a nucleotide sequence encoding the guide RNA.

Aspect 62. The method of aspect 61, further comprising introducing a DNA donor nucleic acid into the cell.

Aspect 63. A method of modulating transcription from a target DNA, modifying a target nucleic acid, or modifying a protein associated with a target nucleic acid, the method comprising contacting the target nucleic acid with: a) a fusion polypeptide of any one of aspects 26-43; and b) a guide RNA comprising: i) an activator region that can bind to and activate the variant CRISPR-Cas effector polypeptide; and ii) a guide sequence that can hybridize with a target region of the target nucleic acid.

Aspect 64. A composition comprising:
a) a variant CRISPR-Cas effector polypeptide of any one of aspects 1-11, or a nucleic acid comprising a nucleotide sequence encoding the variant CRISPR-Cas effector polypeptide; and
b) a guide nucleic acid, or a nucleic acid comprising a nucleotide sequence encoding the guide nucleic acid, wherein the guide nucleic acid comprises: i) an activator region that can bind to and activate the variant CRISPR-Cas effector polypeptide; and ii) a guide sequence that can hybridize with a target region of a target nucleic acid, Aspect 65. The composition of aspect 64, wherein the activator region comprises one or more modifications as set out in Table 1, compared to the following the nucleotide sequence:

```
                                    (SEQ ID NO: 10)
GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAG.
```

Aspect 66, The composition of aspect 64 or aspect 65, wherein the guide nucleic acid comprises the nucleotide sequence:

```
                                    (SEQ ID NO: 90)
GGCGCUUUUAUCUCAUUACUUUGAGAGCCAUCACCAGCGA

CUAUGUCGUAUGGGUAAAGCGCUUAUUUAUCGGAGAAACC

GAUAAAUAAGAAGCAUCAAAG(Nx),
``` wherein N is any nucleotide and x is an integer from 15 to 30 or from 19 to 30.

Aspect 67. The composition of any one of aspects 64-66, wherein the guide RNA is a single-molecule guide RNA.

Aspect 68. The composition of any one of aspects 64-67, wherein the composition comprises a lipid.

Aspect 69. The composition of any one of aspects 64-68, wherein a) and b) are within a liposome.

Aspect 70. The composition of any one of aspects 64-67, wherein a) and b) are within a particle.

Aspect 71. The composition of any one of aspects 64-70, comprising one or more of: a buffer, a nuclease inhibitor, and a protease inhibitor.

Aspect 72. The composition of any one of aspects 64-71, comprising a DNA donor nucleic acid.

Aspect 73. A guide nucleic acid, or a nucleic acid comprising a nucleotide sequence encoding the guide nucleic acid, wherein the guide nucleic acid comprises: i) an activator region that can bind to and activate a variant CRISPR-Cas effector polypeptide according to any one of aspects 1-11; and ii) a guide sequence that can hybridize with a target region of a target nucleic acid, wherein the activator region comprises one or more modifications as set out in Table 1, compared to the following the nucleotide sequence:

```
                                    (SEQ ID NO: 10)
GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAG.
```

Aspect 74. The guide nucleic acid of aspect 73, wherein the guide nucleic acid comprises the nucleotide sequence:

```
                                    (SEQ ID NO: 90)
GGCGCUUUUAUCUCAUUACUUUGAGAGCCAUCACCAGCGA

CUAUGUCGUAUGGGUAAAGCGCUUAUUUAUCGGAGAAACC

GAUAAAUAAGAAGCAUCAAAG(Nx),
``` wherein N is any nucleotide and x is an integer from 15 to 30, and wherein (Nx) comprises a nucleotide sequence that can hybridize with a target region of a target nucleic acid.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Generation and Characterization of CRISPR-Cas Effector Polypeptides and Guide RNAs Materials and Methods CasX Protein Expression and Purification Wildtype and engineered CasX proteins were expressed using Rosetta *Escherichia coli* cells. Competent cells (100 l) were mixed and incubated with the plasmid (100 ng) for 30 minutes on ice. Tubes containing the plasmid and cells were incubated at 42° C. for 35 seconds to induce transformation. After 5 minutes of resting on ice, Luria broth (950 l) was added to the solution and incubated at 37° C. for 1 hour to recover. The cells were transferred to a flask containing Luria broth and 50 mg/ml ampicillin (1:1000) and incubated at 37° C. overnight. 2.7% of the grown culture was added to the main culture containing Terrific broth and 50 mg/ml ampicillin (1:1000). The main culture was incubated at 37° C. until it reached an optical density (OD) of 0.5-0.6. The culture was cooled on ice and protein expression was induced by addition of isopropyl β-d-1-thiogalactopyranoside (IPTG) to a final concentration of 1 mM while incubated at 16° C. and shaking overnight. Cells were harvested by centrifugation (4000 rpm, 4° C.) and resuspended in Lysis buffer (600 mM sodium chloride, 20 mM HEPES, pH 7.5, 10% glycerol, 50 mM imidazole, 1 mM tris(2-carboxyethyl)phosphine (TCEP)). phenylmethylsulfonyl fluoride (PMSF) (0.5 mM) and 4 tablets of Roche protease inhibitor cocktail were added per 100 ml of mixture. The cell suspension was lysed by sonication and pelleted by ultracentrifugation at 35,000 g for 30 minutes.

The soluble lysate was mixed with equilibrated Nickel-Nitrilotriacetic acid (Ni-NTA) agarose beads at 4° C. for 2 hours. Using the gravity-flow column, the Ni-NTA agarose beads were washed using lysis buffer until the eluted protein concentration ceased. To elute the construct, the Ni-NTA beads were incubated overnight at 4° C. in lysis buffer and tobacco etch virus (TEV) protease (final concentration of 1 mg protease/20 mg purified protein). Using the gravity-flow column, the protein of interest was eluted. The flow-through was collected, concentrated using 30 molecular weight cutoff (MWCO)-concentrator (Amicon Ultra, Merck). The solution containing the protein was mixed with lower salt buffer (200 mM sodium chloride, 20 mM HEPES, PH 7.5, 10% glycerol, 1 mM TCEP) and applied to a Heparin column. The protein was eluted using a potassium chloride gradient up to 1 M. The peak containing the active protein was eluted with higher salt concentration which was pooled. The combined fractions were concentrated using 30K MWCO-concentrator (Amicon Ultra, Merck) and applied to a Superdex 200 10/300 column using SEC buffer: 400 mM potassium chloride, 20 mM HEPES, pH 7.5, 10% glycerol, 1 mM TCEP. The protein was concentrated and flash-frozen to use for assays. Engineered and wildtype CasX proteins were expressed and purified using the same method.

sgRNA Preparation

All sgRNA were synthesized using in vitro transcription (IVT). First, to synthesize the DNA template, primers (Integrated DNA Technologies (IDT)) were polymerase chain reaction (PCR) amplified using Q5 polymerase (New England Biolabs). The DNA template (50 μg) along with 10×IVT buffer, 5×NTPs, T7 polymerase, RNase inhibitor and diethylpyrocarbonate (DEPC) were incubated on 37° C. heat blocks for 3-4 hours. The solutions were then treated with DNase by addition of 10× DNase buffer and RNase-free DNase and incubated on 37° C. heat blocks for 30 minutes. The tubes were spun down the and the soluble part was moved to a new tube. After adding 2× formamide, the samples were gel purified by running the products on a 15% urea-PAGE gel. Bands containing the sgRNA were cut out and incubated in water and 1/30 NaOAc at 4° C. overnight. Samples were filtered using 0.22 m Corning filters into 50 ml tubes. Samples were concentrated using 3 kDa MWCO concentrators (Amicon). The sgRNA was then precipitated by adding 100% ethanol. After the samples were spun down to pellet the sgRNA, they were washed with 70% ethanol, resuspended in DEPC H$_2$O, and stored at −80° C. to be used for cleavage assays.

In Vitro Cleavage Assays

For double-stranded DNA (dsDNA) cleavage assays, DNA substrates were 5' labelled using T4 PNK (NEB) by adding γ-$^{32}$P-ATP. CasX proteins were diluted to 2 μM using 1× reaction buffer (400 mM KCl, 5% glycerol, 20 mM Tris-HCl, pH 7.8, 5 mM magnesium chloride, 1 mM dithiothreitol (DTT)). sgRNAs were diluted to 3 M with 1× reaction buffer. The sgRNA and protein samples were then mixed and incubated at room temperature for 1 hour to reconstitute the RNP complex. The final concentration of the CasX-sgRNA was 300 nM and the concentration of radiolabeled probe was 2 nM. Reactions were initiated by mixing CasX-sgRNA and radiolabeled DNA on a 37° C. heat block. Sample aliquots were taken at the following time points: 0, 2, 5, 10, 15, 20, 30, 60, 120, 240, 360 minutes. The aliquots were mixed with formamide loading buffer (formamide, 10 mM EDTA, bromophenol blue, xylene cyanol) and quencher (50 μg/ml heparin, 25 mM EDTA) and were incubated in 95° C. heat blocks for 5 minutes to stop the cleavage reaction. Samples were run on 12% urea-PAGE gels before being dried and visualized using a phosphoimager (Amersham Typhoon, GE Healthcare).

For plasmid cleavage assays, the target DNA sequence was cloned into pUC19 plasmid. For each 100 μl cleavage reaction, 400 nM CasX-sgRNA RNP and 20 nM pUC19 plasmid DNA were incubated in 1× reaction buffer (500 mM NaCl, 5% glycerol, 20 mM Tris-HCl, pH 7.8, 10 mM magnesium chloride, 1 mM DTT) at 37° C. Sample aliquots were taken at the following time points: 0, 10, 20, 30, 60, 120, 240, 360 minutes. The aliquots were mixed with 6×DNA loading buffer (30 mM EDTA, 36% (v/v) glycerol, 0.05% (w/v) Xylene Cyanol FF, 0.05% (w/v) Bromophenol) and then digest with 100 μg/ml Proteinase K for 1 h at 37° C. to quench the reaction. A 1% agarose gel was used to analyze cleavage products.

For the trans-cleavage activity assay, a random 50-nucleotide oligonucleotide substrate was labeled using T4 PNK (NEB) by adding γ-$^{32}$P-ATP. Each reaction included 300 nM CasX protein, 360 nM sgRNA, 450 nM activator, and 2 nM substrate. The trans-cleavage assay was performed and analyzed similarly to the dsDNA cleavage assay, described above.

Plasmid Construction

For human genome editing experiments, DpbCasX plasmid pBLO62.4 (addgene plasmid #123123), PlmCasX plasmid pBLO62.5 (addgene plasmid #123124) were utilized or modified, which were codon-optimized for expression in human cells and contain a SV40 nuclear localization sequence on either terminus (Liu et al., 2019). Short oligonucleotides (IDT) containing the sgRNA spacer sequence were annealed and phosphorylated prior to Golden Gate assembly (BbsI restriction sites) for insertion just downstream of the CasX guide sequence within the plasmids. CasX protein mutants were constructed by PCR amplification of the CasX sequence in two pieces, with primers containing the deletion or insertion sequences. pBLO62.4 and pBLO62.5 were digested with AgeI and BamHI (NEB) and gel electrophoresis was utilized to separate the digested components. The plasmid backbone was excised from the gel and purified with the QIAquick PCR Purification Kit (Qiagen) or the NucleoSpin Gel and PCR Cleanup Kit (Takara) according to the manufacturer's protocol. In-Fusion cloning (Takara) with the Cloning Enhancer was used to insert the PCR amplified mutant CasX sequences within the digested backbone according to the manufacturer's protocol. Plasmids encoding mutant CasX sgRNA scaffolds were constructed similarly to CasX mutant protein plasmids. Plasmids encoding engineered or wildtype CasX proteins were digested using KpnI and PciI (NEB). Gel electrophoresis was used to isolate the digested plasmid backbone. Digested backbone was excised from the gel and purified with the PCR QIAquick PCR Purification Kit (Qiagen) or the NucleoSpin Gel and PCR Cleanup Kit (Takara) according to the manufacturer's protocol. Mutant sgRNA scaffolds were ordered as gBlocks from IDT and cloned into the digested backbone using In-Fusion cloning (Takara). Cloned plasmids were sequence verified by capillary Sanger sequencing (UC Berkeley DNA Sequencing Facility). For the endogenous genome editing experiments, an mNeon fluorescent protein was genetically encoded between the CasX gene and puromycin resistance gene, each separated by self-cleaving 2A peptide sequences. Plasmids were cleaved with BamHI and In-Fusion cloning was utilized as described above to insert a gBlock (IDT) encoding mNeon.

Genome Editing in Fluorescent Reporter Human Cells

Green fluorescent protein (GFP) HEK293 cells were cultured in Dulbecco's Modified Eagle Medium (DMEM) (Gibco) supplemented with 10% fetal bovine serum (FBS) (VWR) and 1% penicillin-streptomycin (Gibco). The MycoAlert *Mycoplasma* Detection Kit (Lonza) was used to routinely test cells for *Mycoplasma*. GFP HEK293 reporter cells were seeded into 96-well plates and transfected 12-18 hours later at 60-70% confluency according to the manufacturer's protocol with lipofectamine 3000 (Life Technologies) and 200 ng of plasmid DNA encoding the wildtype or engineered CasX plasmids. 24 hours post-transfection, GFP HEK293 reporter cells that were successfully transfected were selected by adding 1.5 μg/mL puromycin to the cell culture media for 48 hours. Cell culture media was replaced with media containing fresh 1.5 μg/mL puromycin for an additional 24 hours before replacing with cell culture media without puromycin. Cells were passaged regularly to maintain sub-confluent conditions and then analyzed in 96-well round bottom plates on an Attune NxT Flow Cytometer with an autosampler. Cells were analyzed on the flow cytometer after 5, 7, and 10 days to track the disruption of the GFP gene in cells.

Endogenous Gene Editing

HEK293T cells were cultured in Dulbecco's Modified Eagle Medium (DMEM) (Gibco) supplemented with 10% fetal bovine serum (FBS) (VWR) and 1% penicillin-streptomycin (Gibco). The MycoAlert *Mycoplasma* Detection Kit (Lonza) was used to routinely test cells for *Mycoplasma*. HEK293T cells were plated in 96 well plates and allowed to grow overnight to ~60-70% confluency before transfecting with 200 ng of plasmid and lipofectamine 3000 according to the manufacturer's protocol. 24 hours post-transfection, HEK293T cells that were successfully transfected were selected for by adding 1.5 μg/mL puromycin to the cell culture media for 48 hours. Cell culture media was replaced with media containing fresh 1.5 μg/mL puromycin for an additional 24 hours before replacing with cell culture media without puromycin. Media was removed from the cells and 50 PL of QuickExtract (Lucigen) was added to each well and incubated at room temperature for 10-15 minutes. Cell extracts were then thermocycled at 65° C. for 20 minutes followed by 95° C. for 20 minutes. Amplicons containing the targeted site were amplified via PCR with Q5 polymerase (NEB) and primers containing Illumina adaptor sequences. Amplicons were cleaned with magnetic solid phase reversible immobilization (SPRI) beads (UC Berkeley Sequencing Core) and were run on an Illumina iSeq by the Center for Translational Genomics (Innovative Genomics Institute, UC Berkeley). Over 10,000 reads per sample were routinely achieved. iSeq paired-end reads were analyzed using CRISPResso2 (crispresso.pinellolab.partners.org), using a quantification window of −3 bp, a quantification window size of 30 bp (to account for large deletions), and a plot window size of 30 bp.

Cryo-Electron Microscopy (Cryo-EM) Sample Preparation and Data Collection

The PlmCasX-sgRNA complex was assembled by incubating protein with a 1.25-fold excess of sgRNA for 30 min at room temperature. The ternary complexes were assembled by incubating PlmCasX-sgRNA with a 1.5-fold excess of annealed dsDNA target for 30 min at room temperature. After the complexes were assembled, they were purified by size-exclusion chromatography using a Superdex200 10/300 column. PlmCasX complexes at 10 μM concentration in a buffer containing 20 mM HEPES, pH 7.5, 300 mM KCl, 1 mM DTT, and 0.25% glycerol were aliquoted and stored in LN2 for further usage.

For EM sample preparation of PlmCasX-sgRNAv1-dsDNA, the complex (final concentration 1 μM) was mixed with BS3 cross-linker (final concertation 1 mM) and incubated on ice for 1 hour. 3.7 μL droplets of the sample were placed onto Quantifoil grids (1.2/1.3 m) with freshly coated graphene-oxide film (https://www.biorxiv.org/content/10.1101/2021.03.08.434344v1). After a 1-minute incubation, the grids were blotted for 3 seconds with a blot force of 4 and immediately plunged into liquid ethane using a FEI Vitrobot MarkIV maintained at 8° C. and 100% humidity. Data was acquired using a Thermo Fisher Titan Krios transmission electron microscope operated at 300 keV with an energy filter (GIF quantum 1967), and images were taken at a nominal magnification of ×135,000 (0.9 Å pixel size) with defocus ranging from −0.7 to −2.1 m. Micrographs were recorded using SerialEM on a Gatan K3 Summit direct electron detector operated in super-resolution mode (Mastronarde, 2003). A 5 s exposure fractionated into 50, 100 ms frames with a dose of 10 e-$\text{Å}^{-2}\text{s}_{-1}$ was collected For EM sample preparation of PlmCasX-sgRNAv2-dsDNA, complex (non-crosslinked) at a concentration of 5 μM was used. Immediately after glow-discharging the grid for 14 seconds using a Solaris plasma cleaner, 3.6 μL droplets of the sample were placed onto C-flat grids (2/2 μm). The grids were blotted for 4 seconds with a blot force of 8 and rapidly plunged into liquid ethane using a FEI Vitrobot MarkIV maintained at 8° C. and 100% humidity. Data was acquired by following the same protocol as PlmCasX-sgRNAv1-dsDNA complex but using 3 exposures per hole.

Single Particle Cryo-EM Analysis 46 frames (the first 2 and last 2 frames were skipped) of each image stack in super-resolution mode were aligned, decimated, summed and dose-weighted using Motioncor2 (Zheng et al. (2017) *Nature Methods* 14:331. They were then imported into CryoSparc (Punjani et al. (2009) *Methods* 49:174-180) for patched CTF estimation and particle picking using of 2D class-averages of DpbCasX from a previous study as templates. Particle extraction, ab-initio reconstitution, and 3D classification were performed without 2D classification. Good models from 3D classification were further refined using homogenous refinement. In cases when the post-processing in CryoSparc over-sharpened the map, half-maps generated by CryoSparc were imported into Relion (Kimanius et al., 2016) for post-processing.

Atomic Model Building and Refinement

For PlmCasX-gRNAv1-DNA, an initial model of PlmCasX was first constructed using homology modeling in the Swiss-model sever with the DpbCasX structure (PDB: 6NY2) as reference. The gRNAv1-DNA part was adopted from DpbCasX structure (PDB:6NY2) with manual revision in Coot. The two parts were fitted into the density map of the State I of PlmCasX-gRNAv1-DNA (2.9 Å resolution) and then manually modified in Coot to better fit the density. The entire model was subjected to PHENIX real space refinement (global minimization and ADP refinement) with secondary structure, Ramachandran, rotamer, and nucleic-acid restraints (Liebschner et al. (2019) *Acta Crystallographica Section D: Structural Biology* 75:861-877. The final model was validated using Molprobity (Chen et al. (2010) *Acta Crystallographica Section D: Biological Crystallography* 66:12-21). The atomic model of PlmCasX-gRNAv1-DNA State II were obtained by running flexible fitting on the State I atomic model against the State II cryo-EM map (3.4 Å resolution) with secondary structure restrains in MDFF (Trabuco et al. (2009) *Methods* 49:174-180. The output model was manually rebuilt in Coot (Casanal et al. (2020) *Protein Science* 29:1069-1078 and PHENIX real space refinement was used to improve backbone geometry. The State III atomic model was directly adopted from State I by deleting the Helical-domain, followed by PHENIX real space refinement against the State III cryo-EM map (3.2 Å resolution).

For PlmCasX-gRNAv2-DNA model building, the PlmCasX-gRNAv1-DNA models in State I and State II were used as the starting models. Then, the sgRNA sequence was modified and the structures were manually rebuilt in Coot. PHENIX real space refinements against PlmCasX-gRNAv2-DNA EM maps were used to improve the models. The final models were validated using Molprobity.

Plasmids and oligonucleotides used in this study are summarized in the Table provided in FIG. 19.

Results

Rational design of both CasX and sgRNA yielded two new version of CasX CRISPR-Cas effector polypeptides with improved DNA cleavage activity in vitro.

The amino acid sequence of DpbCasXv2 is shown in FIG. 1A. The amino acid sequence of DpbCasXv1 is shown in FIG. 1B. The amino acid sequence of PlmCasXv2 is shown in FIG. 2A. The amino acid sequence of PlmCasXv1 is shown in FIG. 2B.

The nucleotide sequence of gRNA v1 is as follows:

```
                                    (SEQ ID NO: 91)
GGCGCGUUUAUUCCAUUACUUUGGAGCCAGUCCCAGCGACUA

UGUCGUAUGGACGAAGCGCUUAUUUAUCGGAGAGAAACCGAU

AAGUAAAACGCAUCAAAGNNNNNNNNNNNNNNNNNNNNNNNNN,
where N is any nucleotide
(e.g., any ribonucleotide).
```

The nucleotide sequence of RNA v2 is as follows:

```
                                    (SEQ ID NO: 92)
GGCGCUUUUAUCUCAUUACUUUGAGAGCCAUCACCAGCGA

CUAUGUCGUAUGGGUAAAGCGCUUAUUUAUCGGAGAAACC

GAUAAAUAAGAAGCAUCAAAGNNNNNNNNNNNNNNNNNNNNN

N,
where N is any nucleotide
(e.g., any ribonucleotide).
```

Engineered CasX proteins and sgRNAs were first tested in vitro using $^{32}P$ labeled DNA targets. The DpbCasXv2 together with gRNAv2 cleaved 50% of the DNA target within 1 minute. In comparison, cleavage of the same DNA target with DpbCasXv1 together with gRNAv1 takes up to 13.5 minutes. PlmCasXv2 together with gRNAv2 cleaved 50% of the DNA target within 8 minutes, while PlmCasXv1 together with gRNAv1 cleaved only 10% of the DNA target even after 6 hours. The data are shown in FIG. 3. The data show that both DpbCasXv2 and PlmCasXv2, when complexed with gRNAv2, cleaved target nucleic acid more efficiently than DpbCasXv1 and PlmCasXv1 when complexed with gRNAv1.

FIG. 3 depicts in vitro DNA cleavage activity of DpvCasXv2, DpvCasXv2, PlmCasXv1, and PlmCasXv2, complexed with gRNAv1 or gRNAv2.

Engineered CasX proteins and sgRNAs were further tested in vivo using an eGFP HEK293 cell reporter assay. Ten target sequences were chosen tiled across the eGFP gene and were encoded within the sgRNAv1 or sgRNAv2 along with wildtype CasX (DpbCasXv1 or PlmCasXv1) or engineered CasXv2 (DpbCasXv2 or PlmCasXv2) in a single plasmid. The data are shown in FIG. 4. Use of sgRNAv2 resulted in enhanced editing compared to sgRNAv1 for all ten targets with either PlmCasX construct (PlmCasXv1 or PlmCasXv2), and in eight out of the ten targets for either DpbCasX construct (DpbCasXv1 or DpbCasXv2). On average, among all of the sgRNAs, PlmCasX (PlmCasXv1 or PlmCasXv2) with sgRNAv2 showed a 2.14-fold improvement in eGFP knockout compared to sgRNAv1. PlmCasXv2 showed a similar 2.38-fold improvement with sgRNAv2 compared to sgRNAv1. sgRNAv2 led to a 1.50-fold improvement in editing efficiency compared to sgRNA when complexed with DpbCasX. The same comparison with DpbCasXv2 showed a further 1.77-fold improvement.

FIG. 4 depicts in vivo eGFP editing efficiency of DpbCasXv1, DpbCasXv2, PlmCasXv1, and PlmCasXv2, when complexed with sgRNAv1 or sgRNAv2.

Figure 6C:
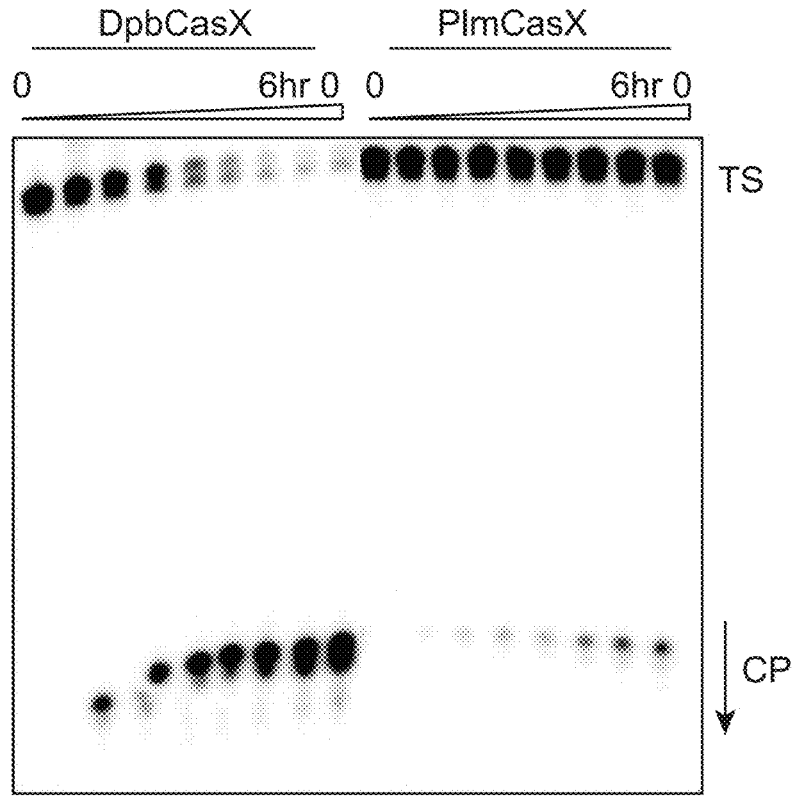
Figure 6D:
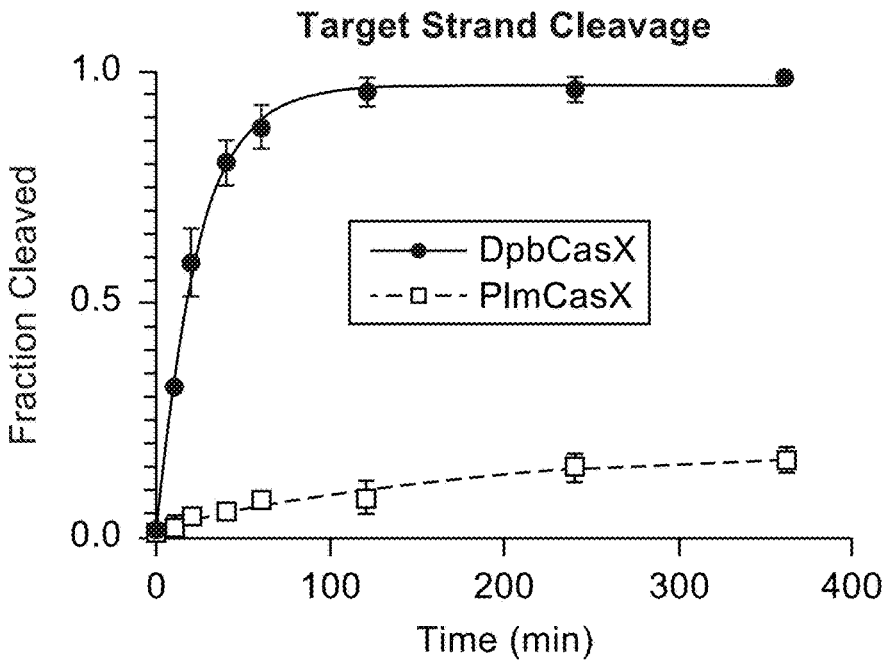
Figures 6E, 6F:
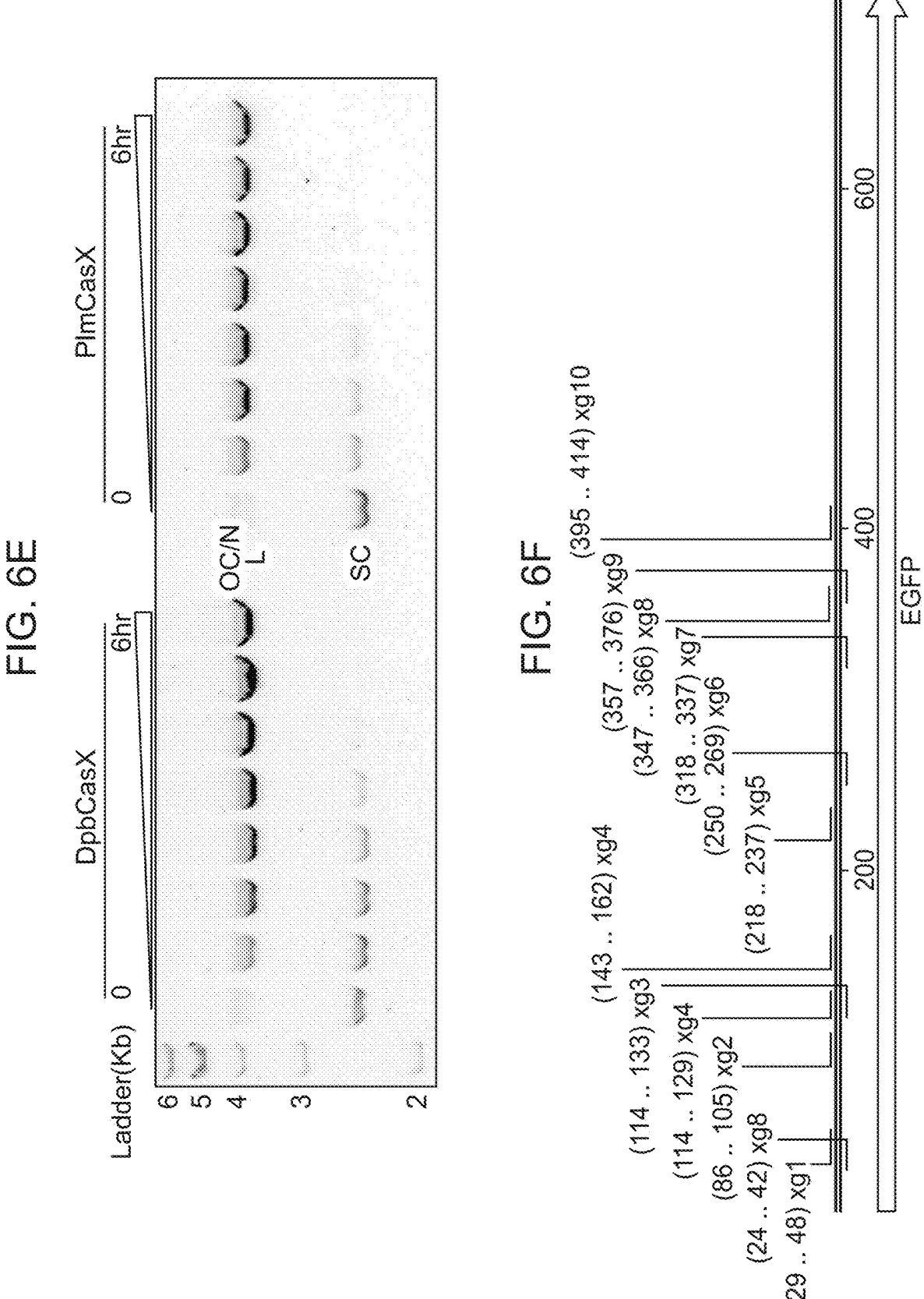

PlmCasX Shows Minimal dsDNA Cleavage Biochemically but Works Robustly in Mammalian Cells An improved protocol (see Materials and Methods) was used to purify wildtype (wt)PlmCasX with similar purity and yield as wtDpbCasX (FIG. 6A and FIG. 6B). PlmCasX eluted 0.3 mL earlier via size exclusion chromatography (FIG. 6A), which suggests apo-PlmCasX (112.66 kDa) is less compact than apo-DpbCasX (112.93 kDa), and may lead to the increased difficulty during expression and purification. In vitro, PlmCasX cleaved just 10% of both the NTS and TS DNA (FIG. 7A, FIG. 6C, and FIG. 6D) compared to DpbCasX with the original sgRNA scaffold—sgRNAv1. However, DpbCasX and PlmCasX showed similar linearization activity on pUC19 (FIG. 6E), which may be due to the supercoiling-induced denaturation bubbles within plasmids. In HEK293 cells stably expressing GFP, plasmid transfection of PlmCasX showed adequate, in some cases even higher, genome editing activity using different GFP-targeting sgRNAv1s compared to DpbCasX (FIG. 7D; FIG. 6F), which suggests PlmCasX is prominent for genome editing by plasmid transfection. The inverted in vitro and in vivo behavior provided further motivation to understand the molecular difference between DpbCasX and PlmCasX. The structural details of PlmCasX were explored; this information was used to improve its biochemical and genome editing capacity through molecular engineering.

FIG. 6A-6F. Targeted DNA cleavage by DpbCasX and PlmCasX. (A) Purification of DpbCasX and PlmCasX by size exclusion chromatography. The representative S200 size exclusion traces by UV280 absorbance are aligned and shown. DpbCasX eluted at 12.2 mL, and PlmCasX eluted at 11.9 mL. (B) sodium dodecyl sulfate-polyacrylamide gel electrophoresis (SDS-PAGE) for DpbCasX and PlmCasX samples taken from the elution peak after size exclusion chromatography. (C) In vitro dsDNA cleavage activity comparison between DpbCasX and PlmCasX revealed by denaturing PAGE. TS denotes the target strand DNA which was $^{32}$P labeled on the 5' end. CP indicates the cleavage product. (D) The TS band density from the cleavage fraction was analyzed based on the input TS band density at the reaction time of 0 min (n=3, mean±s.d.). The k values for DpbCasX and PlmCasX cleavage of the TS were 0.04351 and 0.005978, respectively. (E) In vitro plasmid cleavage activity comparison between DpbCasX and PlmCasX revealed by agarose gel. OC/N indicates the open-circle or nicked plasmids. L indicates the linearized plasmids. SC indicates the super-coiled plasmids. Quantifications are not provided due to the limited sensitivity and linearization range of DNA staining (n=3). (F) The distribution of 10 sgRNAv1 spacers across the genomically integrated GFP gene.

FIG. 7A-7D. Comparison of DNA cleavage efficacy between DpbCasX and PlmCasX. (A) In vitro dsDNA cleavage activity comparison between DpbCasX and PlmCasX revealed by denaturing PAGE. NTS denotes the non-target strand which is $^{32}$P labeled on the 5' end. CP indicates the cleavage product. (B) The cleavage fraction analysis based on the NTS band density compared to the input NTS band density at the reaction time of 0 min. The plot represents six repeated assays (three biological repeats with two technical repeats for each). The k value (calculated by one-phase association model in Prism7) was 0.05031 and 0.004137 for DpbCasX and PlmCasX, respectively. (C) The workflow for human cell genome editing experiments, which were based on disruption of stable GFP expression in HEK293 cells. (D) Human cell genome editing by DpbCasX and PlmCasX with sgRNAv1, measured 10 days after plasmid transfection. The GFP disruption efficacies for 10 GFP guides both for DpbCasX and PlmCasX are shown (n=3 (except PlmCasX sgRNAv1 9, 10, NT; n=2), mean±s.d.). NT indicates the non-targeting sgRNAv1.

The Mobility of the Helical-II Domain Impairs DNA Cutting by PlmCasX

Figure 8A:
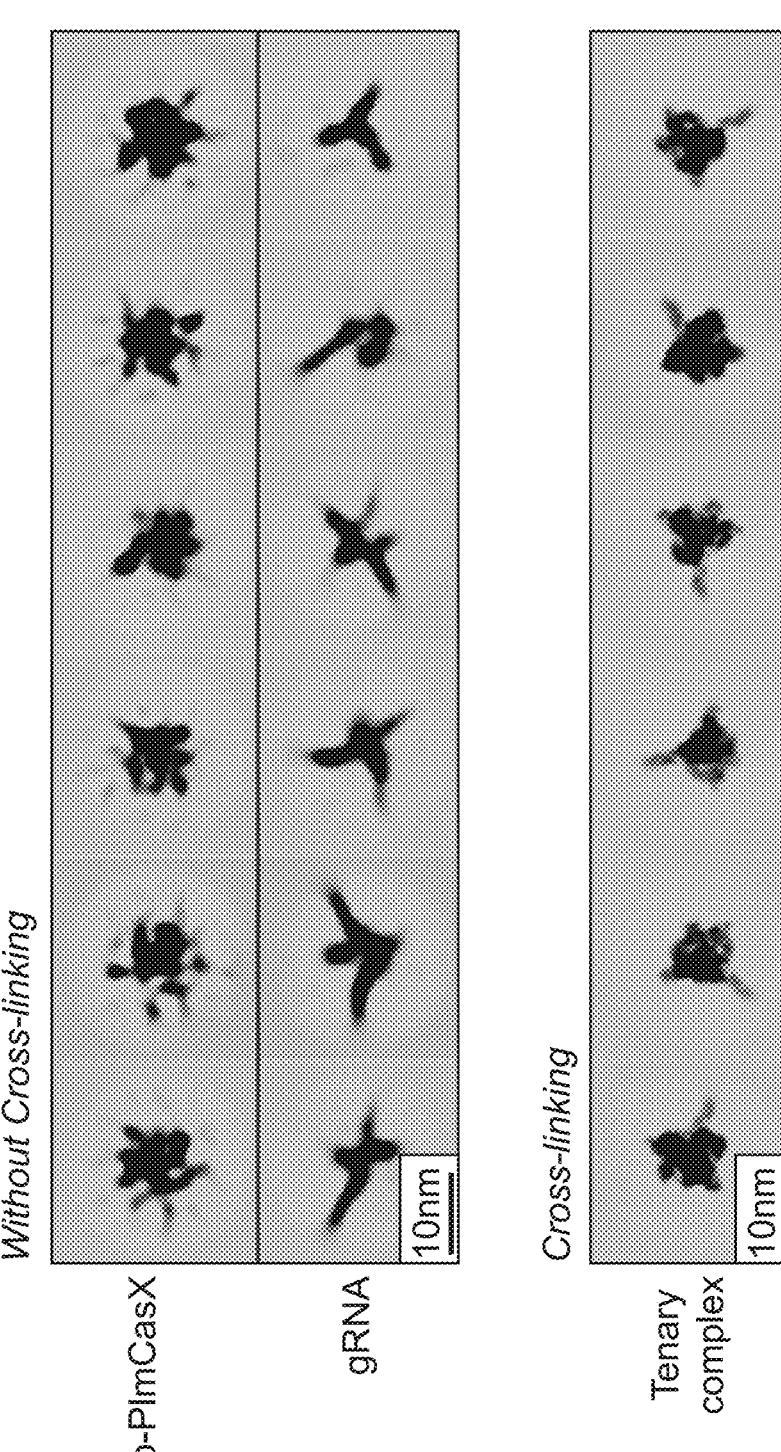
FIG. 8A-8F depict single particle cryo-EM analysis of PlmCasX-sgRNAv1-dsDNA complex.
Figure 8B:
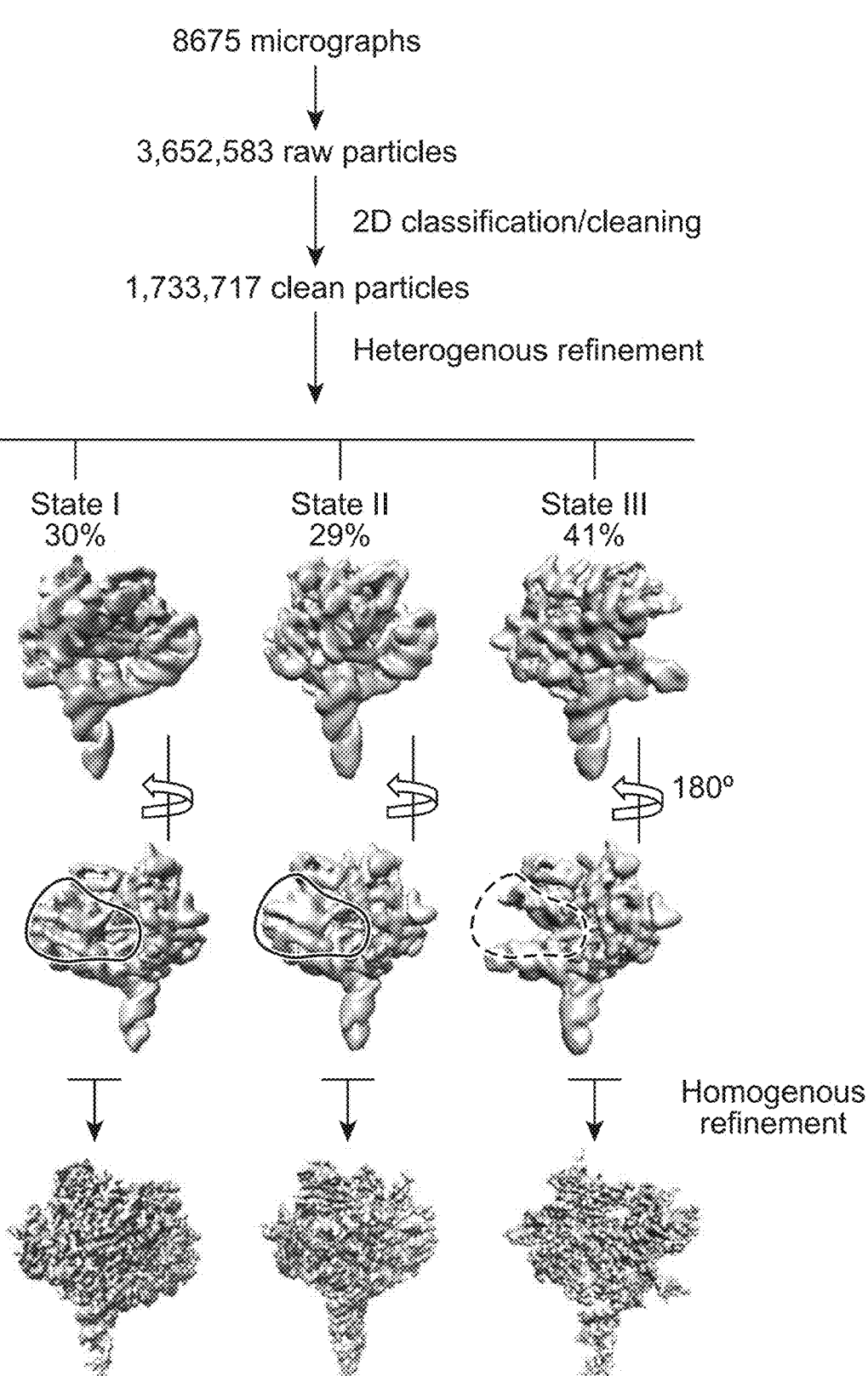
Figure 8C:
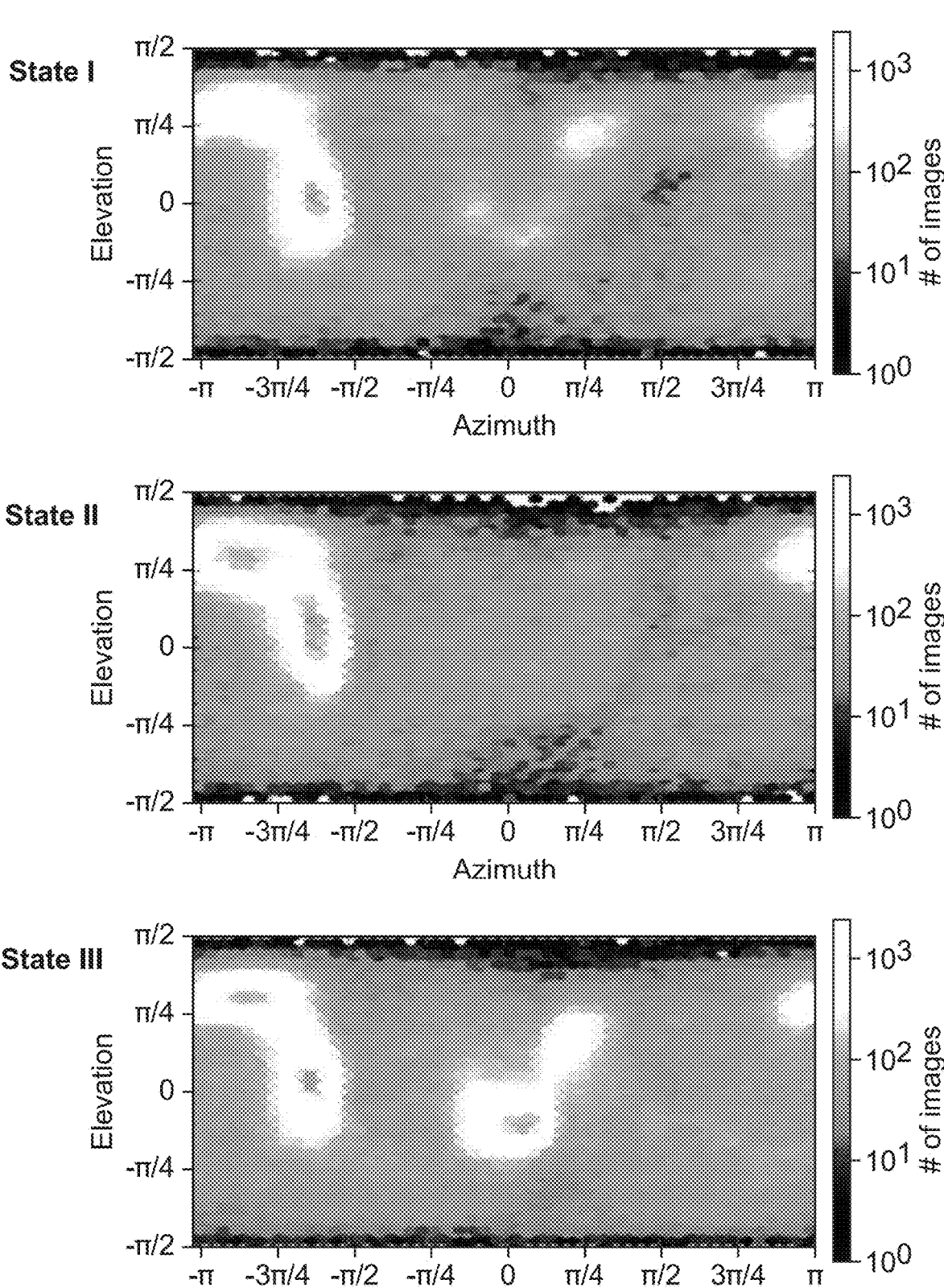
Figure 8D:
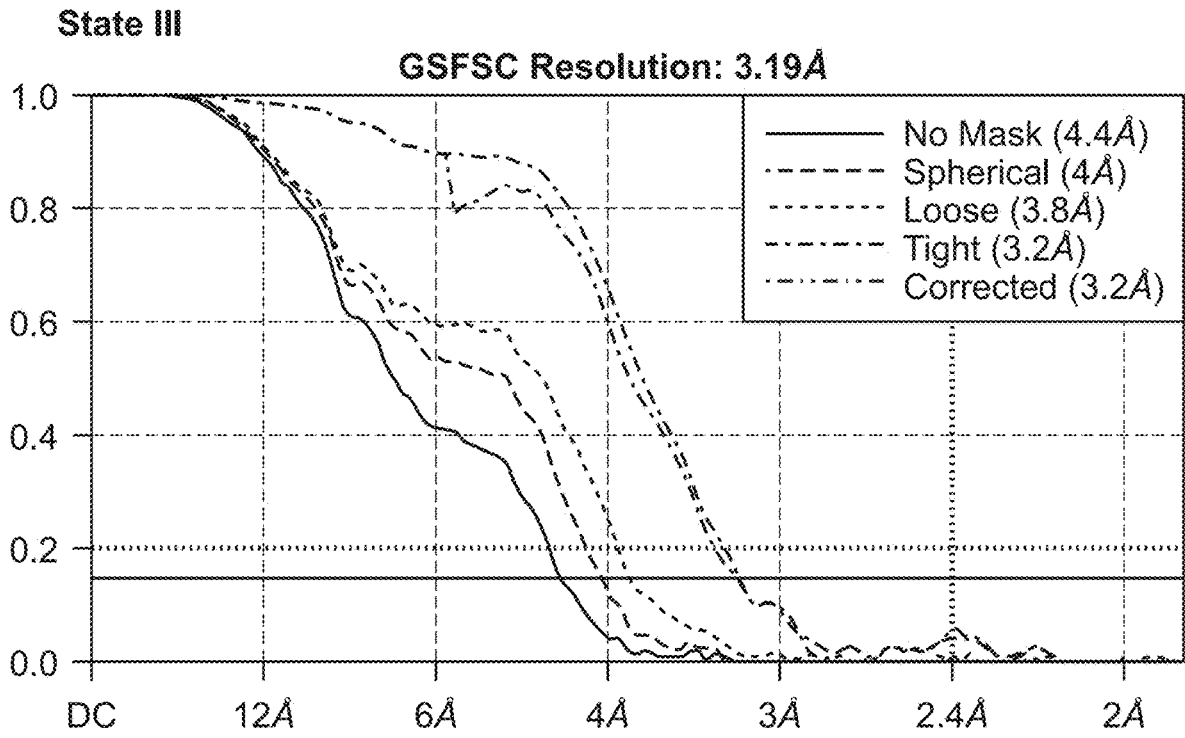
Figure 8E:
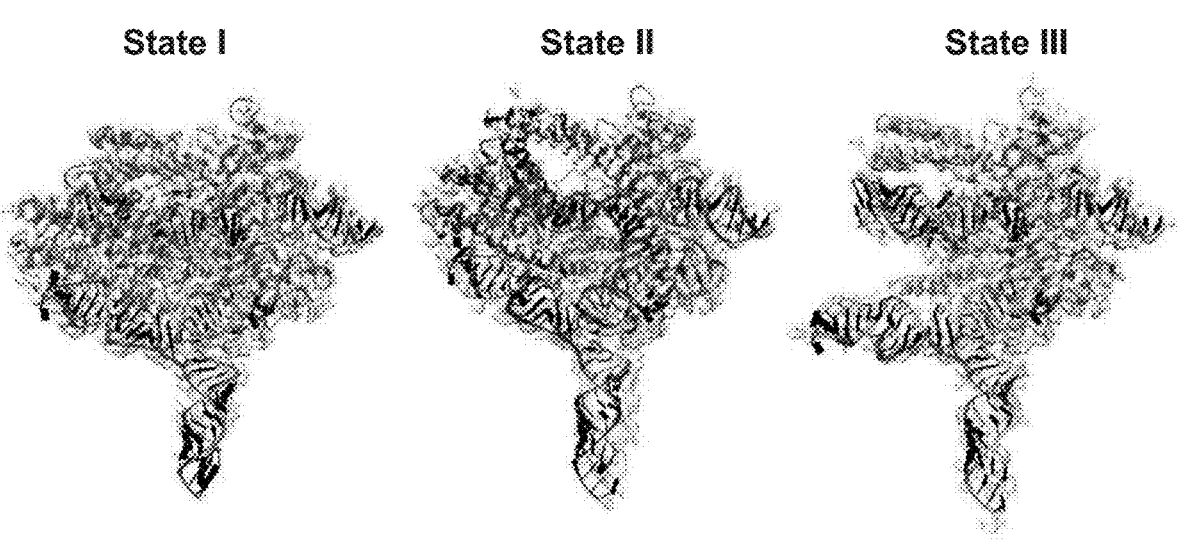
Figure 8F:
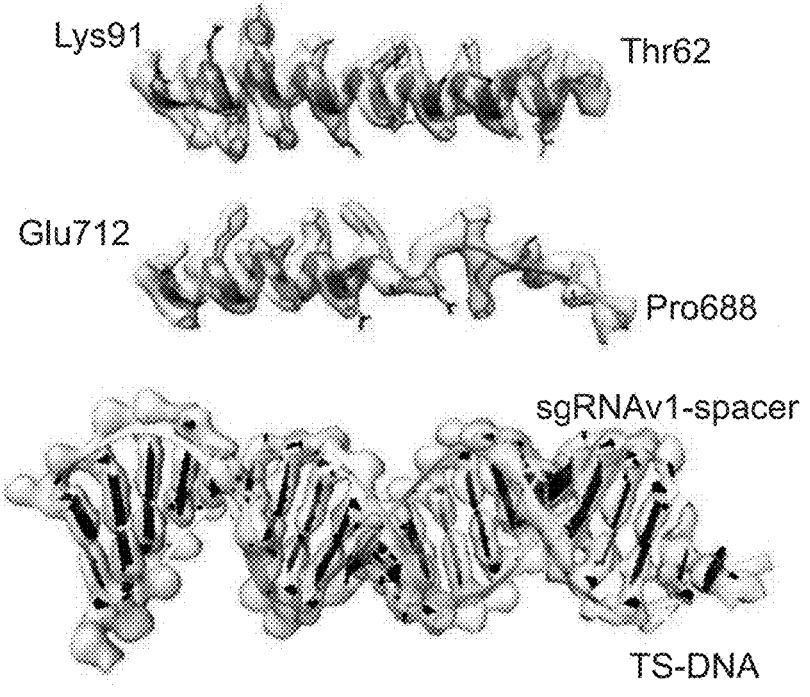
Figure 9A:
Figure 9B:
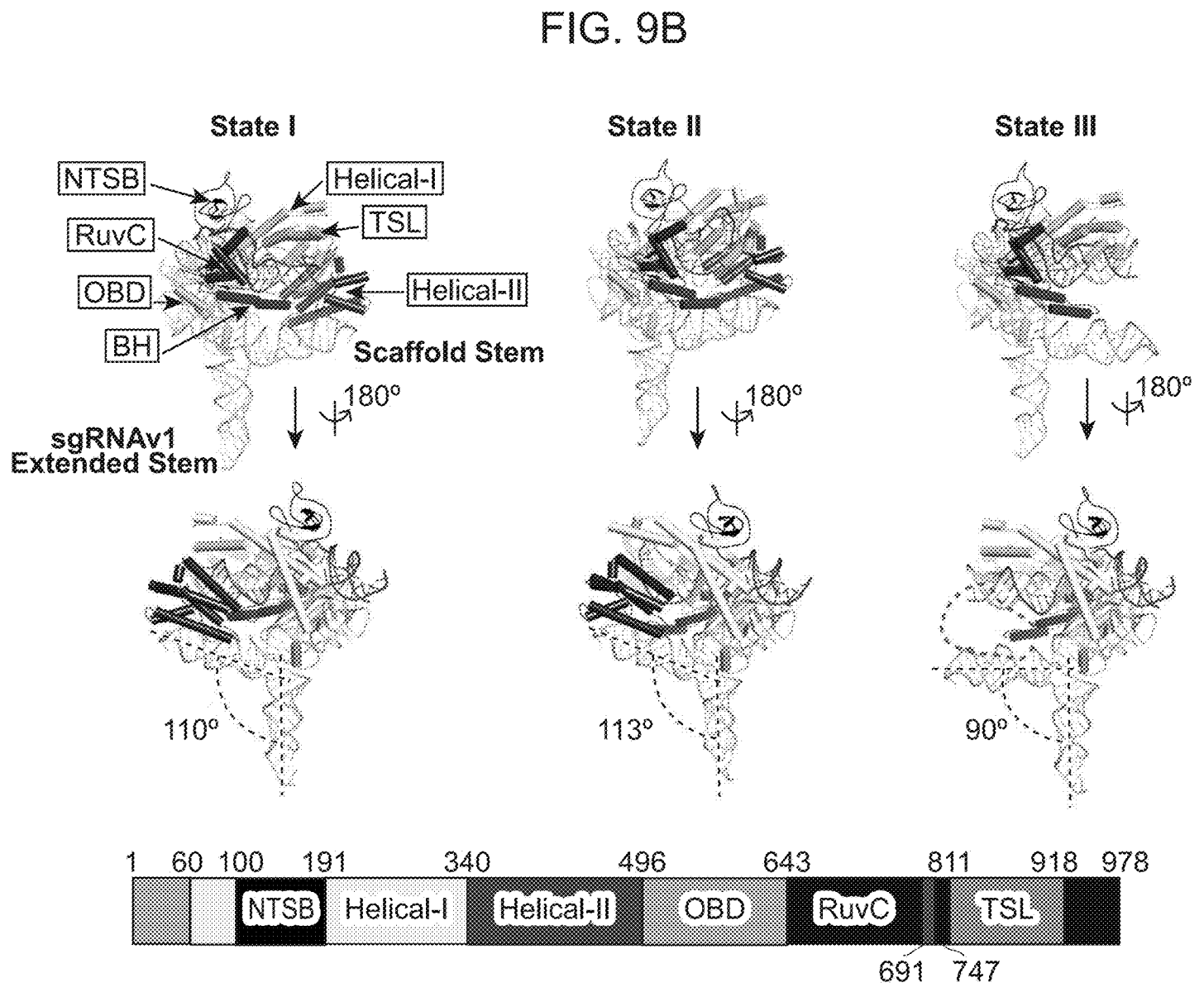

A ternary complex containing deactivated PlmCasX (dPlmCasX), sgRNAv1 (122 nucleotides (nt)) and a complementary DNA substrate (40 base pairs (bp)) was reconstituted; however, it was found that the majority of ternary complex disassembled during cryo-EM grid preparation (FIG. 8A). Crosslinking the complex using BS3 significantly improved the holo-complex stability for single particle cryo-EM analysis (FIG. 8B). 3D classification and refinement identified three conformational populations of the cross-linked complex that were resolved at resolutions of 2.9 Å, 3.4 Å and 3.2 Å (State I, State II and State III, respectively) (FIG. 9A; FIG. 8B-8F). The cryo-EM density maps for States I and II both accounted for the entire complex with all six CasX protein domains (FIG. 9B). They correspond to a NTS DNA cleavage state and a TS DNA cleavage state, respectively (FIG. 9A). These two conformations are similar to those previously described for the DpbCasX ternary complex (Liu et al., 2019).

Figure 7A:
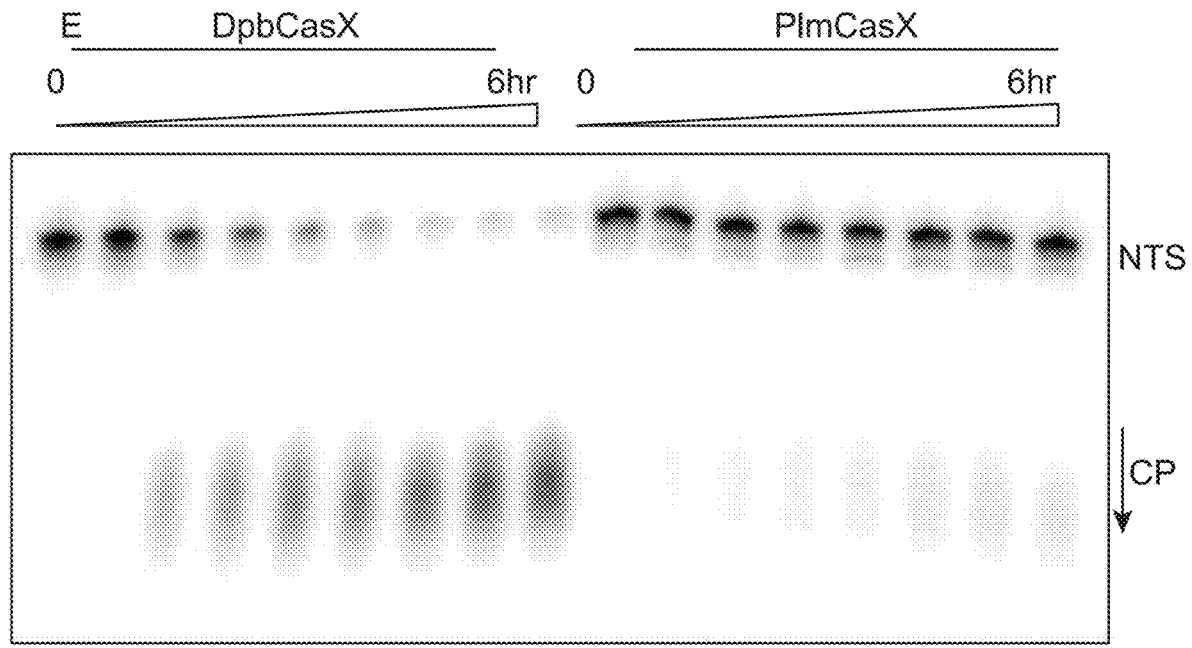
FIG. 7A-7D depict comparison of DNA cleavage efficacy between DpbCasX and PlmCasX.
Figure 7B:
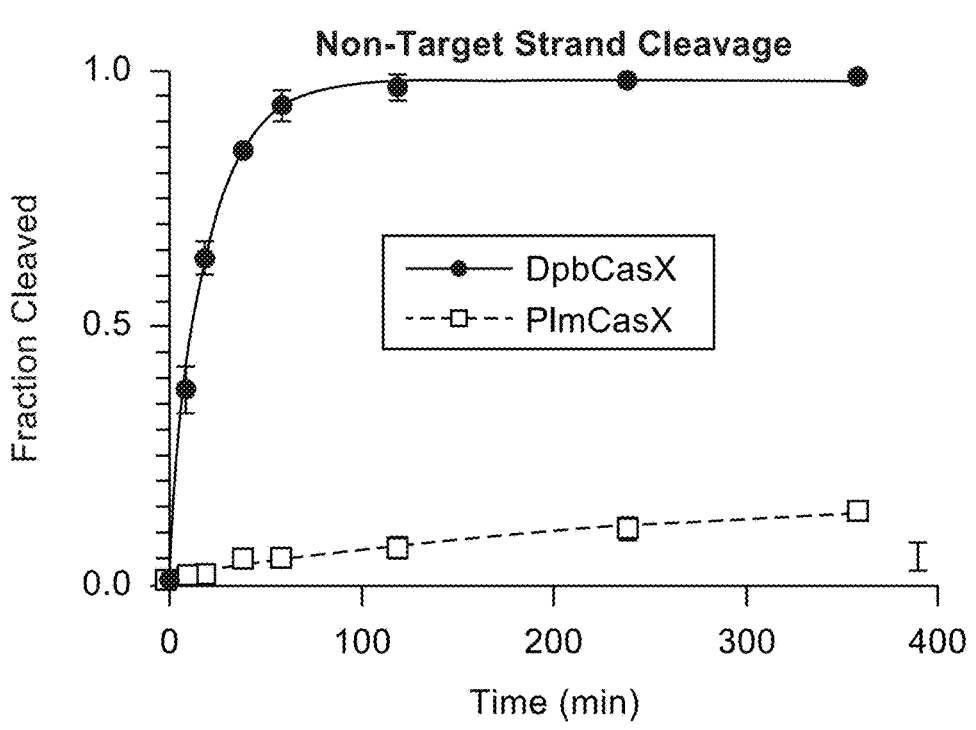
Figures 7C, 7D:
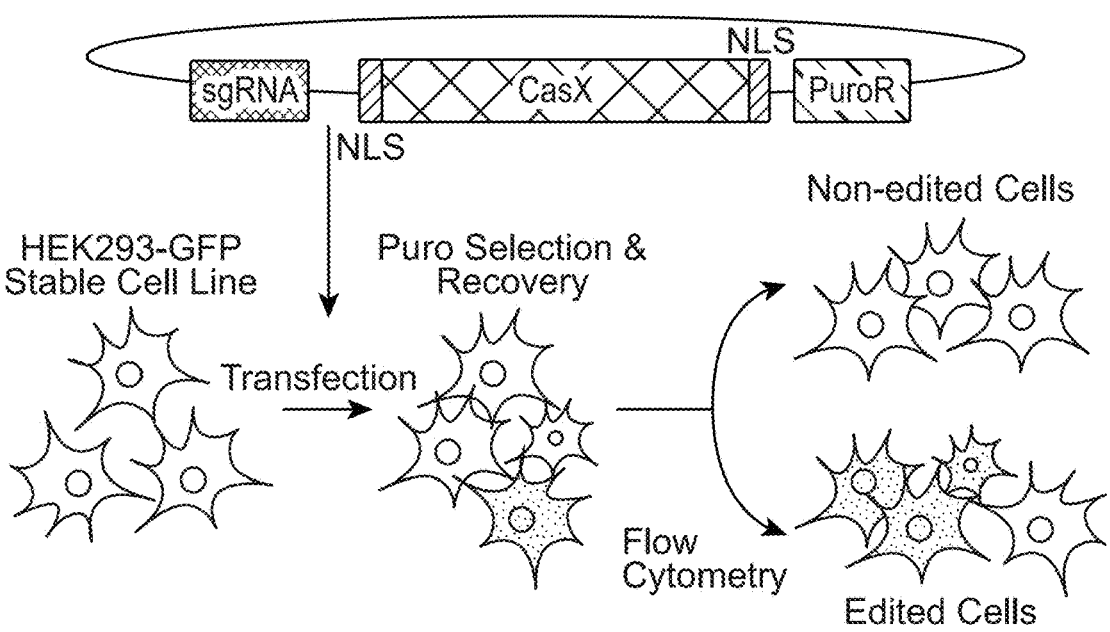
Figure 10A:
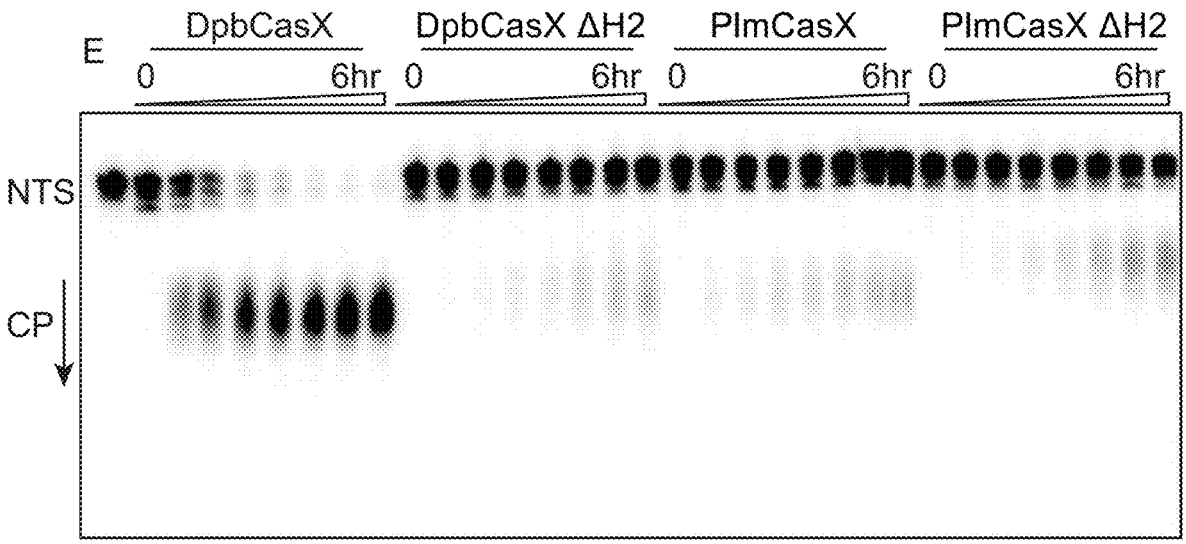
FIG. 10A-10F depict the effect of the Helical-II domain in DpbCasX and PlmCasX on dsDNA cleavage.
Figure 10B:
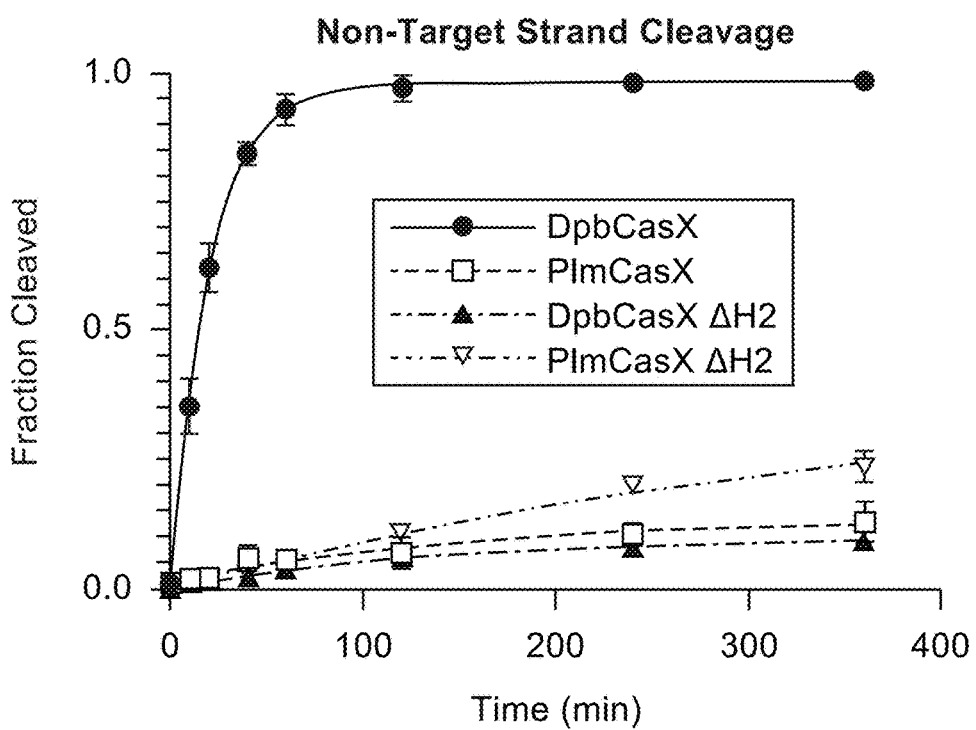
Figure 10C:
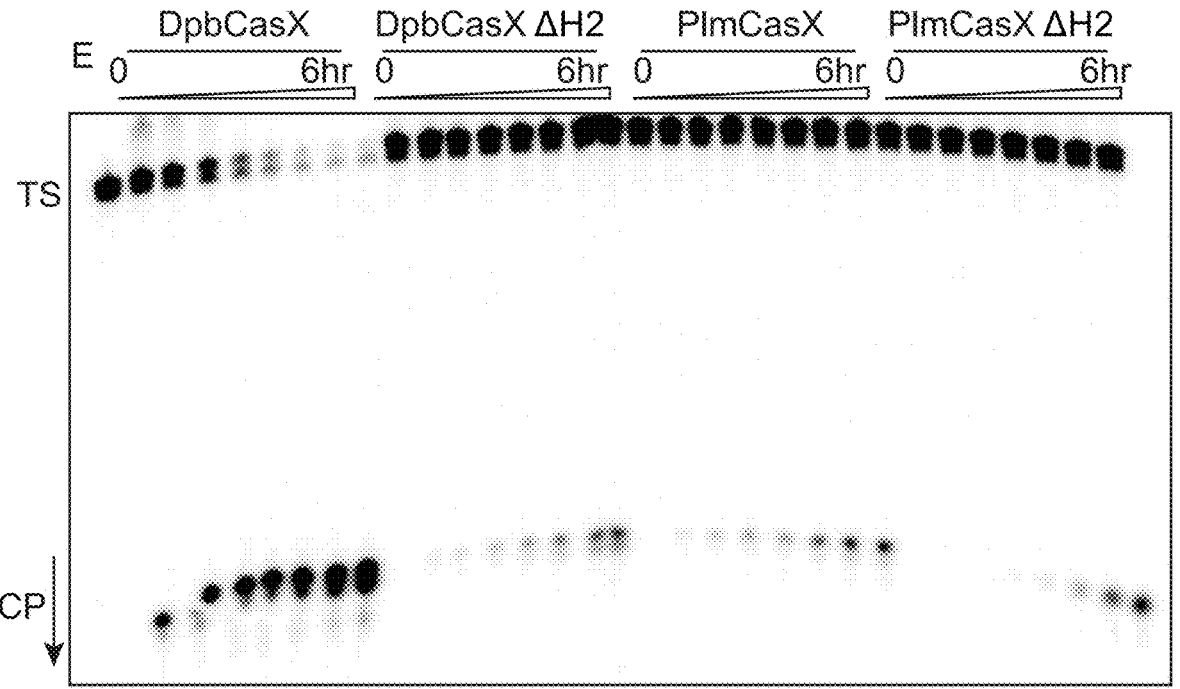
Figure 10D:
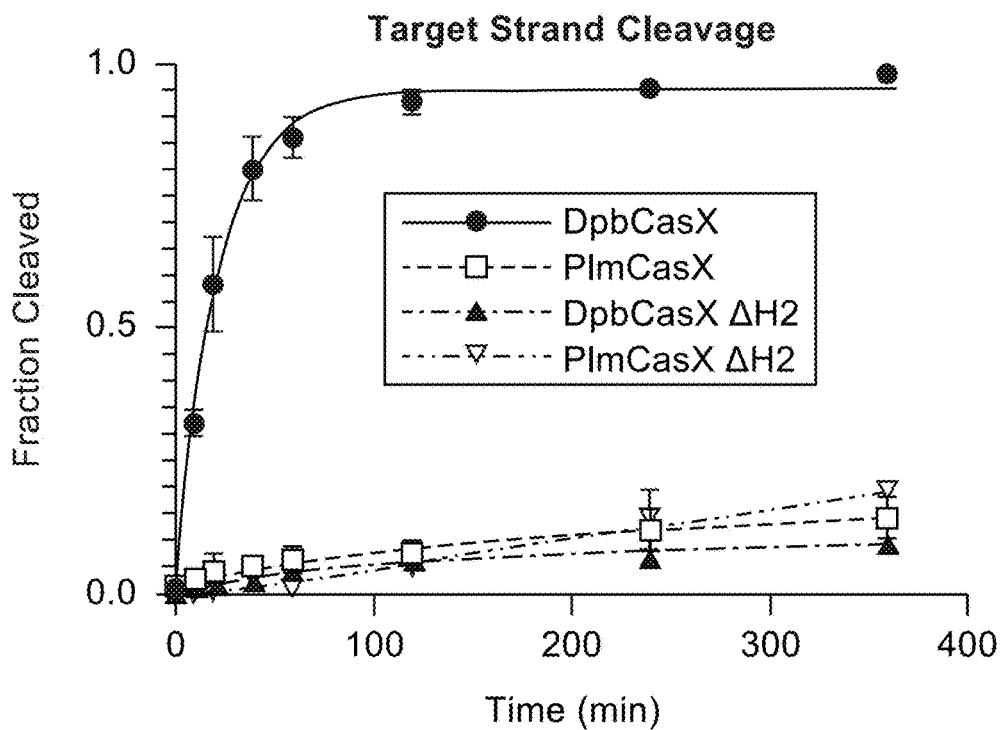
Figure 10E:
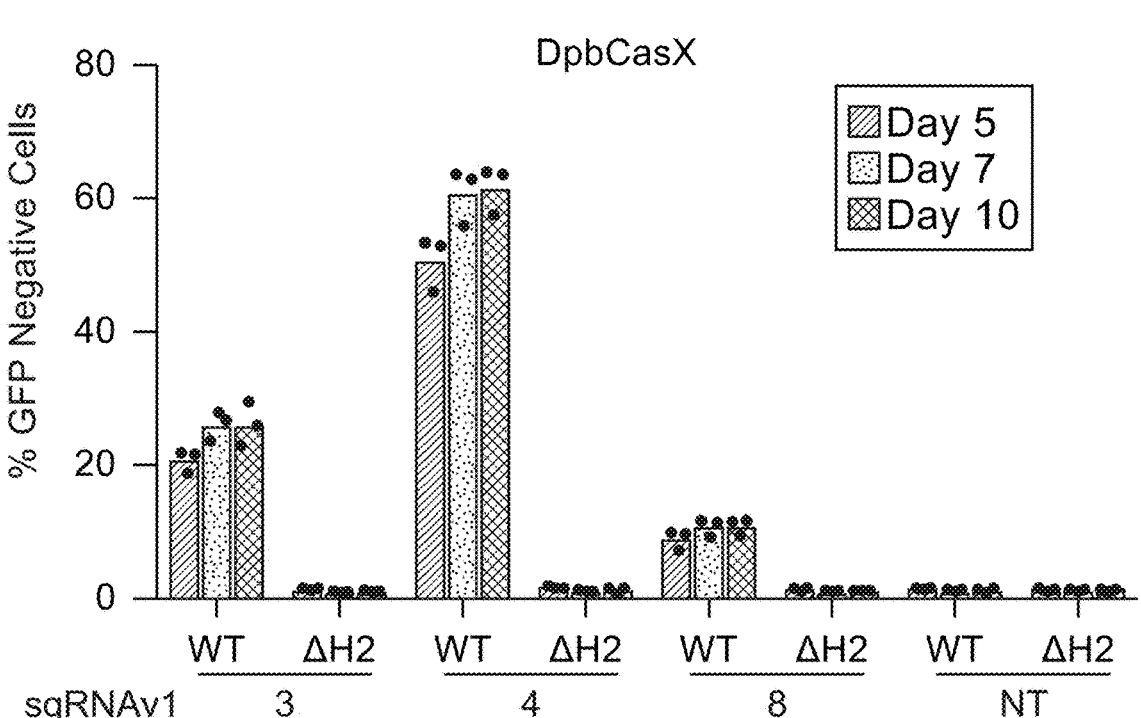
Figure 10F:
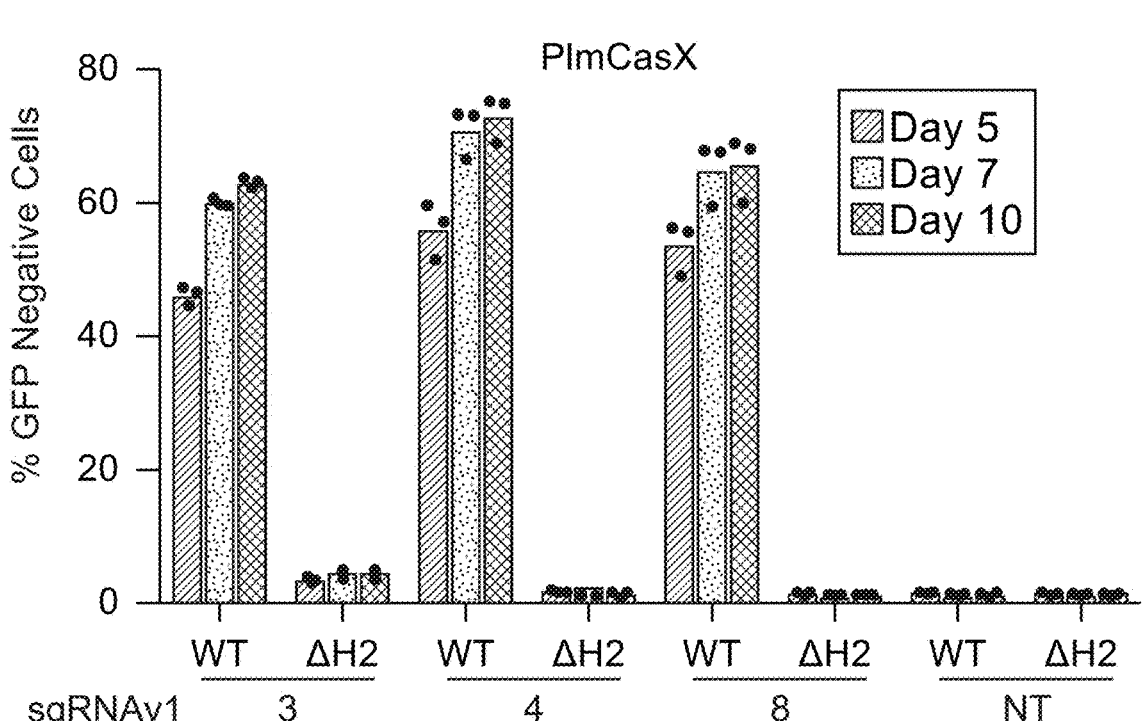

In State III of the PlmCasX ternary complex, the NTS DNA appears loaded into the RuvC domain as in State I, but the density for the Helical-II (H2) domain is missing, most likely due to high flexibility (FIG. 9A; FIG. 8E). By losing the interaction with the H2 domain, the sgRNA scaffold stem in State III is fully exposed and bent about 200 and 23° downward relative to States I and II, respectively (FIG. 9B). Notably, State III accounted for 41% of the entire population of PlmCasX ternary complexes (FIG. 9A; FIG. 8B). For many type V CRISPR nucleases, a stable H2 domain (also termed the REC2 domain) in the ternary complex is structurally important to maintain the active DNA R-loop conformation and assist with DNA cleavage (Liu et al., 2019; Yamano et al., 2016; Yang et al., 2016). It was hypothesized that the presence of State III, with its highly mobile H2 domain, could explain the reduced DNA editing capability of PlmCasX in vitro (FIG. 7A and FIG. 7B). To test this hypothesis, the H2 domain in DpbCasX (DpbCasX ΔH2) was truncated, which resulted in decreased DNA cleavage activity down to a level similar to wtPlmCasX (FIG. 10A-10D). On the other hand, truncation of the H2 domain in PlmCasX (PlmCasX ΔH2) had little to no effect on DNA cleavage as compared to wtPlmCasX (FIG. 10A-10D). These results suggest that the high mobility of the H2 domain in wtPlmCasX largely decreases its in vitro cleavage capability to a minimal level as H2 truncation constructs. It was tested whether PlmCasX ΔH2 and DpbCasX ΔH2 are still capable of genome editing in human cells. Truncation of the H2 domain in both CasXs led to insignificant GFP disruption in HEK293 cells, which demonstrated necessity of the H2 domain for effective genome editing in cells (FIG. 10E and FIG. 10F).

FIG. 8A-8F. Single particle cryo-EM analysis of PlmCasX-sgRNAv1-dsDNA complex. (A) Representative 2D class averages of native and cross-linked (BS3 cross-linking) complexes. (B) The workflow for single particle cryo-EM analysis in CryoSparc. The particles in State I, State II and State III account for 30%, 29% and 41%, respectively, of all the particles used for 3D refinement. The mobile regions across the three states are outlined. (C) Euler angle distribution of the refined particles belonging to the three states. (D) Fourier shell correlation (FSC) curve calculated using two independent half maps. The final resolutions for B-factor corrected maps were 2.9 angstroms (State I), 3.4 angstroms (State II) and 3.2 angstroms (State III). Panels C and D were directly taken from the standard output of CryoSparc. (E) Overall fitting between atomic model and EM map within the three states of PlmCasX-sgRNAv1-dsDNA complex. The atomic models are shown by ribbon cartoon and EM maps are shown by transparent surface. (F) Details of the fitting between atomic model and EM map of State I. The amino acid sidechains are shown.

FIG. 9A-9B. Overall structures of the PlmCasX-sgRNAv1-dsDNA complex. (A) The different structural states of the PlmCasX ternary complex with the sgRNAv1 scaffold revealed by single particle cryo-EM. The top views of refined EM maps for States I, II and III are shown in the top panel. The three maps are shown at the sigma value from 6 to 9. The cartoon model for each map is presented in the bottom panel for better elucidation of substrate DNA loading and cleavage. Referring to the published DpbCasX maps (Liu et al., 2019), the RuvC domain is colored in green, Helical-II in orange and other parts of the protein in blue. The sgRNAv1 and DNA are colored in light gray. The invisible Helical-II (H2) domain in State III is represented with a dashed line. The particle proportions for all functional states within the PlmCasX complex (determined in this study) and DpbCasX complex (Liu et al., 2019) are presented with percentages. (B) The atomic models of the PlmCasX-sgRNAv1-dsDNA complex in three states shown in a front and back view. The domain architecture of the PlmCasX amino acid sequence is shown in the bottom panel. The PlmCasX protein contains NTSB (red), Helical-I (yellow), Helical-II (orange), OBD (aquamarine), RuvC (green) and TSL (pink) domains, and a bridge helix (blue). The sgRNAv1 is in light gray and the dsDNA is in dark gray. The angle between the sgRNAv1 scaffold stem and extended stem (defined by RNA helix rotation axis, black dashed line) was calculated in PyMol. The Helical-II domain region is outlined with a yellow dashed line in State III.

FIG. 10A-10F. Effect of the Helical-II domain in DpbCasX and PlmCasX on dsDNA cleavage. (A) In vitro biochemical dsDNA cleavage activity comparison among DpbCasX, DpbCasX with a Helical-II truncation (DpbCasX ΔH2), PlmCasX and PlmCasX with a Helical-II truncation (PlmCasX ΔH2). TS denotes the target strand DNA which is $^{32}$P labeled on the 5' end. CP indicates the cleavage product. (B) The cleavage fraction analysis based on the NTS band density compared to input NTS band density at the reaction time of 0min (n=3, mean±s.d.). The k values for DpbCasX, PlmCasX, DpbCasX ΔH2 and PlmCasX ΔH2 are 0.04851, 0.006054, 0.006705 and 0.002683, respectively. (C) In vitro dsDNA cleavage activity comparison revealed by 5-primer end $^{32}$P labeled target strand (TS). (D) The cleavage fraction analysis based on the TS band density compared to input TS band density at the reaction time of 0min (n=3, mean±s.d.). The k values for DpbCasX, PlmCasX, DpbCasX ΔH2 and PlmCasX ΔH2 are 0.04445, 0.004754, 0.008223 and $1.741e^{-0005}$, respectively. (E) The genome editing efficacy comparison between wild type DpbCasX (WT) and DpbCasX ΔH2 (ΔH2) constructs with sgRNAv1. sgRNAv1 3, 4 and 8 targeting the GFP gene were tested. NT denote the non-target sgRNAv1 control (n=3, mean±s.d.). Cells were collected and analyzed by flow cytometry at 5, 7 and 10 days after plasmid transfection. (F) The genome editing efficacy comparison between wild type PlmCasX (WT) and PlmCasX ΔH2 (ΔH2) constructs with sgRNAv1.

Nucleotide-Binding Loops in CasX Contribute to R-Loop Assembly and DNA Cutting

Figure 11A:
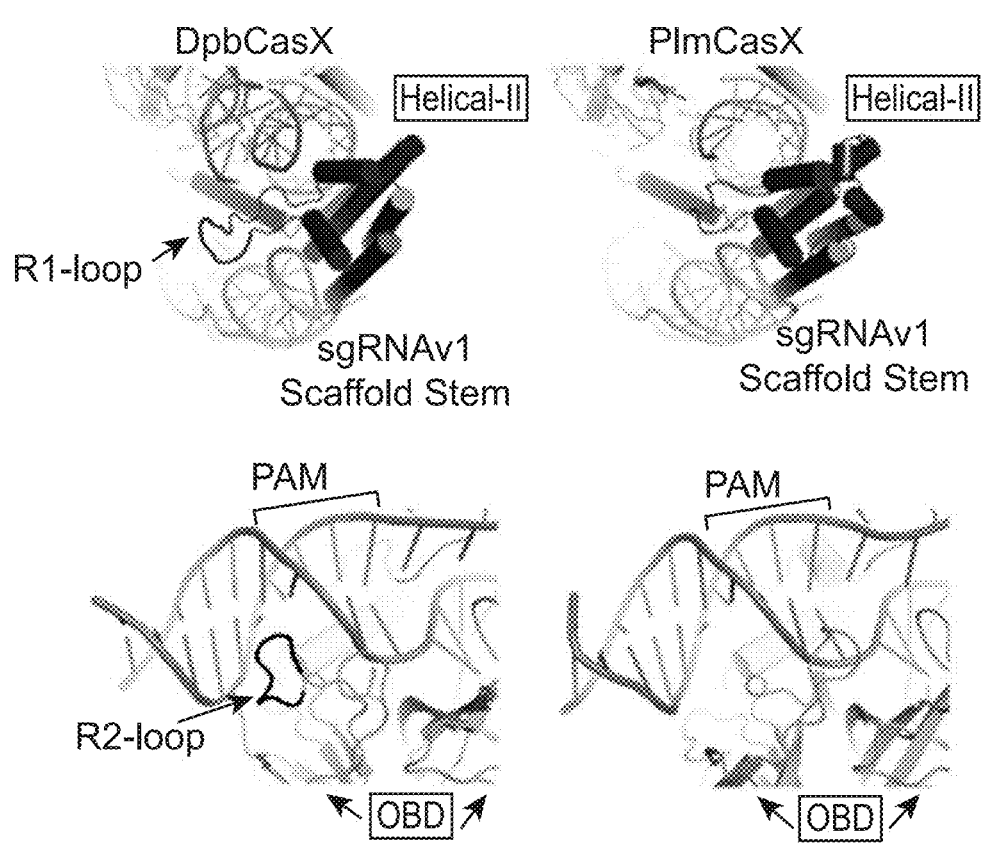
FIG. 11A-11C depict structural comparison between DpbCasX and PlmCasX.
Figure 11B:
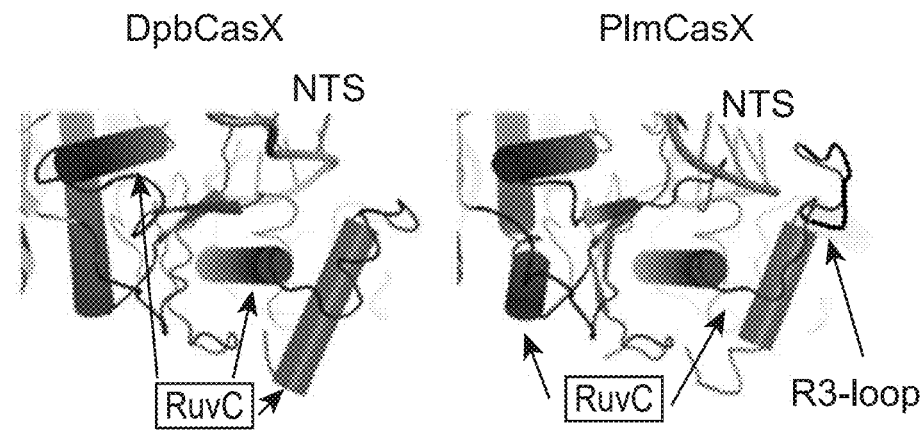
Figure 12B:
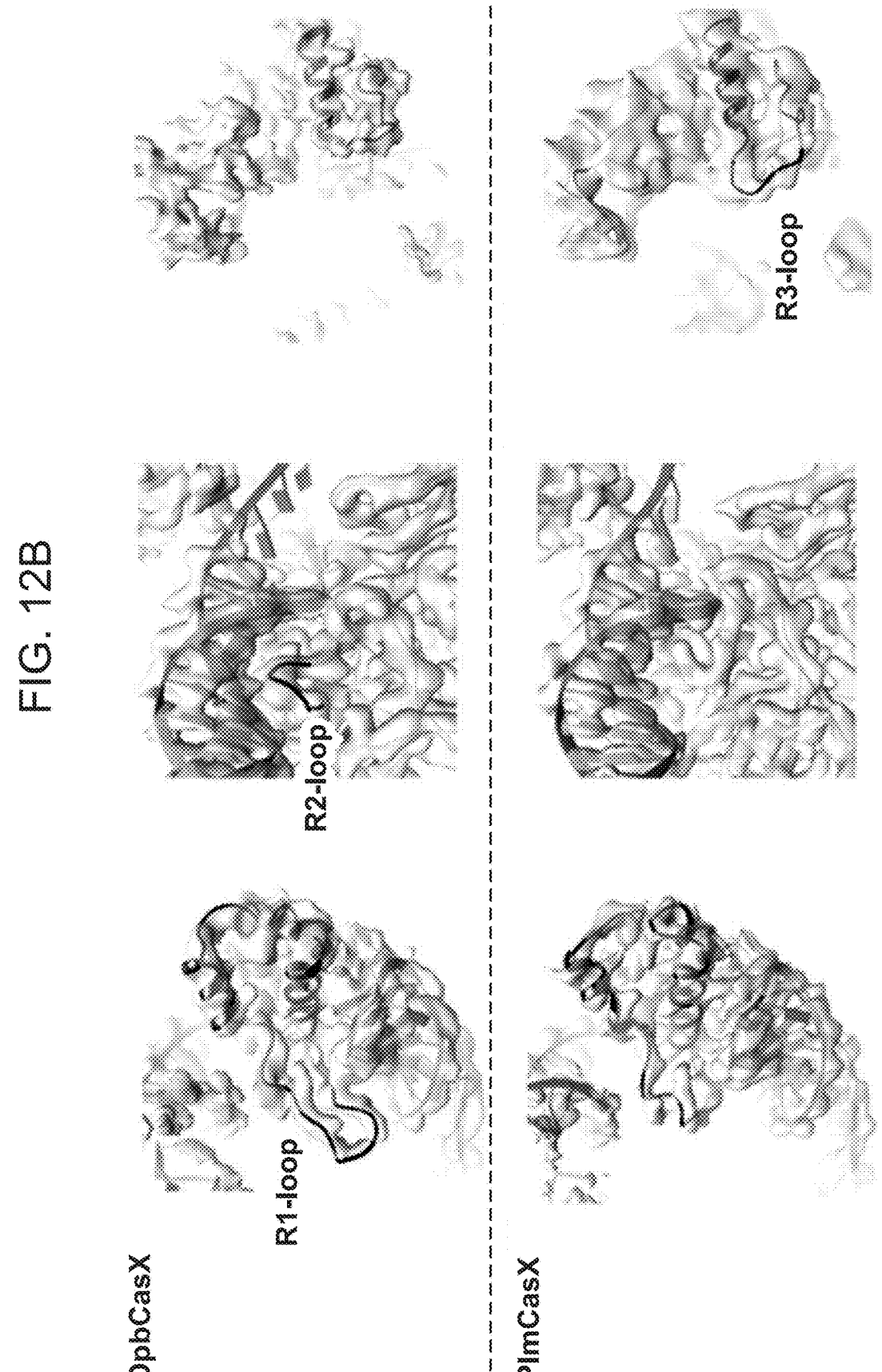
Figure 12C:
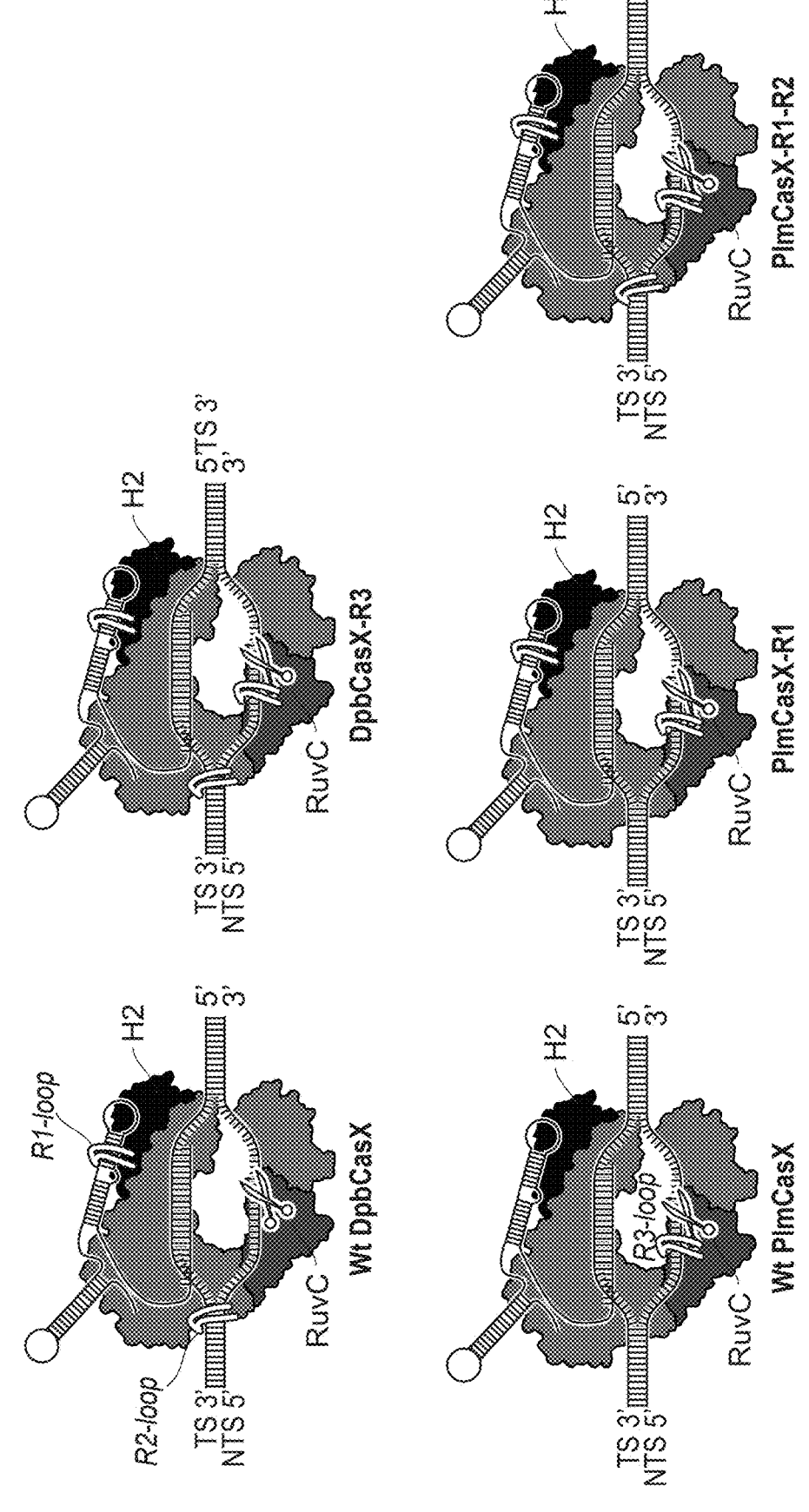
Figure 13A:
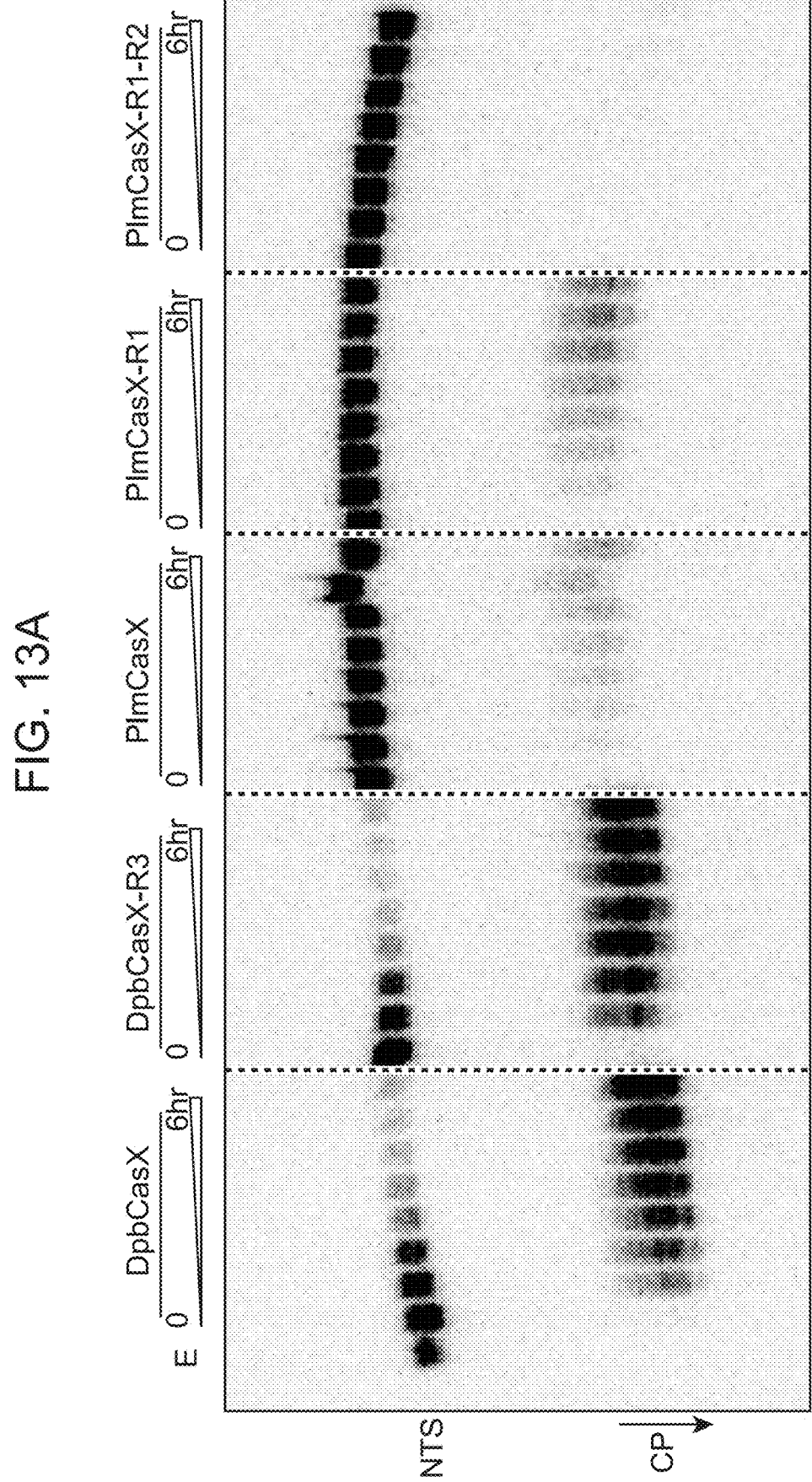
FIG. 13A-13E depict DNA cleavage by CasX protein chimeras.
Figure 13B:
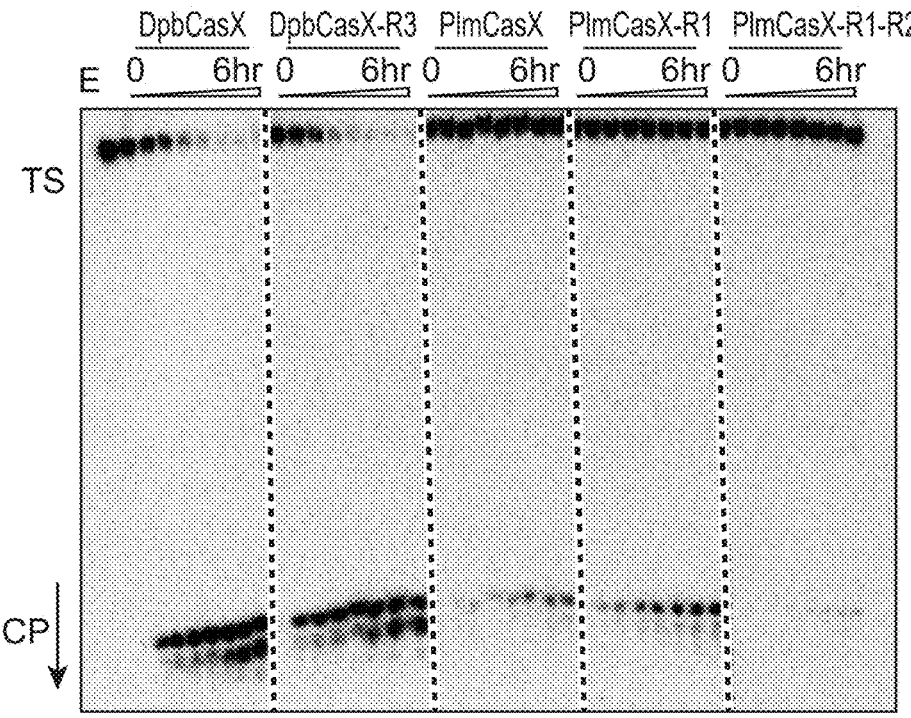
Figure 13C:
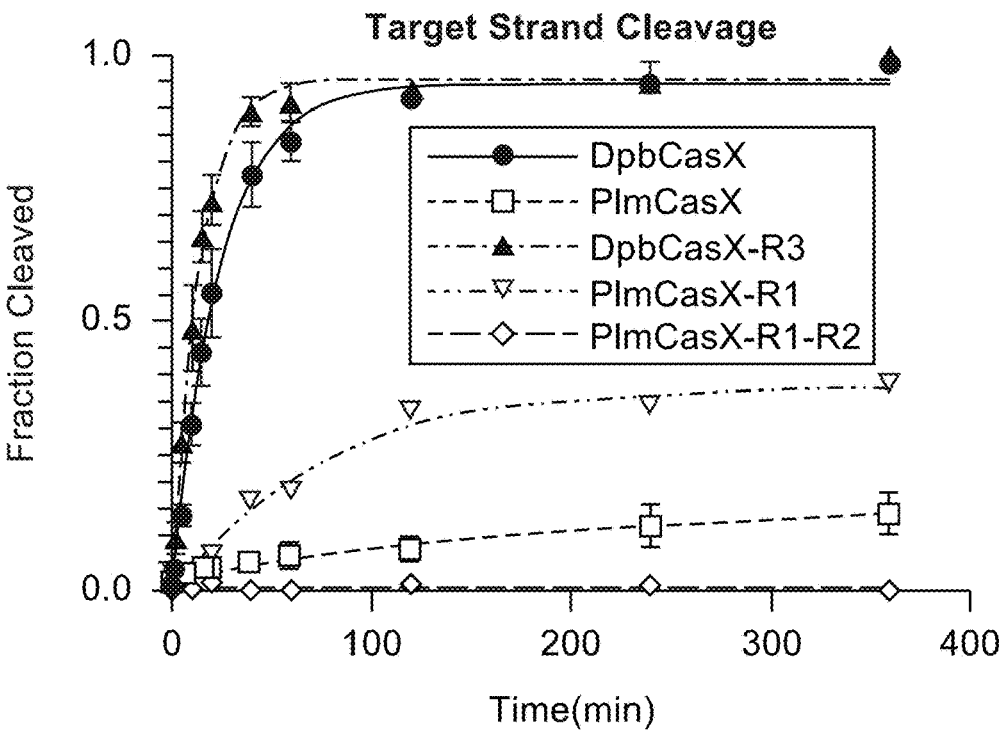
Figure 13D:
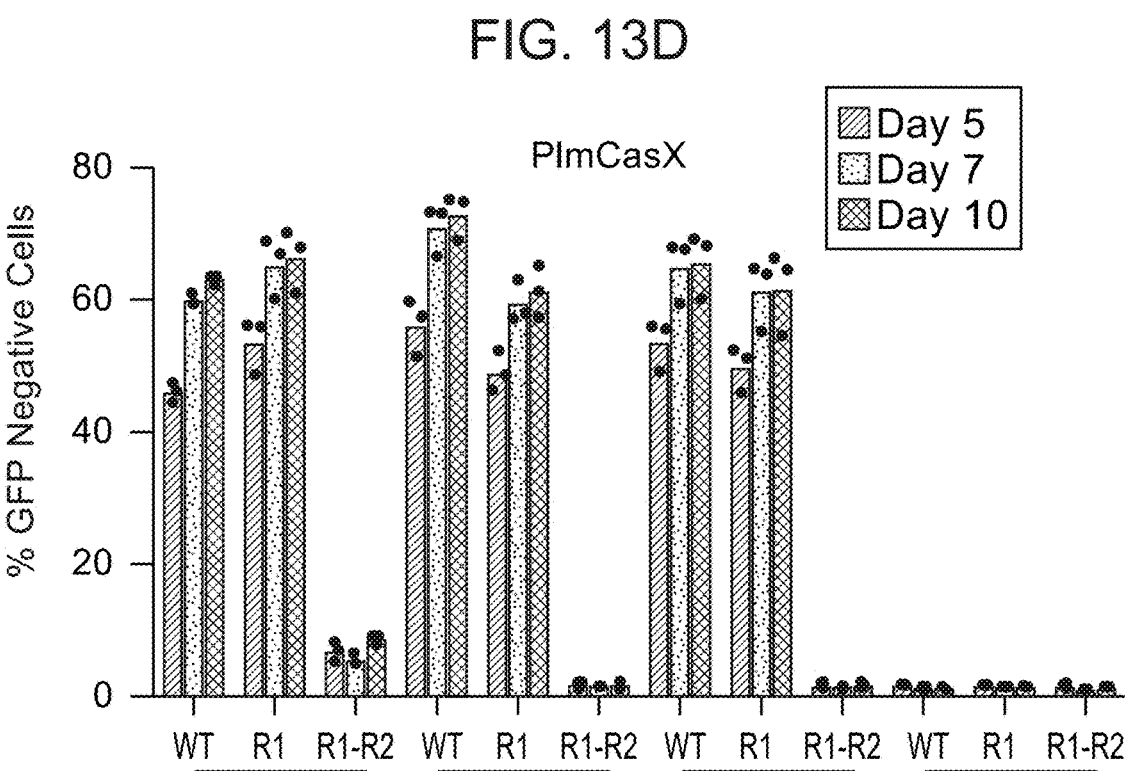
Figure 13E:
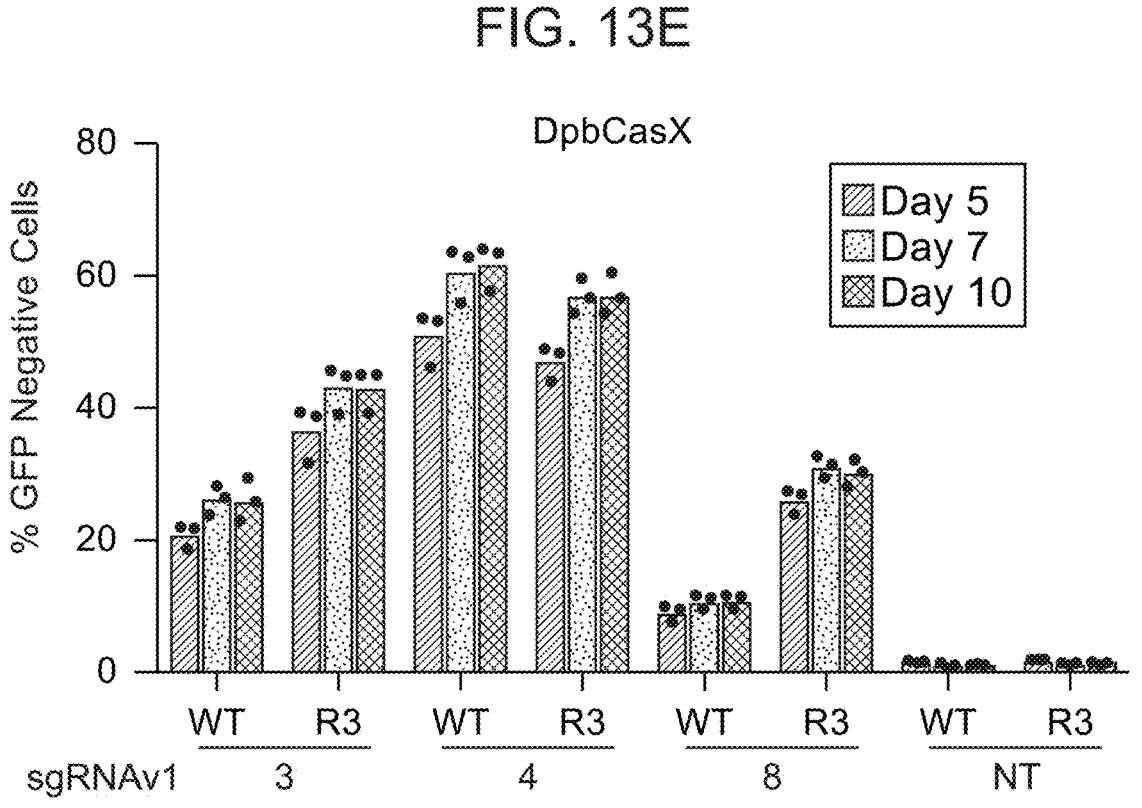

To further understand the structural details that led to unstable assembly and a mobile H2 domain within the PlmCasX ternary complex, a comprehensive analysis of the sequence and structural differences between PlmCasX and DpbCasX in State I was conducted. PlmCasX and DpbCasX share 56% sequence identity overall, with a structural similarity Z score of 33.8 as calculated by the Dali Server (Holm and Laakso, 2016). The protein domains (OBD, Helical-I, Helical-II, RuvC, TSL and BH) of PlmCasX that correspond to those in the DpbCasX structure was identified; and the protein sequence corresponding to the BH domain was redefined based on the better-resolved structural details in PlmCasX (FIG. 9B). Within the context of the same protein architecture, three nucleotide-binding loops were found that exist exclusively in either PlmCasX or DpbCasX and could have relevance to R-loop complex assembly and DNA cleavage (FIG. 11A and FIG. 11B). It was found that the region 1 loop (R1, K390-L396) in the DpbCasX H2 domain, which together with the H2 domain helices forms a deep pocket for tight binding of the sgRNA scaffold stem, likely contributes to the stable assembly of the R-loop complex (FIG. 11A; FIG. 12A and FIG. 12B). R1 is shortened in wtPlmCasX, giving rise to a shallower binding pocket that likely leads to weaker H2 domain-sgRNA binding and eventually the assembly of a less stable R-loop complex (FIG. 11A; FIG. 12A and FIG. 12B). A chimeric PlmCasX with the DpbCasX R1 loop (PlmCasX-R1) showed about 3-fold higher DNA cleavage kinetics in vitro (FIG. 11C; FIG. 12C; FIG. 13A-13C), but similar DNA editing activity in HEK293 cells compared to that of wtPlmCasX (FIG. 13D). The region 2 loop (R2, G520-1526) is only present in the DpbCasX OBD domain and structurally interacts with the PAM proximal region (FIG. 11A; FIG. 12A and FIG. 12B), which may be important for initial steps of dsDNA substrate loading. However, adding R2 to PlmCasX-R1 (PlmCasX-R1-R2) completely disrupted DNA cleavage in vitro and editing in mammalian cells (FIG. 11C; FIG. 12C; FIG. 13A-13D). This result suggests that for R2, interactions with both DNA and the surrounding protein elements are likely important for the proper ternary complex assembly (FIG. 11A). The region 3 loop (R3, Q945-G951) is exclusively present in PlmCasX, and similar to R1, forms a deep active pocket together with the remaining part of the RuvC domain that likely helps to faithfully accommodate and degrade ssDNA substrates (FIG. 11B; FIG. 12A and FIG. 12B). In contrast, the DpbCasX RuvC lacks R3 and contains a shallow active pocket that may have a lower-affinity interaction with a ssDNA substrate (FIG. 11B; FIG. 12B). A chimeric DpbCasX with the PlmCasX R3 (DpbCasX-R3) had about 1.6-fold higher DNA cleavage kinetics in our biochemical cleavage assays (FIG. 11C; FIG. 12C; FIG. 13A-13C), and a 1.6-fold increase in median genome editing efficacy of HEK293 cells across three sgRNAv1s, compared to wtDpbCasX (FIG. 13E).

Figure 11C:
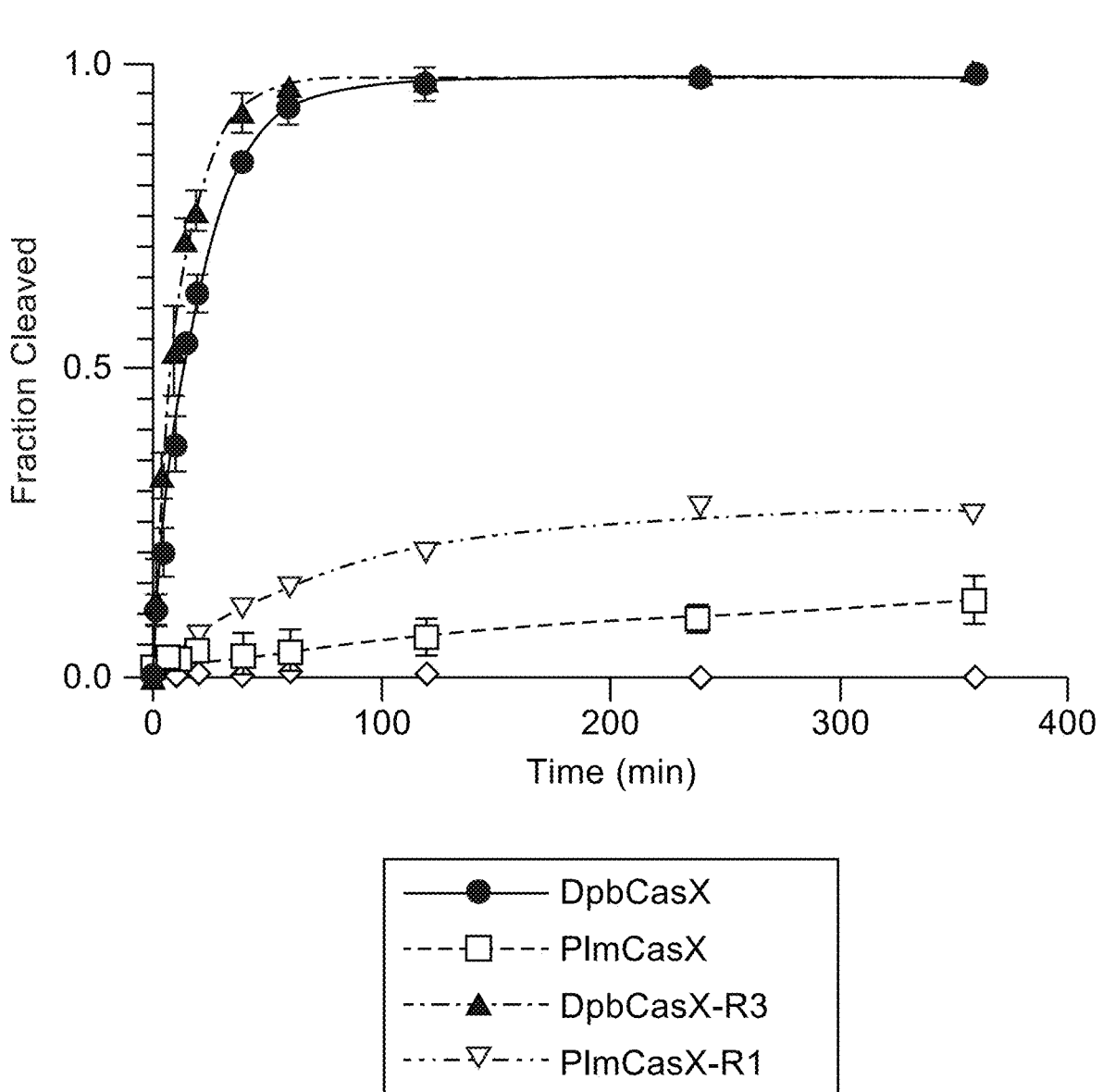

FIG. 11A-11C. Structural comparison between DpbCasX and PlmCasX (A) Region 1 (R1) and region 2 (R2) loops located within DpbCasX but absent from PlmCasX. The protein domains are colored as see in FIG. 9, the sgRNAv1 is seen in light gray and the dsDNA (with PAM region labeled) in blue. (B) Region 3 (R3) loop located within PlmCasX but absent from DpbCasX. (C) Biochemical dsDNA cleavage activity comparison between CasX chimeras with sgRNAv1 (n=3, mean±s.d.). The k values for DpbCasX, PlmCasX, DpbCasX-R3 and PlmCasX-R1 are 0.05065, 0.003569, 0.07993 and 0.012503, respectively.

FIG. 12A-12B. Design of CasX protein chimeras. (A) Amino acid sequence alignment between DpbCasX and PlmCasX using Clustal. Only regions in proximity to loops R1, R2 and R3 are shown for clarity. (B) Details of the fitting between the atomic model and EM map at region 1, 2 and 3. The R1, R2 and R3-loops are colored in red and labeled in each model. For DpbCasX, the published model (PDB code 6NY2) with re-built R1-loop and EM map (EMDB code EMD-8996) was used. In the bottom right panel, the EM map is shown in low-threshold at the sigma value of 3.68 due to the weak density of the R3-loop in the PlmCasX reconstruction. The EM maps in other panels are shown at the sigma value ranging from 6 to 9. (C) Cartoon models for wild type CasX proteins and chimeric designs. The R1, R2 and R3 regions are presented as red loops on the 3D structure.

FIG. 13A-13E. DNA cleavage by CasX protein chimeras. (A) In vitro dsDNA cleavage activity comparison among wild type and CasX chimeras using the gRNAv1 scaffold revealed by denaturing PAGE. NTS denotes the target strand DNA which was $^{32}$P labeled on the 5' end. CP indicates the cleavage product. The fractions were collected at 0 min, 10 mins, 20 mins, 40 mins, 1 hr, 2 hrs, 4 hrs and 6 hrs, respectively. E indicates empty well with labeled DNA but no enzyme. (B) In vitro dsDNA cleavage activity comparison among wild type and CasX chimeras using the gRNAv1 scaffold revealed by denaturing PAGE. The TS was $^{32}$P labeled on the 5' end. The fractions were collected at 0 min, 10 mins, 20 mins, 40 mins, 1 hr, 2 hrs, 4 hrs and 6 hrs, respectively. E indicates empty well with labeled DNA but no enzyme. (C) Plot of DNA cleavage kinetics analyzed based on the TS band density from the cleaved fractions compared to the input TS band density at the reaction time of 0 min (n=3, mean±s.d.). The fractions were collected at 0 min, 10 mins, 20 mins, 40 mins, 1 hr, 2 hrs, 4 hrs and 6 hrs, respectively. k values for DpbCasX, PlmCasX, Dpb-CasX-R3 and PlmCasX-R1 were 0.04189, 0.004144, 0.07236 and 0.01364, respectively. (D) Genome editing efficacy comparison between wild type PlmCasX (WT), PlmCasX-R1 (R1), and PlmCasX-R1-R2 (R1-R2) chimeras with sgRNAv1. (E) Genome editing efficacy comparison between wild type DpbCasX (WT) and DpbCasX-R3 chimera (R3) with sgRNAv1. sgRNAv1 3, 4 and 8 targeting the GFP gene were tested. NT denotes the non-targeting sgR-NAv1 control (n=3, mean). Cells were collected and analyzed by flow cytometry at 5, 7 and 10 days after plasmid transfection.

A New sgRNA Scaffold Promotes the CasX R-Loop Complex Assembly and DNA Cleavage

Figure 14F:
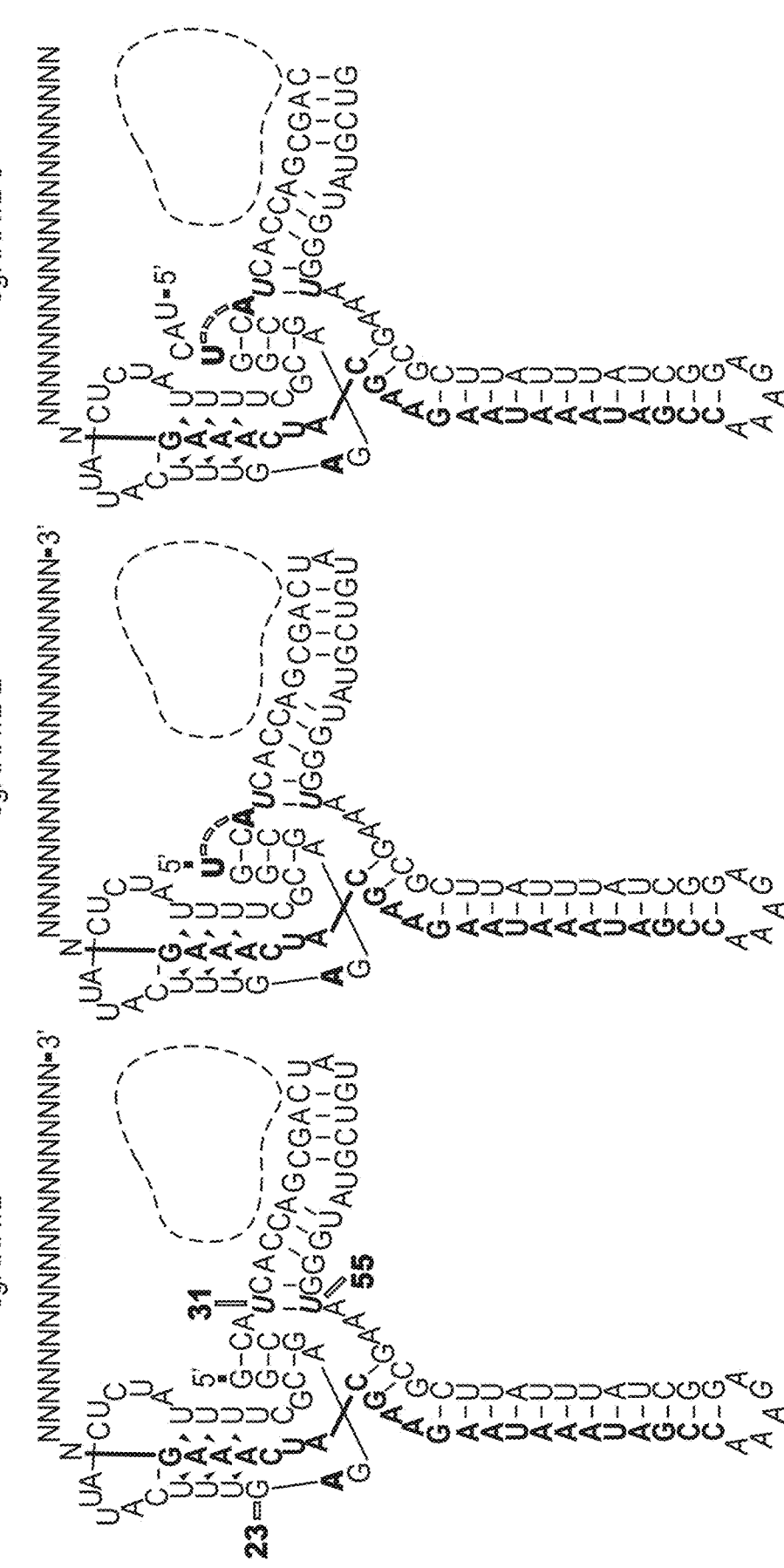
Figure 14G:
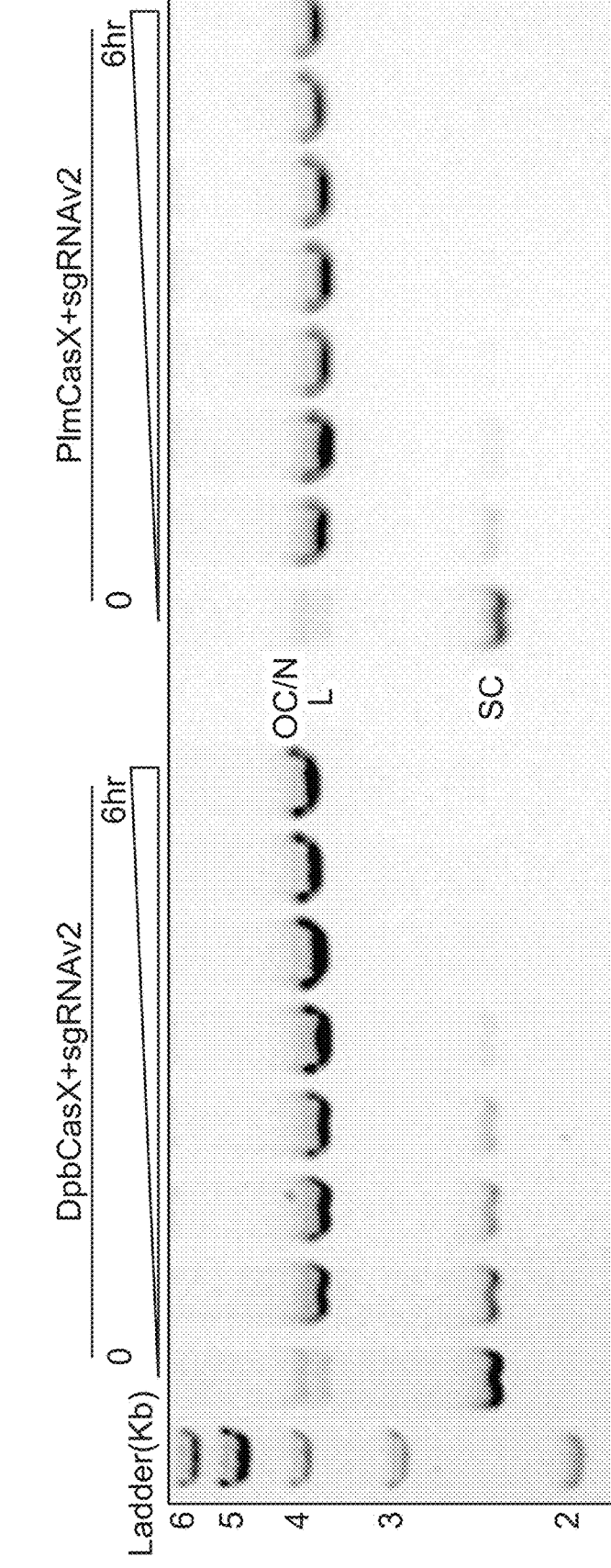
Figure 15A:
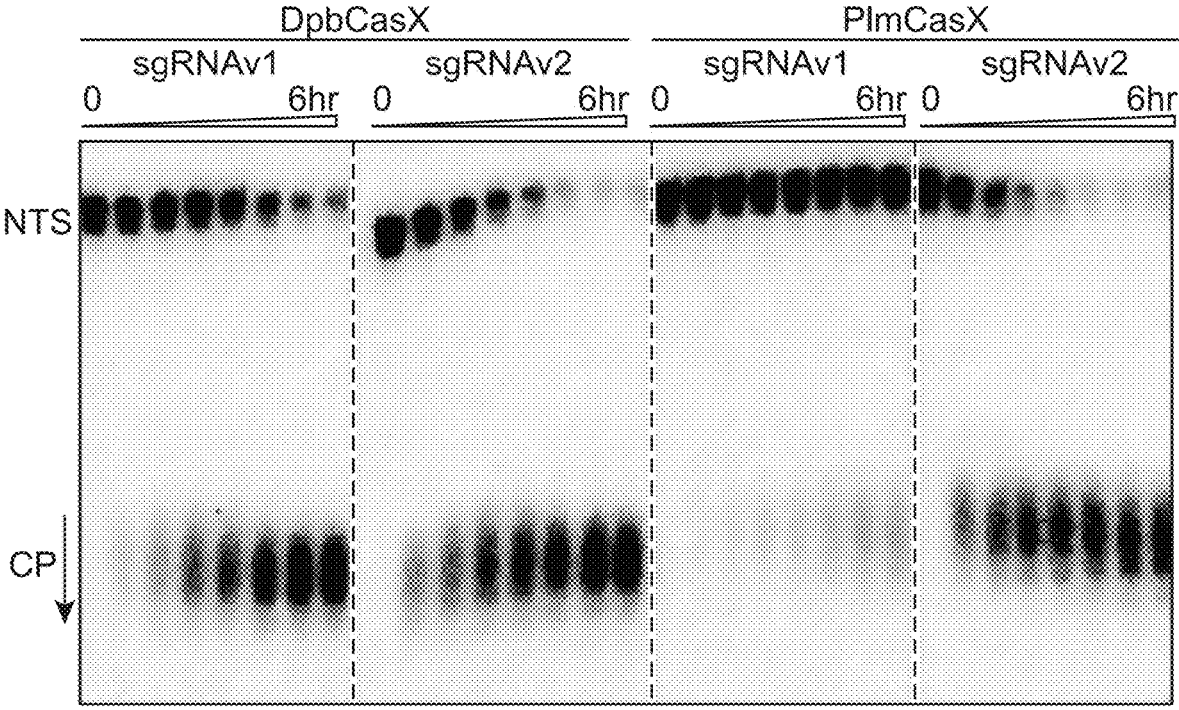
FIG. 15A-15F depict in vitro biochemical cleavage behavior of CasX using sgRNAv2 (FIG. 15C SEQ ID NO:15).
Figure 15B:
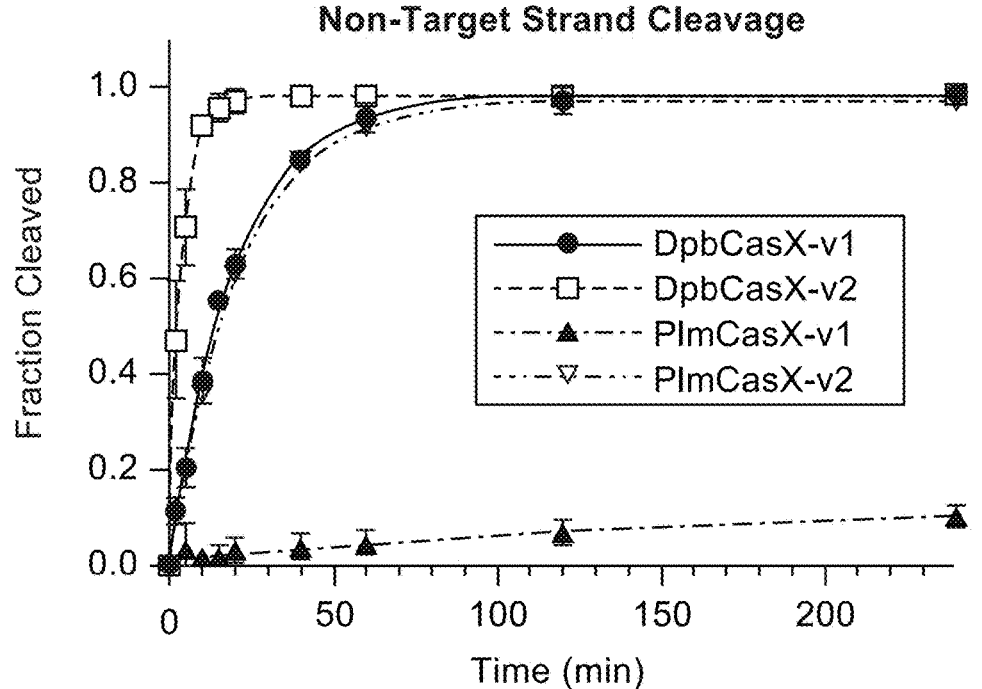

The cryo-EM structures indicate that the weak interaction between the H2 domain and sgRNA scaffold stem likely interferes with R-loop complex assembly and thus decreases the DNA cutting activity of PlmCasX. In addition to engineering the CasX protein, the sgRNA sequence was redesigned to stabilize the scaffold stem for better interaction with the H2 domain and improve DNA cleavage activity in that way. Based on secondary structure prediction and available atomic structures, adding an additional U at the 5' end of the sgRNAv1 could form a new base pairing interaction with A29 and thus limit the mobility of the scaffold stem without changing the structure (hereafter sgRNAv1-2) (FIG. 14A-14C). However, DpbCasX showed lower DNA cleavage activity with sgRNAv1-2 (FIG. 14D and FIG. 14E). Instead, CasX may require a certain level of flexibility within the sgRNA to adopt the necessary conformational changes during the multi-step assembly of the ternary complex (Liu et al., 2019). By structural inspection, the disruption of the G30-C54 base pairing and adding nucleotides after G23 to increase the single stranded linker may increase the flexibility of sgRNA scaffold stem while preserving its predicted secondary structure (FIG. 14B and FIG. 14F). RNA profiling showed that the native PlmCasX tracrRNA sequence also contains additional nucleotides compared to sgRNAv1, which was designed based on the native Dpb-CasX tracrRNA sequence (FIG. 14A). Referring to this structural interpretation and the PlmCasX tracrRNA sequence, the sgRNA design was revised by adding an additional nucleotide A after G23 and swapping the G30-C54 pair to U31-U55 (FIG. 14C and FIG. 14F). The new sgRNA (hereafter sgRNAv2) enhanced both DpbCasX and PlmCasX dsDNA cleavage kinetics by 5.6 and 11-fold, respectively (FIG. 15A and FIG. 15B). Again, adding a U or more nucleotides to the 5' end of sgRNAv2 decreased the dsDNA cleavage activity of PlmCasX (sgRNAv2-2 and sgRNAv2-3) (FIG. 14D and FIG. 14E). Both DpbCasX and PlmCasX also showed increased plasmid linearization activity using sgRNAv2 compared to sgRNAv1 (FIG. 6E and FIG. 14G).

Figure 15C:
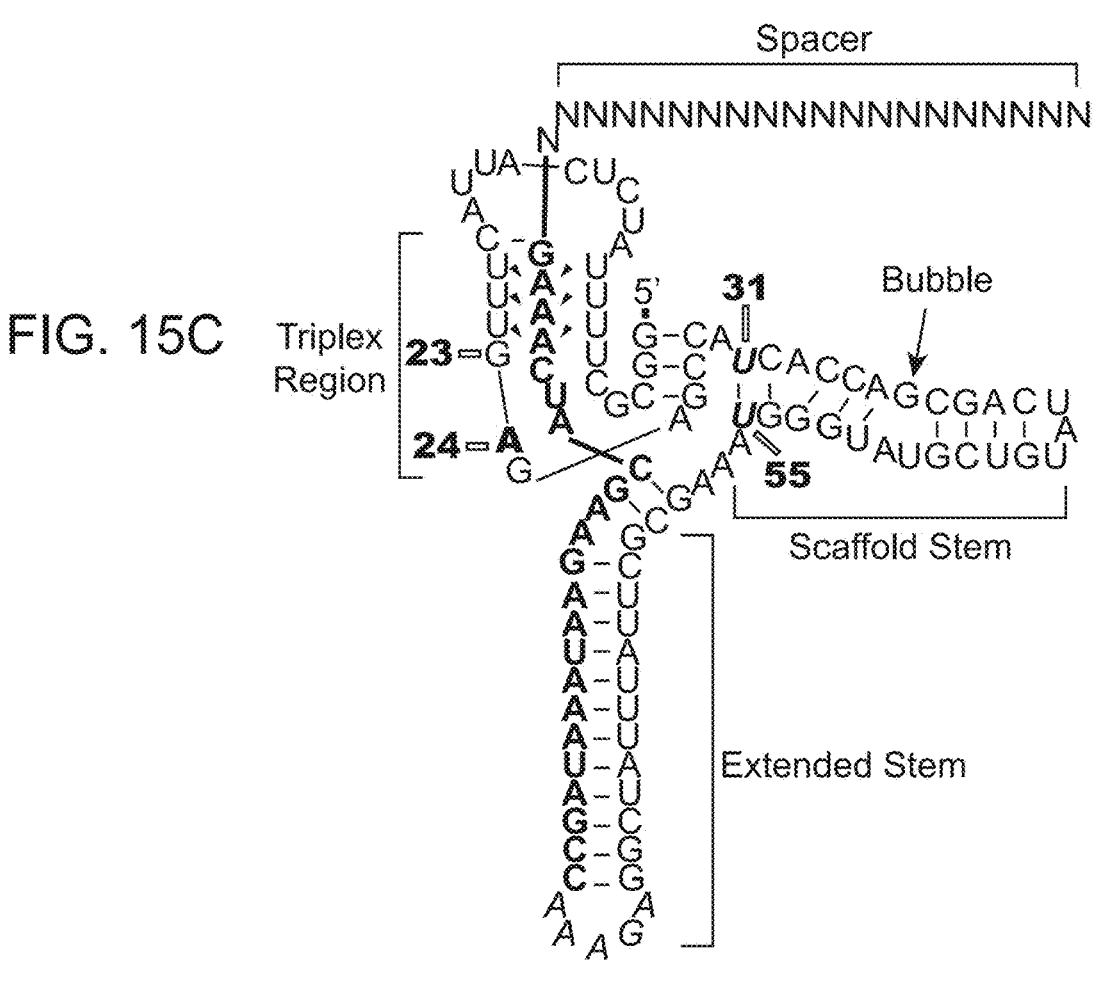
Figure 15D:
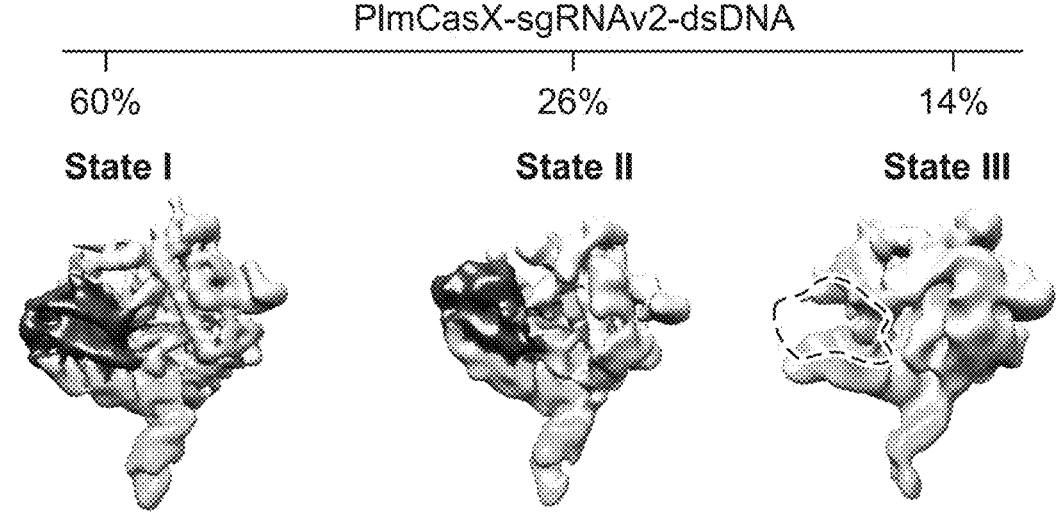
Figure 15E:
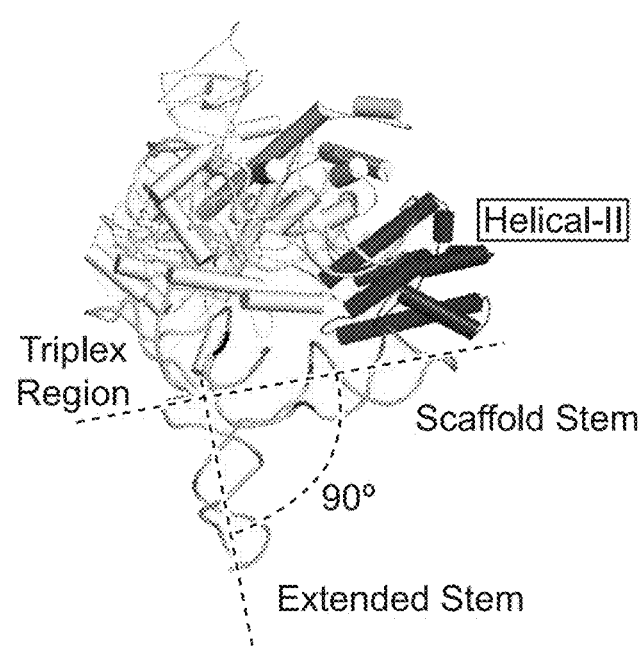
Figure 15F:
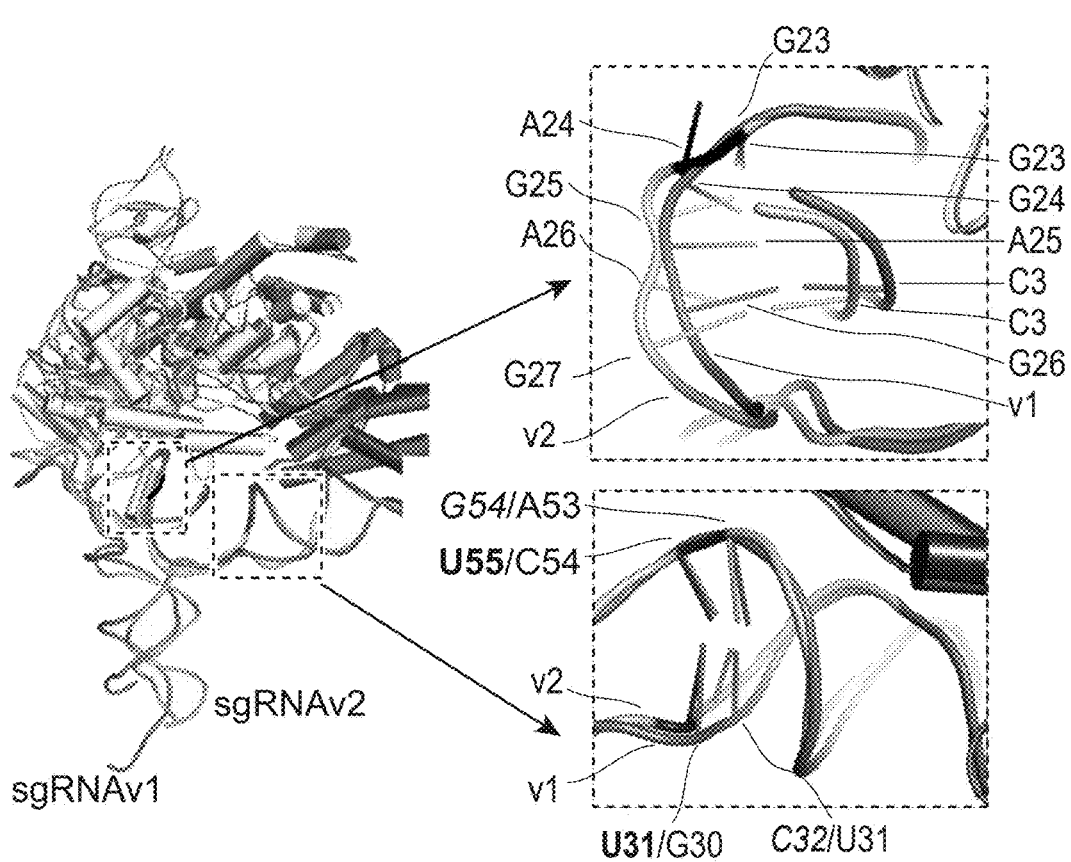
Figure 16A:
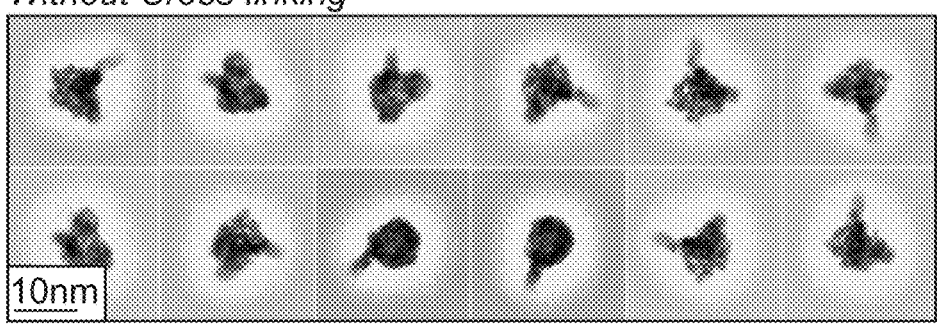
FIG. 16A-16F depict single particle cryo-EM analysis of the PlmCasX-sgRNAv2-dsDNA complex.
Figure 16B:
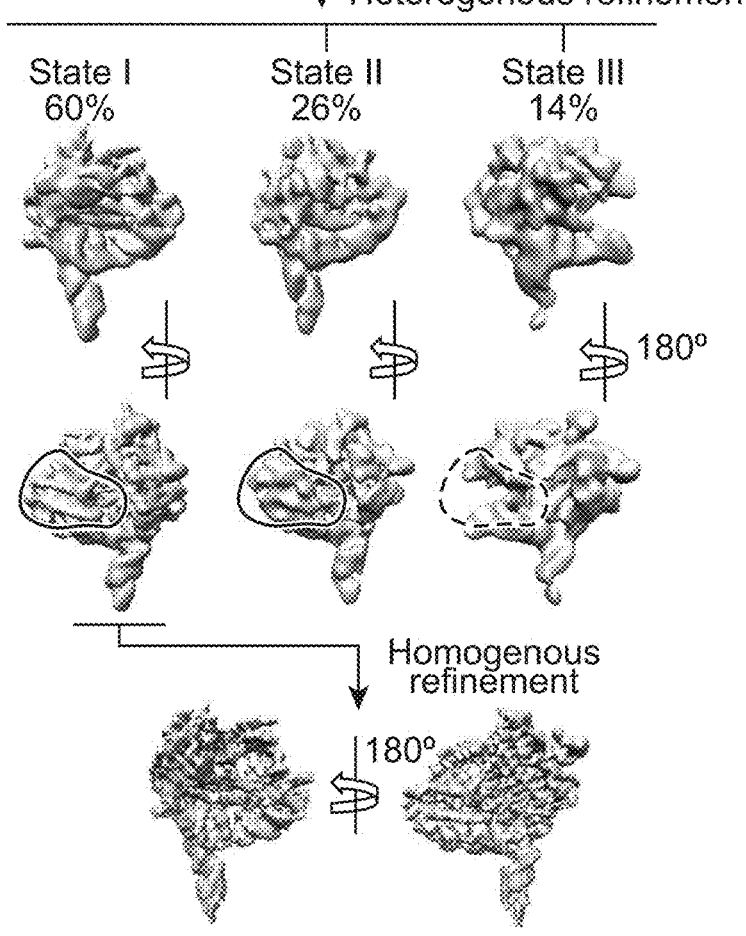
Figure 16C:
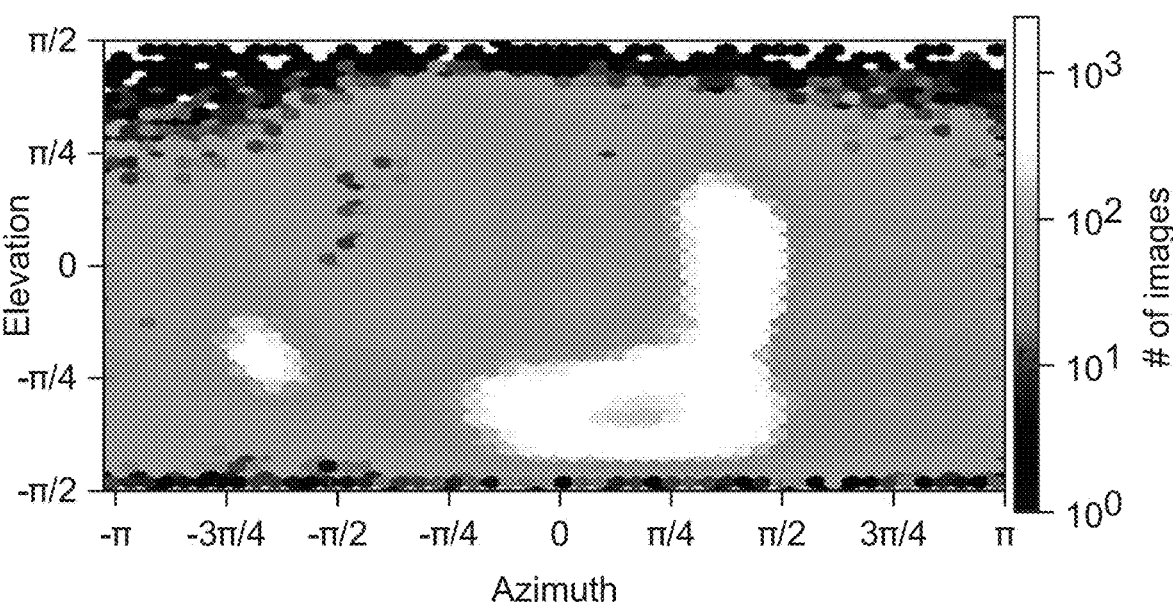
Figure 16D:
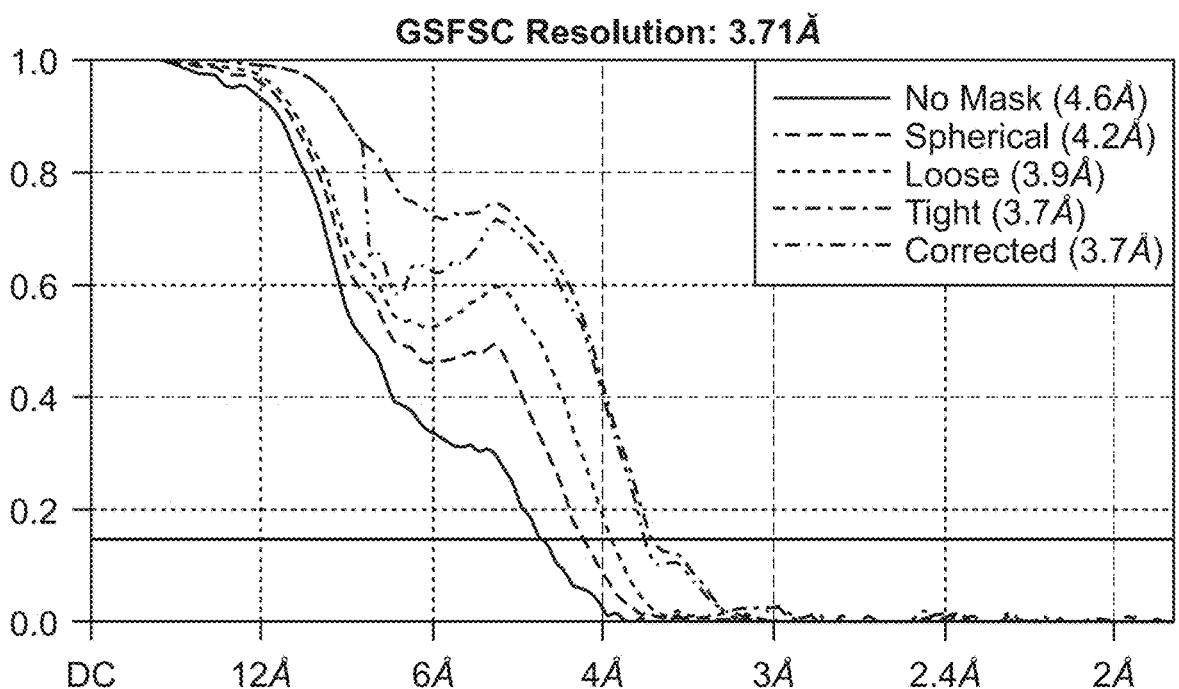
Figure 16E:
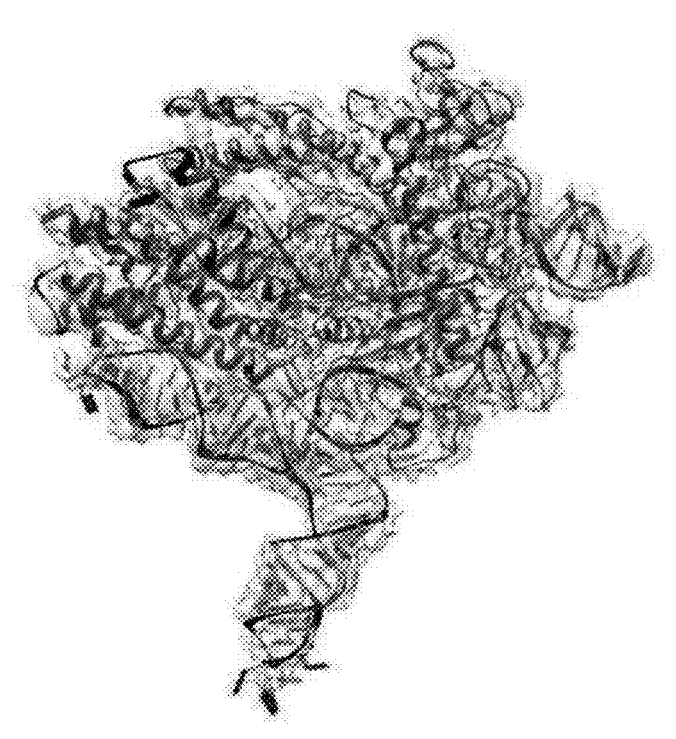
Figure 16F:
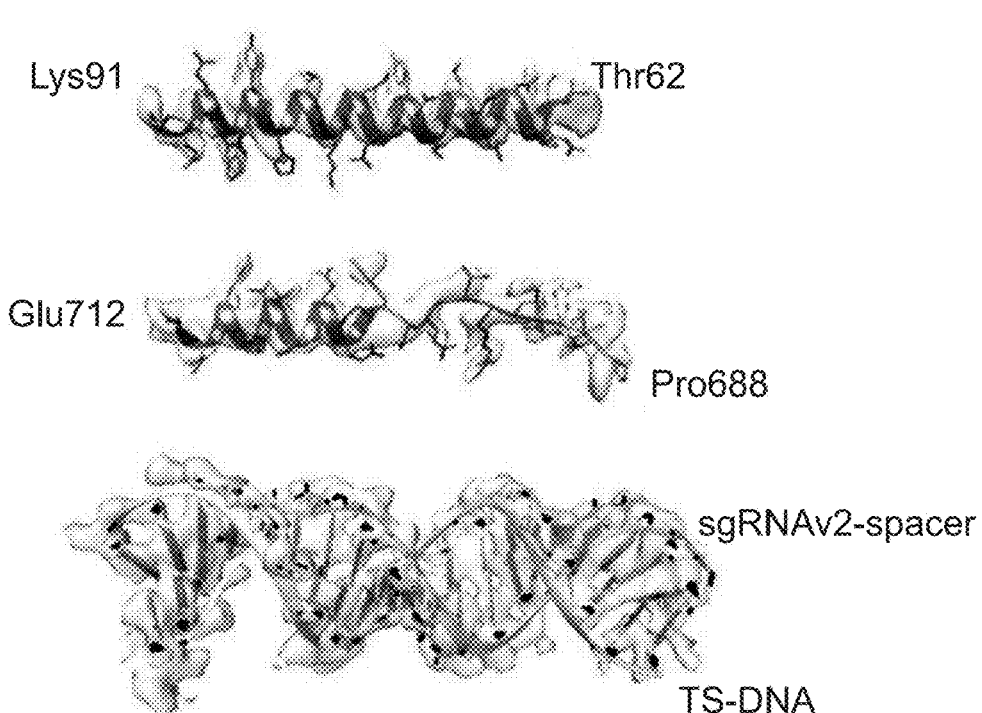

To further investigate whether and how sgRNAv2 helped with the overall stability of the R-loop complex (FIG. 15C), single particle cryo-EM analysis was performed on PlmCasX-sgRNAv2-dsDNA (40 bp). Indeed, the new complex appeared more stable without the need for crosslinking during cryo-EM sample preparation (FIG. 16A). 3D classification showed that only 14% of the PlmCasX-sgRNAv2-dsDNA complexes were present in State III, a sharp decrease from 41% for the PlmCasX-sgRNAv1-dsDNA complexes, presumably due to the higher affinity interaction of the H2 domain with sgRNAv2 (FIG. 15D; FIG. 16B). Further 3D variability analysis for particles from State I of PlmCasX-sgRNAv2-dsDNA indicated that the extended stem of sgR-NAv2 adopts a continuum of states, that may contribute to the limited resolution of the EM map (FIG. 16C and FIG. 16D). Structural comparison of PlmCasX-sgRNAv1-dsDNA and PlmCasX-sgRNAv2-dsDNA showed that the addition of an A after G23 increased the curvature in the single strand RNA linker, and swapping the G30-C54 pair to U31-U55 generated a minor distortion at the end of the sgRNAv2 scaffold stem (FIG. 15E and FIG. 15F; FIG. 16E and FIG. 16F). Meanwhile, the angle between the sgRNA extended stem and scaffold stem decreased from 110° to 90° (FIG. 9B; FIG. 15E). Notably, the structures of the PlmCasX proteins appear indistinguishable between the two complexes (FIG. 15F). Overall, sgRNAv2 increases the stability of the R-loop complex, which could explain the observed increase in DNA cutting activity when complexed with both DpbCasX and PlmCasX.

FIG. 14A-14G. Updated design of the CasX sgRNA. (A) Transcripts from the hypothetical CasX tracrRNA loci revealed by meta-transcriptome sequencing. The coverage axis denotes the number of sequencing reads. The abscissa denotes the genome sequence of the hypothetical tracrRNA region. (B) The structural details for sgRNAv1. The additional U at the 5' end was hypothetically modeled in the top panel. The structural details of the G30-C54 base-paring region in sgRNAv1 are also shown in the bottom panel. (C) The secondary architecture of sgRNAv1 revealed by cryo-EM. The sgRNAv1-2 architecture is modeled based on sgRNAv1. The potential base-pairing between the additional 5' U and A29 is labeled with a dashed line. The Helical-II domain was modeled to indicate the interaction interface with the sgRNA scaffold stem. (D) In vitro dsDNA cleavage activity comparison among different sgRNAs by DpbCasX and PlmCasX. The NTS was $^{32}$P labeled on the 5' end. (E) Cleavage kinetics analysis was based on the NTS band density from the cleaved fractions compared to the input NTS band density at the reaction time of 0 min (n=3, mean±s.d.) (DpbCasX-v2 from FIG. 15A). The fractions were collected from 0 min to 6 hrs. The k values for DpbCasX-v1, DpbCasX-v1-2, DpbCasX-v2, PlmCasX-v1, PlmCasX-v2, PlmCasX-v2-2 and PlmCasX-v2-3 were 0.05065, 0.01087, 0.2817 and 0.004433, 0.04858, 0.009191 and 0.02169, respectively. (F) The hypothetical secondary architectures of sgRNAv2 designs. (G) In vitro plasmid cleavage activity comparison between DpbCasX and PlmCasX with sgRNAv2 revealed by agarose gel. The fractions were collected at 0 min, 10 mins, 20 mins, 40 mins, 1 hr, 2 hrs, 4 hrs and 6 hrs, respectively. OC/N indicates the open-circle or nicked plasmids, L indicates the linearized plasmids and SC indicates the super-coiled plasmids (n=3, representative gel shown).

FIG. 15A-15F. In vitro biochemical cleavage behavior of CasX using sgRNAv2. (A) In vitro dsDNA cleavage activity comparison between DpbCasX and PlmCasX using sgR-NAv1 and sgRNAv2 revealed by denaturing polyacrylamide gel electrophoresis (PAGE). The fractions were collected at 0 min, 10 mins, 20 mins, 40 mins, 1 hr, 2 hrs, 4 hrs and 6 hrs, respectively. (B) Cleavage fraction analysis based on the NTS band density compared to the input NTS band density at the reaction time of 0 min (n=5, mean±s.d.). CasX-v1 denotes the CasX complex using sgRNAv1, while CasX-v2 denotes the CasX complex using sgRNAv2. The k values for DpbCasX-v1, PlmCasX-v1, DpbCasX-v2 and PlmCasX-v2 were 0.05065, 0.004433, 0.2817 and 0.04858, respectively. (C) The secondary architecture of sgRNAv2 revealed by cryo-EM. The key nucleic acid variants in sgRNAv2 compared to sgRNAv1 are marked in green and red. The nucleotide number for G23, A24, U31 and U55 are labeled. (D) The different structural states of the PlmCasX ternary complex with the sgRNAv2 scaffold revealed by single particle cryo-EM. The back views of refined EM maps for State I, State II and State III are shown in the top panel. The three maps were low-pass filtered at 6 Å and shown at the sigma value from 6 to 9 for clear presentation and comparison. The Helical-II domain is colored in orange and sgR-NAv2 in light purple. Other parts of the complex are colored in light gray. The invisible Helical-II domain in State III is represented with the dashed outline. The particle proportions for all functional states within PlmCasX-sgRNAv2-dsDNA complex are presented with percentages. (E) Atomic model of PlmCasX-sgRNAv2-dsDNA in State I. The CasX protein is colored in light gray and sgRNAv2 is shown in light purple. The Helical-II domain is emphasized by highlighting in orange. (F) Structural comparison between PlmCasX-sgRNAv1-dsDNA (all in gray) and PlmCasX-sgRNAv2-dsDNA (CasX in light gray and sgRNAv2 in light purple) complexes in State I. The two structures were aligned in PyMol referring to the PlmCasX protein and dsDNA. The dsDNA models are hidden for better presentation. The zoomed in features for the sgRNA triplex region and scaffold stem are shown in the right panels, with the number of key nucleotides labeled.

Figure 17A:
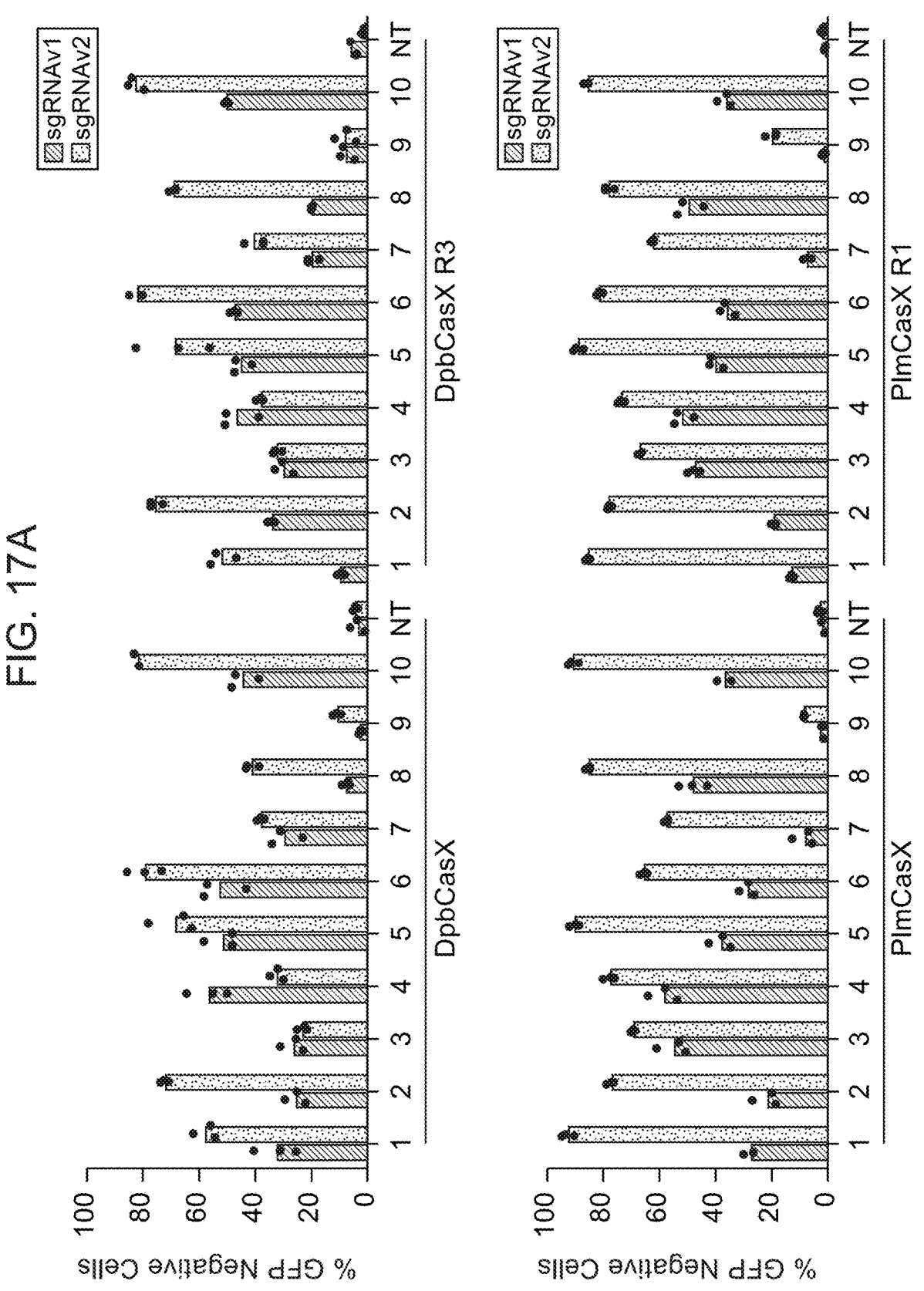

FIG. 16A-16F. Single particle cryo-EM analysis of the PlmCasX-sgRNAv2-dsDNA complex. (A) Representative 2D class averages of the native complex; the scale bar is 10 nm. (B) The workflow for single particle cryo-EM analysis in CryoSparc. The particles in State I, State II and State III account for 60%, 26% and 14%, respectively, of all the particles used for 3D refinement. The mobile regions across the three states are outlined. (C) Euler angle distribution of the refined particles belonging to State I. (D) Fourier shell correlation (FSC) curve calculated using two independent half maps. The final resolutions for B-factor corrected State I map are 3.7 angstroms. Panels C and D are directly taken from the standard output of CryoSparc. (E) Overall fitting between atomic model and EM map of PlmCasX-sgRNAv1-dsDNA complex in State I. The atomic model is shown by ribbon cartoon and EM maps is shown by transparent surface. (F) Details of the fitting between atomic model and EM map of State I. The amino acid sidechains are shown. Improved Versions of CasX for Mammalian Genome Editing Using structure-based engineering of both the CasX protein and sgRNA, improved DNA cleavage by CasX in vitro was achieved (FIG. 11C; FIG. 15B). The newly designed sgRNAs were tested for mammalian cell genome editing and observed a considerable improvement in DNA editing efficacy both for DpbCasX and PlmCasX using ten different sgRNAs targeting HEK293 cells stably expressing GFP (FIG. 17A). The median editing efficacy for DpbCasX and PlmCasX with sgRNAv2 (DpbCasX-v2 and PlmCasX-v2) was 43.50% and 77.25%, respectively, a significant improvement from 31.45% for DpbCasX and 32.95% for PlmCasX by using sgRNAv1 (DpbCasX-v1 and PlmCasX-v1)(FIG. 17B).

Figure 18A:
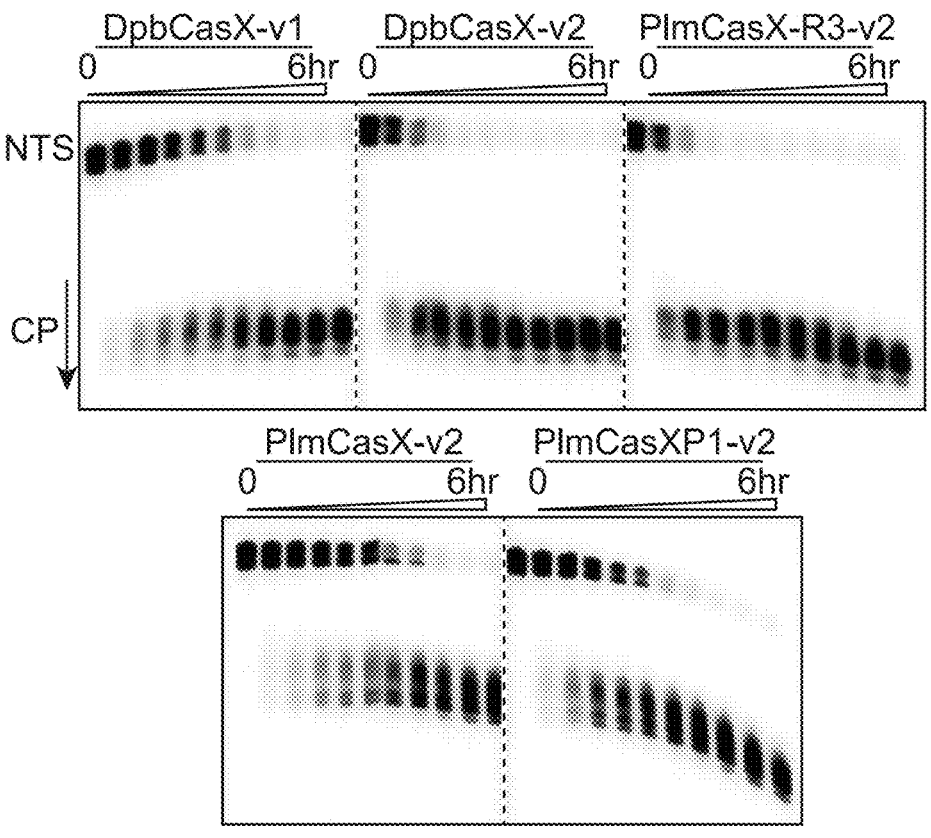
Figure 18B:
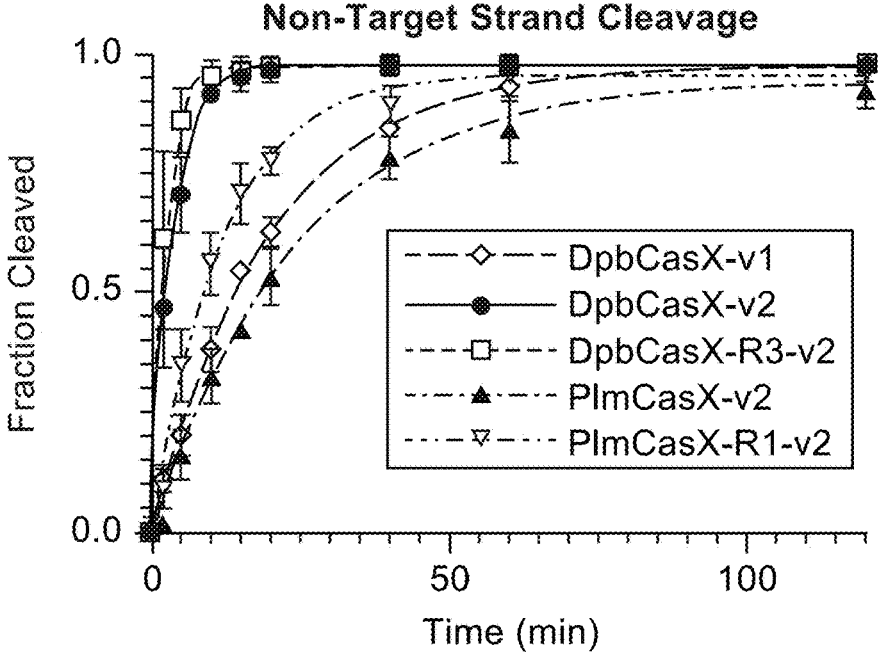

Next, it was tested whether combining both protein chimeras and the new sgRNAv2 could make a yet more effective CasX genome editing tool. Indeed, a combination of DpbCasX-R3 and sgRNAv2 (DpbCasX-R3-v2) outperformed all other combinations of CasX and sgRNA constructs in in vitro dsDNA cleavage activity (FIG. 18A and FIG. 18B) and works robustly for genome editing (median editing efficiency of 56.60%) (FIG. 17B). A combination of PlmCasX-R1 and sgRNAv2 (PlmCasX-R1-v2) showed improved dsDNA cleavage kinetics in vitro (~20-fold increase compared to PlmCasX with sgRNAv1 (PlmCasX-v1)) (FIG. 7B; FIG. 18A and FIG. 18B), and showed the highest median editing efficacy (78.20%) and smallest interquartile range (18.33%) across sgRNAs compared to all other combinations of CasX and sgRNAs in HEK293 cells (FIG. 17B). Unlike Type II CRISPR nucleases like Cas9, sequence specific cis-cleavage by Type V Cas12 nucleases activates non-specific ssDNA trans-cleavage (Chen et al., 2018; Li et al., 2019; Pausch et al., 2020). Our previous data indicated that DpbCasX with sgRNAv1 (DpbCasX-v1) shows minimal trans-activity compared to LbCas12a (Liu et al., 2019). Cleavage assays investigating indiscriminate ssDNA trans-cleavage revealed that the trans-activities of the new CasX enzymes and sgRNAs remain minimal, similar to the original DpbCasX-v1 (FIG. 18C).

Figure 18D:
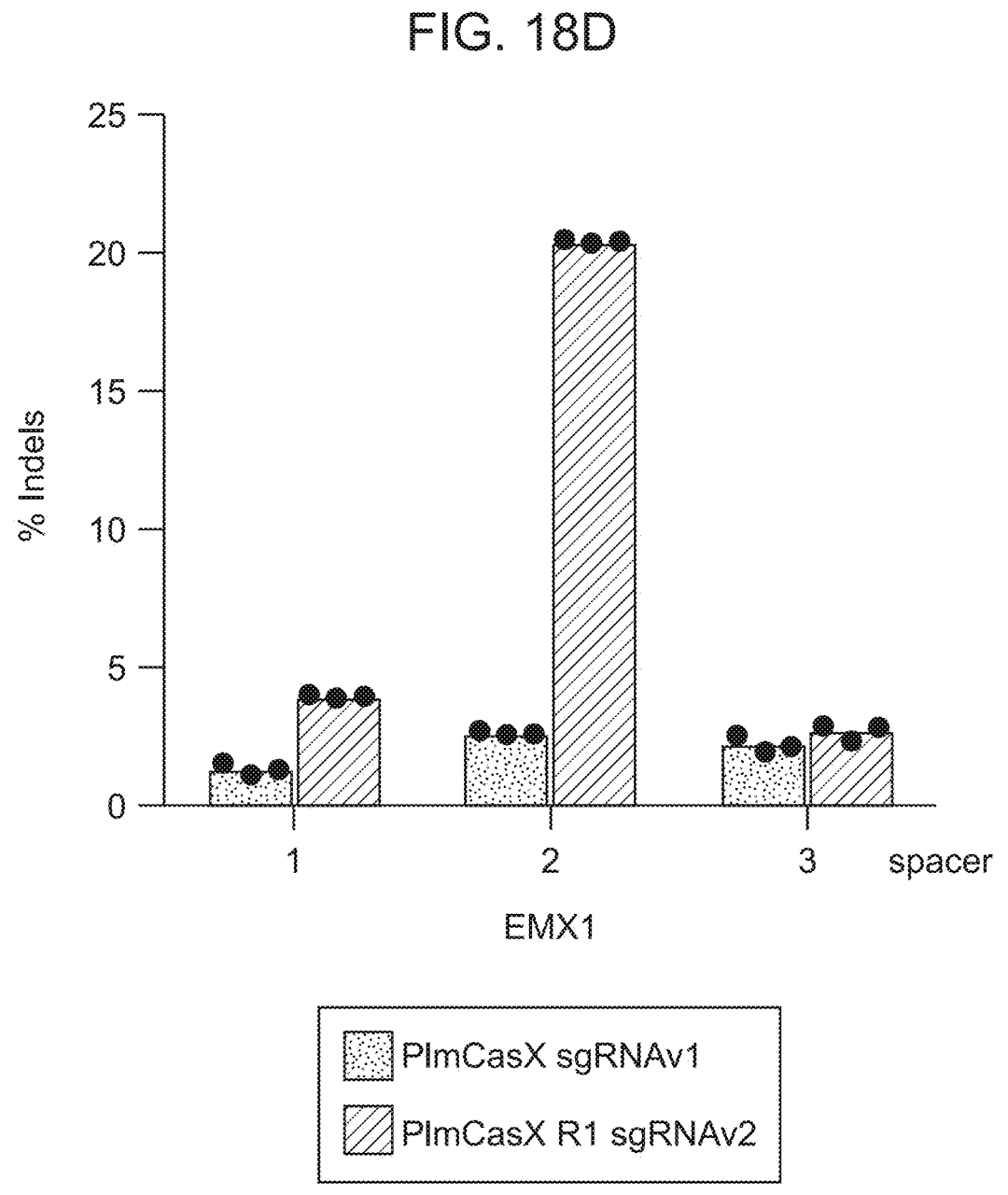
Figure 18E:
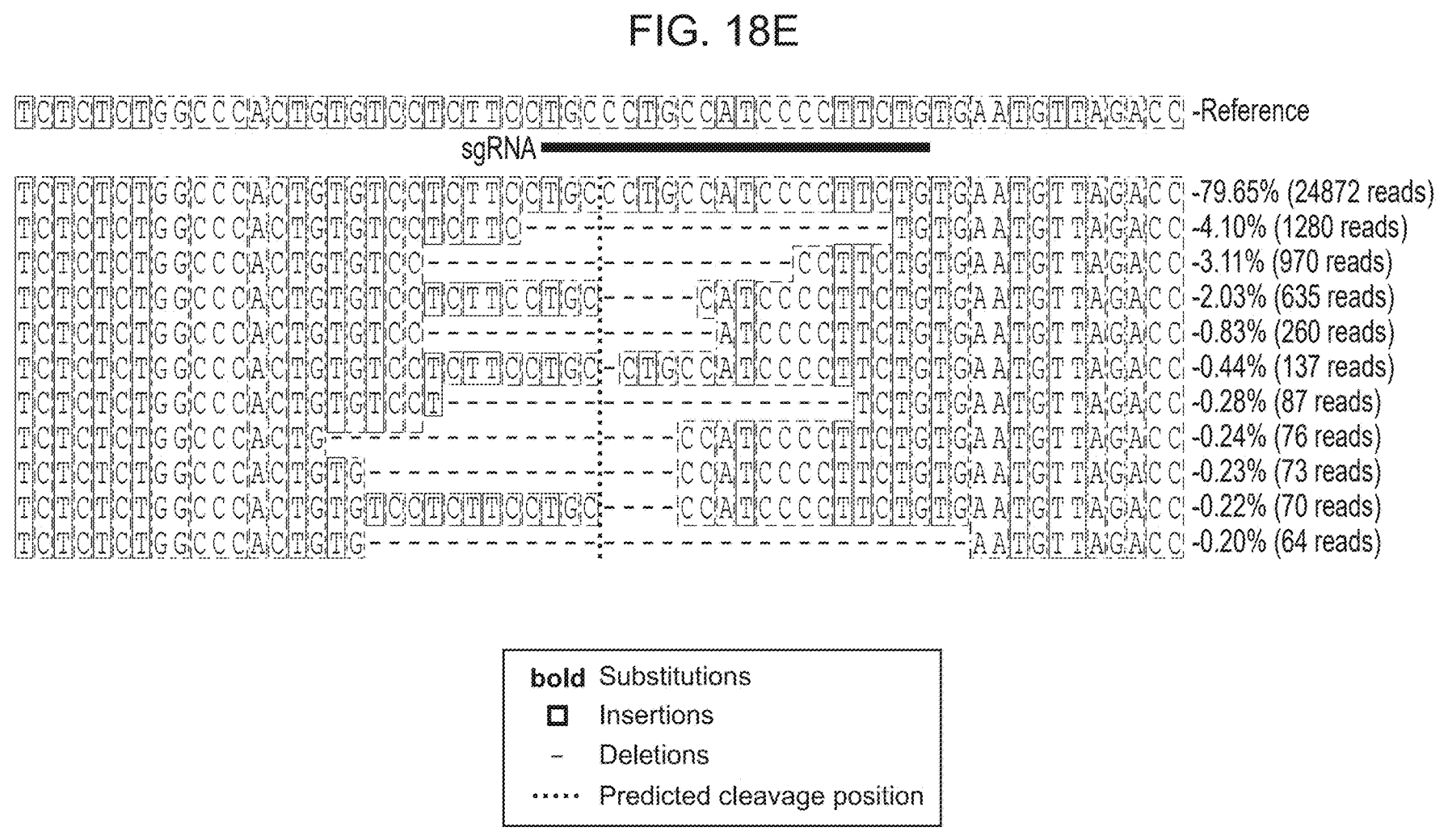

The capacity of PlmCasX-R1-v2, which showed the highest editing efficacy in the fluorescent reporter assay, for endogenous genome editing by targeting the EMX1 gene via plasmid transfection was explored. Next generation sequencing revealed that PlmCasX-R1-v2 generated insertions and deletions (INDELs) at the targeted gene, and notably, showed approximately 7.8-fold higher activity than PlmCasX-v1 for spacer 2 (FIG. 18D). Interestingly, PlmCasX-R1-v2 targeted to EMX1 with spacer 2 generated larger INDELs than seen with other Class II CRISPR nucleases, with the most prevalent INDEL being a 19 bp deletion and the largest INDEL being a 31 bp deletion (FIG. 18E)(Kim et al., 2021; Ran et al., 2015).

FIG. 17A-17B. Improved genome editing by engineered DpbCasX and PlmCasX. (A) Human cell genome editing by DpbCasX, DpbCasX-R3, PlmCasX and PlmCasX-R1 using sgRNAv1 or sgRNAv2 revealed by disruption of genetically encoded GFP. The GFP disruption efficacies for all ten GFP guides are shown (n=3 (except PlmCasX sgRNAv1 9, 10, NT, DpbCasX-R3 sgRNAv1 NT, DpbCasX sgRNAv2 10 and DpbCasX-R3 sgRNAv2 NT; n=2), mean). NT indicates the non-targeting sgRNA. (B) Genome editing efficacy for all ten GFP-targeting sgRNAs as a box and whiskers plot: the box represents the $25^{th}$, $50^{th}$, and $75^{th}$ percentile, the whiskers represent the $10^{th}$ and $9^{th}$ percentile, and outliers are plotted individually.

FIG. 18A-18E. CasX platform with largely enhanced gene editing efficacy. (A) In vitro dsDNA cleavage activity comparison among different sgRNAs by wild type CasX and chimeras. The NTS DNA is $^{32}P$ labeled on the 5' end. (B) Cleavage kinetics analysis was based on the NTS band density from the cleaved fractions compared to the input NTS band density at the reaction time of 0 min (n=3, mean±s.d.). The fractions were collected at 0 min, 2 mins, 5 mins, 10 mins, 15 mins, 20 mins, 40 mins, 1 hr, 2 hrs, 4 hrs and 6 hrs, respectively. k values for DpbCasX-v1, Dpb-CasX-v2, DpbCasX-R3-v2, PlmCasX-v2 and PlmCasX-R1-v2 are 0.05065, 0.2817, 0.4730, 0.04182 and 0.08680 respectively. (C) In vitro trans-ssDNA cleavage activity comparison among different constructs. The trans-ssDNA was ³²P labeled on the 5' end. The fractions were collected at 0 min, 10 mins, 20 mins, 40 mins, 1 hr, 2 hrs, 4 hrs and 6 hrs, respectively (n=3, representative gel shown). (D) Genome editing efficacy comparison between PlmCasX-sgRNAv1 and PlmCasX-R1-sgRNAv2 targeting the EMX1 gene with 3 spacer sequences (1, 2 and 3). Sequences for the three spacers are listed in the table provided in FIG. 19. INDELs were quantified with next generation sequencing of amplicons from the targeted gene site. (E) INDEL distribution generated by PlmCasX-R1-sgRNAv2 with spacer 2 targeting the EMX1 gene.

REFERENCES

Adamcik, J., et al. (2012). Soft Matter 8, 8651-8658.
Burstein, D., et al. (2017). Nature 542, 237.
Cao, et al. (2021). Clinical and translational medicine 11.
Casanal, A., et al. (2020). Protein Science 29, 1069-1078.
Chen, et al. (2010). Nature 578, 229-236.
Doudna, J. A., and Charpentier, E. (2014). Science 346.
Charlesworth, et al. (2019). Nature Medicine 25, 249-254.
Chen, et al. (2018). Science 360, 436-439.
Chen, et al. (2010). Acta Crystallographica Section D: Biological Crystallography 66, 12-21.
Crudele and Chamberlain (2018). Nature Communications 9, 1-3.
Doudna, J. A. (2020). Nature 578, 229-236.
Hille, F., et al. (2018) Cell 172, 1239-1259.
Holm, L., and Laakso, L. M. (2016). Nucleic Acids Research 44, W351-W355
Jiang, F., and Doudna, J. A. (2017). Annual review of biophysics 46, 505-529.
Kim, D. Y., et al. (2021). Nature Biotechnology, 1-9.
Kimanius, D., et al. (2016). Elife 5, e18722.
Kleinstiver, et al. (2019). Nature Biotechnology 37, 276-282.
Koonin, E. V., et al. (2017). Current Opinion in Microbiology 37, 67-78.
Le Rhun, A., et al. (2019). RNA Biology 16, 380-389.
Li, et al. (2019). ACS Synthetic Biology 8, 2228-2237.
Li, et al. (2018). Nature Biotechnology 36, 324-327
Liebschner, D., et al. (2019). Acta Crystallographica Section D: Structural Biology 75, 861-877.
Lin, A., et al. (2017). Elife 6, e24179.
Liu, J.-J., et al. (2019). Nature 566, 218-223.
Makarova, K. S., et al. (2019). Nature Reviews Microbiology, 1-17.
Mastronarde, D. N. (2003). Microscopy and Microanalysis 9, 1182-1183.
Mojica and Rodriguez-Valera (2016). The FEBS Journal 283, 3162-3169.
Pausch, et al. (2020). Science 369, 333-337
Punjani, A., et al. (2017). Nature methods 14, 290.
Ran, et al. (2015). Nature 520, 186-191.
Roberson, E. D. (2019). BMC Genomics 20, 1-5.
Samulski and Muzyczka. (2014). Annual Review of Virology 1, 427-451
Trabuco, L. G., et al. (2009). Methods 49, 174-180.
Wang, et al. (2020). Cell 181, 136-150
Wright, A. V., et al. (2016). Cell 164, 29-44.
Wu, Z., et al. (2021). Nature Chemical Biology, 1-7.
Xu, X., et al. (2021). Molecular Cell. https://doi.org/10.1016/j.molcel.2021.08.008
Yamano, et al. (2016). Cell 165, 949-962.
Yang, et al. (2016). Cell 167, 1814-1828. e1812.
Yang and Patel (2019). Cell Research 29, 345-346
Zetsche, B., et al. (2015). Cell 163, 759-771.
Zhang, L., et al. (2020). Nucleic Acids Research 48, 5037-5053.
Zheng, et al. (2017). Nature Methods 14, 331.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant CRISPR-Cas effector polypeptide comprising an amino acid sequence having at least 85% amino acid sequence identity to SEQ ID NO: 1, wherein the variant CRISPR-Cas effector polypeptide comprises a substitution of the sequence NSNSTEFKSYKSGKQPFVGAWQA (SEQ ID NO:34) of the reference CRISPR-Cas effector polypeptide set forth as SEQ ID NO: 2, wherein said substitution provides for increased binding and/or cleavage of a target nucleic acid compared to the binding and/or cleavage of the target nucleic acid by the reference CRISPR-Cas effector polypeptide.

2. The variant CRISPR-Cas effector polypeptide of claim 1, wherein the variant CRISPR-Cas effector polypeptide exhibits at least 2-fold increased target cleavage of a target nucleic acid compared to the cleavage of the target nucleic acid by the reference CRISPR-Cas effector polypeptide.

3. The variant CRISPR-Cas effector polypeptide of claim 1, the amino acid sequence $X_1$SQEYKX$_2$YX$_3$X$_4$X$_5$KTTGNTDKX$_6$X$_7$FVX$_8$X$_9$WQX$_{10}$ (SEQ ID NO:31), where $X_1$ is Arg, Gln, or Asn; $X_2$ is Lys, His, or Ser; $X_3$ is Gln, Arg, or Asn; $X_4$ is Thr or Ser; $X_5$ is Arg, Asn, Gln, or Gly; $X_6$ is Arg, Gln, or Asn; $X_7$ is Ala, Val, or Pro; $X_8$ is Glu, Asp, or Gly; $X_9$ is Thr, Ser, Ala, or Val; and $X_{10}$ is Ser, Thr, Ala, or Val, replaces the sequence NSN-STEFKSYKSGKQPFVGAWQA (SEQ ID NO:34).

4. The variant CRISPR-Cas effector polypeptide of claim 1, wherein the amino acid sequence RSQEYKKYQTNKTTGNTDKRAFVETWQS (SEQ ID NO:30) replaces the sequence NSN-STEFKSYKSGKQPFVGAWQA (SEQ ID NO:34).

5. The variant CRISPR-Cas effector polypeptide of claim 1, wherein the variant CRISPR-Cas effector polypeptide is a nickase that can cleave only one strand of a double-stranded target nucleic acid.

6. The variant CRISPR-Cas effector polypeptide of claim 1, wherein the variant CRISPR-Cas effector polypeptide is catalytically inactive.

7. The variant CRISPR-Cas effector polypeptide of claim 1, wherein the variant CRISPR-Cas effector polypeptide comprises one or more mutations at a position corresponding to D672, E769, and/or D935 of SEQ ID NO: 1.

8. A composition comprising:
  a) a variant CRISPR-Cas effector polypeptide of claim 1, or a nucleic acid comprising a nucleotide sequence encoding the variant CRISPR-Cas effector polypeptide; and
  b) a guide nucleic acid, or a nucleic acid comprising a nucleotide sequence encoding the guide nucleic acid, wherein the guide nucleic acid comprises: i) an activator region that can bind to and activate the variant CRISPR-Cas effector polypeptide; and ii) a guide sequence that can hybridize with a target region of a target nucleic acid,
  optionally wherein the activator region comprises one or more modifications as set out in Table 1, compared to the following the nucleotide sequence:

```
                                  (SEQ ID NO: 10)
GGCGCGUUUAUUCCAUUACUUUGGAGCCAGUCCCAGCGAC

UAUGUCGUAUGGACGAAGCGCUUAUUUAUCGGAGAGAAAC

CGAUAAGUAAAACGCAUCAAAG.
```

9. The composition of claim 8, wherein the guide nucleic acid comprises the nucleotide sequence:

```
                                  (SEQ ID NO: 90)
GGCGCUUUUAUCUCAUUACUUUGAGAGCCAUCACCAGCGACUAUGUCGU

AUGGGUAAAGCGCUUAUUUAUCGGAGAAACCGAUAAAUAAGAAGCAUCA

AAG(Nₓ),
``` wherein N is any nucleotide and x is an integer from 19 to 30.

10. The composition of claim 8, wherein the guide RNA is a single-molecule guide RNA.

11. The composition of claim 8, wherein the composition comprises a lipid.

12. The composition of claim 8, wherein a) and b) are within a liposome.

13. The composition of claim 8, wherein a) and b) are within a particle.

14. The composition of claim 8, comprising one or more of: a buffer, a nuclease inhibitor, and a protease inhibitor.

15. The composition of claim 8, comprising a DNA donor nucleic acid.

16. A nucleic acid comprising a nucleotide sequence encoding the variant CRISPR-Cas effector polypeptide of claim 1.

17. The nucleic acid of claim 16, wherein the nucleotide sequence is operably linked to a promoter.

18. The nucleic acid of claim 17, wherein the promoter is functional in a eukaryotic cell.

19. The nucleic acid of claim 18, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

20. The nucleic acid of claim 17, wherein the promoter is one or more of: a constitutive promoter, an inducible promoter, a cell type-specific promoter, and a tissue-specific promoter.

21. A recombinant expression vector comprising the nucleic acid of claim 16.

22. The recombinant expression vector of claim 21, wherein the recombinant expression vector is a recombinant adenoassociated viral vector, a recombinant retroviral vector, or a recombinant lentiviral vector.

23. A fusion polypeptide comprising:
  a) a variant CRISPR-Cas effector polypeptide of claim 1; and
  b) one or more heterologous polypeptides.

24. The fusion polypeptide of claim 23, wherein the variant CRISPR-Cas effector polypeptide is a nickase that can cleave only one strand of a double-stranded target nucleic acid.

25. The fusion polypeptide of claim 23, wherein the variant CRISPR-Cas effector polypeptide is catalytically inactive.

26. The fusion polypeptide of claim 24, wherein the variant CRISPR-Cas effector polypeptide comprises one or more mutations at a position corresponding to D672, E769, and/or D935 of SEQ ID NO: 1.

27. The fusion polypeptide of claim 23, wherein the heterologous polypeptide is fused to the N-terminus and/or the C-terminus of the variant CRISPR-Cas effector polypeptide.

28. The fusion polypeptide of claim 23, wherein at least one of the one or more heterologous polypeptides is a nuclear localization signal.

29. The fusion polypeptide of claim 23, wherein the one or more heterologous polypeptides is a targeting polypeptide that provides for binding to a cell surface moiety on a target cell or target cell type.

30. The fusion polypeptide of claim 23, wherein the one or more heterologous polypeptides exhibits an enzymatic activity that modifies target DNA.

31. The fusion polypeptide of claim 30, wherein the heterologous polypeptide exhibits an enzymatic activity selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

32. The fusion polypeptide of claim 30, wherein the heterologous polypeptide exhibits an enzymatic activity selected from: nuclease activity, methyltransferase activity, demethylase activity, deamination activity, depurination activity, integrase activity, transposase activity, and recombinase activity.

33. The fusion polypeptide of claim 23, wherein the heterologous polypeptide exhibits an enzymatic activity that modifies a target polypeptide associated with a target nucleic acid.

34. The fusion polypeptide of claim 33, wherein the heterologous polypeptide exhibits histone modification activity.

35. The fusion polypeptide of claim 33, wherein the heterologous polypeptide exhibits an enzymatic activity selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

36. The fusion polypeptide of claim 23, wherein at least one of the one or more heterologous polypeptides is an endosomal escape polypeptide.

37. The fusion polypeptide of claim 23, wherein at least one of the one or more heterologous polypeptides is a protein that increases or decreases transcription.

38. The fusion polypeptide of claim 37, wherein at least one of the one or more heterologous polypeptides is a transcriptional repressor polypeptide.

39. The fusion polypeptide of claim 37, wherein at least one of the one or more heterologous polypeptides is a transcriptional activation polypeptide.

40. The fusion polypeptide of claim 23, wherein at least one of the one or more heterologous polypeptides is a protein binding polypeptide.

41. A nucleic acid comprising a nucleotide sequence encoding the fusion polypeptide of claim 23.

42. A recombinant expression vector comprising the nucleic acid of claim 41.

43. A cell comprising one or more of:

a) a variant CRISPR-Cas effector polypeptide of claim 1;

b) a nucleic acid comprising a nucleotide sequence encoding a variant CRISPR-Cas effector polypeptide of claim 1;

c) a fusion polypeptide of claim 23;

d) a nucleic acid comprising a nucleotide sequence encoding a fusion polypeptide of claim 23;

e) a guide nucleic acid, wherein the guide nucleic acid comprises: i) an activator region that can bind to and activate the variant CRISPR-Cas effector polypeptide of claim 1; and ii) a guide sequence that can hybridize with a target region of a target nucleic acid; and f) a nucleic acid encoding the guide nucleic acid.

44. The cell of claim 43, wherein the cell is a eukaryotic cell.

45. The cell of claim 44, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

46. The cell of claim 43, wherein the cell is in vitro.

47. The cell of claim 43, wherein the cell is in vivo.

48. A method of modifying a target nucleic acid, the method comprising contacting the target nucleic acid with: a) a variant CRISPR-Cas effector polypeptide of claim 1; and b) a guide nucleic acid, wherein the guide nucleic acid comprises: i) an activator region that can bind to and activate the variant CRISPR-Cas effector polypeptide; and ii) a guide sequence that can hybridize with a target region of a target nucleic acid.

49. The method of claim 48, wherein said modification is cleavage of the target nucleic acid.

50. The method of claim 48, wherein the target nucleic acid is selected from: double stranded DNA, single stranded DNA, RNA, genomic DNA, and extrachromosomal DNA.

51. The method of claim 48, wherein said contacting takes place in vitro outside of a cell.

52. The method of claim 48, wherein said contacting takes place inside of a cell in vitro.

53. The method of claim 48, wherein said contacting takes place inside of a cell in vivo.

54. The method of claim 52, wherein the cell is a eukaryotic cell.

55. The method of claim 54, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

56. The method of claim 52, wherein the cell is a prokaryotic cell.

57. The method of claim 48, wherein said contacting results in genome editing.

58. The method of claim 52, wherein said contacting comprises introducing into the cell:

a) the variant CRISPR-Cas effector polypeptide, or a nucleic acid comprising a nucleotide sequence encoding the variant CRISPR-Cas effector polypeptide; and b) the guide RNA, or a nucleic acid comprising a nucleotide sequence encoding the guide RNA.

59. The method of claim 58, further comprising introducing a DNA donor nucleic acid into the cell.

60. A method of modulating transcription from a target DNA, modifying a target nucleic acid, or modifying a protein associated with a target nucleic acid, the method comprising contacting the target nucleic acid with: a) a fusion polypeptide of claim 23; and b) a guide RNA comprising: i) an activator region that can bind to and activate the variant CRISPR-Cas effector polypeptide; and ii) a guide sequence that can hybridize with a target region of the target nucleic acid.

61. The variant CRISPR-Cas effector polypeptide of claim 7, wherein the variant CRISPR-Cas effector polypeptide comprises one or more mutations corresponding to D672A, E769A, and/or D935A of SEQ ID NO: 1.

62. The method of claim 53, wherein the cell is a eukaryotic cell.

63. The method of claim 62, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

64. The method of claim 53, wherein said contacting comprises introducing into the cell:

a) the variant CRISPR-Cas effector polypeptide, or a nucleic acid comprising a nucleotide sequence encoding the variant CRISPR-Cas effector polypeptide; and b) the guide RNA, or a nucleic acid comprising a nucleotide sequence encoding the guide RNA.

65. The method of claim 64, further comprising introducing a DNA donor nucleic acid into the cell.

* * * * *

SEQUENCE LISTING

```
<160> NUMBER OF SEQ ID NOS: 110

<210> SEQ ID NO 1
<211> LENGTH: 991
<212> TYPE: PRT
<213> ORGANISM: Artificial sequence
<220> FEATURE:
<223> OTHER INFORMATION: synthetic sequence

<400> SEQUENCE: 1

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80
```

-continued

```
Gln Val Tyr Trp Gln Glu Phe Lys Asp Asp His Val Gly Leu Met Cys
                85              90              95

Lys Phe Ala Gln Pro Ala Ser Lys Lys Ile Asp Gln Asn Lys Leu Lys
            100             105             110

Pro Glu Met Asp Glu Lys Gly Asn Leu Thr Thr Ala Gly Phe Ala Cys
            115             120             125

Ser Gln Cys Gly Gln Pro Leu Phe Val Tyr Lys Leu Glu Gln Val Ser
    130             135             140

Glu Lys Gly Lys Ala Tyr Thr Asn Tyr Phe Gly Arg Cys Asn Val Ala
145             150             155             160

Glu His Glu Lys Leu Ile Leu Leu Ala Gln Leu Lys Pro Glu Lys Asp
            165             170             175

Ser Asp Glu Ala Val Thr Tyr Ser Leu Gly Lys Phe Gly Gln Arg Ala
            180             185             190

Leu Asp Phe Tyr Ser Ile His Val Thr Lys Glu Ser Thr His Pro Val
            195             200             205

Lys Pro Leu Ala Gln Ile Ala Gly Asn Arg Tyr Ala Ser Gly Pro Val
    210             215             220

Gly Lys Ala Leu Ser Asp Ala Cys Met Gly Thr Ile Ala Ser Phe Leu
225             230             235             240

Ser Lys Tyr Gln Asp Ile Ile Ile Glu His Gln Lys Val Val Lys Gly
            245             250             255

Asn Gln Lys Arg Leu Glu Ser Leu Arg Glu Leu Ala Gly Lys Glu Asn
            260             265             270

Leu Glu Tyr Pro Ser Val Thr Leu Pro Pro Gln Pro His Thr Lys Glu
            275             280             285

Gly Val Asp Ala Tyr Asn Glu Val Ile Ala Arg Val Arg Met Trp Val
    290             295             300

Asn Leu Asn Leu Trp Gln Lys Leu Lys Leu Ser Arg Asp Asp Ala Lys
305             310             315             320

Pro Leu Leu Arg Leu Lys Gly Phe Pro Ser Phe Pro Val Val Glu Arg
            325             330             335

Arg Glu Asn Glu Val Asp Trp Trp Asn Thr Ile Asn Glu Val Lys Lys
            340             345             350

Leu Ile Asp Ala Lys Arg Asp Met Gly Arg Val Phe Trp Ser Gly Val
            355             360             365

Thr Ala Glu Lys Arg Asn Thr Ile Leu Glu Gly Tyr Asn Tyr Leu Pro
    370             375             380

Asn Glu Asn Asp His Lys Lys Arg Glu Gly Ser Leu Glu Asn Pro Lys
385             390             395             400

Lys Pro Ala Lys Arg Gln Phe Gly Asp Leu Leu Leu Tyr Leu Glu Lys
            405             410             415

Lys Tyr Ala Gly Asp Trp Gly Lys Val Phe Asp Glu Ala Trp Glu Arg
            420             425             430

Ile Asp Lys Lys Ile Ala Gly Leu Thr Ser His Ile Glu Arg Glu Glu
            435             440             445

Ala Arg Asn Ala Glu Asp Ala Gln Ser Lys Ala Val Leu Thr Asp Trp
    450             455             460

Leu Arg Ala Lys Ala Ser Phe Val Leu Glu Arg Leu Lys Glu Met Asp
465             470             475             480

Glu Lys Glu Phe Tyr Ala Cys Glu Ile Gln Leu Gln Lys Trp Tyr Gly
            485             490             495

Asp Leu Arg Gly Asn Pro Phe Ala Val Glu Ala Glu Asn Arg Val Val
```

-continued

```
                    500                 505                 510

Asp Ile Ser Gly Phe Ser Ile Gly Ser Asp Gly His Ser Ile Gln Tyr
            515                 520                 525

Arg Asn Leu Leu Ala Trp Lys Tyr Leu Glu Asn Gly Lys Arg Glu Phe
        530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
                580                 585                 590

Gln Leu Ile Ile Leu Pro Leu Ala Phe Gly Thr Arg Gln Gly Arg Glu
            595                 600                 605

Phe Ile Trp Asn Asp Leu Leu Ser Leu Glu Thr Gly Leu Ile Lys Leu
            610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
                660                 665                 670

Arg Gly Glu Asn Ile Pro Ala Val Ile Ala Leu Thr Asp Pro Glu Gly
                675                 680                 685

Cys Pro Leu Pro Glu Phe Lys Asp Ser Ser Gly Gly Pro Thr Asp Ile
            690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
            755                 760                 765

Glu Asn Leu Ser Arg Gly Phe Gly Arg Gln Gly Lys Arg Thr Phe Met
        770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
            835                 840                 845

Trp Ala Thr Thr Leu Asn Asn Lys Glu Leu Lys Ala Glu Gly Gln Ile
        850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
            900                 905                 910

Arg Phe Ser His Arg Pro Val Gln Glu Gln Phe Val Cys Leu Asp Cys
            915                 920                 925
```

```
Gly His Glu Val His Ala Asp Glu Gln Ala Ala Leu Asn Ile Ala Arg
    930             935             940

Ser Trp Leu Phe Leu Arg Ser Gln Glu Tyr Lys Lys Tyr Gln Thr Asn
945             950             955             960

Lys Thr Thr Gly Asn Thr Asp Lys Arg Ala Phe Val Glu Thr Trp Gln
                965             970             975

Ser Phe Tyr Lys Arg Arg Leu Lys Glu Val Trp Lys Pro Asn Ala
            980             985             990

<210> SEQ ID NO 2
<211> LENGTH: 986
<212> TYPE: PRT
<213> ORGANISM: Artificial sequence
<220> FEATURE:
<223> OTHER INFORMATION: synthetic sequence

<400> SEQUENCE: 2

Met Glu Lys Arg Ile Asn Lys Ile Arg Lys Lys Leu Ser Ala Asp Asn
1               5               10              15

Ala Thr Lys Pro Val Ser Arg Ser Gly Pro Met Lys Thr Leu Leu Val
            20              25              30

Arg Val Met Thr Asp Asp Leu Lys Lys Arg Leu Glu Lys Arg Arg Lys
        35              40              45

Lys Pro Glu Val Met Pro Gln Val Ile Ser Asn Asn Ala Ala Asn Asn
    50              55              60

Leu Arg Met Leu Leu Asp Asp Tyr Thr Lys Met Lys Glu Ala Ile Leu
65              70              75              80

Gln Val Tyr Trp Gln Glu Phe Lys Asp Asp His Val Gly Leu Met Cys
            85              90              95

Lys Phe Ala Gln Pro Ala Ser Lys Lys Ile Asp Gln Asn Lys Leu Lys
        100             105             110

Pro Glu Met Asp Glu Lys Gly Asn Leu Thr Thr Ala Gly Phe Ala Cys
        115             120             125

Ser Gln Cys Gly Gln Pro Leu Phe Val Tyr Lys Leu Glu Gln Val Ser
    130             135             140

Glu Lys Gly Lys Ala Tyr Thr Asn Tyr Phe Gly Arg Cys Asn Val Ala
145             150             155             160

Glu His Glu Lys Leu Ile Leu Leu Ala Gln Leu Lys Pro Glu Lys Asp
            165             170             175

Ser Asp Glu Ala Val Thr Tyr Ser Leu Gly Lys Phe Gly Gln Arg Ala
            180             185             190

Leu Asp Phe Tyr Ser Ile His Val Thr Lys Glu Ser Thr His Pro Val
        195             200             205

Lys Pro Leu Ala Gln Ile Ala Gly Asn Arg Tyr Ala Ser Gly Pro Val
    210             215             220

Gly Lys Ala Leu Ser Asp Ala Cys Met Gly Thr Ile Ala Ser Phe Leu
225             230             235             240

Ser Lys Tyr Gln Asp Ile Ile Ile Glu His Gln Lys Val Val Lys Gly
            245             250             255

Asn Gln Lys Arg Leu Glu Ser Leu Arg Glu Leu Ala Gly Lys Glu Asn
            260             265             270

Leu Glu Tyr Pro Ser Val Thr Leu Pro Pro Gln Pro His Thr Lys Glu
        275             280             285

Gly Val Asp Ala Tyr Asn Glu Val Ile Ala Arg Val Arg Met Trp Val
    290             295             300
```

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
            325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
            355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
            435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
            515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
            565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
    595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
            645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
            675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

-continued

```
Ala Lys Glu Val Glu Gln Arg Arg Ala Gly Gly Tyr Ser Arg Lys Phe
              725                 730                 735

Ala Ser Lys Ser Arg Asn Leu Ala Asp Asp Met Val Arg Asn Ser Ala
              740                 745                 750

Arg Asp Leu Phe Tyr His Ala Val Thr His Asp Ala Val Leu Val Phe
              755                 760                 765

Glu Asn Leu Ser Arg Gly Phe Gly Arg Gln Gly Lys Arg Thr Phe Met
      770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
              805                 810                 815

Gln Tyr Thr Ser Lys Thr Cys Ser Asn Cys Gly Phe Thr Ile Thr Thr
              820                 825                 830

Ala Asp Tyr Asp Gly Met Leu Val Arg Leu Lys Lys Thr Ser Asp Gly
              835                 840                 845

Trp Ala Thr Thr Leu Asn Asn Lys Glu Leu Lys Ala Glu Gly Gln Ile
      850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
              885                 890                 895

Lys Trp Thr Lys Gly Arg Arg Asp Glu Ala Leu Phe Leu Leu Lys Lys
              900                 905                 910

Arg Phe Ser His Arg Pro Val Gln Glu Gln Phe Val Cys Leu Asp Cys
              915                 920                 925

Gly His Glu Val His Ala Asp Glu Gln Ala Ala Leu Asn Ile Ala Arg
      930                 935                 940

Ser Trp Leu Phe Leu Asn Ser Asn Ser Thr Glu Phe Lys Ser Tyr Lys
945                 950                 955                 960

Ser Gly Lys Gln Pro Phe Val Gly Ala Trp Gln Ala Phe Tyr Lys Arg
              965                 970                 975

Arg Leu Lys Glu Val Trp Lys Pro Asn Ala
              980                 985
```

```
<210> SEQ ID NO 3
<211> LENGTH: 985
<212> TYPE: PRT
<213> ORGANISM: Artificial sequence
<220> FEATURE:
<223> OTHER INFORMATION: synthetic sequence

<400> SEQUENCE: 3
```

```
Met Gln Glu Ile Lys Arg Ile Asn Lys Ile Arg Arg Arg Leu Val Lys
1                 5                 10                  15

Asp Ser Asn Thr Lys Lys Ala Gly Lys Thr Gly Pro Met Lys Thr Leu
              20                  25                  30

Leu Val Arg Val Met Thr Pro Asp Leu Arg Glu Arg Leu Glu Asn Leu
              35                  40                  45

Arg Lys Lys Pro Glu Asn Ile Pro Gln Pro Ile Ser Asn Thr Ser Arg
      50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
              85                  90                  95
```

-continued

```
Met Ser Arg Val Ala Gln Pro Ala Pro Lys Asn Ile Asp Gln Arg Lys
            100                 105                 110

Leu Ile Pro Val Lys Asp Gly Asn Glu Arg Leu Thr Ser Ser Gly Phe
            115                 120                 125

Ala Cys Ser Gln Cys Cys Gln Pro Leu Tyr Val Tyr Lys Leu Glu Gln
            130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175

Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
            195                 200                 205

Val Lys Pro Leu Glu Gln Ile Gly Gly Asn Ser Cys Ala Ser Gly Pro
            210                 215                 220

Val Gly Lys Ala Leu Ser Asp Ala Cys Met Gly Ala Val Ala Ser Phe
225                 230                 235                 240

Leu Thr Lys Tyr Gln Asp Ile Ile Leu Glu His Gln Lys Val Ile Lys
                245                 250                 255

Lys Asn Glu Lys Arg Leu Ala Asn Leu Lys Asp Ile Ala Ser Ala Asn
            260                 265                 270

Gly Leu Ala Phe Pro Lys Ile Thr Leu Pro Pro Gln Pro His Thr Lys
            275                 280                 285

Glu Gly Ile Glu Ala Tyr Asn Asn Val Val Ala Gln Ile Val Ile Trp
            290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
            325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
            355                 360                 365

Leu Ala Gly Tyr Lys Arg Gln Glu Ala Leu Leu Pro Tyr Leu Ser Ser
    370                 375                 380

Glu Glu Asp His Lys Lys Arg Glu Gly Ser Leu Glu Asn Pro Lys Lys
385                 390                 395                 400

Phe Ala Arg Tyr Gln Phe Gly Asp Leu Leu Leu His Leu Glu Lys Lys
            405                 410                 415

His Gly Glu Asp Trp Gly Lys Val Tyr Asp Glu Ala Trp Glu Arg Ile
            420                 425                 430

Asp Lys Lys Val Glu Gly Leu Ser Lys His Ile Lys Leu Glu Glu Glu
            435                 440                 445

Arg Arg Ser Glu Asp Ala Gln Ser Lys Ala Ala Leu Thr Asp Trp Leu
    450                 455                 460

Arg Ala Lys Ala Ser Phe Val Ile Glu Gly Leu Lys Glu Ala Asp Lys
465                 470                 475                 480

Asp Glu Phe Cys Arg Cys Glu Leu Lys Leu Gln Lys Trp Tyr Gly Asp
            485                 490                 495

Leu Arg Gly Lys Pro Phe Ala Ile Glu Ala Glu Asn Ser Ile Leu Asp
            500                 505                 510

Ile Ser Gly Phe Ser Lys Gln Tyr Asn Cys Ala Phe Ile Trp Gln Lys
```

-continued

```
              515               520               525

Asp Gly Val Lys Lys Leu Asn Leu Tyr Leu Ile Ile Asn Tyr Phe Lys
    530               535               540

Gly Gly Lys Leu Arg Phe Lys Lys Ile Lys Pro Glu Ala Phe Glu Ala
545               550               555               560

Asn Arg Phe Tyr Thr Val Ile Asn Lys Lys Ser Gly Glu Ile Val Pro
              565               570               575

Met Glu Val Asn Phe Asn Phe Asp Asp Pro Asn Leu Ile Ile Leu Pro
              580               585               590

Leu Ala Phe Gly Lys Arg Gln Gly Arg Glu Phe Ile Trp Asn Asp Leu
              595               600               605

Leu Ser Leu Glu Thr Gly Ser Leu Lys Leu Ala Asn Gly Arg Val Ile
              610               615               620

Glu Lys Thr Leu Tyr Asn Arg Arg Thr Arg Gln Asp Glu Pro Ala Leu
625               630               635               640

Phe Val Ala Leu Thr Phe Glu Arg Arg Glu Val Leu Asp Ser Ser Asn
              645               650               655

Ile Lys Pro Met Asn Leu Ile Gly Ile Asp Arg Gly Glu Asn Ile Pro
              660               665               670

Ala Val Ile Ala Leu Thr Asp Pro Glu Gly Cys Pro Leu Ser Arg Phe
              675               680               685

Lys Asp Ser Leu Gly Asn Pro Thr His Ile Leu Arg Ile Gly Glu Ser
    690               695               700

Tyr Lys Glu Lys Gln Arg Thr Ile Gln Ala Ala Lys Glu Val Glu Gln
705               710               715               720

Arg Arg Ala Gly Gly Tyr Ser Arg Lys Tyr Ala Ser Lys Ala Lys Asn
              725               730               735

Leu Ala Asp Asp Met Val Arg Asn Thr Ala Arg Asp Leu Leu Tyr Tyr
              740               745               750

Ala Val Thr Gln Asp Ala Met Leu Ile Phe Glu Asn Leu Ser Arg Gly
              755               760               765

Phe Gly Arg Gln Gly Lys Arg Thr Phe Met Ala Glu Arg Gln Tyr Thr
              770               775               780

Arg Met Glu Asp Trp Leu Thr Ala Lys Leu Ala Tyr Glu Gly Leu Pro
785               790               795               800

Ser Lys Thr Tyr Leu Ser Lys Thr Leu Ala Gln Tyr Thr Ser Lys Thr
              805               810               815

Cys Ser Asn Cys Gly Phe Thr Ile Thr Ser Ala Asp Tyr Asp Arg Val
              820               825               830

Leu Glu Lys Leu Lys Lys Thr Ala Thr Gly Trp Met Thr Thr Ile Asn
              835               840               845

Gly Lys Glu Leu Lys Val Glu Gly Gln Ile Thr Tyr Tyr Asn Arg Tyr
    850               855               860

Lys Arg Gln Asn Val Val Lys Asp Leu Ser Val Glu Leu Asp Arg Leu
865               870               875               880

Ser Glu Glu Ser Val Asn Asn Asp Ile Ser Ser Trp Thr Lys Gly Arg
              885               890               895

Ser Gly Glu Ala Leu Ser Leu Leu Lys Lys Arg Phe Ser His Arg Pro
              900               905               910

Val Gln Glu Lys Phe Val Cys Leu Asn Cys Gly Phe Glu Thr His Ala
              915               920               925

Asp Glu Gln Ala Ala Leu Asn Ile Ala Arg Ser Trp Leu Phe Leu Arg
    930               935               940
```

-continued

```
Ser Gln Glu Tyr Lys Lys Tyr Gln Thr Asn Lys Thr Thr Gly Asn Thr
945                 950                 955                 960

Asp Lys Arg Ala Phe Val Glu Thr Trp Gln Ser Phe Tyr Arg Lys Lys
                965                 970                 975

Leu Lys Glu Val Trp Lys Pro Ala Val
            980                 985

<210> SEQ ID NO 4
<211> LENGTH: 978
<212> TYPE: PRT
<213> ORGANISM: Artificial sequence
<220> FEATURE:
<223> OTHER INFORMATION: synthetic sequence

<400> SEQUENCE: 4

Met Gln Glu Ile Lys Arg Ile Asn Lys Ile Arg Arg Arg Leu Val Lys
1               5                   10                  15

Asp Ser Asn Thr Lys Lys Ala Gly Lys Thr Gly Pro Met Lys Thr Leu
                20                  25                  30

Leu Val Arg Val Met Thr Pro Asp Leu Arg Glu Arg Leu Glu Asn Leu
            35                  40                  45

Arg Lys Lys Pro Glu Asn Ile Pro Gln Pro Ile Ser Asn Thr Ser Arg
        50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
                100                 105                 110

Leu Ile Pro Val Lys Asp Gly Asn Glu Arg Leu Thr Ser Ser Gly Phe
            115                 120                 125

Ala Cys Ser Gln Cys Cys Gln Pro Leu Tyr Val Tyr Lys Leu Glu Gln
            130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175

Ala Asn Asp Glu Leu Val Thr Tyr Ser Leu Gly Lys Phe Gly Gln Arg
                180                 185                 190

Ala Leu Asp Phe Tyr Ser Ile His Val Thr Arg Glu Ser Asn His Pro
            195                 200                 205

Val Lys Pro Leu Glu Gln Ile Gly Gly Asn Ser Cys Ala Ser Gly Pro
        210                 215                 220

Val Gly Lys Ala Leu Ser Asp Ala Cys Met Gly Ala Val Ala Ser Phe
225                 230                 235                 240

Leu Thr Lys Tyr Gln Asp Ile Ile Leu Glu His Gln Lys Val Ile Lys
                245                 250                 255

Lys Asn Glu Lys Arg Leu Ala Asn Leu Lys Asp Ile Ala Ser Ala Asn
                260                 265                 270

Gly Leu Ala Phe Pro Lys Ile Thr Leu Pro Pro Gln Pro His Thr Lys
            275                 280                 285

Glu Gly Ile Glu Ala Tyr Asn Asn Val Val Ala Gln Ile Val Ile Trp
        290                 295                 300

Val Asn Leu Asn Leu Trp Gln Lys Leu Lys Ile Gly Arg Asp Glu Ala
305                 310                 315                 320
```

-continued

```
Lys Pro Leu Gln Arg Leu Lys Gly Phe Pro Ser Phe Pro Leu Val Glu
             325                 330                 335

Arg Gln Ala Asn Glu Val Asp Trp Trp Asp Met Val Cys Asn Val Lys
             340                 345                 350

Lys Leu Ile Asn Glu Lys Lys Glu Asp Gly Lys Val Phe Trp Gln Asn
             355                 360                 365

Leu Ala Gly Tyr Lys Arg Gln Glu Ala Leu Leu Pro Tyr Leu Ser Ser
        370                 375                 380

Glu Glu Asp Arg Lys Lys Gly Lys Lys Phe Ala Arg Tyr Gln Phe Gly
385                 390                 395                 400

Asp Leu Leu Leu His Leu Glu Lys Lys His Gly Glu Asp Trp Gly Lys
                405                 410                 415

Val Tyr Asp Glu Ala Trp Glu Arg Ile Asp Lys Lys Val Glu Gly Leu
             420                 425                 430

Ser Lys His Ile Lys Leu Glu Glu Glu Arg Arg Ser Glu Asp Ala Gln
             435                 440                 445

Ser Lys Ala Ala Leu Thr Asp Trp Leu Arg Ala Lys Ala Ser Phe Val
        450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
                485                 490                 495

Ile Glu Ala Glu Asn Ser Ile Leu Asp Ile Ser Gly Phe Ser Lys Gln
             500                 505                 510

Tyr Asn Cys Ala Phe Ile Trp Gln Lys Asp Gly Val Lys Lys Leu Asn
             515                 520                 525

Leu Tyr Leu Ile Ile Asn Tyr Phe Lys Gly Gly Lys Leu Arg Phe Lys
        530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
                565                 570                 575

Asp Asp Pro Asn Leu Ile Ile Leu Pro Leu Ala Phe Gly Lys Arg Gln
             580                 585                 590

Gly Arg Glu Phe Ile Trp Asn Asp Leu Leu Ser Leu Glu Thr Gly Ser
        595                 600                 605

Leu Lys Leu Ala Asn Gly Arg Val Ile Glu Lys Thr Leu Tyr Asn Arg
        610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
                645                 650                 655

Gly Ile Asp Arg Gly Glu Asn Ile Pro Ala Val Ile Ala Leu Thr Asp
             660                 665                 670

Pro Glu Gly Cys Pro Leu Ser Arg Phe Lys Asp Ser Leu Gly Asn Pro
             675                 680                 685

Thr His Ile Leu Arg Ile Gly Glu Ser Tyr Lys Glu Lys Gln Arg Thr
        690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735
```

```
Asn Thr Ala Arg Asp Leu Leu Tyr Tyr Ala Val Thr Gln Asp Ala Met
            740                 745                 750

Leu Ile Phe Glu Asn Leu Ser Arg Gly Phe Gly Arg Gln Gly Lys Arg
        755                 760                 765

Thr Phe Met Ala Glu Arg Gln Tyr Thr Arg Met Glu Asp Trp Leu Thr
    770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Ser Ala Asp Tyr Asp Arg Val Leu Glu Lys Leu Lys Lys Thr
            820                 825                 830

Ala Thr Gly Trp Met Thr Thr Ile Asn Gly Lys Glu Leu Lys Val Glu
        835                 840                 845

Gly Gln Ile Thr Tyr Tyr Asn Arg Tyr Lys Arg Gln Asn Val Val Lys
    850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
                885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
        915                 920                 925

Ile Ala Arg Ser Trp Leu Phe Leu Arg Ser Gln Glu Tyr Lys Lys Tyr
    930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
                965                 970                 975

Ala Val
```

```
<210> SEQ ID NO 5
<211> LENGTH: 40
<212> TYPE: DNA
<213> ORGANISM: Artificial sequence
<220> FEATURE:
<223> OTHER INFORMATION: synthetic sequence

<400> SEQUENCE: 5
atcgttatac tttgattttc tgctgcagga tgaaatcccg                          40

<210> SEQ ID NO 6
<211> LENGTH: 40
<212> TYPE: DNA
<213> ORGANISM: Artificial sequence
<220> FEATURE:
<223> OTHER INFORMATION: synthetic sequence

<400> SEQUENCE: 6
cgggatttca tcctgcagca tccccgaccc gtataacgat                          40

<210> SEQ ID NO 7
<211> LENGTH: 122
<212> TYPE: RNA
<213> ORGANISM: Artificial sequence
<220> FEATURE:
<223> OTHER INFORMATION: synthetic sequence
```

-continued

```
<400> SEQUENCE: 7
ggcgcguuua uuccauuacu uuggagccag ucccagcgac uaugucguau ggacgaagcg      60
cuuauuuauc ggagagaaac cgauaaguaa aacgcaucaa aguccugcag cagaaaauca     120
aa                                                                    122

<210> SEQ ID NO 8
<211> LENGTH: 55
<212> TYPE: DNA
<213> ORGANISM: Artificial sequence
<220> FEATURE:
<223> OTHER INFORMATION: synthetic sequence

<400> SEQUENCE: 8
gcccgcggga tttcatcctg cagcagaaaa tcaaagacaa tgaatatttc ggcgc          55

<210> SEQ ID NO 9
<211> LENGTH: 55
<212> TYPE: DNA
<213> ORGANISM: Artificial sequence
<220> FEATURE:
<223> OTHER INFORMATION: synthetic sequence

<400> SEQUENCE: 9
gcgccgaaat attcattgtc tttgattttc tgctgcagga tgaaatcccg cgggc          55

<210> SEQ ID NO 10
<211> LENGTH: 102
<212> TYPE: RNA
<213> ORGANISM: Artificial sequence
<220> FEATURE:
<223> OTHER INFORMATION: synthetic sequence

<400> SEQUENCE: 10
ggcgcguuua uuccauuacu uuggagccag ucccagcgac uaugucguau ggacgaagcg      60
cuuauuuauc ggagagaaac cgauaaguaa aacgcaucaa ag                        102

<210> SEQ ID NO 11
<211> LENGTH: 103
<212> TYPE: RNA
<213> ORGANISM: Artificial sequence
<220> FEATURE:
<223> OTHER INFORMATION: synthetic sequence

<400> SEQUENCE: 11
uggcgcguuu auuccauuac uuuggagcca gucccagcga cuaugucgua uggacgaagc      60
gcuuauuuau cggagagaaa ccgauaaguam aaacgcauca aag                      103

<210> SEQ ID NO 12
<211> LENGTH: 101
<212> TYPE: RNA
<213> ORGANISM: Artificial sequence
<220> FEATURE:
<223> OTHER INFORMATION: synthetic sequence

<400> SEQUENCE: 12
ggcgcuuuua ucucauuacu uugagagcca ucaccagcga cuaugucgua uggguaaagc      60
gcuuauuuau cggagaaacc gauaaauaag aagcaucaaa g                         101

<210> SEQ ID NO 13
<211> LENGTH: 102
<212> TYPE: RNA
<213> ORGANISM: Artificial sequence
```

-continued

<220> FEATURE:
<223> OTHER INFORMATION: synthetic sequence

<400> SEQUENCE: 13
uggcgcuuuu aucucauuac uuugagagcc aucaccagcg acuaugucgu auggguaaag        60
cgcuuauuua ucggagaaac cgauaaauaa gaagcaucaa ag                          102

<210> SEQ ID NO 14
<211> LENGTH: 105
<212> TYPE: RNA
<213> ORGANISM: Artificial sequence
<220> FEATURE:
<223> OTHER INFORMATION: synthetic sequence

<400> SEQUENCE: 14
uacuggcgcu uuuaucucau uacuuugaga gccaucacca gcgacuaugu cguauggguua       60 aagcgcuuau uuaucggaga aaccgauaaa uaagaagcau caaag                       105

<210> SEQ ID NO 15
<211> LENGTH: 121
<212> TYPE: RNA
<213> ORGANISM: Artificial sequence
<220> FEATURE:
<223> OTHER INFORMATION: synthetic sequence

<400> SEQUENCE: 15
ggcgcuuuua ucucauuacu uugagagcca ucaccagcga cuaugucgua uggguaaagc        60
gcuuauuuau cggagaaacc gauaaauaag aagcaucaaa guccugcagc agaaaaucaa       120
a                                                                        121

<210> SEQ ID NO 16
<211> LENGTH: 50
<212> TYPE: DNA
<213> ORGANISM: Artificial sequence
<220> FEATURE:
<223> OTHER INFORMATION: synthetic sequence

<400> SEQUENCE: 16
gtttatttac tttagtcact ccaggattcc aatagatatt tactttgaag                   50

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17
ccggggtggt gcccatcctg                                                    20

<210> SEQ ID NO 18
<211> LENGTH: 20
<212> TYPE: DNA
<213> ORGANISM: Artificial sequence
<220> FEATURE:
<223> OTHER INFORMATION: synthetic sequence

<400> SEQUENCE: 18
gcgtgtccgg cgagggcgag                                                    20

<210> SEQ ID NO 19
<211> LENGTH: 20
<212> TYPE: DNA

-continued

```
<213> ORGANISM: Artificial sequence
<220> FEATURE:
<223> OTHER INFORMATION: synthetic sequence

<400> SEQUENCE: 19
gggtcagctt gccgtaggtg                                              20

<210> SEQ ID NO 20
<211> LENGTH: 20
<212> TYPE: DNA
<213> ORGANISM: Artificial sequence
<220> FEATURE:
<223> OTHER INFORMATION: synthetic sequence

<400> SEQUENCE: 20
tctgcaccac cggcaagctg                                              20

<210> SEQ ID NO 21
<211> LENGTH: 20
<212> TYPE: DNA
<213> ORGANISM: Artificial sequence
<220> FEATURE:
<223> OTHER INFORMATION: synthetic sequence

<400> SEQUENCE: 21
gccgctaccc cgaccacatg                                              20

<210> SEQ ID NO 22
<211> LENGTH: 20
<212> TYPE: DNA
<213> ORGANISM: Artificial sequence
<220> FEATURE:
<223> OTHER INFORMATION: synthetic sequence

<400> SEQUENCE: 22
ggcatggcgg acttgaagaa                                              20

<210> SEQ ID NO 23
<211> LENGTH: 20
<212> TYPE: DNA
<213> ORGANISM: Artificial sequence
<220> FEATURE:
<223> OTHER INFORMATION: synthetic sequence

<400> SEQUENCE: 23
cctcggcgcg ggtcttgtag                                              20

<210> SEQ ID NO 24
<211> LENGTH: 20
<212> TYPE: DNA
<213> ORGANISM: Artificial sequence
<220> FEATURE:
<223> OTHER INFORMATION: synthetic sequence

<400> SEQUENCE: 24
agggcgacac cctggtgaac                                              20

<210> SEQ ID NO 25
<211> LENGTH: 20
<212> TYPE: DNA
<213> ORGANISM: Artificial sequence
<220> FEATURE:
<223> OTHER INFORMATION: synthetic sequence

<400> SEQUENCE: 25
gctcgatgcg gttcaccagg                                              20
```

```
<210> SEQ ID NO 26
<211> LENGTH: 20
<212> TYPE: DNA
<213> ORGANISM: Artificial sequence
<220> FEATURE:
<223> OTHER INFORMATION: synthetic sequence

<400> SEQUENCE: 26
aggaggacgg caacatcctg                                                    20

<210> SEQ ID NO 27
<211> LENGTH: 20
<212> TYPE: DNA
<213> ORGANISM: Artificial sequence
<220> FEATURE:
<223> OTHER INFORMATION: synthetic sequence

<400> SEQUENCE: 27
ctctggccca ctgtgtcctc                                                    20

<210> SEQ ID NO 28
<211> LENGTH: 20
<212> TYPE: DNA
<213> ORGANISM: Artificial sequence
<220> FEATURE:
<223> OTHER INFORMATION: synthetic sequence

<400> SEQUENCE: 28
cagaagggga tggcagggca                                                    20

<210> SEQ ID NO 29
<211> LENGTH: 20
<212> TYPE: DNA
<213> ORGANISM: Artificial sequence
<220> FEATURE:
<223> OTHER INFORMATION: synthetic sequence

<400> SEQUENCE: 29
cctgggccag ggagggaggg                                                    20

<210> SEQ ID NO 30
<211> LENGTH: 28
<212> TYPE: PRT
<213> ORGANISM: Artificial sequence
<220> FEATURE:
<223> OTHER INFORMATION: synthetic sequence

<400> SEQUENCE: 30

Arg Ser Gln Glu Tyr Lys Lys Tyr Gln Thr Asn Lys Thr Thr Gly Asn
1               5                   10                  15

Thr Asp Lys Arg Ala Phe Val Glu Thr Trp Gln Ser
            20                  25

<210> SEQ ID NO 31
<211> LENGTH: 28
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: Xaa is Arg, Gln, or Asn
<220> FEATURE:
<221> NAME/KEY: SITE
<222> LOCATION: (7)..(7)
```

```
<223> OTHER INFORMATION: Xaa is Lys, His, or Ser
<220> FEATURE:
<221> NAME/KEY: SITE
<222> LOCATION: (9)..(9)
<223> OTHER INFORMATION: Xaa is Gln, Arg, or Asn
<220> FEATURE:
<221> NAME/KEY: SITE
<222> LOCATION: (10)..(10)
<223> OTHER INFORMATION: Xaa is Thr or Ser
<220> FEATURE:
<221> NAME/KEY: SITE
<222> LOCATION: (11)..(11)
<223> OTHER INFORMATION: Xaa is Arg, Asn, Gln, or Gly
<220> FEATURE:
<221> NAME/KEY: SITE
<222> LOCATION: (20)..(20)
<223> OTHER INFORMATION: Xaa is Arg, Gln, or Asn
<220> FEATURE:
<221> NAME/KEY: SITE
<222> LOCATION: (21)..(21)
<223> OTHER INFORMATION: Xaa is Ala, Val, or Pro
<220> FEATURE:
<221> NAME/KEY: SITE
<222> LOCATION: (24)..(24)
<223> OTHER INFORMATION: Xaa is Glu, Asp, or Gly
<220> FEATURE:
<221> NAME/KEY: SITE
<222> LOCATION: (25)..(25)
<223> OTHER INFORMATION: Xaa is Thr, Ser, Ala, or Val
<220> FEATURE:
<221> NAME/KEY: SITE
<222> LOCATION: (28)..(28)
<223> OTHER INFORMATION: Xaa is Ser, Thr, Ala, or Val

<400> SEQUENCE: 31

Xaa Ser Gln Glu Tyr Lys Xaa Tyr Xaa Xaa Xaa Lys Thr Thr Gly Asn
1               5                   10                  15

Thr Asp Lys Xaa Xaa Phe Val Xaa Xaa Trp Gln Xaa
            20                  25

<210> SEQ ID NO 32
<211> LENGTH: 14
<212> TYPE: PRT
<213> ORGANISM: Artificial sequence
<220> FEATURE:
<223> OTHER INFORMATION: synthetic sequence

<400> SEQUENCE: 32

Phe Tyr Lys Arg Arg Leu Lys Glu Val Trp Lys Pro Asn Ala
1               5                   10

<210> SEQ ID NO 33
<211> LENGTH: 57
<212> TYPE: PRT
<213> ORGANISM: Artificial sequence
<220> FEATURE:
<223> OTHER INFORMATION: synthetic sequence

<400> SEQUENCE: 33

Asp Glu Gln Ala Ala Leu Asn Ile Ala Arg Ser Trp Leu Phe Leu Phe
1               5                   10                  15

Arg Ser Gln Glu Tyr Lys Lys Tyr Gln Thr Asn Lys Thr Thr Gly Asn
                20                  25                  30

Thr Asp Lys Arg Ala Phe Val Glu Thr Trp Gln Ser Tyr Lys Arg Arg
            35                  40                  45

Leu Lys Glu Val Trp Lys Pro Asn Ala
    50                  55

<210> SEQ ID NO 34
```

```
<211> LENGTH: 23
<212> TYPE: PRT
<213> ORGANISM: Artificial sequence
<220> FEATURE:
<223> OTHER INFORMATION: synthetic sequence

<400> SEQUENCE: 34

Asn Ser Asn Ser Thr Glu Phe Lys Ser Tyr Lys Ser Gly Lys Gln Pro
1               5                   10                  15

Phe Val Gly Ala Trp Gln Ala
            20

<210> SEQ ID NO 35
<211> LENGTH: 11
<212> TYPE: PRT
<213> ORGANISM: Artificial sequence
<220> FEATURE:
<223> OTHER INFORMATION: synthetic sequence

<400> SEQUENCE: 35

His Lys Lys Arg Glu Gly Ser Leu Glu Asn Pro
1               5                   10

<210> SEQ ID NO 36
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: Xaa is His or Arg
<220> FEATURE:
<221> NAME/KEY: SITE
<222> LOCATION: (7)..(7)
<223> OTHER INFORMATION: Xaa is Ser or Thr
<220> FEATURE:
<221> NAME/KEY: SITE
<222> LOCATION: (8)..(8)
<223> OTHER INFORMATION: Xaa is Leu, Val, or Ile
<220> FEATURE:
<221> NAME/KEY: SITE
<222> LOCATION: (10)..(10)
<223> OTHER INFORMATION: Xaa is Asn, Arg, or Gln

<400> SEQUENCE: 36

Xaa Lys Lys Arg Glu Gly Xaa Xaa Glu Xaa Pro
1               5                   10

<210> SEQ ID NO 37
<211> LENGTH: 184
<212> TYPE: PRT
<213> ORGANISM: Artificial sequence
<220> FEATURE:
<223> OTHER INFORMATION: synthetic sequence

<400> SEQUENCE: 37

Pro Leu Val Glu Arg Gln Ala Asn Glu Val Asp Trp Trp Asp Met Val
1               5                   10                  15

Cys Asn Val Lys Lys Leu Ile Asn Glu Lys Lys Glu Asp Gly Lys Val
            20                  25                  30

Phe Trp Gln Asn Leu Ala Gly Tyr Lys Arg Gln Glu Ala Leu Leu Pro
        35                  40                  45

Tyr Leu Ser Ser Glu Glu Asp His Lys Lys Arg Glu Gly Ser Leu Glu
    50                  55                  60

Asn Pro Lys Lys Phe Ala Arg Tyr Gln Phe Gly Asp Leu Leu Leu His
```

-continued

```
65              70              75              80

Leu Glu Lys Lys His Gly Glu Asp Trp Gly Lys Val Tyr Asp Glu Ala
                85              90              95

Trp Glu Arg Ile Asp Lys Lys Val Glu Gly Leu Ser Lys His Ile Lys
            100             105             110

Leu Glu Glu Glu Arg Arg Ser Glu Asp Ala Gln Ser Lys Ala Ala Leu
        115             120             125

Thr Asp Trp Leu Arg Ala Lys Ala Ser Phe Val Ile Glu Gly Leu Lys
    130             135             140

Glu Ala Asp Lys Asp Glu Phe Cys Arg Cys Glu Leu Lys Leu Gln Lys
145             150             155             160

Trp Tyr Gly Asp Leu Arg Gly Lys Pro Phe Ala Ile Glu Ala Glu Asn
            165             170             175

Ser Ile Leu Asp Ile Ser Gly Phe
            180
```

```
<210> SEQ ID NO 38
<211> LENGTH: 4
<212> TYPE: PRT
<213> ORGANISM: Artificial sequence
<220> FEATURE:
<223> OTHER INFORMATION: synthetic sequence

<400> SEQUENCE: 38

Arg Lys Lys Gly
1
```

```
<210> SEQ ID NO 39
<211> LENGTH: 84
<212> TYPE: PRT
<213> ORGANISM: Artificial sequence
<220> FEATURE:
<223> OTHER INFORMATION: synthetic sequence

<400> SEQUENCE: 39

Met Ala Ser Met Ile Ser Ser Ser Ala Val Thr Thr Val Ser Arg Ala
1               5               10              15

Ser Arg Gly Gln Ser Ala Ala Met Ala Pro Phe Gly Gly Leu Lys Ser
            20              25              30

Met Thr Gly Phe Pro Val Arg Lys Val Asn Thr Asp Ile Thr Ser Ile
        35              40              45

Thr Ser Asn Gly Gly Arg Val Lys Cys Met Gln Val Trp Pro Pro Ile
    50              55              60

Gly Lys Lys Lys Phe Glu Thr Leu Ser Tyr Leu Pro Pro Leu Thr Arg
65              70              75              80

Asp Ser Arg Ala
```

```
<210> SEQ ID NO 40
<211> LENGTH: 57
<212> TYPE: PRT
<213> ORGANISM: Artificial sequence
<220> FEATURE:
<223> OTHER INFORMATION: synthetic sequence

<400> SEQUENCE: 40

Met Ala Ser Met Ile Ser Ser Ser Ala Val Thr Thr Val Ser Arg Ala
1               5               10              15

Ser Arg Gly Gln Ser Ala Ala Met Ala Pro Phe Gly Gly Leu Lys Ser
            20              25              30
```

```
Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 41
<211> LENGTH: 85
<212> TYPE: PRT
<213> ORGANISM: Artificial sequence
<220> FEATURE:
<223> OTHER INFORMATION: synthetic sequence

<400> SEQUENCE: 41

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 42
<211> LENGTH: 76
<212> TYPE: PRT
<213> ORGANISM: Artificial sequence
<220> FEATURE:
<223> OTHER INFORMATION: synthetic sequence

<400> SEQUENCE: 42

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 43
<211> LENGTH: 76
<212> TYPE: PRT
<213> ORGANISM: Artificial sequence
<220> FEATURE:
<223> OTHER INFORMATION: synthetic sequence

<400> SEQUENCE: 43

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
```

```
              50              55              60

Pro Leu Lys Val Met Ser Ser Val Ser Thr Ala Cys
65              70              75

<210> SEQ ID NO 44
<211> LENGTH: 72
<212> TYPE: PRT
<213> ORGANISM: Artificial sequence
<220> FEATURE:
<223> OTHER INFORMATION: synthetic sequence

<400> SEQUENCE: 44

Met Ala Gln Ile Asn Asn Met Ala Gln Gly Ile Gln Thr Leu Asn Pro
1               5               10              15

Asn Ser Asn Phe His Lys Pro Gln Val Pro Lys Ser Ser Ser Phe Leu
            20              25              30

Val Phe Gly Ser Lys Lys Leu Lys Asn Ser Ala Asn Ser Met Leu Val
        35              40              45

Leu Lys Lys Asp Ser Ile Phe Met Gln Leu Phe Cys Ser Phe Arg Ile
        50              55              60

Ser Ala Ser Val Ala Thr Ala Cys
65              70

<210> SEQ ID NO 45
<211> LENGTH: 69
<212> TYPE: PRT
<213> ORGANISM: Artificial sequence
<220> FEATURE:
<223> OTHER INFORMATION: synthetic sequence

<400> SEQUENCE: 45

Met Ala Ala Leu Val Thr Ser Gln Leu Ala Thr Ser Gly Thr Val Leu
1               5               10              15

Ser Val Thr Asp Arg Phe Arg Arg Pro Gly Phe Gln Gly Leu Arg Pro
            20              25              30

Arg Asn Pro Ala Asp Ala Ala Leu Gly Met Arg Thr Val Gly Ala Ser
        35              40              45

Ala Ala Pro Lys Gln Ser Arg Lys Pro His Arg Phe Asp Arg Arg Cys
        50              55              60

Leu Ser Met Val Val
65

<210> SEQ ID NO 46
<211> LENGTH: 77
<212> TYPE: PRT
<213> ORGANISM: Artificial sequence
<220> FEATURE:
<223> OTHER INFORMATION: synthetic sequence

<400> SEQUENCE: 46

Met Ala Ala Leu Thr Thr Ser Gln Leu Ala Thr Ser Ala Thr Gly Phe
1               5               10              15

Gly Ile Ala Asp Arg Ser Ala Pro Ser Ser Leu Leu Arg His Gly Phe
            20              25              30

Gln Gly Leu Lys Pro Arg Ser Pro Ala Gly Gly Asp Ala Thr Ser Leu
        35              40              45

Ser Val Thr Thr Ser Ala Arg Ala Thr Pro Lys Gln Gln Arg Ser Val
        50              55              60

Gln Arg Gly Ser Arg Arg Phe Pro Ser Val Val Val Cys
65              70              75
```

<210> SEQ ID NO 47
<211> LENGTH: 57
<212> TYPE: PRT
<213> ORGANISM: Artificial sequence
<220> FEATURE:
<223> OTHER INFORMATION: synthetic sequence

<400> SEQUENCE: 47

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 48
<211> LENGTH: 65
<212> TYPE: PRT
<213> ORGANISM: Artificial sequence
<220> FEATURE:
<223> OTHER INFORMATION: synthetic sequence

<400> SEQUENCE: 48

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65

<210> SEQ ID NO 49
<211> LENGTH: 72
<212> TYPE: PRT
<213> ORGANISM: Artificial sequence
<220> FEATURE:
<223> OTHER INFORMATION: synthetic sequence

<400> SEQUENCE: 49

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 50
<211> LENGTH: 20
<212> TYPE: PRT
<213> ORGANISM: Artificial sequence
<220> FEATURE:

```
<223> OTHER INFORMATION: synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 50

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 51
<211> LENGTH: 20
<212> TYPE: PRT
<213> ORGANISM: Artificial sequence
<220> FEATURE:
<223> OTHER INFORMATION: synthetic sequence

<400> SEQUENCE: 51

Gly Leu Phe His Ala Leu Leu His Leu Leu His Ser Leu Trp His Leu
1               5                   10                  15

Leu Leu His Ala
            20

<210> SEQ ID NO 52
<211> LENGTH: 7
<212> TYPE: PRT
<213> ORGANISM: SV40 virus

<400> SEQUENCE: 52

Pro Lys Lys Lys Arg Lys Val
1               5

<210> SEQ ID NO 53
<211> LENGTH: 16
<212> TYPE: PRT
<213> ORGANISM: Unknown
<220> FEATURE:
<223> OTHER INFORMATION: NLS from nucleoplasmin

<400> SEQUENCE: 53

Lys Arg Pro Ala Ala Thr Lys Lys Ala Gly Gln Ala Lys Lys Lys Lys
1               5                   10                  15

<210> SEQ ID NO 54
<211> LENGTH: 9
<212> TYPE: PRT
<213> ORGANISM: Unknown
<220> FEATURE:
<223> OTHER INFORMATION: c-myc NLS

<400> SEQUENCE: 54
```

```
Pro Ala Ala Lys Arg Val Lys Leu Asp
1               5

<210> SEQ ID NO 55
<211> LENGTH: 11
<212> TYPE: PRT
<213> ORGANISM: Unknown
<220> FEATURE:
<223> OTHER INFORMATION: c-myc NLS

<400> SEQUENCE: 55

Arg Gln Arg Arg Asn Glu Leu Lys Arg Ser Pro
1               5                   10

<210> SEQ ID NO 56
<211> LENGTH: 38
<212> TYPE: PRT
<213> ORGANISM: Unknown
<220> FEATURE:
<223> OTHER INFORMATION: hRNPA1 M9 NLS

<400> SEQUENCE: 56

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 57
<211> LENGTH: 42
<212> TYPE: PRT
<213> ORGANISM: Unknown
<220> FEATURE:
<223> OTHER INFORMATION: IBB domain from importin-alpha

<400> SEQUENCE: 57

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 58
<211> LENGTH: 8
<212> TYPE: PRT
<213> ORGANISM: Unknown
<220> FEATURE:
<223> OTHER INFORMATION: myoma T protein

<400> SEQUENCE: 58

Val Ser Arg Lys Arg Pro Arg Pro
1               5

<210> SEQ ID NO 59
<211> LENGTH: 8
<212> TYPE: PRT
<213> ORGANISM: Unknown
<220> FEATURE:
<223> OTHER INFORMATION: myoma T protein

<400> SEQUENCE: 59

Pro Pro Lys Lys Ala Arg Glu Asp
```

-continued

```
1               5

<210> SEQ ID NO 60
<211> LENGTH: 8
<212> TYPE: PRT
<213> ORGANISM: Homo sapiens

<400> SEQUENCE: 60

Pro Gln Pro Lys Lys Lys Pro Leu
1               5

<210> SEQ ID NO 61
<211> LENGTH: 12
<212> TYPE: PRT
<213> ORGANISM: Mus musculus

<400> SEQUENCE: 61

Ser Ala Leu Ile Lys Lys Lys Lys Lys Met Ala Pro
1               5                   10

<210> SEQ ID NO 62
<211> LENGTH: 5
<212> TYPE: PRT
<213> ORGANISM: Influenza virus

<400> SEQUENCE: 62

Asp Arg Leu Arg Arg
1               5

<210> SEQ ID NO 63
<211> LENGTH: 7
<212> TYPE: PRT
<213> ORGANISM: Influenza virus

<400> SEQUENCE: 63

Pro Lys Gln Lys Lys Arg Lys
1               5

<210> SEQ ID NO 64
<211> LENGTH: 10
<212> TYPE: PRT
<213> ORGANISM: Hepatitus virus

<400> SEQUENCE: 64

Arg Lys Leu Lys Lys Lys Ile Lys Lys Leu
1               5                   10

<210> SEQ ID NO 65
<211> LENGTH: 10
<212> TYPE: PRT
<213> ORGANISM: Mus musculus

<400> SEQUENCE: 65

Arg Glu Lys Lys Lys Phe Leu Lys Arg Arg
1               5                   10

<210> SEQ ID NO 66
<211> LENGTH: 20
<212> TYPE: PRT
<213> ORGANISM: Homo sapiens

<400> SEQUENCE: 66

Lys Arg Lys Gly Asp Glu Val Asp Gly Val Asp Glu Val Ala Lys Lys
1               5                   10                  15
```

Lys Ser Lys Lys
            20

<210> SEQ ID NO 67
<211> LENGTH: 17
<212> TYPE: PRT
<213> ORGANISM: Homo sapiens

<400> SEQUENCE: 67

Arg Lys Cys Leu Gln Ala Gly Met Asn Leu Glu Ala Arg Lys Thr Lys
1               5                   10                  15

Lys

<210> SEQ ID NO 68
<211> LENGTH: 11
<212> TYPE: PRT
<213> ORGANISM: Human immunodeficiency virus type 1

<400> SEQUENCE: 68

Tyr Gly Arg Lys Lys Arg Arg Gln Arg Arg Arg
1               5                   10

<210> SEQ ID NO 69
<211> LENGTH: 12
<212> TYPE: PRT
<213> ORGANISM: Artificial sequence
<220> FEATURE:
<223> OTHER INFORMATION: synthetic sequence

<400> SEQUENCE: 69

Arg Arg Gln Arg Arg Thr Ser Lys Leu Met Lys Arg
1               5                   10

<210> SEQ ID NO 70
<211> LENGTH: 27
<212> TYPE: PRT
<213> ORGANISM: Unknown
<220> FEATURE:
<223> OTHER INFORMATION: Transportan

<400> SEQUENCE: 70

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 71
<211> LENGTH: 33
<212> TYPE: PRT
<213> ORGANISM: Artificial sequence
<220> FEATURE:
<223> OTHER INFORMATION: synthetic sequence

<400> SEQUENCE: 71

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 72
<211> LENGTH: 16
<212> TYPE: PRT
<213> ORGANISM: Artificial sequence -continued

```
<220> FEATURE:
<223> OTHER INFORMATION: synthetic sequence

<400> SEQUENCE: 72

Arg Gln Ile Lys Ile Trp Phe Gln Asn Arg Arg Met Lys Trp Lys Lys
1               5                   10                  15

<210> SEQ ID NO 73
<211> LENGTH: 9
<212> TYPE: PRT
<213> ORGANISM: Artificial sequence
<220> FEATURE:
<223> OTHER INFORMATION: synthetic sequence

<400> SEQUENCE: 73

Arg Lys Lys Arg Arg Gln Arg Arg Arg
1               5

<210> SEQ ID NO 74
<211> LENGTH: 8
<212> TYPE: PRT
<213> ORGANISM: Artificial sequence
<220> FEATURE:
<223> OTHER INFORMATION: synthetic sequence

<400> SEQUENCE: 74

Arg Lys Lys Arg Arg Gln Arg Arg
1               5

<210> SEQ ID NO 75
<211> LENGTH: 11
<212> TYPE: PRT
<213> ORGANISM: Artificial sequence
<220> FEATURE:
<223> OTHER INFORMATION: synthetic sequence

<400> SEQUENCE: 75

Tyr Ala Arg Ala Ala Ala Arg Gln Ala Arg Ala
1               5                   10

<210> SEQ ID NO 76
<211> LENGTH: 11
<212> TYPE: PRT
<213> ORGANISM: Artificial sequence
<220> FEATURE:
<223> OTHER INFORMATION: synthetic sequence

<400> SEQUENCE: 76

Thr His Arg Leu Pro Arg Arg Arg Arg Arg Arg
1               5                   10

<210> SEQ ID NO 77
<211> LENGTH: 11
<212> TYPE: PRT
<213> ORGANISM: Artificial sequence
<220> FEATURE:
<223> OTHER INFORMATION: synthetic sequence

<400> SEQUENCE: 77

Gly Gly Arg Arg Ala Arg Arg Arg Arg Arg Arg
1               5                   10

<210> SEQ ID NO 78
<211> LENGTH: 5
<212> TYPE: PRT
<213> ORGANISM: Artificial sequence
<220> FEATURE:
```

<223> OTHER INFORMATION: synthetic sequence

<400> SEQUENCE: 78

Gly Ser Gly Gly Ser
1               5

<210> SEQ ID NO 79
<211> LENGTH: 6
<212> TYPE: PRT
<213> ORGANISM: Artificial sequence
<220> FEATURE:
<223> OTHER INFORMATION: synthetic sequence

<400> SEQUENCE: 79

Gly Gly Ser Gly Gly Ser
1               5

<210> SEQ ID NO 80
<211> LENGTH: 40
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (5)..(8)
<223> OTHER INFORMATION: The amino acids at positions 5 to 8 are either
      present or absent
<220> FEATURE:
<221> NAME/KEY: SITE
<222> LOCATION: (9)..(12)
<223> OTHER INFORMATION: The amino acids at positions 9 to 12 are either
      present or absent
<220> FEATURE:
<221> NAME/KEY: SITE
<222> LOCATION: (13)..(16)
<223> OTHER INFORMATION: The amino acids at positions 13 to 16 are
      either present or absent
<220> FEATURE:
<221> NAME/KEY: SITE
<222> LOCATION: (17)..(20)
<223> OTHER INFORMATION: The amino acids at positions 17 to 20 are
      either present or absent
<220> FEATURE:
<221> NAME/KEY: SITE
<222> LOCATION: (21)..(24)
<223> OTHER INFORMATION: The amino acids at positions 21 to 24 are
      either present or absent
<220> FEATURE:
<221> NAME/KEY: SITE
<222> LOCATION: (25)..(28)
<223> OTHER INFORMATION: The amino acids at positions 25 to 28 are
      either present or absent
<220> FEATURE:
<221> NAME/KEY: SITE
<222> LOCATION: (29)..(32)
<223> OTHER INFORMATION: The amino acids at positions 29 to 32 are
      either present or absent
<220> FEATURE:
<221> NAME/KEY: SITE
<222> LOCATION: (33)..(36)
<223> OTHER INFORMATION: The amino acids at positions 33 to 36 are
      either present or absent
<220> FEATURE:
<221> NAME/KEY: SITE
<222> LOCATION: (37)..(40)
<223> OTHER INFORMATION: The amino acids at positions 37 to 40 are
      either present or absent

<400> SEQUENCE: 80

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser

-continued

```
              20              25              30
Gly Gly Gly Ser Gly Gly Gly Ser
       35                  40

<210> SEQ ID NO 81
<211> LENGTH: 4
<212> TYPE: PRT
<213> ORGANISM: Artificial sequence
<220> FEATURE:
<223> OTHER INFORMATION: synthetic sequence

<400> SEQUENCE: 81

Gly Gly Ser Gly
1

<210> SEQ ID NO 82
<211> LENGTH: 5
<212> TYPE: PRT
<213> ORGANISM: Artificial sequence
<220> FEATURE:
<223> OTHER INFORMATION: synthetic sequence

<400> SEQUENCE: 82

Gly Gly Ser Gly Gly
1               5

<210> SEQ ID NO 83
<211> LENGTH: 5
<212> TYPE: PRT
<213> ORGANISM: Artificial sequence
<220> FEATURE:
<223> OTHER INFORMATION: synthetic sequence

<400> SEQUENCE: 83

Gly Ser Gly Ser Gly
1               5

<210> SEQ ID NO 84
<211> LENGTH: 5
<212> TYPE: PRT
<213> ORGANISM: Artificial sequence
<220> FEATURE:
<223> OTHER INFORMATION: synthetic sequence

<400> SEQUENCE: 84

Gly Ser Gly Gly Gly
1               5

<210> SEQ ID NO 85
<211> LENGTH: 5
<212> TYPE: PRT
<213> ORGANISM: Artificial sequence
<220> FEATURE:
<223> OTHER INFORMATION: synthetic sequence

<400> SEQUENCE: 85

Gly Gly Gly Ser Gly
1               5

<210> SEQ ID NO 86
<211> LENGTH: 5
<212> TYPE: PRT
<213> ORGANISM: Artificial sequence
<220> FEATURE:
<223> OTHER INFORMATION: synthetic sequence

<400> SEQUENCE: 86
```

-continued

```
Gly Ser Ser Ser Gly
1               5

<210> SEQ ID NO 87
<211> LENGTH: 5
<212> TYPE: PRT
<213> ORGANISM: Artificial sequence
<220> FEATURE:
<223> OTHER INFORMATION: synthetic sequence

<400> SEQUENCE: 87

Gly Gly Gly Gly Ser
1               5

<210> SEQ ID NO 88
<211> LENGTH: 102
<212> TYPE: DNA
<213> ORGANISM: Artificial sequence
<220> FEATURE:
<223> OTHER INFORMATION: synthetic sequence

<400> SEQUENCE: 88
ggcgcgttta ttccattact ttggagccag tcccagcgac tatgtcgtat ggacgaagcg     60
cttatttatc ggagagaaac cgataagtaa aacgcatcaa ag                       102

<210> SEQ ID NO 89
<211> LENGTH: 132
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (103)..(121)
<223> OTHER INFORMATION: n is a, c, g, or u
<220> FEATURE:
<221> NAME/KEY: misc_feature
<222> LOCATION: (122)..(132)
<223> OTHER INFORMATION: Any one or all of the nucleotides at positions
      122 to 132 can either be present or absent and n is a, c, g, or u

<400> SEQUENCE: 89
ggcgcguuua uuccauuacu uuggagccag ucccagcgac uaugucguau ggacgaagcg     60
cuuauuuauc ggagagaaac cgauaaguaa aacgcaucaa agnnnnnnnn nnnnnnnnnn    120
nnnnnnnnnn nn                                                        132

<210> SEQ ID NO 90
<211> LENGTH: 131
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (102)..(116)
<223> OTHER INFORMATION: n is a, c, g, or u
<220> FEATURE:
<221> NAME/KEY: misc_feature
<222> LOCATION: (117)..(131)
<223> OTHER INFORMATION: Any one or all of the nucleotides at positions
      117 to 131 can either be present or absent and n is a, c, g, or u

<400> SEQUENCE: 90
ggcgcuuuua ucucauuacu uugagagcca ucaccagcga cuaugucgua uggguaaagc     60
gcuuauuuau cggagaaacc gauaaauaag aagcaucaaa gnnnnnnnnn nnnnnnnnnn    120
```
nnnnnnnnnn n                                                                                    131

<210> SEQ ID NO 91
<211> LENGTH: 122
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (103)..(122)
<223> OTHER INFORMATION: n is a, c, g, or u

<400> SEQUENCE: 91
ggcgcguuua uuccauuacu uuggagccag ucccagcgac uaugucguau ggacgaagcg      60
cuuauuuauc ggagagaaac cgauaaguaa aacgcaucaa agnnnnnnnn nnnnnnnnnn     120 nn                                                                    122

<210> SEQ ID NO 92
<211> LENGTH: 121
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (102)..(121)
<223> OTHER INFORMATION: n is a, c, g, or u

<400> SEQUENCE: 92
ggcgcuuuua ucucauuacu uugagagcca ucaccagcga cuaugucgua uggguaaagc      60
gcuuauuuau cggagaaacc gauaaauaag aagcaucaaa gnnnnnnnnn nnnnnnnnnn     120 n                                                                     121

<210> SEQ ID NO 93
<211> LENGTH: 210
<212> TYPE: PRT
<213> ORGANISM: Artificial sequence
<220> FEATURE:
<223> OTHER INFORMATION: synthetic sequence

<400> SEQUENCE: 93

Asp Met Gly Arg Val Phe Trp Ser Gly Val Thr Ala Glu Lys Arg Asn
1               5                   10                  15

Thr Ile Leu Glu Gly Tyr Asn Tyr Leu Pro Asn Glu Asn Asp His Lys
            20                  25                  30

Lys Arg Glu Gly Ser Leu Glu Asn Pro Lys Lys Pro Ala Lys Arg Gln
        35                  40                  45

Phe Gly Asp Leu Leu Leu Tyr Leu Glu Lys Lys Tyr Met Asp Glu Lys
    50                  55                  60

Glu Phe Tyr Ala Cys Glu Ile Gln Leu Gln Lys Trp Tyr Gly Asp Leu
65                  70                  75                  80

Arg Gly Asn Pro Phe Ala Val Glu Ala Glu Asn Arg Val Val Asp Ile
                85                  90                  95

Ser Gly Phe Ser Ile Gly Ser Asp Gly His Ser Ile Gln Tyr Arg Asn
            100                 105                 110

Leu Leu Ala Trp Lys Tyr Leu Glu Lys Trp Thr Lys Gly Arg Arg Asp
        115                 120                 125

Glu Ala Leu Phe Leu Leu Lys Lys Arg Phe Ser His Arg Pro Val Gln
    130                 135                 140

```
Glu Gln Phe Val Cys Leu Asp Cys Gly His Glu Val His Ala Asp Glu
145                 150                 155                 160

Gln Ala Ala Leu Asn Ile Ala Arg Ser Trp Leu Phe Leu Asn Ser Asn
                165                 170                 175

Ser Thr Glu Phe Lys Ser Tyr Lys Ser Gly Lys Gln Pro Phe Val Gly
            180                 185                 190

Ala Trp Gln Ala Phe Tyr Lys Arg Arg Leu Lys Glu Val Trp Lys Pro
        195                 200                 205

Asn Ala
    210
```

```
<210> SEQ ID NO 94
<211> LENGTH: 199
<212> TYPE: PRT
<213> ORGANISM: Artificial sequence
<220> FEATURE:
<223> OTHER INFORMATION: synthetic sequence

<400> SEQUENCE: 94
```

```
Glu Asp Gly Lys Val Phe Trp Gln Asn Leu Ala Gly Tyr Lys Arg Gln
1               5                   10                  15

Glu Ala Leu Leu Pro Tyr Leu Ser Ser Glu Glu Asp Arg Lys Lys Gly
            20                  25                  30

Lys Lys Phe Ala Arg Tyr Gln Phe Gly Asp Leu Leu Leu His Leu Glu
        35                  40                  45

Lys Lys His Ala Asp Lys Asp Glu Phe Cys Arg Cys Glu Leu Lys Leu
    50                  55                  60

Gln Lys Trp Tyr Gly Asp Leu Arg Gly Lys Pro Phe Ala Ile Glu Ala
65                  70                  75                  80

Glu Asn Ser Ile Leu Asp Ile Ser Gly Phe Ser Lys Gln Tyr Asn Cys
                85                  90                  95

Ala Phe Ile Trp Gln Lys Asp Gly Ser Trp Thr Lys Gly Arg Ser Gly
            100                 105                 110

Glu Ala Leu Ser Leu Leu Lys Lys Arg Phe Ser His Arg Pro Val Gln
        115                 120                 125

Glu Lys Phe Val Cys Leu Asn Cys Gly Phe Glu Thr His Ala Asp Glu
    130                 135                 140

Gln Ala Ala Leu Asn Ile Ala Arg Ser Trp Leu Phe Leu Arg Ser Gln
145                 150                 155                 160

Glu Tyr Lys Lys Tyr Gln Thr Asn Lys Thr Thr Gly Asn Thr Asp Lys
                165                 170                 175

Arg Ala Phe Val Glu Thr Trp Gln Ser Phe Tyr Arg Lys Lys Leu Lys
            180                 185                 190

Glu Val Trp Lys Pro Ala Val
        195
```

```
<210> SEQ ID NO 95
<211> LENGTH: 123
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (103)..(123)
<223> OTHER INFORMATION: n is a, c, g, or u

<400> SEQUENCE: 95
```

```
ggcgcguuua uuccauuacu uuggagccag ucccagcgac uaugucguau ggacgaagcg      60
```

-continued

```
cuuauuuauc ggagagaaac cgauaaguaa aacgcaucaa agnnnnnnnn nnnnnnnnnn      120 nnn                                                                    123

<210> SEQ ID NO 96
<211> LENGTH: 124
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (104)..(124)
<223> OTHER INFORMATION: n is a, c, g, or u

<400> SEQUENCE: 96
uggcgcguuu auuccauuac uuuggagcca gucccagcga cuaugucgua uggacgaagc       60
gcuuauuuau cggagagaaa ccgauaagua aaacgcauca aagnnnnnnn nnnnnnnnnn      120 nnnn                                                                   124

<210> SEQ ID NO 97
<211> LENGTH: 122
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (102)..(122)
<223> OTHER INFORMATION: n is a, c, g, or u

<400> SEQUENCE: 97
ggcgcuuuua ucucauuacu uugagagcca ucaccagcga cuaugucgua uggguaaagc       60
gcuuauuuau cggagaaacc gauaaauaag aagcaucaaa gnnnnnnnnn nnnnnnnnnn      120 nn                                                                     122

<210> SEQ ID NO 98
<211> LENGTH: 123
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (103)..(123)
<223> OTHER INFORMATION: n is a, c, g, or u

<400> SEQUENCE: 98
uggcgcuuuu aucucauuac uuugagagcc aucaccagcg acuaugucgu auggguaaag       60
cgcuuauuua ucggagaaac cgauaaauaa gaagcaucaa agnnnnnnnn nnnnnnnnnn      120 nnn                                                                    123

<210> SEQ ID NO 99
<211> LENGTH: 126
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (106)..(126)
<223> OTHER INFORMATION: n is a, c, g, or u

<400> SEQUENCE: 99
```

-continued

```
uacuggcgcu uuuaucucau uacuuugaga gccaucacca gcgacuaugu cguaugggua        60
aagcgcuuau uuaucggaga aaccgauaaa uaagaagcau caaagnnnnn nnnnnnnnnn       120 nnnnnn                                                                  126

<210> SEQ ID NO 100
<211> LENGTH: 60
<212> TYPE: DNA
<213> ORGANISM: Artificial sequence
<220> FEATURE:
<223> OTHER INFORMATION: synthetic sequence

<400> SEQUENCE: 100
tctctctggc ccactgtgtc ctcttcctgc cctgccatcc ccttctgtga atgttagacc        60

<210> SEQ ID NO 101
<211> LENGTH: 41
<212> TYPE: DNA
<213> ORGANISM: Artificial sequence
<220> FEATURE:
<223> OTHER INFORMATION: synthetic sequence

<400> SEQUENCE: 101
tctctctggc ccactgtgtc ctcttctgtg aatgttagac c                            41

<210> SEQ ID NO 102
<211> LENGTH: 41
<212> TYPE: DNA
<213> ORGANISM: Artificial sequence
<220> FEATURE:
<223> OTHER INFORMATION: synthetic sequence

<400> SEQUENCE: 102
tctctctggc ccactgtgtc cccttctgtg aatgttagac c                            41

<210> SEQ ID NO 103
<211> LENGTH: 55
<212> TYPE: DNA
<213> ORGANISM: Artificial sequence
<220> FEATURE:
<223> OTHER INFORMATION: synthetic sequence

<400> SEQUENCE: 103
tctctctggc ccactgtgtc ctcttcctgc catccccttc tgtgaatgtt agacc             55

<210> SEQ ID NO 104
<211> LENGTH: 45
<212> TYPE: DNA
<213> ORGANISM: Artificial sequence
<220> FEATURE:
<223> OTHER INFORMATION: synthetic sequence

<400> SEQUENCE: 104
tctctctggc ccactgtgtc catccccttc tgtgaatgtt agacc                        45

<210> SEQ ID NO 105
<211> LENGTH: 59
<212> TYPE: DNA
<213> ORGANISM: Artificial sequence
<220> FEATURE:
<223> OTHER INFORMATION: synthetic sequence

<400> SEQUENCE: 105
tctctctggc ccactgtgtc ctcttcctgc ctgccatccc cttctgtgaa tgttagacc         59
```

-continued

```
<210> SEQ ID NO 106
<211> LENGTH: 39
<212> TYPE: DNA
<213> ORGANISM: Artificial sequence
<220> FEATURE:
<223> OTHER INFORMATION: synthetic sequence

<400> SEQUENCE: 106
tctctctggc ccactgtgtc cttctgtgaa tgttagacc                    39

<210> SEQ ID NO 107
<211> LENGTH: 42
<212> TYPE: DNA
<213> ORGANISM: Artificial sequence
<220> FEATURE:
<223> OTHER INFORMATION: synthetic sequence

<400> SEQUENCE: 107
tctctctggc ccactgccat ccccttctgt gaatgttaga cc                42

<210> SEQ ID NO 108
<211> LENGTH: 44
<212> TYPE: DNA
<213> ORGANISM: Artificial sequence
<220> FEATURE:
<223> OTHER INFORMATION: synthetic sequence

<400> SEQUENCE: 108
tctctctggc ccactgtgcc atccccttct gtgaatgtta gacc              44

<210> SEQ ID NO 109
<211> LENGTH: 56
<212> TYPE: DNA
<213> ORGANISM: Artificial sequence
<220> FEATURE:
<223> OTHER INFORMATION: synthetic sequence

<400> SEQUENCE: 109
tctctctggc ccactgtgtc ctcttcctgc ccatcccctt ctgtgaatgt tagacc  56

<210> SEQ ID NO 110
<211> LENGTH: 29
<212> TYPE: DNA
<213> ORGANISM: Artificial sequence
<220> FEATURE:
<223> OTHER INFORMATION: synthetic sequence

<400> SEQUENCE: 110
tctctctggc ccactgtgaa tgttagacc                              29
```